US011160758B2

(12) United States Patent
Asada et al.

(10) Patent No.: US 11,160,758 B2
(45) Date of Patent: Nov. 2, 2021

(54) MODIFIED RELEASE FORMULATIONS AND USES THEREOF

(71) Applicant: Sunovion Pharmaceuticals Inc., Marlborough, MA (US)

(72) Inventors: Takumi Asada, Hyogo (JP); Gerald R. Galluppi, Marlborough, MA (US); Seth Cabot Hopkins, Northborough, MA (US); Megumi Maruyama, Okayama (JP); Siriporn Toongsuwan, Berlin, MA (US); Yuki Tsushima, Osaka (JP)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 16/892,641

(22) Filed: Jun. 4, 2020

(65) Prior Publication Data

US 2020/0383924 A1 Dec. 10, 2020

Related U.S. Application Data

(60) Provisional application No. 62/944,023, filed on Dec. 5, 2019, provisional application No. 62/872,623, filed (Continued)

(51) Int. Cl.
*A61K 9/20* (2006.01)
*A61K 31/40* (2006.01)
(Continued)

(52) U.S. Cl.
CPC ............ *A61K 9/2054* (2013.01); *A61K 31/40* (2013.01); *A61K 47/38* (2013.01); *A61P 25/18* (2018.01); *A61P 25/24* (2018.01)

(58) Field of Classification Search
None
See application file for complete search history.

(56) References Cited

U.S. PATENT DOCUMENTS 3,459,850 A 8/1969 Riva
3,577,514 A 5/1971 Robinson
(Continued)

FOREIGN PATENT DOCUMENTS

AT 264666 B 9/1968
AU 684745 1/1998
(Continued)

OTHER PUBLICATIONS

Abbas et al., "Amisulpride is a potent 5-HT7 antagonist: relevance for antidepressant actions in vivo," Psychopharmacology, Jul. 2009, 205(1)119-128.
(Continued)

*Primary Examiner* — Bethany P Barham
*Assistant Examiner* — Barbara S Frazier
(74) *Attorney, Agent, or Firm* — Fish & Richardson P.C.

(57) ABSTRACT

Provided are modified release compositions in a solid oral dosage form comprising amisulpride in the form of an unequal mixture of (R)-amisulpride and (S)-amisulpride, or pharmaceutically acceptable salts thereof, where the amount of (R)-amisulpride is greater than the amount of (S)-amisulpride, and medicaments comprising the same used for the treatment of various diseases and disorders, and methods of using same for the treatment of various diseases and disorders, including, but not limited to, dosage regimens. In addition, provided are formulations employing polymorphs of enantiomeric amisulpride.

29 Claims, 70 Drawing Sheets

Related U.S. Application Data on Jul. 10, 2019, provisional application No. 62/856,952, filed on Jun. 4, 2019.

(51) Int. Cl.
  *A61K 47/38* (2006.01)
  *A61P 25/18* (2006.01)
  *A61P 25/24* (2006.01)

(56) References Cited

U.S. PATENT DOCUMENTS

| | | | |
|---|---|---|---|
| 4,294,828 | A | 10/1981 | Thominet et al. |
| 4,590,062 | A | 5/1986 | Jang |
| 4,816,264 | A | 3/1989 | Phillips et al. |
| 4,888,178 | A | 12/1989 | Rotini et al. |
| 5,164,193 | A | 11/1992 | Okada et al. |
| 5,316,772 | A | 5/1994 | Jurgens, Jr. et al. |
| 5,389,129 | A | 2/1995 | Jordan |
| 5,514,384 | A | 5/1996 | Signorino |
| 5,591,455 | A | 1/1997 | Signorino |
| 5,711,967 | A | 1/1998 | Juch |
| 5,837,379 | A | 11/1998 | Chen et al. |
| 5,922,352 | A | 7/1999 | Chen et al. |
| 5,955,500 | A | 9/1999 | Logstreth et al. |
| 6,069,165 | A | 5/2000 | Andrieu et al. |
| 6,169,094 | B1 | 1/2001 | Perrault et al. |
| 6,187,807 | B1 | 2/2001 | Perrault et al. |
| 6,210,710 | B1 | 4/2001 | Skinner |
| 6,210,712 | B1 | 4/2001 | Edgren et al. |
| 6,217,903 | B1 | 4/2001 | Skiner |
| 6,358,525 | B1 | 3/2002 | Guo et al. |
| 6,861,072 | B1 | 3/2005 | Alaux et al. |
| 6,897,242 | B1 | 5/2005 | Somerville et al. |
| 7,815,936 | B2 | 10/2010 | Hasenzahl et al. |
| 7,825,156 | B2 | 11/2010 | Azorin |
| 7,976,871 | B2 | 7/2011 | Vaya et al. |
| 7,985,422 | B2 | 7/2011 | Vaya et al. |
| 8,066,661 | B2 | 11/2011 | Boyd et al. |
| 8,138,169 | B2 | 3/2012 | Oronsky et al. |
| 8,216,609 | B2 | 7/2012 | Vaya et al. |
| 8,263,125 | B2 | 9/2012 | Vaya et al. |
| 8,268,352 | B2 | 9/2012 | Vaya et al. |
| 8,304,431 | B2 | 11/2012 | Buntinx |
| 8,377,994 | B2 | 2/2013 | Gray et al. |
| 8,394,790 | B2 | 3/2013 | Portnoy et al. |
| 8,480,631 | B2 | 7/2013 | Wooton et al. |
| 8,575,172 | B2 | 11/2013 | Wilding et al. |
| 8,579,865 | B2 | 11/2013 | Wooton et al. |
| 8,697,127 | B2 | 4/2014 | Sah |
| 8,876,758 | B2 | 11/2014 | Boyd et al. |
| 8,906,847 | B2 | 12/2014 | Cleemann et al. |
| 8,945,063 | B2 | 2/2015 | Wooton et al. |
| 9,050,343 | B2 | 6/2015 | Peters et al. |
| 9,156,829 | B2 | 10/2015 | Fieldhoue et al. |
| 9,173,953 | B2 | 11/2015 | Rau et al. |
| 9,186,461 | B2 | 11/2015 | Boyd et al. |
| 9,283,192 | B2 | 3/2016 | Mullen et al. |
| 9,421,333 | B2 | 8/2016 | Wooton et al. |
| 9,474,719 | B2 | 10/2016 | Mullen et al. |
| 9,750,881 | B2 | 9/2017 | Wooton et al. |
| 9,827,315 | B2 | 11/2017 | Patel et al. |
| 10,011,588 | B2 | 7/2018 | Fieldhoue et al. |
| 10,137,091 | B2 | 11/2018 | Mullen et al. |
| 10,369,134 | B2 | 8/2019 | Hopkins et al. |
| 10,377,708 | B2 | 8/2019 | Snoonian et al. |
| 10,576,058 | B2 | 3/2020 | Hopkins et al. |
| 10,577,317 | B2 | 3/2020 | Snoonian et al. |
| 10,660,875 | B1 | 5/2020 | Hopkins et al. |
| 10,800,738 | B2 | 10/2020 | Snoonian et al. |
| 10,874,639 | B2 | 12/2020 | Hopkins et al. |
| 2001/0020032 | A1 | 9/2001 | Morris et al. |
| 2003/0096264 | A1 | 5/2003 | Altar et al. |
| 2003/0130334 | A1 | 7/2003 | Muller |
| 2005/0085463 | A1 | 4/2005 | Weiner et al. |
| 2005/0171086 | A1 | 8/2005 | Brodney et al. |
| 2005/0181049 | A1 | 8/2005 | Dong et al. |
| 2005/0250767 | A1 | 11/2005 | Weiner et al. |
| 2005/0281752 | A1 | 12/2005 | Dugger, III |
| 2006/0150989 | A1 | 7/2006 | Migaly |
| 2006/0153916 | A1 | 7/2006 | Vaya et al. |
| 2006/0153925 | A1 | 7/2006 | Andre et al. |
| 2006/0167068 | A1 | 7/2006 | Feuerstein et al. |
| 2006/0167074 | A1 | 7/2006 | Muller |
| 2008/0188464 | A1 | 8/2008 | Green et al. |
| 2008/0188537 | A1 | 8/2008 | Azorin |
| 2008/0280886 | A1 | 11/2008 | Grant et al. |
| 2008/0319041 | A1 | 12/2008 | Digenis et al. |
| 2009/0053329 | A1 | 2/2009 | Peters et al. |
| 2009/0082342 | A1 | 3/2009 | Uldam et al. |
| 2009/0208979 | A1 | 8/2009 | Silver et al. |
| 2009/0269770 | A1 | 10/2009 | Silver et al. |
| 2010/0004262 | A1 | 1/2010 | Wilding et al. |
| 2010/0069356 | A1 | 3/2010 | Gant et al. |
| 2010/0069399 | A1 | 3/2010 | Gant et al. |
| 2010/0074973 | A1 | 3/2010 | Gant et al. |
| 2010/0104643 | A1 | 4/2010 | Wilding et al. |
| 2010/0119622 | A1 | 5/2010 | Gant et al. |
| 2010/0119624 | A1 | 5/2010 | Gant et al. |
| 2010/0143507 | A1 | 6/2010 | Gant et al. |
| 2010/0159033 | A1 | 6/2010 | Gant et al. |
| 2010/0168085 | A1 | 7/2010 | Eisenbach-Schwartz et al. |
| 2010/0234288 | A1 | 9/2010 | Jain et al. |
| 2010/0266711 | A1 | 10/2010 | Gant et al. |
| 2011/0130390 | A1 | 6/2011 | Muller |
| 2011/0136742 | A1 | 6/2011 | Mickle et al. |
| 2011/0136865 | A1 | 6/2011 | Buntinx |
| 2011/0207776 | A1 | 8/2011 | Buntinx |
| 2012/0231092 | A1 | 9/2012 | Oronsky et al. |
| 2013/0022688 | A1* | 1/2013 | Gilbert ............... A61K 47/12 424/649 |
| 2013/0096319 | A1 | 4/2013 | Paghdar et al. |
| 2013/0218086 | A1 | 8/2013 | Wotton et al. |
| 2013/0281410 | A1 | 10/2013 | Renshaw |
| 2014/0031372 | A1 | 1/2014 | Fong et al. |
| 2014/0044786 | A1 | 2/2014 | Wilding et al. |
| 2014/0113912 | A1 | 4/2014 | Loebel et al. |
| 2014/0154328 | A1 | 6/2014 | Sovic Brkicic et al. |
| 2015/0018360 | A1 | 1/2015 | Halse et al. |
| 2015/0057221 | A1 | 2/2015 | Cleemann et al. |
| 2015/0099741 | A1 | 4/2015 | Li et al. |
| 2015/0231126 | A1 | 8/2015 | Peters et al. |
| 2015/0272946 | A1 | 10/2015 | Sato et al. |
| 2016/0032390 | A1 | 2/2016 | Hakonarson et al. |
| 2016/0038596 | A1 | 2/2016 | Wright et al. |
| 2016/0060702 | A1 | 3/2016 | Li et al. |
| 2016/0081987 | A1 | 3/2016 | Lawton et al. |
| 2016/0193151 | A1 | 7/2016 | Noriega Escobar et al. |
| 2016/0348101 | A1 | 12/2016 | Chen et al. |
| 2017/0027958 | A1 | 2/2017 | Patel et al. |
| 2017/0100490 | A1 | 4/2017 | Cleeman et al. |
| 2017/0258787 | A1 | 9/2017 | Sato et al. |
| 2017/0361021 | A1 | 12/2017 | Woonton et al. |
| 2018/0071390 | A1 | 3/2018 | Patel et al. |
| 2018/0111891 | A1 | 4/2018 | Tsai et al. |
| 2018/0116967 | A1* | 5/2018 | Sun ............... A61K 9/2853 |
| 2018/0118967 | A1* | 5/2018 | Liu ............... B41M 5/0011 |
| 2018/0282309 | A1 | 10/2018 | Fieldhoue et al. |
| 2018/0346400 | A9 | 12/2018 | Tsai et al. |
| 2019/0070124 | A1 | 3/2019 | Anavi-Goffer |
| 2019/0083407 | A1 | 3/2019 | Hanna |
| 2019/0105276 | A1 | 4/2019 | William et al. |
| 2020/0165200 | A1 | 5/2020 | Snoonian et al. |
| 2020/0237719 | A1 | 7/2020 | Hopkins et al. |
| 2021/0061759 | A1 | 3/2021 | Snoonian et al. |

FOREIGN PATENT DOCUMENTS

| | | |
|---|---|---|
| CA | 2646779 | 5/2010 |
| CN | 1018988991 | 12/2010 |
| CN | 101987081 | 8/2012 |
| CN | 102600132 | 5/2014 |
| CN | 104725292 | 6/2015 |
| CN | 106995397 | 8/2017 |
| CN | 107049981 | 8/2017 |

(56) References Cited

FOREIGN PATENT DOCUMENTS

| | | |
|---|---|---|
| CN | 107126422 | 9/2017 |
| CN | 109010300 | 12/2018 |
| EP | 1547650 | 6/2005 |
| EP | 1646379 | 4/2006 |
| EP | 1944295 | 7/2008 |
| EP | 1946777 | 7/2008 |
| EP | 2030619 | 3/2009 |
| EP | 2959895 | 3/2009 |
| EP | 2272514 | 1/2011 |
| EP | 2508174 | 10/2012 |
| EP | 2596805 | 5/2013 |
| EP | 2676691 | 12/2013 |
| EP | 3058972 | 8/2016 |
| GB | 2456183 | 7/2009 |
| GE | P20115310 | 10/2011 |
| IN | 1013/MUM2005 | 6/2007 |
| IN | 201641042385 | 6/2018 |
| WO | WO 97/47311 | 12/1997 |
| WO | WO 1998047506 | 10/1998 |
| WO | WO 9929297 | 6/1999 |
| WO | WO 2000/021525 | 4/2000 |
| WO | WO 200023045 | 4/2000 |
| WO | WO 2000032558 | 6/2000 |
| WO | WO 2002053140 | 7/2002 |
| WO | WO 2002102297 | 12/2002 |
| WO | WO 3037379 | 5/2003 |
| WO | WO 2003042654 | 5/2003 |
| WO | WO 2004012699 | 2/2004 |
| WO | WO 2004012700 | 2/2004 |
| WO | WO 2004103262 | 12/2004 |
| WO | WO 2005004860 | 1/2005 |
| WO | WO 2005/053796 | 6/2005 |
| WO | WO 2005051358 | 6/2005 |
| WO | WO 2005053796 | 6/2005 |
| WO | WO 2005084654 | 9/2005 |
| WO | WO 2005092392 | 10/2005 |
| WO | WO 2006079547 | 8/2006 |
| WO | WO 2006106425 | 10/2006 |
| WO | WO 2007061896 | 5/2007 |
| WO | WO 2007110878 | 10/2007 |
| WO | WO 2007128349 | 11/2007 |
| WO | WO 2007133802 | 11/2007 |
| WO | WO 2007137224 | 11/2007 |
| WO | WO 2008038003 | 4/2008 |
| WO | WO 2008050341 | 5/2008 |
| WO | WO 2008065500 | 6/2008 |
| WO | WO 2008070296 | 6/2008 |
| WO | WO 2008116024 | 9/2008 |
| WO | WO 2008155357 | 12/2008 |
| WO | WO 2009017453 | 2/2009 |
| WO | WO 2009035473 | 3/2009 |
| WO | WO 2009036056 | 3/2009 |
| WO | WO 2009039461 | 3/2009 |
| WO | WO 2009095479 | 8/2009 |
| WO | WO 2009126931 | 10/2009 |
| WO | WO 2010020642 | 2/2010 |
| WO | WO 2010023690 | 3/2010 |
| WO | WO 2010056065 | 5/2010 |
| WO | WO 2010058314 | 5/2010 |
| WO | WO 2010075275 | 7/2010 |
| WO | WO 2010085452 | 7/2010 |
| WO | WO 2010108116 | 9/2010 |
| WO | WO 2011012722 | 2/2011 |
| WO | WO 2011057199 | 5/2011 |
| WO | WO 2011060363 | 5/2011 |
| WO | WO 2011082337 | 7/2011 |
| WO | WO 2011107749 | 9/2011 |
| WO | WO 2011107750 | 9/2011 |
| WO | WO 2011107755 | 9/2011 |
| WO | WO 2011110854 | 9/2011 |
| WO | WO 2012002583 | 1/2012 |
| WO | WO 2012006959 | 1/2012 |
| WO | WO 2012016646 | 2/2012 |
| WO | WO 2012037457 | 3/2012 |
| WO | WO 2012065102 | 5/2012 |
| WO | WO 2012065110 | 5/2012 |
| WO | WO 2012088441 | 6/2012 |
| WO | WO 2012118562 | 9/2012 |
| WO | WO 2012136816 | 10/2012 |
| WO | WO 2012158492 | 11/2012 |
| WO | WO 2013003586 | 1/2013 |
| WO | WO 2013016727 | 1/2013 |
| WO | WO 2013040164 | 3/2013 |
| WO | WO 2013122554 | 8/2013 |
| WO | WO 2014065437 | 5/2014 |
| WO | WO 2014178065 | 11/2014 |
| WO | WO 2015085004 | 6/2015 |
| WO | WO 2015/124932 | 8/2015 |
| WO | WO 2015154025 | 10/2015 |
| WO | WO 2015154030 | 10/2015 |
| WO | WO 2016020573 | 2/2016 |
| WO | WO 2016/111725 | 7/2016 |
| WO | WO 2016109359 | 7/2016 |
| WO | WO 2016162695 | 10/2016 |
| WO | WO 2016166679 | 10/2016 |
| WO | WO 2016186968 | 11/2016 |
| WO | WO 2017/049294 | 3/2017 |
| WO | WO 2017/149387 | 9/2017 |
| WO | WO 2017/149392 | 9/2017 |
| WO | WO 2018/015915 | 1/2018 |
| WO | WO 2018077157 | 5/2018 |
| WO | WO 2018/200381 | 11/2018 |
| WO | WO 2019113079 | 6/2019 |
| WO | WO 2019113084 | 6/2019 |
| WO | WO 2020/247627 | 12/2020 |

OTHER PUBLICATIONS

Babichev, "Interaction between regions of the hypothalamus regulating hypophyseal gonadotropic function in female rats," Neurosci Behav Physiol., Jul.-Sep. 1972, 5(3):195-199.

Bard et al., "Cloning of a novel human serotonin receptor (5-HT7) positively linked to adenylate cyclase," J Biol Chem, Nov. 5, 1993, 268(31):23422-23426.

Barrett, "Aspects of cognitive function in healthy volunteers administered antipsychotic drugs and in patients with bipolar disorder," Queen's University Belfast (United Kingdom), ProQuest Dissertations Publishing, 2001. U151775. (Abstract only).

BioOrganics, "R-Amisulpride," [retrieved on Mar. 22, 2018], retrieved from: <www.bioorganics.biz/product_details.php?id=BO%ADA67%AD009#1/2>, 2 pages.

Bonaventure et al., "Selective blockade of 5-hydroxytryptamine (5-HT)7 receptors enhances 5-HT transmission, antidepressant-like behavior, and rapid eye movement sleep suppression induced by citalopram in rodents.," J Pharmacol Exp Ther., May 2007, 321(2):690-698.

Bonaventure et al., "Translational evaluation of JNJ-18038683, a 5-hydroxytryptamine type 7 receptor antagonist, on rapid eye movement sleep and in major depressive disorder.," Aug. 2012, J Pharmacol Exp Ther., 342(2):429-440.

Boulu, "Behavioral and neurochemical methods in research on new psychotropics," Ann Pharm Fr, 1998, 56(2):54-59.

Carta et al., "An Open Label Follow-up Study on Amisulpride in the add-on Treatment of Bipolar 1 Patients," Clinical Practive and Epidemiology in Mental Health, Aug. 24, 2006, 2:19.

Cassano et al., "Efficacy and safety of amisulpride 50 mg versus paroxetine 20 mg in major depression: a randomized, double-blind, parallel group study," Int Clin Psychopharmacol., Jan. 2002, 17(1):27-32.

Castelli et al., "(−)S amisulpride binds with high affinity to cloned dopamine D(3) and D(2) receptors," Euro Journal of Pharma., Nov. 5, 2001, 432:143-147.

Cates et al., "Effects of lurasidone in behavioral models of depression. Role of the 5-HT, receptor subtype," Neuropharmacology, Jul. 2013, 70:211-217.

Chaggar et al., "Effect of antipsychotic medications on glucose and lipid levels," J Clin Pharmacol, May 2011, 51(5):631-638.

Chen et al., "Second-generation antipsychotics in major depressive disorder: update and clinical perspective," Curr Opin Psychiatry., Jan. 2011, 24(1):10-17.

(56) References Cited

OTHER PUBLICATIONS

Clinicaltrials.gov, "[18 Fluorine(F)]DOPA Determinants and Predictors of Treatment Response in Psychosis (DPTP)," NCT02880995, Aug. 26, 2016, [retrieved on Dec. 4, 2018] retrieved from URL<https://clinicaltrials.gov/ct2/show/NCT02880995>, 8 pages.

Clinicaltrials.gov, "A Four-week Clinical Trial Investigating Efficacy and Safety of Cannabidiol as a Treatment for Acutely Ill Schizophrenic Patients," NCT02088060, Mar. 8, 2018, [retrieved on Dec. 4, 2018] retrieved from URL<https://clinicaltrials.gov/ct2/show/NCT02088060>, 8 pages.

Clinicaltrials.gov, "A Randomized, Double-blind, Comparison of the Efficacy and Safety of Amisulpride Versus Low-dose Amisulpride Plus Low-dose Sulpiride in the Treatment of Schizophrenia," NCT01615185, Mar. 1, 2016, [retrieved on Dec. 3, 2018] retrieved from URL<https://clinicaltrials.gov/ct2/show/NCT01615185>, 8 pages.

Clinicaltrials.gov, "Amisulpride Augmentation in Clozapine-unresponsive Schizophrenia (AMICUS)," NCT01246232, Apr. 1, 2015, [retrieved on Dec. 3, 2018] retrieved from URL<https://clinicaltrials.gov/ct2/show/NCT01246232>, 8 pages.

Clinicaltrials.gov, "Amisulpride Augmentation Therapy for Clozapine-resistant Schizophrenic Patients (M1106)," NCT01105481, Apr. 16, 2010, [retrieved on Dec. 3, 2018] retrieved from URL<https://clinicaltrials.gov/ct2/show/NCT01105481>, 7 pages.

Clinicaltrials.gov, "Amisulpride in Schizophrenic Acute Phase Patients (ASAP)," NCT00436371, Sep. 5, 2008, [retrieved on Dec. 3, 2018] retrieved from URL<https://clinicaltrials.gov/ct2/show/NCT0043671>, 5 pages.

Clinicaltrials.gov, "Amisulpride in Schizophrenic Patients," NCT00331981, Apr. 10, 2008, [retrieved on Dec. 3, 2018] retrieved from URL<https://clinicaltrials.gov/ct2/show/NCT00331981>, 5 pages.

Clinicaltrials.gov, "An Investigation of Early life Stress and Depression", NCT 017101258, Dec. 28, 2016, [retrieved on Jul. 22, 2017] retrieved from URL<https://clinicaltrials.gov/ct2/show/NCT01701258?term=amisulpride&draw=1>, 6 pages.

Clinicaltrials.gov, "An Observational Drug Utilization Study of Asenapine in the United Kingdom (P08308)," NCT01498770, Jun. 7, 2017, [retrieved on Jul. 22, 2017] retrieved from URL<https://clinicaltrials.gov/ct2/show/NCT01498770?term=amisulpride&draw=1>, 6 pages.

Clinicaltrials.gov, "An Observational Study on Atypical Antipsychotics Long-term Treatment Patients With Schizophrenia," NCT02640911, Aug. 1, 2017, [retrieved on Dec. 4, 2018] retrieved from URL<https://clinicaltrials.gov/ct2/show/NCT02640911>, 6 pages.

Clinicaltrials.gov, "An Observational Study on Metabolic Syndrome Parameters in Schizophrenia Patients Treated With Atypical Antipsychotics (MESSAGE)," NCT00448630, Jul. 7, 2010, [retrieved Dec. 4, 20018] retrieved from URL<https://clinicaltrials.gov/ct2/show/NCT00448630>, 8 pages.

Clinicaltrials.gov, "Antipsychotic Induced Structural and Functional Brain Changes (APIC)," NCT02435095, Dec. 22, 2017, [retrieved on Dec. 4, 2018] retrieved from URL<https://clinicaltrials.gov/ct2/show/NCT02435095>, 10 pages.

Clinicaltrials.gov, "Association of Amisulpride Response in Schizophrenia With Brain Image (ARB)," NCT02095938, Mar. 26, 2014, [retrieved Dec. 3, 2018] retrieved from URL<https://clinicaltrials.gov/ct2/show/NCT02095938>, 9 pages.

Clinicaltrials.gov, "Bergen Psychosis Project 2—the Best Intro Study (BP2)," NCT01446328, Jan. 30, 2018, [retrieved on Dec. 4, 2018] retrieved from URL<https://clinicaltrials.gov/ct2/show/NCT01446328>, 7 pages.

Clinicaltrials.gov, "Cannabidiol as a Different Type of an Antipsychotic: Drug Delivery and Interaction Study (CBD-IS)," NCT02051387, Mar. 8, 2018, [retrieved on Dec. 4, 2018] retrieved from URL<https://clinicaltrials.gov/ct2/show/NCT02051387>, 7 pages.

Clinicaltrials.gov, "Characterize the Modulatory Effects of Dopamine D2/D3 Receptor Agonist and Antagonist Drugs on Compulsive Behaviors," NCT00471588, Sep. 15, 2014, [retrieved on Dec. 4, 2018] retrieved from URL<https://clinicaltrials.gov/ct2/show/NCT00471588>, 7 pages.

Clinicaltrials.gov, "Clinical Trial to Evaluate the Efficacy of Treatment vs Discontinuation in a First Episode of Non-affective Psychosis (NONSTOP)," NCT01765829, Dec. 5, 2014, [retrieved on Dec. 4, 2018] retrieved from URL<https://clinicaltrials.gov/ct2/show/NCT01765829>, 10 pages.

Clinicaltrials.gov, "Clozapine Versus Amisulpride in Treatment-resistant Schizophrenia Patients (ClozAmi)," NCT01448499, Dec. 9, 2015, [retrieved on Dec. 3, 2018] retrieved from URL<https://clinicaltrials.gov/ct2/show/NCT01448499>, 7 pages.

Clinicaltrials.gov, "Comparison of Antipsychotic Combination Treatment of Olanzapine and Amisulpride to Monotherapy," NCT01609153, Jan. 23, 2017, [retrieved on Jul. 22, 2017] retrieved from URL<https://clinicaltrials.gov/ct2/show/NCT01609153?term=amisulpride&draw=1>, 7 pages.

Clinicaltrials.gov, "Comparison of Valproate-Amisulpride and Valproate-Haloperidol in Bipolar I Patients," NCT00126009, Apr. 8, 2008, [retrieved on Jul. 22, 2017] retrieved from URL<https://clinicaltrials.gov/ct2/show/NCT00126009?term=amisulpride&draw=1>, 5 pages.

Clinicaltrials.gov, "Dopamine and Opioid Receptor Antagonists Reduce Cue-induced Reward Responding and Reward Impulsivity," NCT02557984, Sep. 23, 2015, [retrieved on Dec. 4, 2018] retrieved from URL<https://clinicaltrials.gov/ct2/show/NCT02557984>, 8 pages.

Clinicaltrials.gov, "Early Pharmacological and Psychological Intervention for Late Prodromal States of Psychosis," NCT00204061, Dec. 24, 2014, [retrieved on Dec. 4, 2018] retrieved from URL<https://clinicaltrials.gov/ct2/show/NCT00204061>, 7 pages.

Clinicaltrials.gov, "Effect of Atypical Antipsychotic Drugs Olanzapine and Amisulpride on Glucose Metabolism," NCT01160991, Aug. 3, 2010, [retrieved on Dec. 3, 2018] retrieved from URL https://clinicaltrials.gov/ct2/show/NCT01160991>, 7 pages.

Clinicaltrials.gov, "Effectiveness and Safety of Amisulpride in Chinese Patients With Schizophrenia (ESCAPE)," NCT01795183, Jan. 22, 2015, [retrieved on Dec. 3, 2018] retrieved from URL<https://clinicaltrials.gov/ct2/show/NCT01795183>, 6 pages.

Clinicaltrials.gov, "Efficacy of an Early Antipsychotic Switch in Case of Poor Initial Response to the Treatment of Schizophrenia," NCT01029769, May 27, 2015, [retrieved on Jul. 22, 2018], retrieved from URL<https://clinicaltrials.gov/ct2/show/NCT01029769?term=amisulpride&draw=1>, 4 pages.

Clinicaltrials.gov, "Efficacy Study on Cognitive Functions in Schizophrenic Patients (AMIMIND)," NCT00761670, Dec. 9, 2010, [retrieved on Dec. 3, 2018] retrieved from URL<https://clinicaltrials.gov/ct2/show/NCT00761670>, 7 pages.

Clinicaltrials.gov, "Enhancing Recovery in Early Schizophrenia," NCT02926859, Mar. 8, 2018, [retrieved on Dec. 4, 2018] retrieved from URL<https://clinicaltrials.gov/ct2/show/NCT02926859>, 9 pages.

Clinicaltrials.gov, "European Phase III Study of APD421 in PONV," NCT01991821, Jan. 12, 2015, [retrieved on Dec. 4, 2018] retrieved from URL<https://clinicaltrials.gov/ct2/show/NCT01991821>, 5 pages.

Clinicaltrials.gov, "Evaluation of Negative Symptoms and Cognitive Function After Administration of Antipsychotics in Healthy Volunteer," NCT01185418, Aug. 20, 2010, [retrieved on Dec. 4, 2018] retrieved from URL<https://clinicaltrials.gov/ct2/show/NCT01185418>, 6 pages.

Clinicaltrials.gov, "Evaluation of the Antipsychotic Efficacy of Cannabidiol in Acute Schizophrenic Psychosis (CBD-CT1)," NCT00628290, Mar. 18, 2008, [retrieved on Dec. 4, 2018] retrieved from URL<https://clinicaltrials.gov/ct2/show/NCT00628290>, 6 pages.

Clinicaltrials.gov, "Identification and Treatment Response Prediction of Antipsychotic-Related Metabolic Syndrome," NCT00956189, Jan. 3, 2013, [retrieved on Dec. 3, 2018] retrieved from URL<https://clinicaltrials.gov/ct2/show/NCT00956189>, 6 pages.

Clinicaltrials.gov, "Investigation of the Safety, Tolerability and Potential Therapeutic Effects of JNJ-40411813 in Patients With Schizophrenia," NCT01323205, May 30, 2014, [retrieved on Dec. 4, 2018] retrieved from URL<https://clinicaltrials.gov/ct2/show/NCT01323205>, 8 pages.

Clinicaltrials.gov, "Metabolic Side-effects for Second-generation Antipsychotics," NCT01280396, Jan. 28, 2011, [retrieved on Jul. 22, 2017] retrieved from URL<https://clinicaltrials.gov/ct2/show/NCT01280396?term=amisulpride&draw=1>, 4 pages.

(56) References Cited

OTHER PUBLICATIONS

Clinicaltrials.gov, "Metoclopramide as Treatment of Clozapine-induced Hypersalivation," NCT02222220, Aug. 21, 2014, [retrieved on Dec. 4, 2018] retrieved from URL<https://clinicaltrials.gov/ct2/show/NCT02222220>, 7 pages.

Clinicaltrials.gov, "Modulation of Regional Brain Activation in Schizophrenic Patients by Pharmacological Therapy," NCT00419653, Sep. 16, 2008, [retrieved on Dec. 4, 2018] retrieved from URL<https://clinicaltrials.gov/ct2/show/NCT00419653>, 6 pages.

Clinicaltrials.gov, "Optimisation of Antipsychotic Drug Use in Older People," NC01454453, Oct. 19, 2011, [retrieved on Dec. 4, 2018] retrieved from URL<https://clinicaltrials.gov/ct2/show/NCT01454453>, 6 pages.

Clinicaltrials.gov, "Optimization of Treatment and Management of Schizophrenia in Europe (OPTIMISE)," NCT01248195, Nov. 3, 2016, [retrieved Jul. 22, 2017] retrieved from URL<https://clinicaltrials.gov/ct2/show/NCT01248195?term=amisulpride&draw=1>, 6 pages.

Clinicaltrials.gov, "Optimization of Treatment and Management of Schizophrenia in Europe (OPTIMISE): Substudy Site Copenhagen," NCT0155814, Oct. 25, 2016, [retrieved Jul. 22, 2017] retrieved from URL<https://clinicaltrials.gov/ct2/show/NCT01555814?term=amisulpride&draw=1>, 5 pages.

Clinicaltrials.gov, "Pan European Collaboration on Antipsychotic Naive Schizophrenia (PECANS)," NCT01154829, May 26, 2016, [retrieved on Dec. 4, 2018] retrieved from URL<https://clinicaltrials.gov/ct2/show/NCT01154829>, 7 pages.

Clinicaltrials.gov, "Pharmacovigilance in Gerontopsychiatric Patients (GAP)," NCT02374567, Feb. 23, 2017, [retrieved on Jul. 22, 2017] retrieved from URL<https://clinicaltrials.gov/ct2/show/NCT02374567?term=amisulpride&draw=1>, 8 pages.

Clinicaltrials.gov, "Phase IIIb Study of APD421 in Combination as PONV Prophylaxis," NCT02337062, Aug. 4, 2017, [retrieved on Dec. 4, 2018] retrieved from URL<https://clinicaltrials.gov/ct2/show/NCT02337062>, 7 pages.

Clinicaltrials.gov, "SOLIACS: Solian Solution in the Acute Setting," NCT00245674, Apr. 10, 2008, [retrieved on Dec. 3, 2018] retrieved from URL<https://clinicaltrials.gov/ct2/show/NCT00245674>, 5 pages.

Clinicaltrials.gov, "Study Assessing SEP-363856 in Male and Female Volunteers With High or Low Schizotype Characteristics," NCT01972711, Feb. 23, 2016, [retrieved Dec. 4, 2018] retrieved from URL<https://clinicaltrials.gov/ct2/show/NCT01972711>, 9 pages.

Clinicaltrials.gov, "Study of APD421 as PONV Treatment (no Prior Prophylaxis)," NCT02449291, Aug. 5, 2016, [retrieved Dec. 4, 2018] retrieved from URL<https://clinicaltrials.gov/ct2/show/NCT02449291>, 6 pages.

Clinicaltrials.gov, "Study of APD421 as PONV Treatment (Prior Prophylaxis)," NCT02646566, Jan. 24, 2017, [retrieved Dec. 4, 2018] retrieved from URL<https://clinicaltrials.gov/ct2/show/NCT02646566>, 7 pages.

Clinicaltrials.gov, "Switching to Abilify Trial (SWAT)," NCT00304616, Dec. 17, 2009, [retrieved on Dec. 4, 2018] retrieved from URL<https://clinicaltrials.gov/ct2/show/NCT00304616>, 6 pages.

Clinicaltrials.gov, "Tardive Dyskinesia and Cognitive Function (TD)," NCT00926965, Jun. 24, 2009, [retrieved on Dec. 4, 2018] retrieved from URL<https://clinicaltrials.gov/ct2/show/NCT00926965>, 6 pages.

Clinicaltrials.gov, "The Effects of Dopamine on Reward Processing," NCT01253421, Dec. 27, 2016, [retrieved on Jul. 22, 2017] retrieved from URL<https://clinicaltrials.gov/ct2/show/NCT01253421?term=amisulpride&draw=1>, 5 pages.

Clinicaltrials.gov, "Thorough QT Study of Intravenous Amisulpride," NCT02661594, Nov. 29, 2018, [retrieved on Dec. 3, 2018] retrieved from URL<https://clinicaltrials.gov/ct2/show/NCT02661594>, 11 pages.

Clinicaltrials.gov, "US Phase III Study of APD421 in PONV," NCT01991860, Sep. 6, 2018, [retrieved on Dec. 4, 2018] retrieved from URL<https://clinicaltrials.gov/ct2/show/NCT01991860>, 5 pages.

Clinicaltrials.gov, Search Results, Jul. 25, 2018, 25 pages.

Clinicaltrials.gov,"Benzamide Derivates as Treatment of Clozapine-induced Hypersalivation (CIH)," NCT00534573, Jul. 26, 2012, Jul. 26, 2012, [retrieved on Dec. 3, 2018] retrieved from URL<https://clinicaltrials.gov/ct2/show/NCT00534573>, 6 pages.

Clinicaltrials.gov,"Evaluation of the Necessity of Long-term Pharmacological Treatment with Antipsychotics in Schizophrenic Patients," NCT02307396, Feb. 29, 2016, [retrieved on Jul. 22, 2017] retrieved from URL<https://clinicaltrials.gov/ct2/show/NCT02307396?term=amisulpride&draw=1>, 5 pages.

Clinicaltrials.gov. "Safety and Efficacy of Aripiprazole and Ziprasidone Among Schizophrenic Patients With Metabolic Syndrome," NCT01714011, Nov. 27, 2012, [retrieved on Dec. 4, 2018] retrieved from URL<https://clinicaltrials.gov/ct2/show/NCT01714011>, 8 pages.

Coukell et al., "A Review of its Pharmacodynamic and Pharmacokinetic Properties and Therapeutic Efficacy in the Management of Schizophrenia," Drug Evaluation, Sep. 1996, 6(3):237-256.

Coulouvrat et al., "Safety of amisulpride (Solian): a review of 11 clinical studies," International Clinical Psychopharmacology, Jul. 1999, 14(4):209-218.

de Winter et al., "Structure of the Neuropeptic Drug 4-Amino-N-1-[(1-ethyl-2-pyrrolidinyl)methyl]-5-(ethylsulfonyl)-2-methoxybenzamide (Amisulpride)," Acta Cryst., Feb. 15, 1990, 46(2):313-317.

DeVane et al., "Clinical Pharmacokinetics of Quetiapine," Drug Disposition, 2001, 40(7):509-522.

Donahue et al., "(S)-amisulpride as a discriminative stimulus in C57BL/6 mice and its comparison to the stimulus effects of typical and atypical antipsychotics," Eur J Pharmacolo., Jul. 5, 2014, 734(1):15-22.

Donahue, "Characterization of the Discriminative Stimulus Properties of the Atypical Antipsychotic Amisulpride in C57BL/6 Mice," Thesis for the degree of Doctor of Philosophy, Virginia Commonwealth University, Department of Psychology, Nov. 2014, 141 pages.

Donahue, "Discriminative stimulus properties of he atypical antipsychotic amisulpride: comparison to its isomers and to other benzamide derivatives, antipsychotic, antidepressant, and antianxiety drugs in C57BL/6 mice," Psychopharmacology, Dec. 2017, 234(23-24):3507-3520.

Farde et al., "Positron emission tomographic analysis of central D1 and D2 dopamine receptor occupancy in patients treated with classical neuroleptics and clozapine. Relation to extrapyramidal side effects," Arch Gen Psychiatry., Jul. 1992, 49:538-544.

Gao et al., "Efficacy of typical and atypical antipsychotics for primary and comorbid anxiety symptoms or disorders: a review," J Clin Psychiatry, Sep. 2006, 67(9):13727-1340.

Grunder et al., "The 'atypicality' of antipsychotics: a concept re-examined and re-defined," Nat Rev Drug Discov., Mar. 2009, 8(3):197-202.

Guscott et al., "Genetic knockout and pharmacological blockade studies of the 5-HT7 receptor suggest therapeutic potential in depression," Neuropharmacology, Mar. 2005, 48(4):492-502.

Hardoy et al., "Adjunctive amisulpride to fluvoxamine in major depression: Early ssri onset of action," European psychiatry, 2000, 15:s325.

Harvey et al., "Effect of lurasidone dose on cognition in patients with schizophrenia: post-hoc analysis of a long-term, double-blind continuation study," Schizophr Res., Aug. 2015, 166(1-3):334-338.

Harvey et al., "Effect of lurasidone on neurocognitive performance in patients with schizophrenia: a short-term placebo- and active-controlled study followed by a 6-month double-blind extension," Eur Neuropsychopharmocol., Nov. 2013, 23(11):1373-1382.

Hedlund et al., "5-HT7 receptor inhibition and inactivation induce antidepressantlike behavior and sleep pattern," Biol Psychiatry., Nov. 15, 2005, 58(10):831-837.

Hedlund et al., "The 5-HT7 receptor and disorders of the nervous system: an overview," Psycopharmacology, Oct. 2009, 206(3):345-354.

International Search Report and Written Opinion in International Application No. PCT/US2018/63859, dated Mar. 26, 2019, 23 pages.

International Search Report and Written Opinion in International Application No. PCT/US2018/63865, dated Mar. 25, 2019, 13 pages.

(56) References Cited

OTHER PUBLICATIONS

Jakovcevska-Kujundziska et al., "Amisulpride in combination with maprotiline in the treatment of psychotic depression—a clinical experience," European NeuroPsychopharmacology, Oct. 2003, 13:s193.
Kapur et al., "A Positron Emission Tomography Study of Quetiapine in Schizophrenia," Arch Gen Psychiatry, Jun. 2000, 57:553-559.
Kapur et al., "Clinical and Theoretical Implications of 5-HT2 and D2 Receptor Occupancy of Clozapine, Risperidone, and Olanzapine in Schizophrenia," Am J Psychiatry, Feb. 1999, 156:2.
Kaul et al., "Comparative evaluation of amisulpride and escitalopram on Hamilton Depression Rating Scale among depression patients in a tertiary care teaching hospital in Nepal," Int J Med Sci Public Health., 2015, 4(5):642-646.
Keshipeddy et al., "Nonracemic Antifolates Stereoselectively Recruit Alternate Cofactors and Overcome Resistance in *S. aureus*", Journal of the American Chemical Society, Jun. 22, 2015, 137:8983-8990.
Komossa et al., "Second-generation antipsychotics for major depressive disorder and dysthymia," Cochrane Database Syst Rev., Dec. 8, 2010, (12):CD008121.
La Fougere et al., "D2 receptor occupancy during high- and low-dose therapy with the atypical antipsychotic amisulpride: a 123I-iodobenzamide Spect study.," J Nucl Med., Jun. 2005, 46(6):1028-1033.
Lecrubier et al., "Amisulpride versus imipramine and placebo in dysthymia and major depression. Amisulpride Study Group," J Affect Disord., Apr. 1997, 43(2):95-103.
Leopoldo et al., "Serotonin 5-HT7 receptor agents: Structure-activity relationships and potential therapeutic applications in central nervous system disorders," Pharmacol Ther., Feb. 2011, 129(2):120-148.
Leucht et al., "Comparative efficacy and tolerability of 15 antipsychotic drugs in schizophrenia: a multiple-treatments meta-analysis," Lancet, Sep. 14, 2013, 382(9896):951-962.
Lopez-Monoz et al., "Bipolar disorder as an emerging pathology in the scientific literature: a bibliometric approach," J Affect Disord, Jun. 2006, 92(2-3):161-170.
Lovenberg et al., "A novel adenylyl cyclase-activating serotonin receptor (5-HT7) implicated in the regulation of mammalian circadian rhythms," Neuron, Sep. 1993, 11(3):449-458.
Mamo et al., "Quetiapine Extended-Release Versus Immediate-Release Formulation: A Positron Emission Tomography Study," J Clin PsyChiatry, Jan. 2008, 69(1):81-86.
Marchese et al., "Effect of the Amisulpride Isomers on Rat Catalepsy," European Journal of Pharmacology, May 24, 2002, 444(1-2):69-74.
Moller et al., "Antipsychotic and antidepressive effects of second generation antipsychotics," Eur Arch Psychiatry Clin Neurosci., Jun. 2005, 255(3):190-201.
Montgomery, "Dopaminergic deficit and the role of amisulpride in the treatment of mood disorders," Int Clin Psychopharmacol., Dec. 2002, 17 Suppl 4:S9-15.
Morgan et al., "Characterization of the Antiociceptive Effects of the Individual Isomers of Methadone After Acute and Chronic Administrations," Behav Pharmacol., Sep. 2011, 22(5-6):548-557.
Morita et al., "HTR7 Mediates Seratonergic Acute and Chronic Itch," Neuron, Jul. 1, 2015, 87(1):124-138.
Nelson et al., "Atypical antipsychotic augmentation in major depressive disorder: a meta-analysis of placebo-controlled randomized trials," Am J Psychiatry, Sep. 2009, 166(9):980-991.
Nikiforuk et al., "Effects of the selective 5-HT7 receptor antagonist SB-269970 and amisulpride on ketamine-induced schizophrenia-like deficits in rats," PLoS One., Jun. 11, 2013, 8(6):e66695.
Nikiforuk, "Targeting the Serotonin 5-HT7 Receptor in the Search for Treatments for CNS Disorders: Rationale and Progress to Date," CNS Drugs, Apr. 2015, 29(4):265-275.
No Author, "Dementia and Mental Illness: Findings on Dementia Detailed by Investigators at Department of Medicine (Antipsychotic Drug Use and the Risk of Seizures: Follow-up Study with a nested Case-Control Analysis)," Biotech Week; Atlanta, ProQuest document ID 1715999653, Sep. 30, 2015, 3 pages.

Nyberg et al., "Suggested Minimal Effective Dose of Risperidone Based on PET-Measured D2 5-HT2A Receptor Occupancy in Schizophrenic Patients," Am J Psychiatry., Jun. 1999, 156:873-875.
Palovics et al., "Separation of the Mixtures of Chiral Compounds by Crystallization," Advances in Crystallization Processes, Apr. 27, 2012, retrieved from URL <https://www.intechopen.com/books/advances-in-crystallization-processes/separation-of-the-mixtures-of-chiral-compounds-by-crystallization>, pp. 1-38.
Papp and Wieronska, "Antidepressant-like activity of amisulpride in two animal models of depression," Journal of Psychopharmacology, 2000, 14(1):46-52.
Pawar et al., "Evaluation of antidepressant like property of amisulpride per se and its comparison with fluoxetine and olanzapine using forced swimming test in albino mice," Acta Pol Pharma., May-Jun. 2009, 66(3):327-331.
Popovic et al., "Number needed to treat analyses of drugs used for maintenance treatment of bipolar disorder,", Psychopharmacology, Feb. 2011, 213(4):657-667.
Roix et al., "Effect of the antipsychotic agent amisulpride on glucose lowering and insulin secretion," Diabetes, Obesity and Metabolism, Apr. 2012, 14(4):329-334.
Rybakowski et al., "Treatment of depression in first episode of schizophrenia: results from EUFEST," Eur Neuropsychopharmacol., Dec. 2012, 22(12):875-882.
Sarkisyan et al., "The 5-HT(7) receptor as a mediator and modulator of antidepressant-like behavior," Behave Brain Res., May 1, 2010, 209(1):99-108.
Smeraldi, "Amisulpride versus fluoxetine in patients with dysthymia or major depression in partial remission: a double-blind, comparative study," J Affect Disord., Feb. 1998, 48(1):47-56.
Spina et al., "Metabolic drug interactions with newer antipsychotics: a comparative review," Basic Clin Pharmacol Toxicol, Jan. 2007, 100(1):4-22.
Suppes et al., "Lurasidone for the Treatment of Major Depressive Disorder With Mixed Features: A Randomized, Double-Blind, Placebo-Controlled Study," Am J Psychiatry., Apr. 1, 2016, 174(4):400-407.
Taubel et al., "Thorough QT study of the effect of intravenous amisulpride on QTc Interval in Caucasian and Japanese healthy subjects," British Journal of Clinical Pharmacology, Feb. 2017, 83(2):339-348.
Thomas et al., "Amisulpride Plus Valproate vs Haloperidol Plus Valproate in the Treatment of Acute Mania of Bipolar I Patients: A Multicenter, Open-label Randomized, Comparative Trial," Original Research, 2008, 4(3):675-686.
Thomas et al., "SB-656104-A, a Novel Selective 5-HT7 Receptor Antagonist, Modulates REM Sleep in Rats," British Journal of Pharmacology, Jun. 2003, 139(4):705-714.
Toronto Research Chemicals, "R-Amisulpride," 2017, [retrieved on Mar. 20, 2017], retrieved from: URL<https://www.trc-canada.com/product-detail/?CatNum=A633255&CAS=71675-90-6&Chemical_Name=R-Amisulpride&Mol_Formula=$C_{17}H_{27}N_3O_4S$>, 2 pages.
Vanelle et al., "Metabolic control in patients with comorbid schizophrenia and depression treated with amisulpride or olanzapine," European Neuropsychopharmacology, Oct. 2004, 14(3):S284.
Vernaleken et al., "High striatal occupancy of D2-like dopamine receptors by amisulpride in the brain of patients with schizophrenia," Int J Neuropsychopharmacol., Dec. 2004, 7(4):421-430.
Vieta et al. "An open-label study of amisulpride in the treatment of mania," The Journal of Clinical Psychiatry, May 2005, 66(5):575-8.
Wesolowska et al., "Enhancement of the anti-immobility action of antidepressants by a selective 5-HT7 receptor antagonist in the forced swimming test in mice," Eur J Pharmacol., Jan. 19, 2007, 555(1):43-47.
Willner et al., "Dopaminergic mechanism of antidepressant action in depressed patients," J. Affect Disord., May 2005, 86(1):37-45.
Yatham et al., "Canadian Network for Mood and Anxiety Treatments (CANMAT) and International Society for Bipolar Disorders (ISBD) collaborative update of CANMAT guidelines for the management of patients with bipolar disorder: update 2009," Bipolar Disord., May 2009, 11(3):225-255.
Zhang et al., "Crystal Structures and physicochemical properties of amisulpride polymorphs," Journal of Pharmaceutical and Biomedicinal Analysis, Jun. 5, 2017, 140:252-257.

(56) References Cited

OTHER PUBLICATIONS

Zhou et al., "Atypical Antipsychotic Augmentation for Treatment-Resistant Depression: A Systematic Review and Network Meta-Analysis," Int J Neuropsychopharmacol, May 25, 2015, 18(11):pyv060.
Al-Khatib et al., "What Clinicians Should Know About the QT Interval," JAMA, 2003, 289(16):2120-2127.
Asada, T., et al., "An Innovative Method for the Preparation of High API-Loaded Hollow Spherical Granules for Use in Controlled-Release Formulation", International Journal of Pharmaceutics, 523:167-175 (2017).
Asada, T., et al., "Formulation of a Poorly Water-Soluble Drug in Sustained-Release Hollow Granules with a High Viscosity Water-Soluble Polymer Using a Fluidized Bed Rotor Granulator", International Journal of Pharmaceutics, 541:246-252 (2018).
Asada, T., et al., "Mechanism of the Formation of Hollow Spherical Granules Using a High Shear Granulator", European Journal of Pharmaceutical Sciences, 117:371-378 (2018).
Berge et al., "Pharmaceutical Salts," J. Pharmaceutical Sciences, 1977, 66:1-19.
Canal, M., et al., "Lack of Effect of Amisulpride on the Pharmacokinetics and Safety of Lithium", International Journal of Neuropsychopharmacology, 6:103-109 (2003).
Chhabra, V. and Bhatia, M.S., "Amisulpride: A Brief Review", Delhi Psychiatry Journal, 10(2):140-143 (2007).
Colonna, L., et al., "Long-Term Safety and Efficacy of Amisulpride in Subchronic or Chronic Schizophrenia", International Clinical Psychopharmacology, 15:13-22 (2000).
Davey, "How to correct the QT interval for the effects of heart rate in clinical studies," J. Pharmacol. Toxicol. Methods, 2002, 48:3-9.
Dos Santos Pereira, J.N., et al., "The Poorly Membrane Permable Antipsychotic Drugs Amisulpride and Sulpiride are Substrates of the Organic Cation Transporters from the SLC22 Family", The AAPS Journal, 16(6):1247-1258 (2014).
El Ela, A.A., et al., "Identification of P-Glycoprotein Substrates and Inhibitors Among Psychoative Compounds—Implications for Pharmacokinetics of Selected Substrates", Journal of Pharmacy and Pharmacology, 56:967-975 (2004).
Fox, G.M., et al., "Intravenous Amisulpride Does Not Meaningfully Prolong the QTc Interval at Doses Effective for the Management of Posoperative Nausea and Vomiting", Anasthetic Clinical Pharmacology, ahead of print issue:10 pages (2019).
Grandy, D.K., et al., "Cloning of the cDNA and Gene for a Human D2 Dopamine Receptor", Proc Natl Acad Sci USA, 86:9762-9766 (1989).
Hayes, G., et al., "Structural Subtypes of the Dopamine D2 Receptor are Functionally Distinct: Expression of the Cloned D2A and D2B Subtypes in a Heterlogous Cell Line", Molecular Endocrinology, 6:920-926 (1992).
Hillgren, K.M., et al., "Emerging Transporters of Clinical Importance: An Update from the International Transporter Consortium", Nature, 94(1):52-63 (2013).
Hu et al., "Mixed Specifier for Bipolar Mania and Depression: Highlights of DSM-5 Changes and Implications for Diagnosis and Treatment in Primary Care," Prim. Care Companion CNS Disord., 2014, 16(2):PCC.13r01599.
Hartter, S., et al., "How Does the Benzamide Antipsychotic Amisulpride get into the Brain?—an in Vitro Approach Comparing Amisulpride with Clozapine", Neuropsychopharmacology, 28:1916-1922 (2003).
Isbister, G.K., et al., "Amisulpride Deliberate Self-Poisoning Causing Severe Cardiac Toxicity Including QT Prolongation and Torsades de Pointes", Med J Aust., 184:354-356 (2006).
Kim, E., et al., "Predicting Brain Occupancy from Plasma Levels Using PET: Superiority of Combining Pharmacokinetics with Pharmacodynamics While Modeling the Relationship", Journal of Cerebral Blood Flow & Metabolism, 32:759-768 (2012).
Krause, M., et al., "Anitpsychotic Drugs for Patients with Schizophrenia and Predominant Prominent Negative Symptoms: A Systematic Review and Meta-Analysis", Eur Arch Psychiatry Clin Neurosci., 268(7):625-639 (2018).

Le Foll, B., et al., "Occupancy of Dopamine D3 and D2 Receptors by Buspirone: A[11C]-(+)-PHNO PET Study in Humans", Neuropsychopharmacology, 41:529-537 (2016).
Li,J-X, "Imidaoline I2, Receptors: An Update", Pharmacol Ther, 178:48-56 (2017).
Macrae et al., "Mercury: visualization and analysis of crystal structures," J. Appl. Cryst., 2006, 39:453-457.
Mortimer, A., et al., "A Double-Blind, Randomized Comparative Trial of Amisulpride Versus Olanzapine for 6 Months in the Treatment of Schizophrenia", Int Clin Psychopharmacol, 19:63-69 (2004).
Panicker et al., "Intra- and interreader variability in QT interval measurement by tangent and threshold methods in a central electrocardiogram laboratory," J. Electrocardiol., 2009, 42:348-52.
Porsolt, R.D., et al., "Behavioural Despair in Rats: A New Model Sensitive to Antidepressant Treatment", Eur J Pharmacol., 47:379-391 (1978).
Reeves et al., "Therapeutic window of dopamine D2/3 receptor occupancy to treat psychosis in Alzheimer's disease," Brain, 2017, 140(4):1117-1127.
Reeves, S., et al., :Therapeutic Window of Dopamine D2/3 Receptor Occupancy to Treat Psychosis in Alzheimer's Disease, Brain a Journal of Neurology, pp. 1118-1127 (2017).
Rein, w., et al., "Safety Profile of Amisulpride in Short- and Long-Term Use", Acta Pschiatr. Scan. Suppl., 400:23-27 (2000).
Rosenzweig, P., et al., "A Review of the Pharmacokinetics, Tolerability and Pharmacodynamics of Amisulpride in Healthy Volunteers", Human Psychopharmacology, 17:1-13 (2002).
Roth, B.L., et atl., "Binding of Typical and Atypical Antipsychotic Agents to 5-Hydroxytryptamine-6 and 5-Hydroxytryptamine-7 Receptors", the Journal of Pharmacology and Experimental Therapeutics, 268(3):1403-1410 (1994).
Rothman, R.B., et al., "Evidence for Possible Involvement of 5-HT(2B) Receptors in the Cardiac Valvulopathy Associated with Fenfluramine and Other Serotonergic Medications", Circulation, 102:2836-2847 (2000).
Sechter, D., et al., "Amisulpride vs. Risperidone in Chronic Schizophrenia: Results of a 6-Month Double-Blind Study", Neuropsychopharmacology, 27:1071-1081 (2002).
Shapiro, D.A., et al., "Aripiprazole, a Novel Atypical Antipsychotic Drug with a Unique and Robust Pharmacology", Neuropsychopharmacology, 28(8):1400-1411 (2003).
Shen, Y., et al., "Molecular Cloning and Expression of a 5-Hyderoxytryptamine7 Serotonin Receptor Subtype", the Journal of Biological Chemistry, 268(24):18200-18204 (1993).
Silveira da Mota Neto, J.I., et al., Amisulpride for Schizophrenia (Review), the Cochrane Library, Chochran Database of Systematic Reviews, Issue 2, Article No. CD001357 (2013).
Solian® Tablets and Solution, Product Information, 13 pages, Jun. 28, 2012.
Tauscher, J., et al., "Significant Dissociation of Brain and Plasma Kinetics with Antipsychotics", Molecular Psychiatry, 7:317-321 (2002).
Uchida et al., "Therapeutic Window for Striatal Dopamine D2/3 Receptor Occupancy in Older Patients With Schizophrenia: A Pilot PET Study," the American J. of Geriatric Psychiatry, 2014, 22(1):1007-1016.
Vanhauwe, J.F., et al., "Comparison of the Ligand Binding and Signaling Properties of Human Dopamine D(2) and D(3) Receptors in Chinese Hamster Ovary Cells", J Pharmacol Exp Ther., 290(2):908-916 (1999).
Zamek-Gliszczynski, M.J., et al., "ITC Recommendations for Transporter Kinetic Parameter Estimation and Translational Modeling of Transport-Mediated PK and DDIs in Humans", Nature, 94(1):64-79 (2013).
(No Author Listed), "Amisulpride Compound Summary," PubChem, 2020, retrieved on Oct. 27, 2020, retrieved from URL: https://pubchem.ncbi.nlm.nih.gov/compound/amisulpride, 41 pages.
(No Author Listed), "Amisulpride Product Information," Cayman Chemical, May 13, 2020, 1 page.
(No Author Listed), "Amrix Highlights of Prescribing Information," Teva Pharmaceuticals, Apr. 2019, 19 pages.

(56) References Cited

OTHER PUBLICATIONS (No Author Listed), "Cyclobenzaprine Compound Summary," PubChem, 2020, retrieved on Oct. 27, 2020 retrieved from URL: https://pubchem.ncbi.nlm.nih.gov/compound/cyclobenzaprine, 55 pages.
(No Author Listed), "Cyclobenzaprine Hydrochloride (cyclobenzaprine hydrochloride) dose, indications, adverse effects, and interactions," PDR.net, 2020, retrieved from URL: https://www.pdr.net/drug-summary/Cyclobenzaprine-Hydrochloride-cyclobenzaprine-hydrochloride-3089.1153, retrieved on Oct. 23, 2020, 20 pages.
(No Author Listed), "Flexeril (Cyclobenzaprine HCL) Tablets," McNeil Pediatrics, Apr. 2013, 13 pages.
(No Author Listed), "Solian," Sanofi-Synthelabo (India) Pvt Ltd., dated Apr. 20, 2017, 7 pages.
Boyer et al., "Treatment of Negative Symptoms in Schizophrenia with Amisulpride," British Journal of Psychiatry, 1995, 166:68-72.
Boyer et al., "Amisulpride Versus Amineptine and Placebo for the Treatment of Dysthymia," Neuropsychobiology, 1999, 39:25-32.
Bressan et al., "Prolactinemia is Uncoupled from Central D2/D3 Dopamine Receptor Occupancy in Amisulpride Treated Patients," Psychopharmacology, 2004, 175:367-373.
Cortes-Altamirano et al., "Review: 5-HT1, 5-HT3 and 5-HT7 Receptors and their Role in the Modulation of Pain Response in the Central Nervous System," Current Neuropharmacology, 2018, 16:210-221.
Curran et al., "Amisulpride: A review of its use in the management of schizophrenia," Drugs, 2001, 61:2123-2150.
Darrion et al., "Improvement of Schizophrenic Patients with Primary Negative Symptoms Treated with Amisulpride," Am J Psychiatry, 1999, 156:610-616.
Gao et al., "Antipsychotic-Induces Extrapyramidal Side Effects in Bipolar Disorder and Schizophrenia—a Systematic Review," J Clin Psychopharmacol, 2008, 28:203-209.
Gefvert et al., "D2 and 5HT2A Receptor Occupancy of Different Doses of Quetiapine in Schizophrenia: A PET Study," European Neuropsychopharmacology, 2001, 11:105-110.
Ghaemi et al., "Extrapyramidal Side Effects with Atypical Neuoleptics in Bipolar Disorder," Progress in Neuo-Psychopharmacology & Biological Psychiatry, 2006, 30:209-213.
Girgis et al., "In vivo binding of antipsychotics to D3 and D2 receptors: a PET study in baboons with [11C]-(+)-PHNO," Neuropsychopharmacology, 2010, 36(4):867-95.
Hedlund et al., "Functional, Molecular and Pharmacological Advances in F-HT7 Receptor Research," Trends in Pharmacological Sciences, 2004, 25(9):481-486.
Huhn et al., "Comparative Efficacy and Tolerability of 32 Oral Antipsychotics for the Acute Treatment of Adults with Multi-episode Schizophrenia: A Systematic Review and Network Meta-analysis," Lance, 2019, 394:939-951.
International Search Report and Written Opinion in International Appln. No. PCT/US2020/036084, dated Oct. 19, 2020, 21 pages.
International Search Report and Written Opinion in International Appln. No. PCT/US2020/036118, dated Oct. 23, 2020, 41 pages.
Ji et al., "Amisulpride for Schizophrenia (Review)" the Cochrane Collaboration and the Cochrane Library, 2002, 2:102 pages.
King et al., "Guidelines for the Use of Antipsychotic Drug Studies in Healthy Volunteers," Journal of Psychopharmacology, 1997, 11(3):201-209.
Krison et al., "Efficacy and Acceptability of Acute Treatments for Persistent Depressive Disorder: A Network Meta-analysis," Depression and Anxiety, 2014, 31:621-630.
Loo et al., "Amisulpride Versus Placebo in the Medium-Term Treatment of the Negative Symptoms of Schizophrenia," British Journal of Psychiatry, 1997, 170:18-22.
Martinot et al., "Central D2 Receptor Blockade and Antipsychotic Effects of Neuroleptics. Preliminary Study with Positron Emission Tomography," Psychiatr & Psychobiol, 1990, 5:231-240.
Martinot et al., "In vivo Characteristics of Dopamine D2 Receptor Occupancy by Amisulpride in Schizophrenia," Psychopharmacology, 1996, 124:154-158.
Matthys et al., "Role of the 5-HT7 Receptor on the Central Nervous System: From Current Status to Future Perspectives," Mol Neurobiol., 2011, 43:228-253.
McKeage et al., "Amisulpride a Review of its Use in the Management of Schizophrenia," CNS Drugs, 2004, 18(13):933-956.
Meltzer et al., "Placebo-Controlled Evaluation of Four Novel Compounds for the Treatment of Schizophrenia and Schizoaffective Disorder," Am J Psychiatry, 2004, 161:975-984.
Meltzer et al., "The Ratios of Serotonin 2 and Dopamine 2 Affinities Differentiate Atypical and Typical Antipsychotic Drugs," Psychopharmacol Bull, 1989, 25:390-392.
Meneses "5-HT System and Cognition," Neuroscience and Biobehavioral Reviews, 1999, 23:1111-1125.
Miller et al., "Treatment of Neuroleptic Induced Akathisia with the 5-HT2 Antagonist Ritanserin," Psycopharmacology Bulletin, 1990, 26(3):373-376.
Monti et al., "Microinjection of the 5-HT7 Receptor Antagonist SB-269970 into the Rat Brainstem and Basal Forebrain: Site-dependent Effects on REM Sleep," Pharmacology, Biochemistry and Behavior, 102:373-380.
Monti et al., "The Serotonin 5-HT7 Receptor Agonist LP-44 Microinjected into the Dorsal Raphe Nucleus Suppresses REM Sleep in the Rat," Bhavioural Brain Research, 2008, 191:184-189.
Monti, et al., "The Role of Serotonin 5-HT7 Receptor in Regulating Sleep and Wakefulness," Ref Neurosci, 2014, 25:429-437.
Moresco et al., "Cerebral D2 and 5-HT2 Receptor Occupancy in Schizophrenic Patients Treated with Olanzapine of Clozapine," Journal of Psychopharmacology, 2004, 18(3):355-365.
Nordstrom et al., "High 5-HT2 Receptor Occupancy in Clozapine Treated Patients Demonstrated by PET," Psychopharmacology, 1993, 110:365-367.
Nuss et al., "The Use of Amisulpride in the Treatment of Acute Psychosis," Therapeutics and Clinical Risk Management, 2007, 3(1):3-11.
Poyurovsky et al., "Seretonergic Agents in the Treatment of Acute Neuoleptic-Induced Akathisia: Open-Label Study of Buspirone and Mianserin," International Clinical Psychopharmacology, 1997, 12:263-268.
Ramaekers et al., "Psychomotor, Cognitive, Extrapyramidal, and Affective Functions of Healthy Volunteers During Treatment with an Atypical (Amisulpride) and a Classic (Haloperidol) Antipsychotic," Journal of Clinical Psychopharmacology, 1999, 19(3):209-221.
Shelton et al., "5-HT7 Receptor Deletion Enhances REM Sleep Suppression Induced by Selective Serotonin Reuptake Inhibitors, but not by Direct Stimulation of 5-HT1A Receptor," Neuropharmacology, 56:448-454.
Shelton et al., "Selective Pharmacological Blockade of the 5-HT7 Receptor Attenuates Light and 8-OH-DPAT Induced Phase Shifts of Mouse Circadian Wheel Running Activity," Frontiers in Behavioral Neuroscience, 2015, 8(Article 453):8 pages.
Sparshatt et al., "Amisulpride-Dose, Plasma Concentration, Occupancy and Response: Implications for Therapeutic Drug Monitoring," Acta Psychiatr Scand, 2009, 120:416-428.
Tauscher et al., "Striatal Dopamin-2 Receptor Occupancy as Measured with [123I]iodobenzamide and SPECT Predicted the Occurrence of EPS in Patients Treated with Atypical Antipsychotics and Haloperidol," Psychopharmacology, 2002, 162:42-49.
Weil, "Cyclobenzaprine extended release for acute low back and neck pain," Future Medicine Ltd., 2009, 6(6): 871-881.

\* cited by examiner

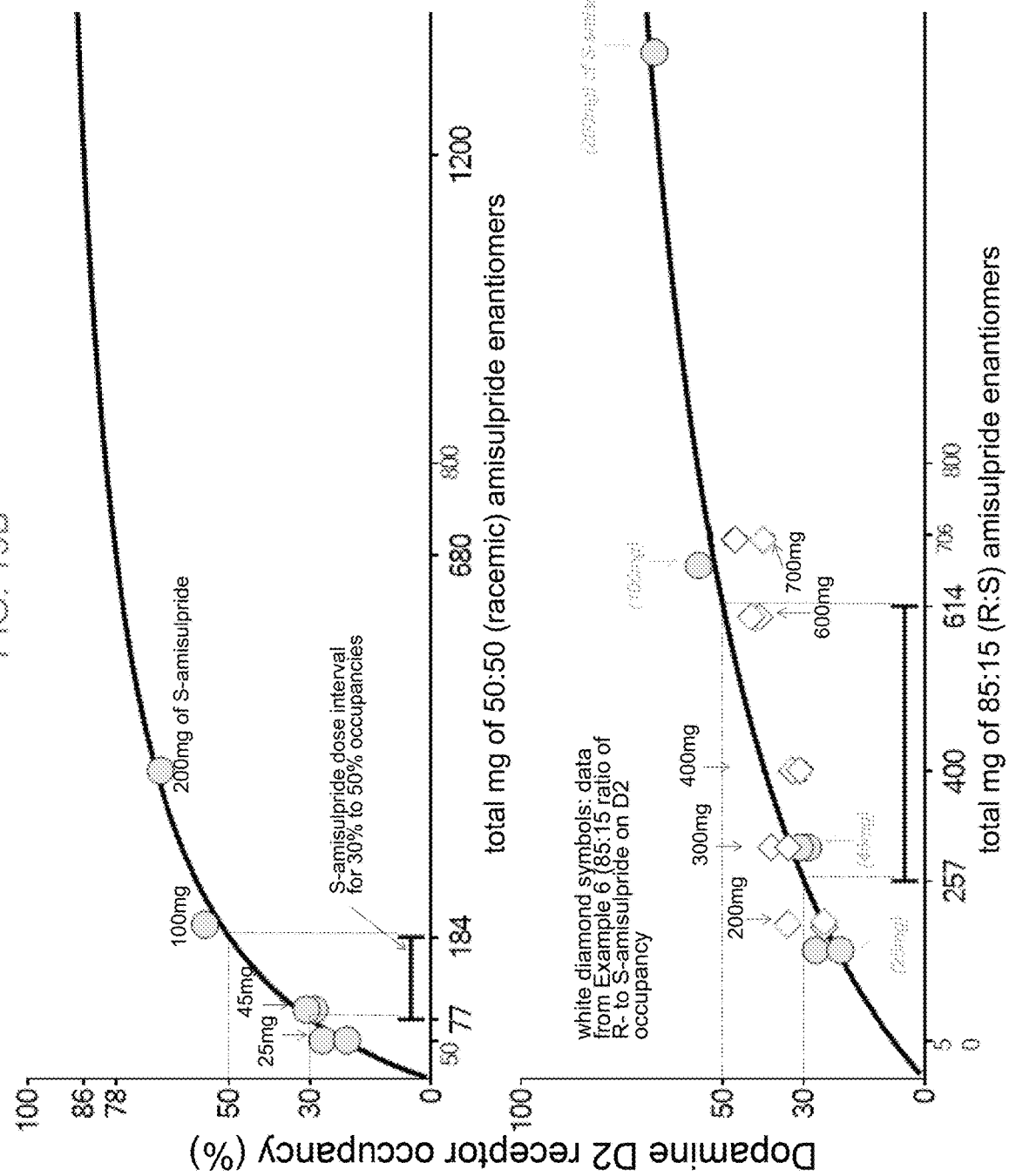

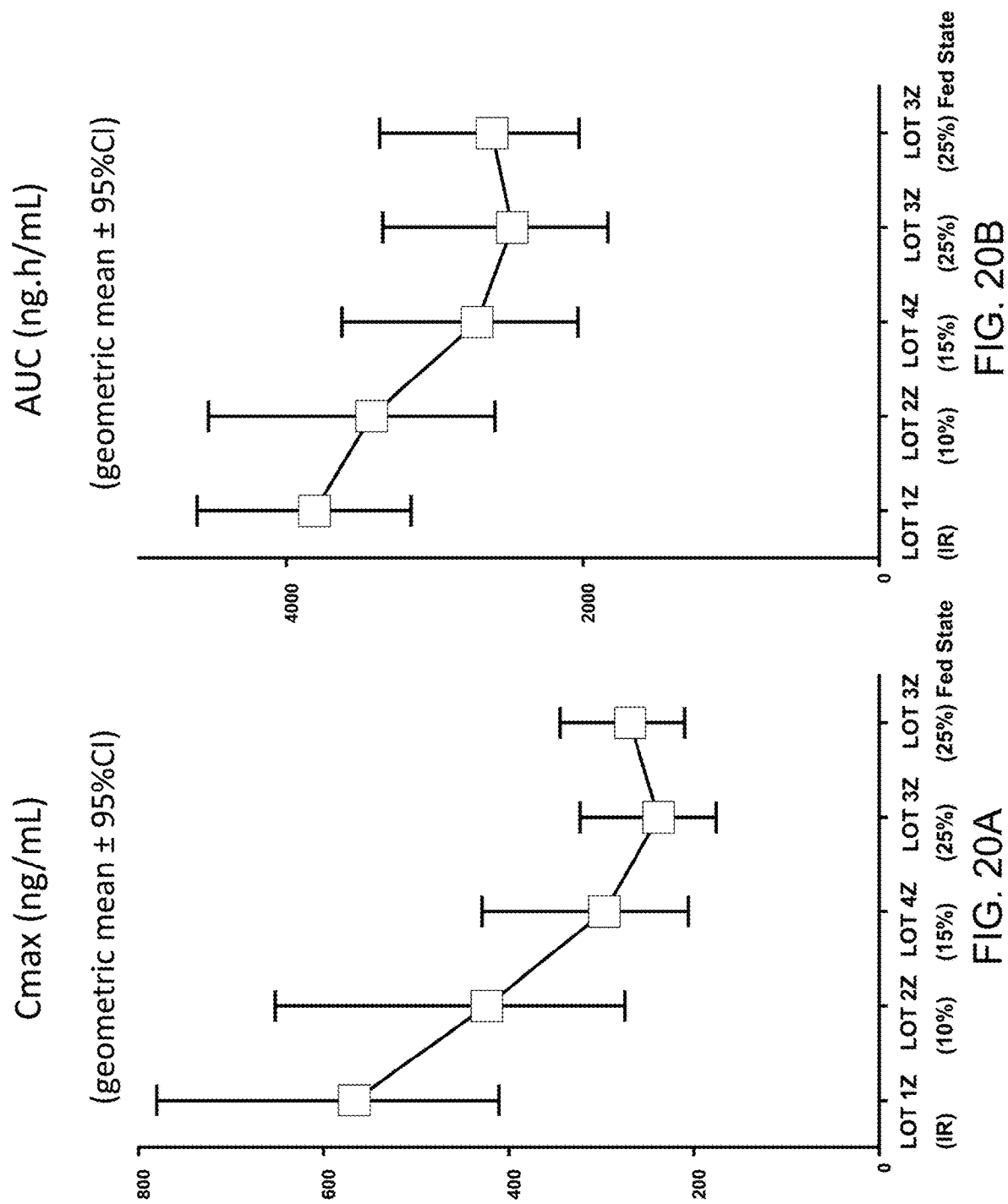

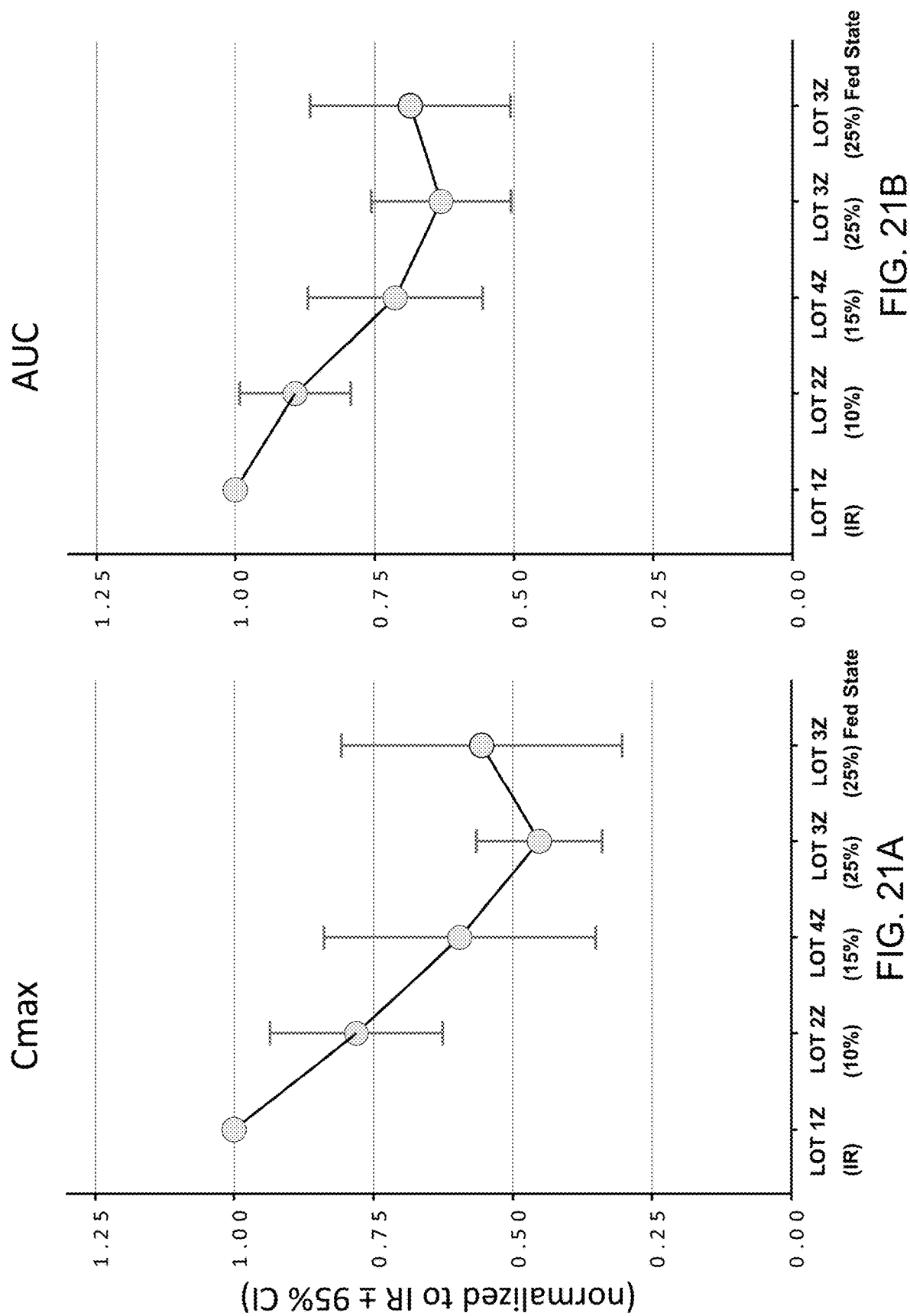

MODIFIED RELEASE FORMULATIONS AND USES THEREOF

FIELD OF THE INVENTION

The present disclosures relate to modified release pharmaceutical compositions of non-racemic amisulpride and methods and uses thereof.

BACKGROUND

Amisulpride is a member of the chemical class benzamide, and has the chemical name 4-amino-N-[(1-ethylpyrolidin-2-yl)methyl]-5-ethylsulfonyl-2-methoxy-benzamide. The chemical structure of amisulpride is as follows:

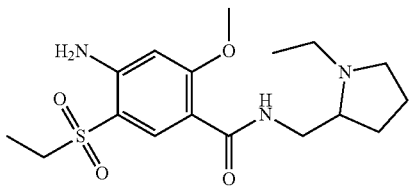

There is a need for better treatments of psychiatric and mood disorders, including schizophrenia, depression, bipolar disorder and in particular depression associated with bipolar disorder. For example, psychiatrists indicate that about 25% of patients across all bipolar disorders are refractory during a manic episode, while about 70% are refractory during a depressive episode. Thus, there is a need for drugs that remit depressive symptoms in bipolar patients.

Dopamine receptor antagonists are one class of drugs used to treat psychiatric disorders, however efficacious $D_2$ occupancy levels are also related to deleterious side effects. A need also therefore exists for central nervous system drugs (CNS) and in particular psychiatric drugs for the treatment of depression and diseases and disorders with a depressive component, that provide a therapeutic effect with no or reduced side effects and in particular side effects associated with dopamine $D_2$ receptor occupancy.

Racemic amisulpride is sold under the tradename Solian® as 400 mg tablet and as a solution for the treatment of acute and chronic schizophrenic disorders, in which positive symptoms (such as delusions, hallucinations, thought disorders) and/or negative symptoms (such as blunted affect, emotional and social withdrawal) are prominent, including patients characterized by predominant negative symptoms, with a recommended total daily dose of 400-800 mg. However, movement related adverse events including tremor, rigidity, hypokinesia, hypersalivation, akathisia, dyskinesia are listed as "very common" in the label for racemic amisulpride in the 400-800 mg/day dosage range. Such extrapyramidal symptoms are commonly associated with antipsychotic drugs employing dopamine receptor blockade. Typically, extrapyramidal symptoms are observed at high dopamine receptor occupancy, e.g., at about 70-75% occupancy.

Other adverse events and side effects associated with amisulpride include prolongation of the QT interval and increase in prolactin which may lead to galactorrhoea, amenorrhoea, gynaecomastia, breast pain, erectile dysfunction. The QT interval represents the duration of ventricular depolarization and subsequent repolarization. QT interval prolongation creates an electrophysiological environment that favors the development of ventricular tachyarrhythmias, the most clinically significant being Torsades de Pointes (TdP) which can lead to ventricular fibrillation and sudden cardiac death. Patients taking one or more than one QT prolonging drug concomitantly, have an enhanced risk of TdP. Therefore, there is need for better psychiatric drugs and drug formulations with reduced side effects such as QT interval prolongation.

Thus there is a need for an amisulpride composition which has reduced adverse events and a greater safety profile. There is a further need for an amisulpride composition which can effectively treat bipolar symptoms accompanied with depression more effectively than current compositions.

SUMMARY

These and other objectives make use of the unexpected discovery by the inventors of modified release formulations of non-racemic amisulpride compositions that provide a therapeutic effect that is the substantially the same as that of an immediate release formulation of the same amisulpride dosage, but with reduced side effects. The present inventors have discovered modified release pharmaceutical formulations of amisulpride that can provide substantially the same efficacy as comparable immediate release formulations at both lower blood plasma maximum concentrations (Cmax) and total blood plasma concentration (AUC). Thus, in various aspect and embodiments, provided are modified release pharmaceutical formulations of amisulpride with substantially the same efficacy as comparable immediate release formulations but with reduced adverse events and side effects.

It has further been discovered by the inventors that the behavior of amisulpride observed in their studies cannot be accounted for with, and is counter-intuitive to, traditional models. The studies have shown that amisulpride exhibits: (1) time-hysteresis: the clearance from plasma is rapid compared to the washout of brain occupancy, (2) dose-response: occupancy increases with dose and receptor binding is not saturated, and (3) lack-of-accumulation: brain occupancy does not accumulate substantially to steady state. The inventors have developed a novel distribution model, that accurately captures the three key observations above: time-hysteresis, dose-response, and lack-of-accumulation; and how the reduced blood plasma exposures with modified release (MR) formulations in the various embodiments of the present inventions can still attain brain D2 receptor occupancies equivalent to those observed for immediate release (IR) formulations.

In various aspects and embodiments, provided are modified release formulations of amisulpride that can provide an occupancy of dopamine D2 receptors (as a measure for antipsychotic drug efficacy, e.g., in the treatment of mania, depression, bipolar disorders, schizophrenia, etc.) that is at least 85% of the dopamine D2 receptors occupancy achieved by an immediate release composition having the same total daily amount of amisulpride but with a blood plasma Cmax of amisulpride that is less than about 80% of the Cmax and an AUC from 0 to 24 hours after administration ($AUC_{0-24}$) of amisulpride that is less than about 80% of the $AUC_{0-24}$ achieved by an immediate release composition having the same total daily amount of amisulpride. In various aspects and embodiments, provided are modified release formulations of amisulpride with reduced drug induced QT prolongation compared to immediate release formulations having the same total amount of amisulpride.

As used herein, the terms "AUC", "Cmax", "Cmin", "Tmax", and "QT interval prolongation", unless stated otherwise, when used in the descriptions herein encompass average, mean, and geometric mean values of a population. That is for the sake of conciseness in description phrasing such as "average, mean, and/or geometric mean values" has not been included as it is to be understood the disclosures herein are generally applicable, mutatis mutandis.

In various aspects and embodiments, provided are modified release formulations of non-racemic amisulpride compositions that provide a therapeutic effect at lower amisulpride blood plasma levels (both Cmax and AUC) than immediate release formulations with substantially the same D2 dopamine receptor antagonism and 5-HT$_7$ serotonin receptor antagonism. In various aspects and embodiments, provided are modified release formulations of non-racemic amisulpride compositions with reduced drug induced QT prolongation compared to immediate release formulations with substantially the same D2 dopamine receptor antagonism and 5-HT$_7$ serotonin receptor antagonism.

The present inventors have discovered that the presence of amisulpride enantiomers in a subject's blood plasma is shorter than the brain D2 dopamine receptor occupancy. The present inventors have also discovered modified release pharmaceutical formulations of amisulpride that can achieve the same brain D2 dopamine receptor occupancy, but at lower amisulpride blood plasma concentrations (e.g. Cmax, AUC, and both Cmax and AUC), than immediate release formulations with comparable brain D2 dopamine receptor occupancy.

In addition, the present inventors have discovered modified release pharmaceutical formulations of amisulpride that improve the therapeutic index of amisulpride. For example, in various aspects and embodiments, the present inventors have discovered modified release pharmaceutical formulations of amisulpride that provide the substantially similar pharmacodynamics (e.g. efficacy) as immediate release formulations but with improved pharmacokinetics (e.g. lower Cmax) and/or reduced side effects (e.g. reduced QT prolongation).

It has been previously discovered that the R and S amisulpride isomers have different properties. The R isomer is a selective serotonin antagonist. In contrast the S isomer is a highly selective D2 dopamine antagonist. The present inventors provide modified release formulations using amisulpride compositions tailored to provide specific antagonism effects against the D2 dopamine receptors and the 5-HT$_7$ receptors independent of one another. In various aspects and embodiments, the amisulpride compositions used in the modified release formulations have been previously shown in immediate release formulations to provide the ability to adjust the D2 dopamine and 5-HT$_7$ receptors antagonism activity and reduce the adverse effects associated with racemic amisulpride of comparable total dosage amounts. The modified release formulations reduce even further the adverse effects associated with racemic amisulpride of comparable total dosage amounts. In short, the present inventors have discovered modified release formulations of these non-racemic amisulpride compositions that provide substantially the same benefits in the treatment of bipolar symptoms and depression as comparable immediate release formulations of non-racemic amisulpride compositions but with reduced side effects in various embodiments.

In various aspects and embodiments, the non-racemic amisulpride compositions used in the modified release formulations provide the ability to adjust release of the active pharmaceutical ingredients (i.e. enantiomers of amisulpride) such that the D2 dopamine and 5-HT$_7$ receptors antagonism activity (associated, respectively, with S amisulpride and R amisulpride) can be achieved at lower blood concentration levels than for comparable immediate release formulations of comparable total dosage amounts. Thus, in various aspects and embodiments, the modified release formulations reduce the adverse effects associated with comparable immediate release formulations of the comparable non-racemic amisulpride compositions, and reduce even further the adverse effects associated with racemic amisulpride of comparable total dosage amounts. Adverse effects associated with racemic amisulpride include, but are not limited to, Extrapyramidal Symptoms (EPS), akathisia, sedation, metabolic parameters such as weight gain, glucose and lipids, prolactin related events, sexual dysfunction and manic depression. Adverse effects associated with both amisulpride enantiomers include, but are not limited to, QT prolongation. In various aspects and embodiments, the degree of reduction is determined by the decrease in Cmax.

In various aspects and embodiments, provided are various modified release formulations, methods and medicaments comprising and/or employing amisulpride in the form of an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, that can provide the discovered antidepressant activity of (R)-(+)-amisulpride while maintaining the mood stabilization activity of (S)-(−)-amisulpride and decreasing the undesirable side effects associated with immediate release formulations of amisulpride. In various aspects and embodiments, modified release formulations decrease the undesirable side effects associated with higher levels of dopamine D2 receptor blockade associated with (S)-(−)-amisulpride. In various aspects and embodiments, modified release formulations decrease the undesirable amisulpride side effect of drug induced QT prolongation.

It has been discovered by the inventors that modified release formulations of a fixed-dose combination of amisulpride enantiomers, defined in various embodiments by the contribution of 5-HT$_7$ occupancy relative to D2 occupancy, exhibit clinical benefit by allowing physicians to treat subjects with a dominant 5-HT$_7$ pharmacodynamics while still maintaining a dose-responsive underlying dopamine D2 activity for a combined, and in various embodiments improved, clinical benefit in depressive disorders, whilst reducing one or more side effects associated with comparable immediate release formulations.

In various aspects and embodiments, there are provided modified release pharmaceutical compositions in a solid oral dosage form comprising amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, and one or more pharmaceutically acceptable excipients. The one or more pharmaceutically acceptable excipients may include an extended release agent.

In various aspects and embodiments, when the modified release pharmaceutical composition is administered to a subject population, it results in a maximum QT interval prolongation of less than about 0.45 milliseconds (ms), less than about 0.30 milliseconds (ms), less than about 0.20 milliseconds (ms), less than about 0.10 milliseconds (ms), less than 0.05 milliseconds (ms), or less than 0.02 milliseconds (ms) per 10 mg of amisulpride over the time period of 12 hours after administration.

In various aspects and embodiments, when the modified release pharmaceutical composition is administered to a subject population, it results in a maximum QT interval prolongation over the time period of 12 hours after administration that is at least about 75%, about 65%, about 60%, about 55%, or about 50% less than that of an immediate release composition having the same total daily amount of amisulpride as the modified release pharmaceutical composition.

In various aspects and embodiments, when the modified release pharmaceutical composition is administered to a subject population, it results in a maximum QT interval prolongation over the time period of 12 hours after administration that is at least about 75%, about 65%, about 60%, about 55%, or about 50% less than that of the immediate release composition described in Table 25 and having the same total daily amount of amisulpride as the modified release pharmaceutical composition.

In various aspects and embodiments, when a modified release pharmaceutical composition comprising about 200 mg of total amisulpride is administered to a subject population, it results in a maximum QT interval prolongation over the time period of 12 hours after administration that is less than about 10 milliseconds (ms), about 9 ms, about 8 ms, about 7 ms, about 6 ms, or about 5 ms relative to baseline.

In various aspects and embodiments, when a modified release pharmaceutical composition comprising about 200 mg of total amisulpride is administered to a subject population, it results in QT interval prolongation at geometric mean Cmax that is less than about 10 milliseconds (ms), about 9 ms, about 8 ms, about 7 ms, about 6 ms, or about 5 ms relative to baseline.

In various aspects and embodiments, the solid oral dosage form, when dissolution tested using in vitro gastrointestinal simulation dissolution test releases (a) less than about 30% of amisulpride after about 1 hour, releases more than about 20% and less than about 60% of amisulpride after about 3 hours, and releases more than about 30% and less than about 100% of amisulpride mixture after about 6 hours; (b) less than about 30% of amisulpride after about 1 hour, releases more than about 20% and less than about 60% of amisulpride after about 3 hours, and releases more than about 30% and less than about 75% of amisulpride after about 6 hours; (c) less than about 20% of amisulpride after about 1 hour, releases more than about 20% and less than about 50% of amisulpride after about 3 hours, and releases more than about 30% and less than about 75% of amisulpride after about 6 hours; (d) more than about 30% and less than about 50% of amisulpride after about 6 hours; (e) no more than about 30% of amisulpride after about 1 hour, releases between about 30% and about 75% of amisulpride after about 3 hours, and releases more than about 75% of amisulpride after about 12 hours; or (f) more than about 75% of amisulpride after about 6 hours.

In various aspects and embodiments, the solid oral dosage form, when dissolution tested using the two-stage in vitro dissolution test described in Table 5 in the paddle apparatus described in United States Pharmacopeia Convention (USP) Apparatus 2 of Chapter 711 Dissolution; USP41-NF36 General Chapter <711> Dissolution releases (a) less than about 30% of amisulpride after about 1 hour, releases more than about 20% and less than about 60% of amisulpride after about 3 hours, and releases more than about 30% and less than about 100% of amisulpride mixture after about 6 hours; (b) less than about 30% of amisulpride after about 1 hour, releases more than about 20% and less than about 60% of amisulpride after about 3 hours, and releases more than about 30% and less than about 75% of amisulpride after about 6 hours; (c) less than about 20% of amisulpride after about 1 hour, releases more than about 20% and less than about 50% of amisulpride after about 3 hours, and releases more than about 30% and less than about 75% of amisulpride after about 6 hours; (d) more than about 30% and less than about 50% of amisulpride after about 6 hours; (e) no more than about 30% of amisulpride after about 1 hour, releases between about 30% and about 75% of amisulpride after about 3 hours, and releases more than about 75% of amisulpride after about 12 hours; or (f) more than about 75% of amisulpride after about 6 hours.

As used herein, the term "two-stage in vitro gastrointestinal simulation dissolution test" refers to an in vitro test designed to simulate the solution pH conditions of the stomach (stage 1) and small intestine (stage 2) of a human in a fasted state. The pH of the first stage is between about 1.2 to 3.5, and the pH of the second stage is between about 6 to about 7.4. The sample to be tested (e.g. tablet, capsule) is placed in the liquid medium of the first stage for about an hour (to simulate residence time in the stomach) prior to the medium being adjust to those of the second stage (to simulate transition to the higher pH environment of the small intestine). The dissolution medium is stirred during the test with a paddle apparatus, substantially in accord with either that described by the United States Pharmacopeia Convention (USP) Apparatus 2 of Chapter 711 Dissolution; USP41-NF36 General Chapter <711> Dissolution or that described by the paddle method of Japanese Pharmacopeia (JP) General test<6.10>, as harmonized with Ph. Eur. <2.9.3> and USP <711>. The paddle apparatus is operated between about 50 to about 75 rpm in both stages; and the temperature of the dissolution medium in both stages is maintained at about 37° C.

In various aspects and embodiments, when the modified release pharmaceutical composition is administered to a subject population, it is effective in minimizing fluctuations between Cmin and Cmax of amisulpride. In various aspects and embodiments, the modified release pharmaceutical compositions are effective in minimizing the difference between Cmin and Cmax of amisulpride compared to the immediate release composition described in Table 25 and having the same total daily amount of amisulpride as the modified release pharmaceutical composition wherein the value of Cmin is at about 9 hours after administration.

In various aspects and embodiments, the modified release pharmaceutical composition, when administered to a subject population, is effective in providing a population mean ratio of Cmax/Cmin of amisulpride that is less than about 2, less than about 1.9, or less than about 1.8, wherein the value of Cmin is at about 9 hours after administration.

In various aspects and embodiments, when the modified release pharmaceutical composition is administered to a subject population (i) the area under the curve (AUC) of blood plasma concentration versus time of amisulpride from administration to Tmax ($AUC_{0-Tmax}$) is less than about 17%, less than about 16%, less than about 15%, less than about 14%, less than about 13%, or less than about 12% of the area under the curve from administration to infinity ($AUC_{0-INF}$); and (ii) Tmax of amisulpride is between about 4 and about 6 hours after administration.

In various aspects and embodiments, when the modified release pharmaceutical composition is administered to a subject population (i) the area under the curve (AUC) of blood plasma concentration versus time of amisulpride from administration to Tmax ($AUC_{0-Tmax}$) is less than about 19%, less than about 18%, less than about 17%, less than about 16%, less than about 15%, less than about 14%, less than about 13%, or less than about 12% of the area under the curve from administration to 48 hours ($AUC_{0-48}$); and (ii) Tmax of amisulpride is between about 4 and about 6 hours after administration.

In various aspects and embodiments, when the modified release pharmaceutical composition is administered to a subject population, it provides a plasma concentration profile substantially the same as the profile of Lot 4Z in FIG. 22B, Lot 4Z in FIG. 22F, Lot 3Z in FIG. 22C, Lot 3Z in FIG. 22H, Lot 3Z in FIG. 22J, Lot 3Z with subjects in a fed state in FIG. 22I, Lot 3Z with subjects in a fed state in FIG. 22D, of Lot 5Z in FIG. 22G, or Lot 6Z in FIG. 22K.

In various aspects and embodiments, when the modified release pharmaceutical composition is administered to a subject population, it provides a blood plasma Cmax of amisulpride that is less than about 75%, less than about 65%, less than about 60%, less than about 55%, or less than about 50% of the Cmax achieved by the immediate release having the same total daily amount of amisulpride as the modified release pharmaceutical composition. In various aspects and embodiments, when the modified release pharmaceutical composition is administered to a subject population, it provides a blood plasma Cmax of amisulpride that is less than about 45%, less than about 40%, less than about 35%, or less than about 30% of the Cmax achieved by the immediate release having the same total daily amount of amisulpride as the modified release pharmaceutical composition. In various embodiments, an immediate release composition has the same total daily amount of (R)-(+)-amisulpride and (S)-(−)-amisulpride as in the modified release pharmaceutical composition.

In various aspects and embodiments, when the modified release pharmaceutical composition is administered to a subject population, it provides a blood plasma Cmax of amisulpride that is less than about 75%, less than about 65%, less than about 60%, less than about 55%, or less than about 50% of the Cmax achieved by the immediate release composition described in Table 25 and having the same total daily amount of amisulpride as the modified release pharmaceutical composition. In various aspects and embodiments, when the modified release pharmaceutical composition is administered to a subject population, it provides a blood plasma Cmax of amisulpride that is less than about 45%, less than about 40%, less than about 35%, or less than about 30% of the Cmax achieved by the immediate release composition described in Table 25 and having the same total daily amount of amisulpride as the modified release pharmaceutical composition. In various embodiments, the immediate release composition has the same total daily amount of (R)-(+)-amisulpride and (S)-(−)-amisulpride as in the modified release pharmaceutical composition.

In various aspects and embodiments, when the modified release pharmaceutical composition is administered to a subject population, it provides a blood plasma Cmax of amisulpride that is less than about 75%, less than about 65%, less than about 55%, or less than about 50% of the Cmax achieved by an immediate release composition having the same total daily amount of amisulpride as the modified release pharmaceutical composition, and when administered to a subject population provides a AUC from 0 to 48 hours after administration ($AUC_{0-48}$) of amisulpride that is at least about 60%, at least about 70%, or at least about 75% of the $AUC_{0-48}$ achieved by an immediate release composition having the same total daily amount of amisulpride as the modified release pharmaceutical composition.

In various aspects and embodiments, when the modified release pharmaceutical composition is administered to a subject population, it provides a blood plasma Cmax of amisulpride that is less than about 75%, less than about 65%, less than about 55%, or less than about 50% of the Cmax achieved by the immediate release composition described in Table 25 and having the same total daily amount of amisulpride as the modified release pharmaceutical composition, and when administered to a subject population provides a AUC from 0 to 48 hours after administration ($AUC_{0-48}$) of amisulpride that is at least about 60%, at least about 70%, or at least about 75% of the $AUC_{0-48}$ achieved by the immediate release composition described in Table 25 and having the same total daily amount of amisulpride as the modified release pharmaceutical composition.

In various aspects and embodiments, when the modified release pharmaceutical composition is administered to a subject population, it provides a AUC from 0 to 48 hours after administration ($AUC_{0-48}$) of amisulpride that is: (a) at least about 40% of the $AUC_{0-48}$ achieved by an immediate release composition having the same total daily amount of amisulpride as the modified release pharmaceutical composition, (b) at least about 50% of the $AUC_{0-48}$ achieved by an immediate release composition having the same total daily amount of amisulpride as the modified release pharmaceutical composition (c) at least about 60% of the $AUC_{0-48}$ achieved by an immediate release composition having the same total daily amount of amisulpride as the modified release pharmaceutical composition, (d) at least about 70% of the $AUC_{0-48}$ achieved by an immediate release composition having the same total daily amount of amisulpride as the modified release pharmaceutical composition, (e) at least about 75% of the $AUC_{0-48}$ achieved by an immediate release composition having the same total daily amount of amisulpride as the modified release pharmaceutical composition, and/or (f) at least about 80% of the $AUC_{0-48}$ achieved by an immediate release composition having the same total daily amount of amisulpride.

In various aspects and embodiments, when the modified release pharmaceutical composition is administered to a subject population, it provides a AUC from 0 to 48 hours after administration ($AUC_{0-48}$) of amisulpride that is: (a) at least about 40% of the $AUC_{0-48}$ achieved by the immediate release composition described in Table 25 and having the same total daily amount of amisulpride as the modified release pharmaceutical composition, (b) at least about 50% of the $AUC_{0-48}$ achieved by the immediate release composition described in Table 25 and having the same total daily amount of amisulpride as the modified release pharmaceutical composition, (c) at least about 60% of the $AUC_{0-48}$ achieved by the immediate release composition described in Table 25 and having the same total daily amount of amisulpride as the modified release pharmaceutical composition, (d) at least about 70% of the $AUC_{0-48}$ achieved by the immediate release composition described in Table 25 and having the same total daily amount of amisulpride as the modified release pharmaceutical composition, (e) at least about 75% of the $AUC_{0-48}$ achieved by the immediate release composition described in Table 25 and having the same total daily amount of amisulpride as the modified release pharmaceutical composition, and/or (f) at least about 80% of the $AUC_{0-48}$ achieved by the immediate release composition described in Table 25 and having the same total daily amount of amisulpride.

In various aspects and embodiments, the modified release pharmaceutical compositions, and methods of treatment refer to a subject population and provision of certain effects thereto, and/or parameters that are those of a subject population (e.g. a subject population average). It is to be understood that when such reference is made to a subject population or in a subject population the effect is that determined from the overall effect in the subject population, e.g. the subject population average of a measured parameter, the subject population geometric mean of a measured parameter, etc. It is not required that any one subject exhibit the effect as specified, nor is it required that every subject exhibit the effect as specified; rather it is the value of the effect (e.g. QT interval, Cmax, Cmin, Tmax, AUC, D2 occupancy, etc.) for the population. As described herein, the value for an effect when used in the descriptions herein encompass average, mean, and geometric mean values of a population. That is for the sake of conciseness in description phrasing such as "average, mean, and/or geometric mean values" has not been included as it is to be understood the disclosures herein are generally applicable, mutatis mutandis.

In various aspects and embodiments, the effects of a modified release pharmaceutical compositions, and methods of treatment using the same, are compared to an immediate release formulation and/or a comparable immediate release formulation having the same total daily amount of amisulpride. It is to be understood that such comparable immediate release formulations are those that are substantially similar in formulation composition to the corresponding modified release formulations except where the extended release agent in the modified release formulation has been replaced by substantially the same filler as used in the modified release formulation, with the understanding that minor variations in excipients such as, e.g., lubricants, glidants and binders, necessary for dosage form formation are acceptable. For example, in various embodiments, modified release formulations are compared to an immediate release formulation substantially similar to that of Lot 1D, and the comparable immediate release formulation is that of Lot 1D; and in various embodiments, modified release formulations are compared to an immediate release formulation substantially similar to that of Lot 1Z, and the comparable immediate release formulation is that of Lot 1Z.

These and other objects, features, and advantages of the inventions will become apparent from the following detailed description of the various aspects and embodiments of the inventions taken in conjunction with the accompanying tables and drawings.

All published documents cited herein are hereby incorporated herein by reference in their entirety.

BRIEF DESCRIPTION OF THE DRAWINGS

FIG. 1A presents data for the formulations of Table 1; FIG. 1B presents data for the formulations of Table 2; FIG. 1C presents data for the formulations of Table 3A; FIG. 1D presents data for the formulations of Tables 24A and 24B.

FIG. 2A is a 50× image of the IR particles, FIG. 2B is a 50× image of Lot SC30, and FIG. 2C is a 50× image of Lot SC60.

FIG. 5A presents data on the % inhibition of dopamine D2 receptor binding; FIG. 5B presents data on the % inhibition of serotonin 5-HT7 receptor binding; and FIG. 5C presents data on relative receptor affinity (5-HT7: D2) for various mixtures of (R)-amisulpride and (S)-amisulpride.

FIG. 7A presents data comparing vehicle to 10 mg/kg and 100 mg/kg of (R)-amisulpride, and FIG. 7B presents data comparing vehicle to 10 mg/kg, 30 mg/kg and 100 mg/kg of (R)-amisulpride.

FIG. 7C presents data comparing vehicle to 30 mg/kg and 100 mg/kg of 85:15 ratio (R:S-amisulpride) and racemic amisulpride in REM sleep time (min). FIG. 7D presents data comparing vehicle to 30 mg/kg and 100 mg/kg of 85:15 ratio (R:S-amisulpride) and racemic amisulpride in NREM sleep time (min). FIG. 7E presents data comparing vehicle to 30 mg/kg and 100 mg/kg of 85:15 ratio (R:S-amisulpride) and racemic amisulpride in WAKE time (min).

FIG. 10A presents data from human clinical studies on the binding to dopamine D2 receptors of an 85:15 ratio by weight percentage (w/w %) of (R)-amisulpride to (S)-amisulpride, FIG. 10B illustrates data on a racemic (50:50 ratio by weight percentage mixture of (R)-amisulpride to (S)-amisulpride), and FIG. 10C illustrates the substantial overlap of the 5-HT$_7$ effect with 30% to 50% D2 receptor occupancy that may be achieved with administration of an 85:15 ratio by weight percentage (w/w %) mixture of (R)-amisulpride to (S)-amisulpride. In FIG. 10B the mg designations within the field of the graph indicate the amount of the indicated enantiomer in the racemic mixture. In FIG. 10C the grey shaded circles are the data for (S)-amisulpride from FIG. 10B plotted on the FIG. 10C x-axis as the total mg amount required to deliver the indicated amount of (S)-amisulpride in the (R)-amisulpride:(S)-amisulpride (85:15) mixture, the dark shaded circles are the data for (R)-amisulpride from FIG. 10B plotted on the FIG. 10C x-axis as the total mg amount required to deliver the indicated amount of (R)-amisulpride in the (R)-amisulpride:(S)-amisulpride (85:15) mixture, and the white diamond symbols are data for the administration of an 85:15 ratio by weight percentage (w/w %) mixture of (R)-amisulpride to (S)-amisulpride.

FIG. 11A presents a DSC thermogram; FIG. 11B a XRPD pattern; and FIG. 11C a micrograph image.

FIG. 12A presents a DSC thermogram; FIG. 12B a XRPD pattern; FIG. 12C a micrograph image; and FIG. 12D a DVS water sorption isotherm.

FIGS. 19A, 19B, and 19C present analytical data on the effects of mixtures of amisulpride.

FIG. 19A presents data from human clinical studies on the effects of (R)-amisulpride (dark circles) on 5-HT$_7$ shown by suppression of REM sleep from Example 5, where the x-axis in the top graph is 50:50 racemic amisulpride, and the x-axis in the bottom graph is 85:15 ratio by weight percentage (w/w %) of R:S-amisulpride.

FIG. 19B presents data from human clinical studies on the binding to dopamine D2 receptors of (S)-amisulpride and an 85:15 ratio by weight percentage (w/w %) of (R)-amisulpride to (S)-amisulpride. The x-axis in the top graph is 50:50 racemic amisulpride. The top graph shows the amount of (S)-amisulpride (grey circles) has on D2 occupancy based on data from Example 4. The x-axis in the bottom graph is 85:15 ratio of (R)-amisulpride to (S)-amisulpride, showing the amount of (S)-amisulpride (grey circles) and 85:15 ratio (white diamonds) have on D2 occupancy based on data from Example 4 and Example 6, respectively.

FIG. 19C illustrates the substantial overlap of the 5-HT$_7$ effect with 30% to 50% D2 receptor occupancy that may be achieved with administration of an 85:15 ratio by weight percentage (w/w %) mixture of (R)-amisulpride to (S)-amisulpride. The x-axis in the top graph is the total amount of racemic amisulpride. The mg designations indicate the amount of the indicated enantiomer in the racemic mixture. The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-HT$_7$. The x-axis in the bottom graph is the total amount of 85:15 ratio R:S amisulpride. The mg designations indicate the amount of the indicted enantiomer in the 85:15 ratio mixture. The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-HT$_7$. The white diamonds are data for the 85:15 ratio R:S amisulpride from Example 6 (D2 occupancy).

FIGS. 20A and 20B present, respectively, the geometric mean of Cmax and AUC for the subjects of Example 7A, the error bars represent the 95% confidence intervals.

FIGS. 21A and 21B present, respectively, average Cmax and AUC for the subjects of the study of Example 7A, Part 1, the error bars represent the ±95% confidence intervals. The values for Cmax and AUC have been normalized for each subject to the Cmax and AUC value of that subject when administered the IR tablet, i.e. a tablet having a composition substantially similar to that of Lot 1Z.

In FIGS. 21D and 21E the values for Cmax and AUC have been normalized for each subject to the Cmax and AUC value of that subject when administered the IR tablet, i.e. a tablet having a composition substantially similar to that of Lot 1Z. Two squares are shown for Lot 3Z in FIGS. 21D and 21E, one square presenting data for Lot 3Z administered in the fed state, and the other for Lot 3Z administered in a fasted state, see Table 28B.

FIGS. 22A-22D present data for subjects who were successfully administered all of the formulations of Part 1 of Example 7A (n=12) that is for subjects who each administered Lot 1Z, Lot 2Z, Lot 4Z, Lot 3Z, and Lot 3Z fed state. FIG. 22A presents data on Lot 2Z compared to Lot 1Z, FIG. 22B presents data on Lot 4Z compared to Lot 1Z in Example 7A Part 1, FIG. 22C presents data on Lot 3Z compared to Lot 1Z in Example 7A Part 1, and FIG. 22D presents data on Lot 3Z when a subject is in a fed state (taken within 30 minutes after a meal), compared to Lot 1Z in Example 7A Part 1.

FIGS. 22E-22K present data where all subjects were included (for example, for Lot 1Z (IR) n=17, for Lot 2Z (10%) n=15, Lot 4Z (15%) n=14, Lot 5Z (20%) n=18, Lot 3Z (25%) n=16, Lot 3Z (25% fed state) n=12, and for Lot 6Z (40%) n=17.

FIG. 22E presents data on Lot 2Z compared to Lot 1Z for all subjects administered Lot 2Z or 1Z in Example 7A Part 1.

FIG. 22F presents data on Lot 4Z compared to Lot 1Z for all subjects administered Lot 4Z or 1Z in Example 7A Part 1.

FIG. 22G presents data on Lot 5Z compared to Lot 1Z in Example 7A Part 2 for all subjects administered Lot 5Z or 1Z in Example 7A Part 2.

FIG. 22H presents data on Lot 3Z compared to Lot 1Z for all subjects administered Lot 3Z or 1Z in Example 7A Part 1.

FIG. 22I presents data on Lot 3Z when a subject is in a fed state (taken within 30 minutes after a meal) compared to Lot 1Z for all subjects administered Lot 3Z in a fed state or 1Z in Example 7A Part 1.

FIG. 22J presents data on Lot 3Z compared to Lot 1Z for all subjects administered Lot 3Z or 1Z in Example 7A Part 2.

FIG. 22K presents data on Lot 6Z compared to Lot 1Z for all subjects administered Lot 6Z or 1Z in Example 7A Part 2.

FIGS. 24A and 24B present data on percentage D2 receptor occupancy for subjects 27.5±1 hour following the first dose, and FIGS. 24 C and 24D present data on percentage D2 receptor occupancy for subjects 27.5±1 hour following the seventh dose. The error bars represent the ±90% confidence intervals.

DETAILED DESCRIPTION

Figure 1A:
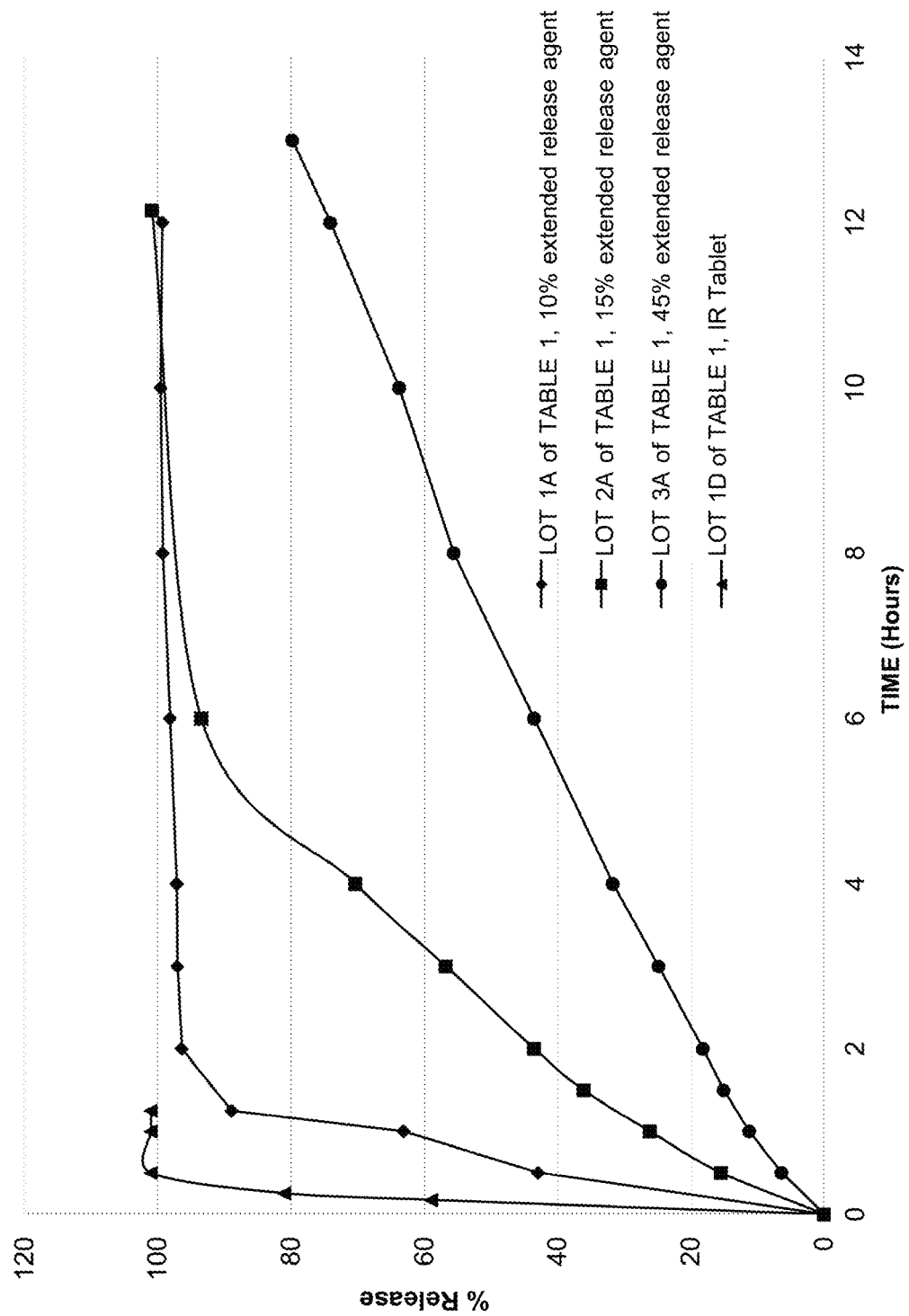
FIGS. 1A-1D present various in vitro dissolution profiles for various modified release pharmaceutical matrix tablet formulations of 85:15 (R:S-amisulpride); where

Reference in the specification to "one embodiment," "an embodiment," "one aspect," or "an aspect" means that a particular, feature, structure or characteristic described in connection with the embodiment or aspect is included in at least one embodiment or aspect of the teachings.

As used herein, the recitation of "amisulpride," unless expressly further limited, refers to amisulpride in any enantiomeric ratio including, equal mixtures of R-amisulpride and S-amisulpride, pure R-amisulpride, pure S-amisulpride, and unequal mixtures of R-amisulpride and S-amisulpride. In addition, as used herein, the recitation of "amisulpride," unless expressly further limited, includes pharmaceutically acceptable salts of amisulpride. As used herein, the term "racemic amisulpride" refers to a 50:50 mixture by weight of (R)-amisulpride and (S)-amisulpride.

As used herein the term "extended release agent" means an excipient that lowers the rate of gastric dissolution of amisulpride in a solid oral dosage form formulation such that the amisulpride is released over an extended time. Extended release agents include, but are not limited to, polymer coatings, polymer matrix systems, enzyme-activated systems, systems that respond to changes in physical conditions, such as, e.g., pH, etc., agents that are hydrophilic, agents that are hydrophobic, etc.

As used herein, the phrase "QT interval" refers to the heart rate corrected QT interval as determined using Fridericia's formula $QTcF=QT/\sqrt[3]{RR}$, that is herein "QT interval" refers to QTcF. As used herein the phrase "QT interval prolongation" refers to the change in the QTcF interval relative to the baseline QTcF interval. i.e., (ΔQTcF).

As used herein, the term "fed state" refers to the metabolic state shortly after ingestion of a meal. Measurements of a fed state pharmacokinetic parameters, such as for example, $C_{max}$, $T_{max}$, AUC can be conducted as follows. Following an overnight fast of at least 10 hours, subjects consume a meal comprising 150, 250, and 400-600 calories from protein, carbohydrate, and fat, respectively. This meal should be consumed about 30 minutes prior to administration of the drug product and subjects should eat this meal in 30 minutes or less. No food should be allowed for at least 4 hours post-dose. Water can be allowed as desired except for one hour before and after drug product administration.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthaleneslfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates.

As used herein, the term "subject," to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); and mammals used for the testing of pharmaceuticals.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

As used herein, the terms "treatment," "treat," and "treating" refer to alleviating, inhibiting, and/or reducing one or more signs or symptoms of a disease, condition, or disorder. In various embodiments, treatment may be administered after one or more symptoms have developed. Treatment may also be continued after symptoms have resolved, for example to prevent or delay their recurrence.

As used herein, the term "therapeutic index" is a comparison of the amount of a drug that causes the therapeutic effect to the amount that causes one or more undesired effects, such as adverse events and/or side effects.

As used herein, the phrase "on a free base basis" indicates that the amount of amisulpride (R and S-amisulpride) is measured based on the molecular weight of amisulpride free base. Unless specified otherwise, the weight amount described herein for amisulpride (e.g., racemic, R, S, or unequal mixtures of R and S amisulpride) refers to the free base. For example, in a mixture of 85:15 ratio of R:S-amisulpride by weight, the amount of amisulpride is measured based on the molecular weight of R and S-amisulpride free base unless stated otherwise.

The compounds disclosed herein can include isotopes. Isotopes include those atoms having the same atomic number but different mass numbers. For example, isotopes of hydrogen include tritium and deuterium. In some embodiments, one or more atoms of the compounds can be replaced or substituted with isotopes of the atoms in natural or non-natural abundance. In some embodiments, one or more hydrogen atoms in a compound of the present disclosure can be replaced or substituted by deuterium.

As used herein, and unless otherwise specified, the term "about", when used in connection with a numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. In some embodiments, the numeric value or range of values vary by 5%.

As used herein, and unless otherwise specified, the term "therapeutically effective" when used in connection with the pharmaceutical compositions of the present inventions means a biological or medical response which is sought or desired, for example, by a researcher or physician, such as improved treatment, healing, prevention or elimination of a disease, syndrome, condition, complaint, disorder or side-effects or also the reduction in the advance of a disease, complaint or disorder. The term "therapeutically effective amount" when used in connection with the pharmaceutical compositions of the present inventions means an amount of a medicament or of an active pharmaceutical ingredient that is therapeutically effective. For example, in various aspects and embodiments, a therapeutically effective amount for the treatment of a depressive disorder (e.g. depressive episodes associated with a bipolar disorder) is an amount that provides an average occupancy of dopamine D2 receptors between about 20% and about 60% (e.g. as measured and described herein). In various aspects and embodiments, a therapeutically effective amount for the treatment of a depressive disorder (e.g. depressive episodes associated with a bipolar disorder) is an amount that reduces depressive symptoms as measured by the reduction in total score on a questionnaire employing the Montgomery-Åsberg Depression Rating Scale (MADRS) and/or the self-rating version MADRS-S.

The term "therapeutically effective blood plasma concentration" when used in connection with the pharmaceutical compositions of the present inventions means an active pharmaceutical ingredient blood plasma concentration that is therapeutically effective.

Other abbreviations not explicitly described herein have their normal meanings in the art.

It is to be understood that AUC and $AUC_{0-INF}$ are determined as is normal in the art. Specifically, $AUC_{0-INF}$ was determined from the formula: $AUC_{0-INF} = AUC_{0-last} + C_{last}/$ λz; where "last" is the last time point for which the blood plasma concentration (C) was measured, and where λz=a first-order rate constant associated with the terminal (log-linear) portion of the blood plasma concentration curve. The value for λz was determined by linear regression analysis of the time vs. log of the blood plasma concentration data.

The present disclosures relate to modified release formulations of pharmaceutical compositions comprising unequal mixtures of amisulpride enantiomers, medicaments for the treatment of a disorder comprising modified release formulations of unequal mixtures of amisulpride enantiomers, methods of treating a disorder in a subject with modified release formulations of pharmaceutical compositions comprising unequal mixtures of amisulpride enantiomers, and methods of inhibiting dopamine D2 activity and serotonin 5-HT7 activity in a subject with modified release formulations comprising unequal mixtures of amisulpride enantiomers.

In various aspects, the disorder which the medicaments and methods treat comprise one or more of a: psychiatric disorder; mood disorder; depressive disorder; as an adjunctive treatment of major depressive disorder; bipolar disorder; bipolar depression; schizophrenia; negative symptoms of schizophrenia; treatment resistant depression (TRD); schizoaffective disorder; anxiety disorder; obsessive-compulsive disorder; behavior disturbances associated with a neurocognitive disorder; conduct disorder; neurological disorder; medication-induced movement disorder; and motor disorder.

Amisulpride has a single asymmetric center and as a result exists in two enantiomeric forms: R-4-Amino-N-[(1-ethyl-2-pyrrolidinyl)methyl]-5-(ethylsulfonyl)-2-methoxybenzamide (also referred to as: (R)-(+)-4-amino-N-[(1-ethylpyrrolidin-2-yl)methyl]-5-(ethylsulfonyl)-2-methoxybenzamide, and under the IUPAC name as 4-amino-5-(ethanesulfonyl)-N-{[(2R)-1-ethylpyrrolidin-2-yl]methyl}-2-methoxybenzamide), abbreviated herein as (R)-(+)-amisulpride or (R)-amisulpride; and S-4-Amino-N-[(1-ethyl-2-pyrrolidinyl)methyl]-5-(ethylsulfonyl)-2-methoxybenzamide (also referred to as: (S)-(−)-4-amino-N-[(1-ethylpyrrolidin-2-yl)methyl]-5-(ethylsulfonyl)-2-methoxybenzamide, and under the IUPAC name as 4-amino-5-(ethanesulfonyl)-N-{[(2S)-1-ethylpyrrolidin-2-yl]methyl}-2-methoxybenzamide), abbreviated herein as (S)-(−)-amisulpride or (S)-amisulpride. These two enantiomeric forms have the following chemical structures:

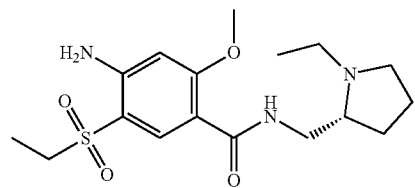 [SMILES: CCN1CCCC1CNC(=O)c1cc(S(=O)(=O)CC)c(N)cc1OC]

R-4-Amino-N-[(1-ethyl-2-pyrrolidinyl)methyl]-5-(ethylsulfonyl)-2-methoxybenzamide, (R)-amisulpride

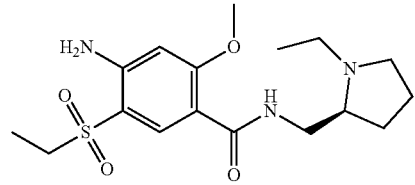

S-4-Amino-N-[(1-ethyl-2-pyrrolidinyl)methyl]-5-(ethylsulfonyl)-2-methoxybenzamide (S)-amisulpride Dopamine $D_2$-related side effects are well-known from clinical experience. It has been observed that the incidence of extrapyramidal side effects increases when occupancy exceeds the 80% threshold and studies have shown that extrapyramidal side effects occur even at about 70-75% occupancy (G. Grunder, et al., Nature, 8, 198-202, (2009); Nyberg, et al., Am. J. Psychiatry, 156, 873-875 (1999); Farde, et al. Arch. Gen. Psychiatry, 49, 538-544 (1992)). However, it is believed that very high D2/3 receptor occupancy is not only associated with but generally required for effectiveness against the positive symptoms of schizophrenia and that the antipsychotic effects of dopamine receptor antagonists occur within a therapeutic window between 60 and 80% striatal D2/3 receptor occupancy. (G. Grunder, et al., Nature, 8, 198-202, (2009)).

Dopamine $D_2$-related side effects are also known from clinical experience with racemic amisulpride and include Extrapyramidal Symptoms (EPS), Tardive Dyskinesia (TD), and Akathisia. (C. Coulouvrat et al., International Clinical Psychopharmacology, Vol 14, No. 4, 209-218 (1999)). It has been determined that in general $D_2$ occupancy greater than about 67% results in side-effects that limit the ability of the underlying 5-$HT_7$ pharmacodynamics to contribute to clinical benefit as a function of dose. (Farde, et al. Arch. Gen. Psychiatry, 49, 538-544 (1992). The impact of $D_2$ occupancy is associated with age with EPS events being noted in older patients with Alzheimer's at occupancies of about 60%; clinically meaningful responses were seen at occupancies of 43%. (Reeves et al., Brain, 140, 1117-1127). Similar results were also obtained with older patients in general. (Uchida et al., The American J. of Geriatic Pyschiatry, 22 (1) 1007-1016).

Selective serotonin 5-HT7 antagonists are known to modulate rapid eye movement (REM) sleep in rodents and humans (Bonaventure et al, 2012). In general, REM suppression is understood to be a translational biomarker of serotonergic antidepressant-like activity appropriate for selecting human doses. The 5-HT7 receptor has been shown, through various pharmacological tools (receptor-specific agonists and antagonists) and through the use of knockout models, to be involved in the central regulation of sleep and circadian rhythms, mood, and cognition. These same three domains are often critically impaired in mood disorders such as major depressive disorder and bipolar disorder, as well as in psychotic disorders.

The present inventors have demonstrated that various modified release formulations having amisulpride in the form of an unequal mixture of the (R)-(+)-amisulpride and (S)-(−)-amisulpride, or pharmaceutically acceptable salts thereof, can provide substantially similar or improved efficacy (e.g. in the treatment of bipolar disorder, depressive episodes associated with bipolar disorder, and/or depression) compared to comparable immediate release formulations whilst reducing undesired side effects, such as, for example, drug induced QT prolongation and/or those associated with higher levels of dopamine $D_2$ receptor blockade.

The beating of the heart is due to precisely controlled regularly spaced waves of myocardial excitation and contraction, arising from ion-based depolarization and repolarization. The electrical currents during depolarization and repolarization can be measured by leads placed on the body in specific locations (the electrocardiogram) to measure the electrical waves. The P-wave in an electrocardiogram represents a wave of depolarization in the atrium. When the entire atria becomes depolarized, the wave returns to zero, and after 0.1 seconds the ventricle is entirely depolarized resulting in the QRS complex seen in the electrocardiogram (ECG). The three peaks of the QRS complex are due to the way the current spreads in the ventricles. The QRS complex is followed by the T-wave, or repolarization of the ventricle. The QT interval is measured from the beginning of the QRS complex to the end of the T wave on the standard ECG. The QT interval represents the duration till the completion of the repolarization, phase of the cardiac myocyte (or the depolarization and repolarization of the ventricle). Prolongation of the QT interval, can result in ventricular arrhythmias, and sudden death.

Amisulpride is a drug well known to induce QT interval prolongation, evidencing a substantially linear increase of prolongation with plasma concentration. (See, Taubel et al., Br. J. Clin. Pharmacology, 83, pp. 339-348 (2017)). The dangers associated with drug induced QT prolongation are also well known: "Although a QT interval of at least 500 milliseconds generally has been shown to correlate with a higher risk of Torsades de Pointes, there is no established threshold below which prolongation of the QT interval is considered free of proarrhythmic risk" (see Al-Khatib et al., JAMA, 289 (16), pp 2120-2127 (2003)). Therefore, there is need for better amisulpride formulations with reduced side effects such as QT interval prolongation.

In various aspects and embodiments, provided are various modified release formulations, methods and medicaments comprising an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, that can provide the antidepressant activity of (R)-(+)-amisulpride while maintaining the mood stabilization activity of (S)-(−)-amisulpride and decreasing the undesirable side effects associated with comparable immediate release formulations. In various aspects and embodiments, the modified release formulations decrease the undesirable side effects associated with higher levels of dopamine $D_2$ receptor blockade associated with (S)-(−)-amisulpride. In various aspects and embodiments, the modified release formulations decrease the undesirable side effect of drug induced QT prolongation associated with both enantiomers of amisulpride.

In various aspects and embodiments, the modified release compositions are provided in a solid oral dosage form comprising amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-ami sulpride; and one or more pharmaceutically acceptable excipients. In various embodiments, the one or more pharmaceutically acceptable excipients include one or more extended release agents.

In various aspects and embodiments, when the modified release composition is administered to a subject population, it provides over the time period of 12 hours after administration a maximum QT interval prolongation of: (a) less than about 0.45 milliseconds (ms) per 10 mg of amisulpride; (b) less than about 0.30 milliseconds (ms) per 10 mg of amisulpride; (c) less than about 0.20 milliseconds (ms) per 10 mg of amisulpride; (d) less than about 0.15 milliseconds (ms) per 10 mg of amisulpride; (e) less than about 0.10 milliseconds (ms) per 10 mg of amisulpride; (f) less than about 0.05 milliseconds (ms) per 10 mg of amisulpride; or (g) less than about 0.02 milliseconds (ms) per 10 mg of amisulpride.

In various aspects and embodiments, the modified release compositions can reduce the population average maximum QT interval prolongation over the time period of about 12 hours after administration to a subject population relative to that for a comparable immediate release formulation.

For example, in various embodiments, the modified release compositions when administered to a subject population result in a population average maximum QT interval prolongation over the time period of about 12 hours after administration that is: (a) at least about 75%, at least about 70%, at least about 65%, at least about 60%, at least about 55%, or at least about 50% less than that of the immediate release composition described in Table 25 and having the same total daily amount of amisulpride as the modified release composition.

A variety of methods are known to the medical art to measure a person's QT interval. The QT interval represents the duration of ventricular depolarization and subsequent repolarization. Herein, the following method is used to determine "QT interval prolongation." Electrocardiograms (ECGs) are recorded using a digital 12-lead Holter ECG device (for example, such as a Mortara H12+, Mortara Instruments, Milwaukee, Wis.) at a sampling rate of 1000 samples/second (1000 HZ). The Holter ECG recordings are started at least about 1 hour before dosing with the active pharmaceutical ingredient (API) being evaluated and continued for at least 12 hours and preferably until 24 hours after dosing. Ten ECG replicate measurements are made at least at the following time points and within 7 minutes of the time point: 45, 30, and 15 minutes before dosing (baseline) and at 1, 2, 3, 4, 6, 8, 10, and 12 hours (and optionally 24 hours) after dosing. As heart rate can affect the measurements, subjects are in a supine position during measurement.

The determination of QT interval prolongation herein for an API should exclude ECGs that exhibit morphological abnormalities, such as of the P wave, QRS complex, ST segment, T wave, U wave, rhythm and axis.

The ECGs are to be read and interpreted by a qualified cardiologist. The QT interval is measured from the initiation of the QRS complex (first deflection of the QRS complex) to the point of where the T wave returns to the isoelectric baseline. The end of the T wave is identified as the intersection of the descending part of the T wave (positive T wave) with the isoelectric line. If a U wave interrupts the T wave before it returns to baseline, the QT interval is measured as the nadir between T and U waves. If it is not clear whether the second deflection towards the descending part of the T wave is a part of the T wave or a U wave, then it is included in the QT interval. (see, e.g., Panicker G K, et al. "Intra- and interreader variability in QT interval measurement by tangent and threshold methods in a central electrocardiogram laboratory." *J Electrocardiol.* 2009; 42:348-52).

The first five beats in a single lead with at least three consecutive complexes during normal rhythm, is used to measure the QT and preceding RR intervals. The PR interval and QRS duration measurements are made in the appropriate leads. Heart rate (HR) is calculated from the mean RR value. The QT interval has an inverse relationship with heart rate and shortens with increasing heart rate. As QT interval varies with change in heart rate, a heart rate correction formulae is used to transform the measure QT interval into a heart rate independent corrected value known as the QTc interval. The QTc value is intended to represent the QT interval at a standardized heart rate of 60 bpm.

The QT interval values are corrected for the effect of heart rate using the Fridericia's formula $QTcF=QT/\sqrt[3]{RR}$. QTcF of a given time point is calculated from the mean QT value and the mean RR interval value at that time point. QT interval prolongation is determined as the mean change from baseline values using the calculated QTcF values. Accordingly the "QT interval prolongation" at a time point is the mean QTcF change from baseline values (ΔQTcF).

It is to be understood that Bazett's (QTcB) formula, QTcB=QT/√RR, is another commonly used correction formula but QTcF has been chosen here for evaluation of QT prolongations instead of Bazett's formula because Bazett's formula does not adequately correct for the effect of heart rate and is known to overcorrect at high heart rates. (see, e.g., Davey P., "How to correct the QT interval for the effects of heart rate in clinical studies." *J. Pharmacol Toxicol Methods.* 2002; 48; 3-9). It is also to be understood that in double-blind clinical trials placebo adjusted change from baseline values of QTcF (ΔΔQTcF) however mean QTcF change from baseline values (ΔQTcF) have been chosen for use here as they do not require a double-blind protocol to determine and ECG measurements during normal clinical visits do not make use of placebos.

Modified Release Formulations

In various aspects and embodiments, the modified release compositions in a solid oral dosage form comprise amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients. In various embodiments, the one or more pharmaceutically acceptable excipients include one or more extended release agents.

In various aspects and embodiments, the amisulpride comprises one or more amisulpride enantiomers of crystalline Form A and/or Form A'.

In various embodiments, the modified release compositions make use of a distinct polymorphs of (R)-(+)-amisulpride and (S)-(−)-amisulpride; referred to as Form A for the free base crystalline form of (R)-amisulpride, and Form A' for the free base crystalline form of (S)-amisulpride, and described in further detail herein. In various embodiments the enantiomeric amisulpride is provided in one or more of high polymorph purity, chiral purity, and chemical purity. In various embodiments, one or both of the active pharmaceutical ingredients (R)-amisulpride and (S)-amisulpride are crystalline compounds, respectively, of Form A and Form A'.

It is to be understood that when an amisulpride enantiomer is said to be present in a certain weight amount, and such enantiomeric amisulpride is provided as a pharmaceutically acceptable salt thereof, that the weight amount refers to the amisulpride enantiomer portion exclusive of the salt portion, that is as the free base. Accordingly, it is to be understood that when a weight ratio of (R)-(+)-amisulpride to (S)-(−)-amisulpride is recited, it is the weight ratios only of the amisulpride portions exclusive of any salt portion especially if only one of the amisulpride enantiomers is present as a pharmaceutically acceptable salt thereof or the amisulpride enantiomers are present as different pharmaceutically acceptable salts.

In various aspects and embodiments, the modified release composition comprises a total amount of amisulpride between about 25 mg and about 1000 mg, between about 50 mg and about 750 mg, between about 50 mg and about 300 mg, or between about 100 mg and about 300 mg.

In various embodiments, the compositions comprise a ratio of (R)-(+)-amisulpride to (S)-(−)-amisulpride, or pharmaceutically acceptable salts thereof, that is in the range between about 65:35 to about 90:10 by weight of the free base, between about 80:20 to about 88:12 by weight of the free base, or about 85:15 by weight of the free base.

In various aspects and embodiments, the modified release compositions comprise a total amount of amisulpride from about 100 mg to about 1000 mg, from about 150 mg to about 800 mg, from about 100 mg to about 150 mg, from about 150 mg to about 200 mg, from about 200 mg to about 300 mg, from about 300 mg to about 400 mg, from about 400 mg to about 500 mg, from about 600 mg to about 700 mg, from about 700 mg to about 800 mg, about 100 mg, about 200 mg, about 300 mg, about 400 mg, about 500 mg, about 600 mg, about 700 mg, or about 800 mg, by weight of the free base. In such compositions, the ratio of (R)-(+)-amisulpride to (S)-(−)-amisulpride is in the range between about 65:35 to about 90:10 by weight of the free base, between about 80:20 to about 88:12 by weight of the free base, or about 85:15 by weight of the free base.

In various aspects and embodiments, the modified release compositions comprise about 85 mg to about 600 mg of (R)-(+)-amisulpride, or pharmaceutically acceptable salts thereof, by weight of the free base; about 15 mg to about 100 mg of (S)-(−)-amisulpride, or pharmaceutically acceptable salts thereof, by weight of the free base; wherein the enantiomeric ratio of (R)-(+)-amisulpride to (S)-(−)-amisulpride in the modified release compositions is about 65:35 to about 88:12 by weight of the free base.

In various aspects and embodiments, the modified release compositions comprise about 170 mg to about 340 mg of (R)-(+)-amisulpride, or pharmaceutically acceptable salts thereof, by weight of the free base; about 30 mg to about 60 mg of (S)-(−)-amisulpride, or pharmaceutically acceptable salts thereof, by weight of the free base; wherein the enantiomeric ratio of (R)-(+)-amisulpride to (S)-(−)-amisulpride in the modified release compositions is about 65:35 to about 88:12 by weight of the free base.

In various aspects and embodiments, the modified release compositions comprise an amount about 170 mg of (R)-(+)-amisulpride, or a pharmaceutically acceptable salt thereof, by weight of the free base; and an amount about 30 mg of (S)-(−)-amisulpride, or a pharmaceutically acceptable salt thereof, by weight of the free base.

In various aspects and embodiments, the modified release compositions comprise an amount about 340 mg of (R)-(+)-amisulpride, or a pharmaceutically acceptable salt thereof, by weight of the free base; and an amount about 60 mg of (S)-(−)-amisulpride, or a pharmaceutically acceptable salt thereof, by weight of the free base.

In various aspects and embodiments, the modified release compositions comprise (R)-(+)-amisulpride and (S)-(−)-amisulpride, or pharmaceutically acceptable salts thereof, in a ratio of R-amisulpride to S amisulpride from about 65:35 to about 90:10; from about 75:25 to about 88:12, and from about 80:20 to about 88:12, by weight of the free base.

In various aspects and embodiments, the ratio of (R)-amisulpride to (S)-amisulpride, or pharmaceutically acceptable salts thereof, is about 65:35, about 66:34, about 67:33, about 68:32, about 69:31, about 70:30, about 71:29, about 72:28, about 73:27, about 74:26, or about 75:25, by weight of the free base.

In various aspects and embodiments, the ratio of (R)-amisulpride to (S)-amisulpride, or pharmaceutically acceptable salts thereof, is about 80:20, about 81:19, about 82:18, about 83:17, about 84:16, about 85:15, about 86:14, about 87:13, about 88:12, about 89:11, or about 90:10, by weight of the free base.

In various aspects and embodiments, the ratio of (R)-amisulpride to (S)-amisulpride, or pharmaceutically acceptable salts thereof, is about 80:20, by weight of the free base or about 85:15, by weight of free base.

It is to be understood that pharmaceutically acceptable excipients, include, but are not limited to, one or more binders, bulking agents, buffers, fillers, stabilizing agents, surfactants, wetting agents, lubricating agents, diluents, disintegrants, plasticizers, viscosity enhancing or reducing agents, emulsifiers, anti-tacking agents, suspending agents, preservatives, antioxidants, opaquing agents, glidants, processing aids, colorants, sweeteners, taste-masking agents, perfuming agents, flavoring agents, diluents and other known additives to provide an elegant presentation of the drug or aid in the manufacturing of a medicament or pharmaceutical product comprising the modified release compositions described herein. Examples of carriers and excipients are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005.

In various aspects and embodiments the modified release compositions comprise one or more pharmaceutically acceptable excipients, carriers, adjuvants, or vehicles, and are formulated as a solid oral dosage form. In various embodiments, the solid oral dosage form is in the form of a powder, tablet, caplet, or capsule. In various embodiments the solid oral dosage form comprises a tablet, and in various embodiments the solid oral dosage form comprises a capsule.

In various embodiments, the modified release compositions are formulated (for example, with respect to active ingredient amounts) to be administered once, twice, three times, or four times daily.

It is to be understood that the total amount of the amisulpride in the form of an unequal mixture of (R)-(+)-amisulpride and (S)-(−)-amisulpride, or pharmaceutically acceptable salts thereof, need not be provided in a single dosage unit form, e.g. a single tablet, capsule, etc. In various embodiments, the modified release composition is provided in dosage unit forms such that, for example, the administration of two of the dosage unit forms will result in administration of amisulpride in the desired combined amount of the (R)-amisulpride and (S)-amisulpride.

For example, various embodiments provide dosage unit forms comprising a total combined amount of (R)-amisulpride and (S)-amisulpride of about 100 mg (a 100 mg tablet/capsule), and comprising about 85 mg (R)-amisulpride and about 15 mg (S)-amisulpride. Accordingly, administration of two of these tablets/capsules, containing 100 mg of amisulpride mixture, would result in administration of a total combined amount of (R)-amisulpride and (S)-amisulpride of about 200 mg; whilst administration of four of these tablets/capsules would result in administration of a total combined amount of (R)-amisulpride and (S)-amisulpride of about 400 mg. It is further to be understood that with the addition of excipients and extended release agent a tablet containing 100 mg, for example, of amisulpride will weigh more than 100 mg.

In various aspects and embodiments, all excipients comply with the respective The United States Pharmacopeia (USP), The Japanese Pharmacopoeia (JP), Japanese Pharmaceutical Excipients (JPE), The European Pharmacopoeia (Ph. Eur.), and/or The National Formulary (NF) monograph.

The modified release compositions are in various embodiments formulated in dosage unit form for ease of administration and uniformity of dosage. The expression "dosage unit form" as used herein refers to a physically discrete unit of agent appropriate for the subject to be treated.

Tablet Formulations

In various embodiments, modified release compositions are provided as solid oral dosage forms in the form of a tablet comprising an intragranular component (granules) and an extragranular component; the intragranular component comprising (a) amisulpride in the form of a mixture of (R)-amisulpride and (S)-amisulpride in a ratio of R:S amisulpride between 60:40 to 40:60; 65:35 to 90:10, 80:20 to 88:12, or 85:15 by weight of the free base and (b) one or more pharmaceutically acceptable excipients; and the extragranular component comprising an extended release agent.

In various embodiments, the granules comprise between about 60% to about 80% by weight of amisulpride in the form of a mixture of (R)-amisulpride and (S)-amisulpride, between about 10% to about 30% by weight of filler, between about 1% to about 5% by weight of binder; all weight percentages being exclusive of any solvent (e.g. water) removed during processing. In various embodiments, the resultant tablet (granules plus extragranular component) comprises between about 20% to about 70% by total tablet weight of granules, between about 10% to about 50% by total tablet weight of extended release agent, and a combined amount of both extragranular and intragranular filler that is between about 6% to about 60% by total tablet weight. In various embodiments, the combined amount of both extragranular and intragranular filler that is between about 10% to about 50% by total tablet weight.

In various embodiments, the granules comprise between about 60% to about 80% by weight of the total of both enantiomers of amisulpride, between about 10% to about 30% by weight of filler, between about 1% to about 5% by weight of binder; all weight percentages being exclusive of any solvent (e.g. water) removed during processing.

In various embodiments, the granules comprise between about 70% to about 80% by weight of the total of both enantiomers of amisulpride, between about 20% to about 25% by weight of filler, between about 1% to about 5% by weight of binder; all weight percentages being exclusive of any solvent (e.g. water) removed during processing.

In still further embodiments, the granules comprise between about 75% by weight of weight of the total of both enantiomers of amisulpride, about 22% by weight of filler, about 3% by weight of binder; all weight percentages being exclusive of any solvent (e.g. water) removed during processing.

In various embodiments, the resultant tablet (granules plus extragranular component) comprises between about 20% to about 70% by total tablet weight of granules, between about 10% to about 50% by total tablet weight of extended release agent, and a combined amount of both extragranular and intragranular filler that is between about 6% to about 60% by total tablet weight.

In various embodiments, the combined amount of both extragranular and intragranular filler is between about 10% to about 50% by total tablet weight. In some embodiments, the resultant tablet (granules plus extragranular component) comprises between about 20% to about 70% by total tablet weight of granules, between about 10% to about 50% by total tablet weight of extended release agent, between about 0% to about 60% of extragranular filler, and between about 0% to about 2% of a lubricant by total tablet weight.

In various embodiments, the resultant tablet (granules plus extragranular component) comprises between about 45% to about 65% by total tablet weight of granules, between about 10% to about 35% by total tablet weight of extended release agent, and between about 0% to about 40% total tablet weight of extragranular filler, and between about 0% to about 2% total tablet weight of a lubricant.

In various aspects and embodiments, the ratio of the weight percentage of both enantiomers of amisulpride relative to the total combined weight percentage of the filler and binder in the granule is about 3:1.

In various aspects the ratio of the weight percentage of both enantiomers of amisulpride relative to the total combined weight percentage of the extragranular filler and extended release agent is about 1:1 to 1:0.8.

In various aspects and embodiments, granulated granules exhibit a D50 particle size of between about 180 microns to about 250 microns, between about 170 microns to about 190 microns, between about 175 microns to about 185 microns, between about 180 microns to about 205 microns, between about 205 microns to about 220 microns, or between about 220 microns to about 240 microns.

In various aspects and embodiments, blended granules plus extragranular component exhibit a D50 particle size of between about 180 microns to about 250 microns. between about 80 microns to about 120 microns, between about 90 microns to about 110 microns, between about 180 microns to about 205 microns, between about 205 microns to about 220 microns, or between about 220 microns to about 240 microns.

In still some further aspects and embodiments, the blended granules plus an extragranular component are compressed into tablets with a compression force of between 5-15 kN to produce tablets having a hardness between about 70 N and about 170 N.

In various embodiments of 200 mg Matrix Tablet Formulations, (R)-amisulpride, (S)-amisulpride and D-mannitol are separately delumped with a screen mill. The delumped (R)-amisulpride, delumped (S)-amisulpride, delumped D-mannitol, and partly pregelatinized starch are granulated by spraying aqueous solution of partially hydrolyzed polyvinyl alcohol in a wet high-shear granulator, and wet granules are passed through a screening mill to give sized granules. D-mannitol and hypromellose are blended with the sized granules in a blender. Subsequently, magnesium stearate is blended with the granules in a blender. The blended granules are compressed into core tablets with a rotary press.

In various embodiments, examples of diluents and fillers include, but are not limited to, D-mannitol, dicalcium phosphate dibasic, dibasic calcium phosphate, anhydrous dibasic calcium phosphate, lactose (e.g., lactose monohydrate, lactose anhydrous, lactose monohydrate), microcrystalline cellulose, starch (e.g., pregelatinized starch, partly pregelatinized starch, and corn starch), powdered cellulose, and sorbitol. It is to be understood that more than one type of diluent and/or filler can be used in a tablet of the present inventions and that the diluent and/or filler in the granules can be the same or different than that used in the extragranular component of the tablet.

In various embodiments, examples of binders include, but are not limited to, partially hydrolyzed polyvinyl alcohol, polyvinyl alcohol, methylcellulose, polyvinylpyrrolidone, copovidone, cellulose derivatives, shellac, zein, gelatin, polymethacrylates, synthetic resins, acrylates, and combinations thereof.

In various embodiments, the extended release agents include matrix formers such as cellulosic ethers, polymer coatings, polymer matrix systems, enzyme-activated systems, and systems that respond to changes in physical conditions, such as pH, etc. Suitable polymers include, but are not limited to, pH independent polymers and pH dependent polymers. The extended release agent may be hydrophillic or hydrophobic in nature. It is to be understood that more than one type of extended release agent can be used in an oral dosage form of the present inventions.

Examples of pH dependent polymers include, but are not limited to, an alginate material, a carboxyvinyl polymer or sodium salts of carboxymethyl cellulose.

Examples of pH independent polymers include, but are not limited to, hydroxy propyl methyl cellulose, hydroxy propyl ethyl cellulose, hydroxy propyl cellulose, hydroxy ethyl cellulose, methyl cellulose, xanthan gum, polyethylene oxide, ammonio methacrylate copolymers type A and B as described in USP, polyacrylate dispersion 30% as described in Ph. Eur., or combinations thereof.

In various embodiments, examples of extended release agents include, but are not limited to, hydroxypropylcellulose (HPC) and hydroxypropyl methylcellulose (HPMC) (a.k.a. hypromellose), used alone or in combination with other extended release agents.

In various embodiments, used together with one or more disintegrants, such as, for example, croscarmellose sodium and crospovidone, to adjust the release profile. For example, in various embodiments, the hydrophillic polymer will act as matrix to retard the dissolution of the solid oral dosage form and one or more disintegrants absorb water to speed hydration of a hydrophillic matrix.

In various embodiments, examples of glidants and antitacking agents include, but are not limited to, Aerosil 200, light anhydrous silicic acid, colloidal silica, talc, calcium silicate, magnesium silicate, colloidal silicondioxide, and combinations thereof.

In various embodiments, examples of lubricants include, but are not limited to, magnesium stearate, sodium stearyl fumarate, talc (e.g., micronized talc), and combinations thereof.

In various embodiments, examples of lubricants include, but are not limited to, magnesium stearate, sodium stearyl fumarate, talc, polyethylene glycol, calcium stearate, aluminum stearate, potassium stearate, zinc stearate, talc (e.g., micronized talc), sodium stearyl fumarate, silica, hydrogenated castor oil, hydrated silicon dioxide, magnesium silicate, light anhydrous silicic acid, synthetic aluminum silicate, heavy anhydrous silicic acid, silicon dioxide, carnauba wax, titanium oxide, and combinations thereof.

In various embodiments, examples of surfactants include, but are not limited to, sodium dodecyl sulfate, ammonium lauryl sulfate, other alkyl sulfates, dodecyl betaine, dodecyl dimethylamine oxide, alkyl polyethylene oxide, copolymers of polyethylene oxide, and copolymers of polypropylene oxide, (alternatively called poloxamers). Additional surfactants include polyethoxylated tocopheryl succinate, polyoxyethylene castor oil, polyethoxylated castor oil, polyoxyethylene sorbitan monolaurate (Tween®20), polyoxyethylene sorbitan monopalmitate (Tween®40), polyoxyethylene sorbitan monostearate (Tween®60), polyoxyethylene sorbitan monooleate (Tween®80), polyethylene glycol monostearate (Polyoxyl 40 stearate).polyoxyethylene-polyoxypropylene copolymers, octylphenolethoxylate, and combinations thereof.

In various embodiments, examples of plasticizers include, but are not limited to, one or more of triethyl citrate, PEG 6000, PEG8000, glyceryl monopalmetostearate, glyceryl monostearate, dibutyl phthalate, macrogol, triethyl citrate, polyethylene glycol, propylene glycol, polypropylene glycol, sorbitol sorbitan solution, triacetin, glycerin, glycerol fatty acid, glycerol esters of fatty acids, silicon oil, acetyltriethyl citrate, diethyl phthalate, tributyl citrate, dibutyl phthalate, acetyltributyl citrate, dibutyl sebacate, glycerol triacetate, acetylated monoglyceride, and combinations thereof.

In various embodiments, one or more of ethylcellulose and aminoalkylmethacrylate copolymer RS are the polymers, and triethyl citrate is the plasticizer.

In is to be understood that pharmaceutical compositions, and in particular solid oral dosage forms can comprise coatings, such a films, for example as an aid in swallowing or to maintain dosage form integrity upon handling, and such customary coatings are included in various embodiments of the present inventions. In various embodiments, such coatings comprise one or more coating agents, colorants (a.k.a. coloring agents), opaquing agents (a.k.a. opacifiers), polishing agents, etc.

In various embodiments, examples of opaquing agents and colorants include, but are not limited to, titanium oxide, titanium dioxide, iron oxide yellow (a.k.a. yellow ferric oxide), iron oxide red (a.k.a. red ferric oxide), and talc, and combinations thereof.

In various embodiments, the modified release tablets have a composition substantially in accord with that set forth in Table 1. The tablets of Table 1 each comprise 200 mg of amisulpride in the form of a mixture of (R)-amisulpride and (S)-amisulpride, where (R)-amisulpride and (S)-amisulpride are in the ratio R:S of 85:15, and varying amounts of extended release agent.

TABLE 1

| Compositions Matrix Tablets 200 mg | | | | | |
|---|---|---|---|---|---|
| | Component | Function | Lot 1A (10%) mg/tab | Lot 2A (15%) mg/tab | Lot 3A (45%) mg/tab |
| Intra-granular | (R)-amisulpride | API | 170 | 170 | 170 |
| | (S)-amisulpride | API | 30 | 30 | 30 |
| component | D-Mannitol*1 | Filler | 29.5 | 29.5 | 29.5 |
| | Pregelatinized starch | Filler | 29.5 | 29.5 | 29.5 |
| | Polyvinyl alcohol | Binder | 5.5 | 5.5 | 5.5 |
| | Purified water*2 (binder solvent) | Solvent | 72 | 72 | 72 |
| Subtotal (granule component)*5 | | | 264.5 | 264.5 | 264.5 |
| Extra-granular component | Hypromellose*3 | Extended release agent | 50.0 | 75.0 | 225.5 |
| | D-Mannitol*4 | Filler | 178.0 | 153.0 | 2.5 |
| | Magnesium stearate | Lubricant | 7.5 | 7.5 | 7.5 |
| Total tablet weight | | | 500 | 500 | 500 |

*1 Crystalline powder, Pearlitol 50C (Roquette)
*2 Water is removed during processing.
*3 Metolose SR 90SH-100SR (Shin Etsu)
*4 Spray dried powder, Pearlitol 100SD (Roquette)
*5 After water removed during processing In various embodiments, the modified release tablets having a composition substantially in accord with that set forth in Table 2. The tablets of Table 2 each comprise 200 mg of amisulpride in the form of a mixture of (R)-amisulpride and (S)-amisulpride where (R)-amisulpride and (S)-amisulpride are in the ratio R:S of 85:15, and varying amounts of extended release agent.

TABLE 2

| Compositions Matrix Tablets 200 mg | | | | | | | |
|---|---|---|---|---|---|---|---|
| Component | | Function | Lot 1B (10%) mg/tab | Lot 2B (15%) mg/tab | Lot 3B (25%) mg/tab | Lot 4B (35%) mg/tab | Lot 5B (45%) mg/tab |
| Intra-granular component | (R)-amisulpride | API | 170 | 170 | 170 | 170 | 170 |
| | (S)-amisulpride | API | 30 | 30 | 30 | 30 | 30 |
| | D-Mannitol*1 | Filler | 29.5 | 29.5 | 29.5 | 29.5 | 29.5 |
| | Partly pregelatinized starch | Filler | 29.5 | 29.5 | 29.5 | 29.5 | 29.5 |
| | Polyvinyl alcohol | Binder | 8 | 8 | 8 | 8 | 8 |
| | Purified water*2 (binder solvent) | Solvent | 72 | 72 | 72 | 72 | 72 |
| Subtotal (granule component)*5 | | | 267.0 | 267.0 | 267.0 | 267.0 | 267.0 |
| Extra-granular component | Hypromellose*3 | Extended release | 50.0 | 75.0 | 125.0 | 175.0 | 225.5 |
| | D-Mannitor*4 | Filler | 175.5 | 150.5 | 100.5 | 50.5 | – |
| | Magnesium stearate | Lubricant | 7.5 | 7.5 | 7.5 | 7.5 | 7.5 |
| Total tablet weight (mg) | | | 500 | 500 | 500 | 500 | 500 |

*1: Crystalline powder, Pearlitol 50C (Roquette)
*2: Water is removed during processing.
*3: Metolose SR 90SH-100SR (Shin Etsu)
*4: Spray dried powder, Pearlitol 100SD (Roquette)
*5: After water removed during processing In various embodiments, the modified release tablets have a composition substantially in accord with that set forth in Tables 3A, 3B, 3C, 3D and 3E. The tablets of Tables 3A and 3B each comprise 200 mg of amisulpride in the form of a mixture of (R)-amisulpride and (S)-amisulpride where (R)-amisulpride and (S)-amisulpride are in the ratio R:S of 85:15, and varying amounts of extended release agent. The tablets of Tables 3C, 3D and 3E comprise either 100 mg or 200 mg of amisulpride in the form of a mixture of (R)-amisulpride and (S)-amisulpride where (R)-amisulpride and (S)-amisulpride are in the ratio R:S of 85:15.

TABLE 3A

Compositions Matrix Tablets 200 mg

| | Component | Function | Lot 1C (10%) mg/tab | Lot 2C (25%) mg/tab | Lot 3C (15%) mg/tab |
|---|---|---|---|---|---|
| Intra-granular component | (R)-amisulpride | API | 170 | 170 | 170 |
| | (S)-amisulpride | API | 30 | 30 | 30 |
| | D-Mannitol[*1] | Filler | 29.5 | 29.5 | 29.5 |
| | Pregelatinized starch | Filler | 29.5 | 29.5 | 29.5 |
| | Polyvinyl alcohol | Binder | 5.5 | 5.5 | 5.5 |
| | Purified water[*2] (binder solvent) | Solvent | 72 | 72 | 72 |
| Subtotal (granule component)[*5] | | | 264.5 | 264.5 | 264.5 |
| Extra-granular component | Hypromellose[*3] | Extended release agent | 50.0 | 125.0 | 75.0 |
| | D-Mannitol[*4] | Filler | 178.0 | 103.0 | 153.0 |
| | Magnesium stearate | Lubricant | 7.5 | 7.5 | 7.5 |
| Total tablet weight (mg) | | | 500 | 500 | 500 |

[*1]Crystalline powder, Pearlitol 50C (Roquette)
[*2]Water is removed during processing.
[*3]Metolose SR 90SH-100SR (Shin Etsu)
[*4]Spray dried powder, Pearlitol 100SD (Roquette)
[*5]After water removed during processing

TABLE 3B

Compositions Matrix Tablets 200 mg

| | Component | Function | Lot 5C (20%) mg/tab | Lot 6C (40%) mg/tab |
|---|---|---|---|---|
| Intra-granular component | (R)-amisulpride | API | 170 | 170 |
| | (S)-amisulpride | API | 30 | 30 |
| | D-Mannitol[*1] | Filler | 29.5 | 29.5 |
| | Pregelatinized starch | Filler | 29.5 | 29.5 |
| | Polyvinyl alcohol | Binder | 5.5 | 5.5 |
| | Purified water[*2] (binder solvent) | Solvent | 72 | 72 |
| Subtotal (granule component)[*5] | | | 264.5 | 264.5 |
| Extra-granular component | Hypromellose[*3] | Extended release agent | 100.0 | 200.0 |
| | D-Mannitol[*4] | Filler | 128.0 | 28.0 |
| | Magnesium stearate | Lubricant | 7.5 | 7.5 |
| Total tablet weight | | | 500 | 500 |

[*1]Crystalline powder, Pearlitol 50C (Roquette)
[*2]Water is removed during processing.
[*3]Metolose SR 90SH-100SR (Shin Etsu)
[*4]Spray dried powder, Pearlitol 100SD (Roquette)
[*5]After water removed during processing

TABLE 3C

Compositions Matrix Tablets 100 mg and 200 mg

| | | | Quantity (mg/tab) | | | |
|---|---|---|---|---|---|---|
| | | | Lot 7C (25%) Round, 11 mm | Lot 8C (25%) Round, 11 mm | Lot 9C (25%) Oval, 11.2 × 8.7 mm | Lot 10C (25%) Oval, 11.2 × 8.7 mm |
| Tablet shape, dimensions | | Function | mg/tab | mg/tab | mg/tab | mg/tab |
| Intra-granular component | (R)-amisulpride | API | 85 | 170 | 85 | 170 |
| | (S)-amisulpride | API | 15 | 30 | 15 | 30 |
| | D-Mannitol [*1] | Filler | 14.75 | 29.5 | 14.75 | 29.5 |
| | Pregelatinized starch | Filler | 14.75 | 29.5 | 14.75 | 29.5 |
| | Polyvinyl alcohol | Binder | 4 | 8 | 4 | 8 |
| | Purified water [*2] | Solvent | q.s. | q.s. | q.s. | q.s. |
| Subtotal (granule component) [*5] | | | 133.5 | 267 | 133.5 | 267 |
| Extra-granular component | Hypromellose [*3] | Extended release agent | 125 | 125 | 100 | 100 |
| | D-Mannitol [*4] | Filler | 231.5 | 98 | 158.5 | 25 |
| | Aerosil 200 | Glidant | 2.5 | 2.5 | 2 | 2 |
| | Magnesium stearate | Lubricant | 7.5 | 7.5 | 6 | 6 |
| Uncoated tablet weight | | | 500 | 500 | 400 | 500 |
| Film coating component | HPMC (TC-5R) | Coating agent | 6.25 | 6.25 | 6 | 6 |
| | Macrogol 400 | Coating agent | 0.625 | 0.625 | 0.6 | 0.6 |
| | Titanium dioxide | Coating agent | 3.125 | 3.125 | 3 | 3 |
| | Talc | Coating agent | 2.25 | 2.25 | 2.16 | 2.16 |
| | Iron oxide yellow | Color | 0.175 | 0.175 | 0.168 | 0.168 |

TABLE 3C-continued

Compositions Matrix Tablets 100 mg and 200 mg

| | | Quantity (mg/tab) | | | |
|---|---|---|---|---|---|
| | | Lot 7C (25%) Round, 11 mm | Lot 8C (25%) | Lot 9C (25%) Oval, 11.2 × 8.7 mm | Lot 10C (25%) |
| Tablet shape, dimensions | Function | mg/tab | mg/tab | mg/tab | mg/tab |
| Iron oxide red | Color | 0.075 | 0.075 | 0.072 | 0.072 |
| Carnauba wax | Polishing agent | 0.01 | 0.01 | 0.01 | 0.01 |
| Total film-coated tablet weight (mg) | | 512.51 | 512.51 | 412.01 | 412.01 |

[*1]: Crystalline powder, Pearlitol 50C (Roquette)
[*2]: Water is removed during processing,
[*3]: Metolose SR 905H-100SR (Shin Etsu) (viscosity: 100mPa. s)
[*4]: Spray dried powder, Pearlitol 100SD (Roquette)
[*5]: After water removed during processing
q.s. means quantum sufficiat (as much as necessary)

TABLE 3D

Compositions Matrix Tablets 100 mg and 200 mg

| | | | Quantity (mg/tab) | | | |
|---|---|---|---|---|---|---|
| | Total API (mg) | Function | Lot 11C (25%) 200 mg/tab | Lot 12C (25%) 200 mg/tab | Lot 13C (25%) 100 mg/tab | Lot 14C (25%) 100 mg/tab |
| Intra-granular component | (R)-amisulpride | API | 170 | 170 | 85 | 85 |
| | (S)-amisulpride | API | 30 | 30 | 15 | 15 |
| | Mannitol[*1] | Filler | 29.5 | 29.5 | 14.75 | 14.75 |
| | Partly Pregelatinized starch[*6] | Filler | 29.5 | 29.5 | 14.75 | 14.75 |
| | Polyvinylalcohol[*7] | Binder | 8 | 8 | 4 | 4 |
| | Purified water[*2] | Solvent | q.s. | q.s. | q.s. | q.s. |
| Subtotal (granule component) [*5] | | | 267 | 267 | 133.5 | 133.5 |
| Extra-granular component | Hypromellose[*3] | Extended release agent | 125 | 125 | 125 | 125 |
| | Mannitol[*4] | Filler | 95.5 | 95.5 | 114 | 114 |
| | Partly Pregelatinized starch[*8] | Filler | — | — | 115 | 115 |
| | Light anhydrous silicic acid (Aerosil200) | Glidant | 2.5 | 2.5 | 2.5 | 2.5 |
| | Sodium stearyl fumarate (PRUV) | Lubricant | 10 | 10 | 10 | 10 |
| Uncoated tablet weight | | | 500 | 500 | 500 | 500 |
| Film coating | Hypromellose (TC-5R) | Coating agent | 3.75 | 6.25 | 3.75 | 6.25 |
| | Macrogol 400 | Coating agent | 0.375 | 0.625 | 0.375 | 0.625 |
| | Titanium dioxide | Coating agent | 1.875 | 3.125 | 1.875 | 3.125 |
| | Talc | Coating agent | 1.35 | 2.25 | 1.35 | 2.25 |
| | Iron oxide yellow | Color | 0.105 | 0.175 | 0.105 | 0.175 |
| | Iron oxide red | Color | 0.045 | 0.075 | 0.045 | 0.075 |
| | Purified water[*2] | Solvent | q.s. | q.s. | q.s. | q.s. |
| | Carnauba wax | Polishing agent | 0.01 | 0.01 | 0.01 | 0.01 |
| Total film-coated tablet weight [*5] | | | 507.51 | 512.51 | 507.51 | 512.51 |

[*1]: Crystalline powder, Pearlitol 50C (Roquette)
[*2]: Water is removed during processing.
[*3]: Metolose SR 905H-100SR (Shin Etsu)
[*4]: Spray dried powder, Pearlitol 100SD (Roquette)
[*5]: After water removed during processing
[*6]: PCS PC-10 (Asahi Kasei)
[*7]: GOHSENOL EG-05P (Mitsubishi Chemical)
[*8]: Starch 1500G (Colorcon)
q.s. means quantum sufficiat (as much as necessary)

TABLE 3E

Compositions Matrix Tablets 100 mg and 200 mg

| | | | Quantity (mg/tab) | | | |
|---|---|---|---|---|---|---|
| | Total API (mg) | Function | Lot 15C (25%) 200 mg/tab | Lot16C (25%) 200 mg/tab | Lot 17C (25%) 100 mg/tab | Lot 18C (25%) 100 mg/tab |
| | (R)-amisulpride | API | 170 | 170 | 85 | 85 |
| | (S)-amisulpride | API | 30 | 30 | 15 | 15 |
| Intra-granular component | Mannitol *1 | Filler | 29.5 | 29.5 | 14.75 | 14.75 |
| | Partly Pregelatinized starch *6 | Filler | 29.5 | 29.5 | 14.75 | 14.75 |
| | Polyvinylalcohol *7 | Binder | 8 | 8 | 4 | 4 |
| | Purified water *2 | Solvent | q.s. | q.s. | q.s. | q.s. |
| Subtotal (granule component) *5 | | | 267 | 267 | 133.5 | 133.5 |
| | Hypromellose *3 | Extended release agent | 125 | 125 | 125 | 125 |
| | Mannitol *4 | Filler | 100.5 | 100.5 | 119 | 119 |
| Extra-granular component | Partly Pregelatinized starch *8 | Filler | — | — | 115 | 115 |
| | Light anhydrous silicic acid (Aerosil200) | Glidant | 2.5 | 2.5 | 2.5 | 2.5 |
| | Magnesium stearate | Lubricant | 5 | 5 | 5 | 5 |
| Uncoated tablet weight | | | 500 | 500 | 500 | 500 |
| | Hypromellose (TC-5R) | Coating agent | 3.75 | 6.25 | 3.75 | 6.25 |
| | Macrogol 400 | Coating agent | 0.375 | 0.625 | 0.375 | 0.625 |
| | Titanium dioxide | Coating agent | 1.875 | 3.125 | 1.875 | 3.125 |
| Film coating | Talc | Coating agent | 1.35 | 2.25 | 1.35 | 2.25 |
| | Iron oxide yellow | Color | 0.105 | 0.175 | 0.105 | 0.175 |
| | Iron oxide red | Color | 0.045 | 0.075 | 0.045 | 0.075 |
| | Purified water *2 | Solvent | q.s. | q.s. | q.s. | q.s. |
| | Carnauba wax | Polishing agent | 0.01 | 0.01 | 0.01 | 0.01 |
| Total film-coated tablet weight *5 | | | 507.51 | 512.51 | 507.51 | 512.51 |

*1: Crystalline powder, Pearlitol 50C (Roquette)
*2: Water is removed during processing.
*3: Metolose SR 905H-100SR (Shin Etsu)
*4: Spray dried powder, Pearlitol 100SD (Roquette)
*5: After water removed during processing
*6: PCS PC-10 (Asahi Kasei)
*7: GOHSENOL EG-05P (Mitsubishi Chemical)
*8: Starch 1500G (Colorcon)
q.s. means quantum sufficiat (as much as necessary)

TABLE 4

Figure 1B:
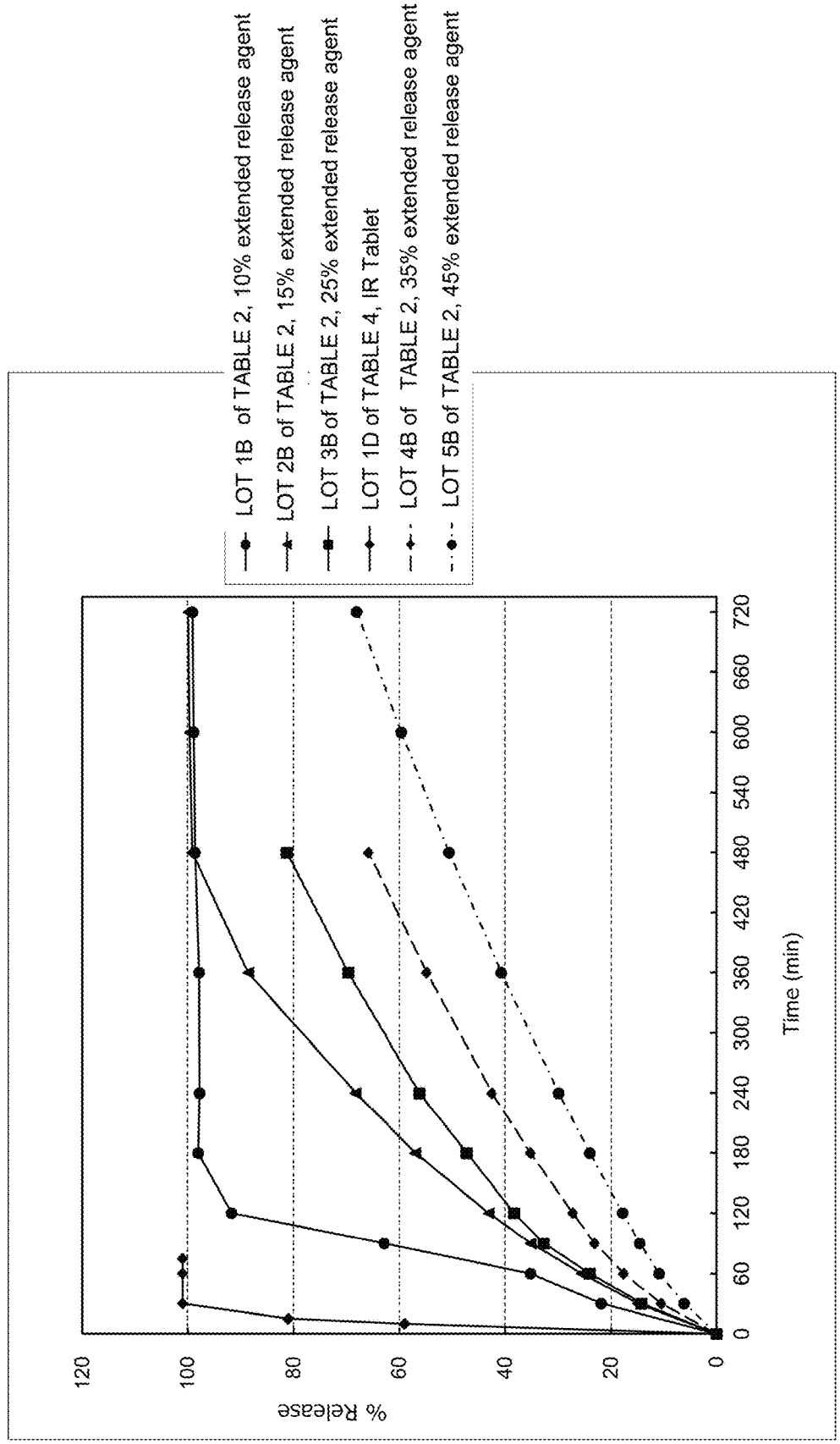

Composition IR Tablet (Lot 1D) of FIG. 1A and FIG. 1B

| Component | Function | Lot 1D (mg/tablet) |
|---|---|---|
| Core Tablet | | |
| (R)-amisulpride | API | 170.0 |
| (S)-amisulpride | API | 30.0 |
| D-Mannitol | Filler | 167.5 |
| Partly pregelatinized starch | Filler | 100.0 |
| Partially hydrolyzed polyvinyl alcohol | Binder | 10.0 |
| Purified water*2 | Granulation Solvent | q.s. |
| Croscarmellose sodium | Disintegrant | 15.0 |
| Magnesium stearate | Lubricant | 7.5 |
| Weight of Core tablet | | 500.0 |
| Film Coat Suspension | | |
| Hypromellose | Coating agent | 3.78 |
| Macrogol 400 | Coating agent | 0.38 |
| Titanium oxide | Coating agent | 1.89 |
| Talc | Coating agent | 1.36 |
| Yellow ferric oxide | Coloring agent | 0.11 |
| Red ferric oxide | Coloring agent | 0.05 |
| Purified water | Coating solvent | q.s. |
| Carnauba wax | Polishing agent | 0.01 |
| Total Weight | | 507.58 | q.s. means quantum sufficiat (as much as necessary)

TABLE 4 provides the formulation of the immediate release tablets comprising 200 mg of combined amount of (R)-amisulpride and (S)-amisulpride in the ratio (R:S) of 85:15, for which dissolution data is provided in FIGS. 1A and 1B.

In various aspects and embodiments, the modified release composition, when tested using a two-stage in vitro dissolution test set forth in Table 5 and the accompanying description, (a) releases no more than about 40% of amisulpride after 2 hours and releases greater than about 80% of amisulpride in less than about 12 hours; (b) releases less than about 40% of amisulpride after 1 hour, releases more than about 20% and less than about 60% of amisulpride after 3 hours, and releases more than about 30% and less than 100% of amisulpride after 6 hours; (c) releases less than about 30% of amisulpride after 1 hour, releases more than about 20% and less than about 60% of amisulpride after 3 hours, and releases more than about 30% and less than about 75% of amisulpride after 6 hours; (d) releases less than about 20% of amisulpride after 1 hour, releases more than about 20% and less than about 50% of amisulpride after 3 hours, and releases more than about 30% and less than about 75% of amisulpride after 6 hours; (e) releases more than about 30% and less than about 50% of amisulpride after 6 hours; (f) releases between about 30% and 75% of amisulpride after about 3 hours, and releases more than about 75% of amisulpride after about 12 hours; or (g) releases more than about 75% of amisulpride after about 6 hours.

TABLE 5

In-vitro Dissolution Test Parameters
Modified Release Tablet Formulations

| Medium: | 0-60 minutes 500 mL 0.01M HCl, pH 2.0 |
| --- | --- |
| | For pH Switch |
| | Add 400 mL of 0.15M Na3PO4 |
| | (pre-heat to 37° C.), pH 6.8 ± 0.05 |
| Dissolution type: | USP II(Paddles) |
| Paddle Speed: | 75 rpm |
| Volume of Medium: | 0-60 minutes 500 mL |
| | 60 minutes onwards 900 mL |
| Temperature: | 37.0° C. (±0.5) |
| Sampling time points: | Stage 1: 0.5, 1 |
| | Stage 2: 1.5, 2, 3, 4, 6, 8, 10, 12 hours followed |
| | by infinity for 1 hour @ 250 rpm |
| Sampling Type: | Automatic with filter 10 μm full flow |
| Sampling Volume: | 1.5 mL |

The in vitro dissolution profiles of the modified release (MR) formulations in FIGS. 1A, 1B, 1C and 1D were acquired using a paddle apparatus substantially in accord with that described by the United States Pharmacopeia Convention (USP) Apparatus 2 of Chapter 711 Dissolution; USP41-NF36 General Chapter <711> Dissolution. The apparatuses were operated as described in Table 5. Amisulpride release was determined from 1.5 ml samples taken from the medium and analyzed using HPLC with a Kinetex Biphenyl, 4.6×100 mm, 2.6 μm (P/N: 00D-4622-E0) column and UV detector set to 280 nm at the time points indicated in the figures.

TABLE 6

In-vitro Dissolution Test Parameters IR Tablet Formulations

| Medium: | 1$^{st}$ Fluid for dissolution test of JP, pH 1.2 |
| --- | --- |
| | (containing sodium chloride, hydrochloric |
| | acid, and water, e.g. 2.0 g of |
| | sodium chloride, 7.0 mL of hydrochloric |
| | acid in water to make 1000 mL) |
| Dissolution type: | JP General Test <6.10> Apparatus 2 |
| Paddle Speed: | 50 rpm (first 60 minutes) |
| Volume of Medium: | 900 mL |
| Temperature: | 37.0° C. (±0.5) |
| Sampling time points: | 5, 10, 15, 30, 45, 60 minutes (at 50 rpm) |
| | and 75 minutes (at 250 rpm) |
| Sampling Type: | Manual |
| Sampling Volume: | 5 mL |

The in vitro dissolution profiles of the IR formulations in FIGS. 1A and 1B were acquired using a paddle apparatus substantially in accord with that described by the paddle method of Japanese Pharmacopeia (JP) General test<6.10>, which was harmonized with Ph. Eur. <2.9.3> and USP <711>. The apparatuses were operated as described in Table 6. The amount of amisulpride dissolved in the dissolution medium was determined by reversed phase isocratic HPLC method, using a Kinetex Biphenyl, 4.6×100 mm, 2.6 μm (P/N: 00D-4622-E0) column and UV detector set to 280 nm at the time points indicated in the figures.

The dissolution tests of the IR formulations was discontinued prior to the 60 minute mark as all API (i.e. all (R)-amisulpride and (S)-amisulpride) had been released.

The data plotted in FIGS. 1A, 1B, 1C, and 1D are also provided, respectively, in Tables 7, 8, 9A and 9B below.

TABLE 7

Data of FIG. 1A

| Time (hours) | IR Lot 1D (% API released) | Lot 1A (10%) (% API released) | Lot 2A (15%) (% API released) | Lot 3A (45%) (% API released) |
| --- | --- | --- | --- | --- |
| 0 | 0 | 0 | 0 | 0 |
| 0.17 | 59 | | | |
| 0.25 | 81 | | | |
| 0.5 | 101 | 42.9 | 15.5 | 6.4 |
| 1 | 101 | 63.1 | 26.2 | 11.2 |
| 1.25 | 101 | 88.9 | | |
| 1.5 | | | 36.1 | 15.1 |
| 2 | | 96.4 | 43.5 | 18.2 |
| 3 | | 97.0 | 56.8 | 24.9 |
| 4 | | 97.1 | 70.4 | 31.7 |
| 6 | | 98.1 | 93.5 | 43.5 |
| 8 | | 99.2 | | 55.6 |
| 10 | | 99.6 | | 63.8 |
| 12 | | 99.3 | | 74.1 |
| 12.5 | | 100.8 | 100.8 | |
| 13 | | | | 79.8 |

TABLE 8

Data of FIG. 1B (data is % API released vs Time)

| Time (minutes) | Lot 1D IR | Lot 1B (10%) | Lot 2B (15%) | Lot 3B (25%) | Lot 4B (35%) | Lot 5B (45%) |
| --- | --- | --- | --- | --- | --- | --- |
| 0 | 0 | 0 | 0 | 0 | 0 | 0 |
| 10 | 59 | | | | | |
| 15 | 81 | | | | | |
| 30 | 101 | 21.9 | 14.9 | 14.1 | 10.4 | 6.1 |
| 60 | 101 | 35.2 | 25.6 | 24.0 | 17.6 | 10.8 |
| 75 | 101 | | | | | |
| 90 | | 62.9 | 35.1 | 32.7 | 23.1 | 14.5 |
| 120 | | 91.7 | 43.1 | 38.3 | 27.2 | 17.8 |
| 180 | | 98.0 | 57.0 | 47.3 | 35.2 | 24.0 |
| 240 | | 97.7 | 68.3 | 56.2 | 42.5 | 29.9 |
| 360 | | 97.8 | 88.6 | 69.7 | 54.8 | 40.7 |
| 480 | | 98.6 | 99.1 | 81.3 | 65.9 | 50.6 |
| 600 | | 98.9 | 99.6 | | | 59.6 |
| 720 | | 99.1 | 99.9 | | | 68.1 |
| 735 | | 100.0 | 100.9 | | | 88.4 |

TABLE 9A

Figure 1C:
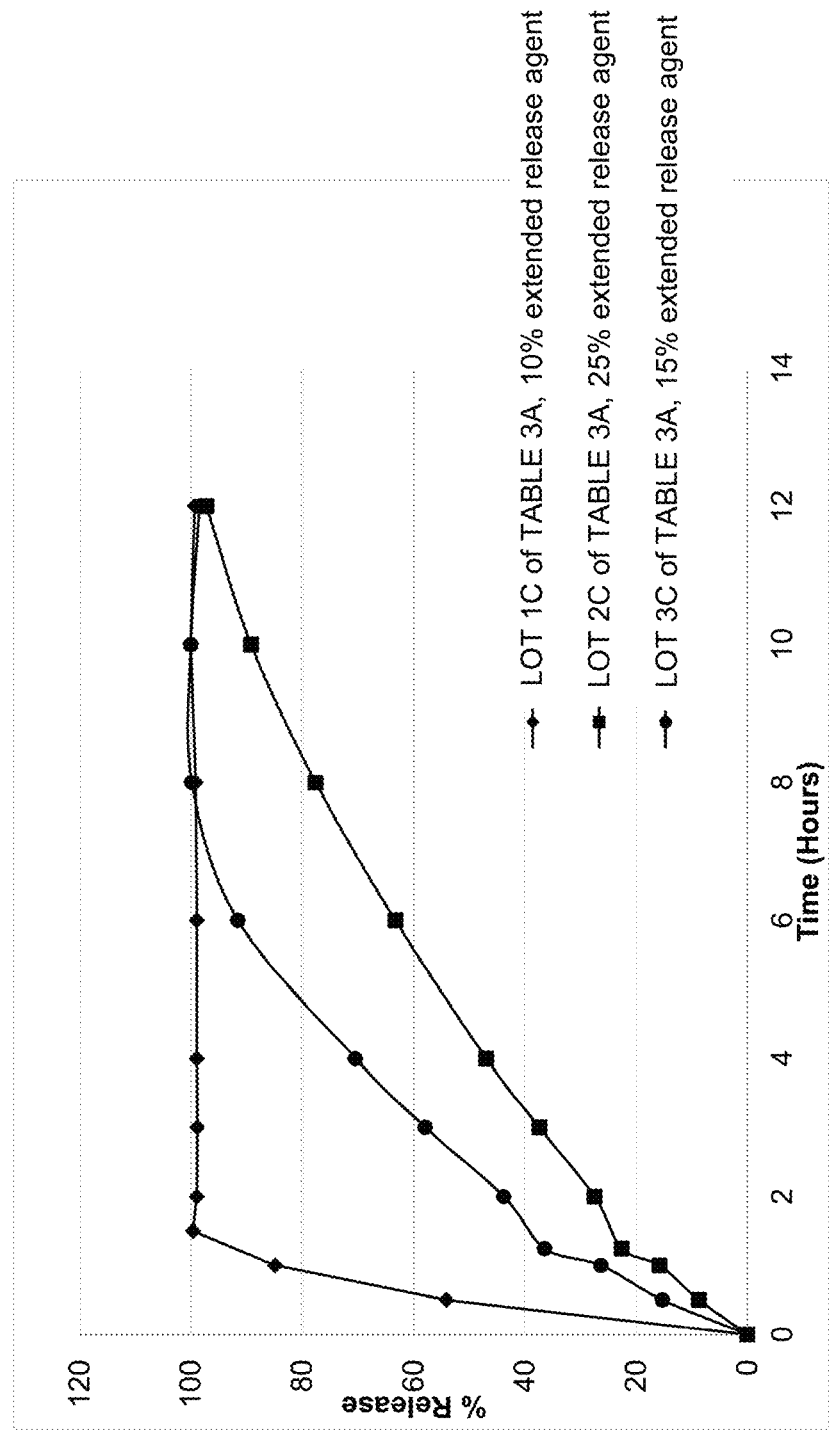

Data of FIG. 1C (data is % API released vs Time)

| Time (hours) | Lot 1C (10%) (% API released) | Lot 3C (15%) (% API released) | Lot 2C (25%) (% API released) |
| --- | --- | --- | --- |
| 0 | 0 | 0 | 0 |
| 0.5 | 54.1 | 15.3 | 8.7 |
| 1 | 84.8 | 26.3 | 15.8 |
| 1.5 | 99.6 | 36.4 | 22.6 |
| 2 | 98.9 | 43.8 | 27.5 |
| 3 | 98.8 | 57.9 | 37.4 |
| 4 | 98.9 | 70.5 | 47 |
| 6 | 98.9 | 91.5 | 63.3 |
| 8 | 99.1 | 99.8 | 77.6 |
| 10 | 100.0 | 100.0 | 89.2 |
| 12 | 99.3 | 98.4 | 97.2 |

TABLE 9B

Figure 1D:
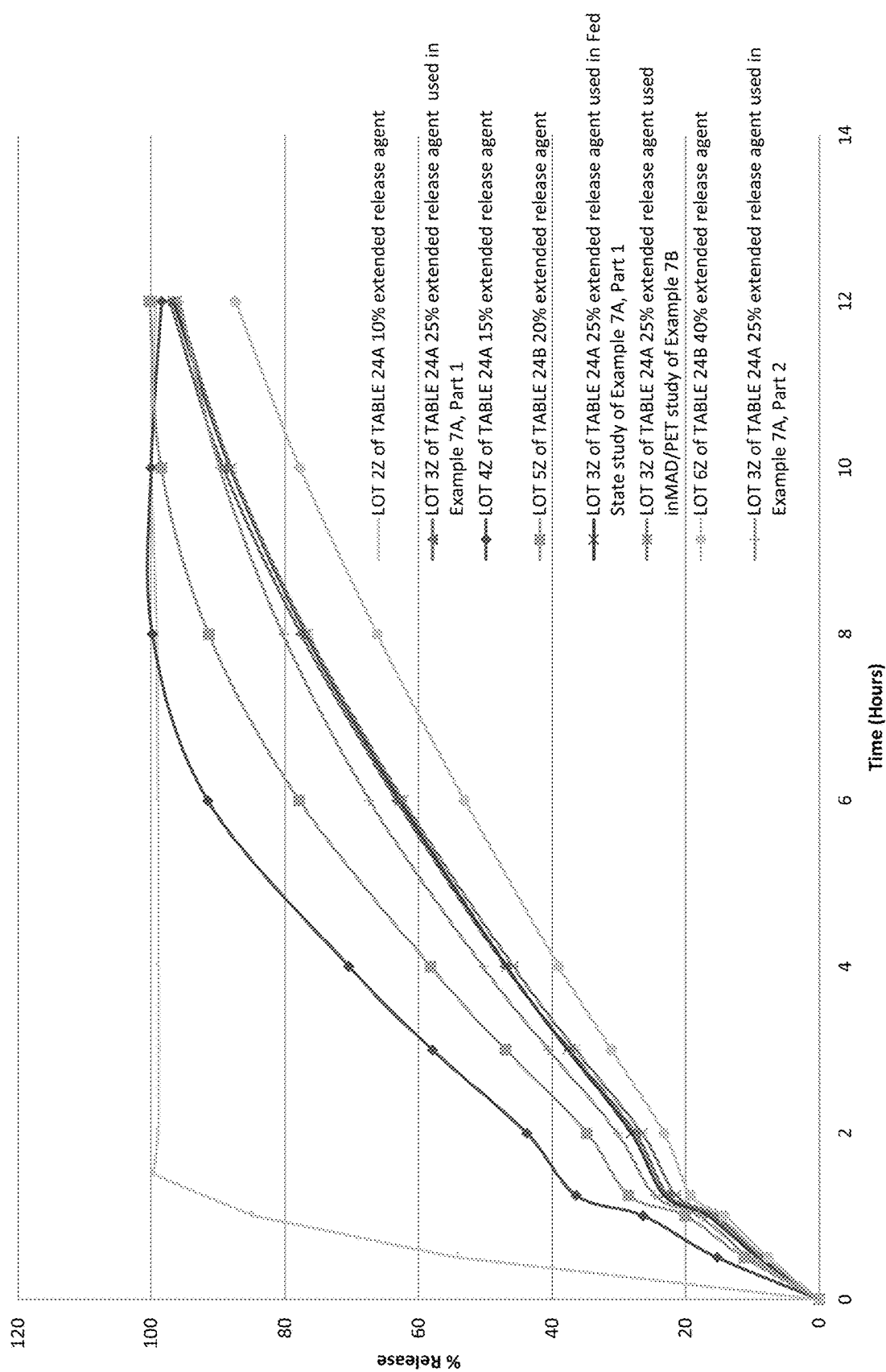

Data of FIG. 1D (data is % API released vs Time)

| Time (hours) | Lot 2Z (10%) | Lot 4Z (15%) | Lot 3Z (25%) Part 1 | Lot 3Z (25%) Part 2 | Lot 3Z (25%) fed state* | Lot 3Z (25%) MAD/PET** | Lot 5Z (20%) | Lot 6Z (40%) |
|---|---|---|---|---|---|---|---|---|
| 0 | 0 | 0 | 0 | 0 | 0 | 0 | 0 | 0 |
| 0.5 | 54.1 | 15.3 | 8.7 | 10.2 | 9.1 | 8.4 | 11.2 | 7.6 |
| 1 | 84.8 | 26.3 | 15.8 | 17.9 | 16.7 | 15.3 | 20 | 14.2 |
| 1.5 | 99.6 | 36.4 | 22.6 | 24.6 | 23.2 | 21.4 | 28.5 | 19.2 |
| 2 | 98.9 | 43.8 | 27.5 | 30.2 | 28.1 | 26.5 | 34.8 | 23.2 |
| 3 | 98.8 | 57.9 | 37.4 | 40.6 | 37.7 | 36.5 | 47 | 31.1 |
| 4 | 98.9 | 70.5 | 47 | 50.4 | 46.8 | 45.8 | 58.2 | 39 |
| 6 | 98.9 | 91.5 | 63.3 | 67.4 | 62.8 | 62.3 | 77.9 | 53.1 |
| 8 | 99.1 | 99.8 | 77.6 | 80.3 | 76.9 | 76.6 | 91.4 | 66.2 |
| 10 | 100.0 | 100.0 | 89.2 | 89.8 | 88.2 | 88 | 98.5 | 77.8 |
| 12 | 99.3 | 98.4 | 97.2 | 95.7 | 96.7 | 96.2 | 100.2 | 87.4 |

*Tablet batch of Lot 3Z formulation used in fed state study of Example 7A, Part 1
**Tablet batch of Lot 3Z formulation used in MAD / PET Imaging study of Example 7B

TABLE 9C

Figure 1E:
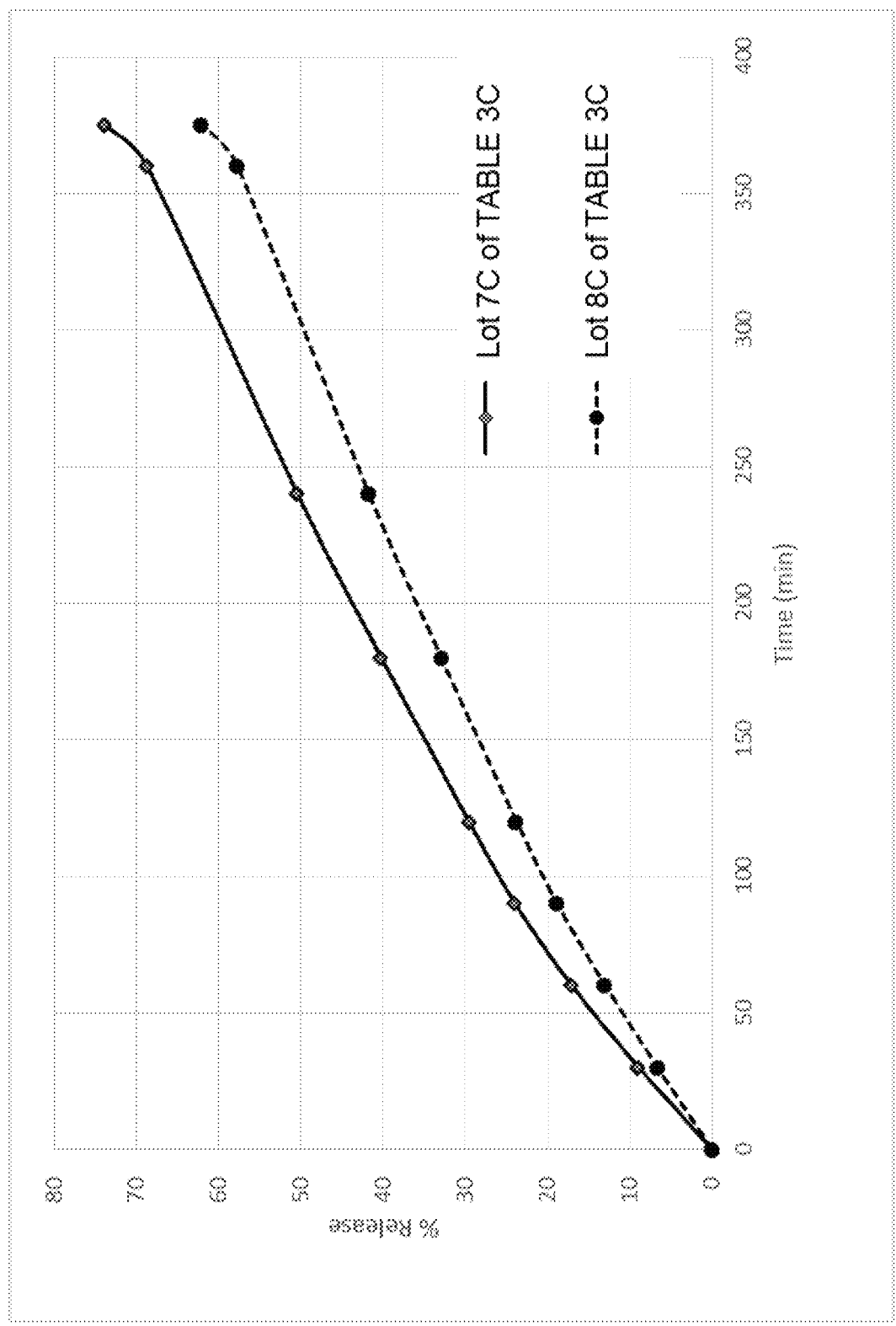
FIG. 1E presents data for the formulations of Table 3C.

Data of FIG. 1E (data is % API released vs Time)

| Time (hours) | Lot 7C (25%) 100 mg | Lot 8C (25%) 200 mg |
|---|---|---|
| 0 | 0 | 0 |
| 0.5 | 9.0 | 6.7 |
| 1 | 17.1 | 13.0 |
| 1.5 | 24.0 | 18.9 |
| 2 | 29.6 | 23.8 |
| 3 | 40.3 | 33.0 |
| 4 | 50.5 | 41.8 |
| 6 | 68.8 | 57.8 |
| 6.25 | 74.0 | 62.1 |

In various embodiments, the modified release composition has a release profile substantially in accord with that for Lot 1A (of Table 1) in FIG. 1A, Lot 2A (of Table 1) in FIG. 1A, Lot 3A (of Table 1) in FIG. 1A, Lot 1B (of Table 2) in FIG. 1B, Lot 2B (of Table 2) in FIG. 1B, Lot 3B (of Table 2) in FIG. 1B, Lot 4B (of Table 2) in FIG. 1B, Lot 5B (of Table 2) in FIG. 1B, Lot 1C (of Table 3A) in FIG. 1C, Lot 2C (of Table 3A) in FIG. 1C, Lot 3C (of Table 3A) in FIG. 1C, Lot 7C (of Table 3C) in FIG. 1E, or Lot 8C (of Table 3C) in FIG. 1E, when tested using a two-stage in vitro dissolution test set forth in Table 5 and the accompanying description.

In various embodiments, the modified release composition has a release profile substantially in accord with that for Lot 2Z (of Table 24A) in FIG. 1D, Lot 3Z (of Table 24A) in FIG. 1D, Lot 3Z (of Table 24A) in FIG. 1D fed state batch, Lot 3Z (of Table 24A) in FIG. 1D MAD/PET imaging batch, Lot 4Z (of Table 24A) in FIG. 1D, Lot 5Z (of Table 24B) in FIG. 1D, or Lot 6Z (of Table 24B) in FIG. 1D, when tested using a two-stage in vitro dissolution test set forth in Table 5 and the accompanying description.

A variety of procedures can be used to make the modified release tablets described herein. For example, the modified release tablets of Tables 1-3A, 3B, 4, 24A, 24B and 25, were made as follows. The active pharmaceutical ingredients ((R)-amisulpride and (S)-amisulpride) and D-mannitol (Pearitol 50C) were separately delumped with a screen mill. The delumped API, delumped D-mannitol and partly pregelatinized starch were granulated by spraying aqueous solution of partially hydrolyzed polyvinyl alcohol in a wet high-shear granulator, and wet granules were passed through a screening mill and dried in a fluid bed granulator. The resultant granules were then passed through a screening mill to give sized granules. D-mannitol (Pearitol 100SD) and hypromellose were then blended with the sized granules in a blender. Subsequently, magnesium stearate was blended with the granules in a blender. The blended granules were then compressed into core tablets with a rotary press.

More specifically, prior to mixing the active pharmaceutical ingredients ((R)-amisulpride and (S)-amisulpride) with the various excipients to form granules, the (R)-amisulpride and (S)-amisulpride are separately delumped. The delumping employed a Powrex (Quadro) Co mill QC-194S, configured with a round bar impeller and round holed screen having screen size 1.397 mm(055R), with a spacer size of 0.200, and the impeller operated with a low rotating speed of 743 min$^{-1}$. D-Mannitol was also delumped by a similar procedure.

Granulation was achieved using a Powrex FM-VG-05 (total capacity: 5 L) Granulator, configured with a blade of straight type 35° (rotating at 400 rpm), cross screws of 60 mm×3 plates, (rotating at 3000 rpm), seal air pressures of 30 NL/min (Blade), 20 NL/min (Cross screw), a two fluid nozzle spray gun (with spray gun nozzle size of 1.0 mm operated at a spray rate of 10 g/min, a spray air pressure of 0.03 MPa, and a temperature control jacket set as required for various steps in the process.

The binder was first prepared as a 10% solid concentration placed in purified water is heated above 80° C. and partially hydrolyzed polyvinyl alcohol was dissolved in the heated water by propeller mixer. In addition, as required, other excipients were delumped prior to combination.

To produce granules and tablets substantially in accord with those of Tables 1-3A, 3B, 4, 24A, 24B and 25, the binder was added for introduction via the spray guns, and delumped mannitol, partly pregelatinized starch, delumped (R)-amisulpride and delumped (S)-amisulpride were mixed briefly in a plastic bag. The resultant mixture was added to the granulator container and blended for 1 min., then the sprayer started to start spraying the binder. After spraying, all granules in the container, including granules adhered on surface of container, blade, cross screw, lid, are scraped off and the loss of water on drying determined.

The resultant granules were then wet sized prior to combination with the extra-granular component. The granules were wet sized using a Powrex (Quadro) Co mill QC-194S, configured with a round bar impeller and round holed screen having screen size: 3.962 mm(156R), with a spacer size of 0.225, and the impeller operated with a low rotating speed of 900 min$^{-1}$. The granules were fed manually over 2-3 min (for a 300 g scale feed).

The wet sized granules were then dried using a Powrex FD-MP-01 (total capacity: 0.6-3 L), with an inlet air flow of 0.7-1.0 m$^3$/hr having an inlet air temperature of 80° C. The wet sized granules were added to the container and drying started. The drying was stopped when the outlet air temperature reached 40° C., and the granules tested for loss of water; loss on drying (LOD) should be NMT 2.0%.

The granules and extra-granule components were blended using a Tsutsui scientific instrument S-3 (V-blender, total capacity: 2 L) as follows. The sized granules were added to the container of the blender, then the extended release agent (e.g. hypromellose) and filler (e.g., D-mannitol) were added, and the material blended for 15 min at 40 rpm. A portion of the blended granules were removed and mixed with a lubricant (e.g., magnesium stearate), the mixture passed through an appropriate sieve (e.g., a 850 μm sieve), and the sieved mixture added back to the blender container, and blended for 5 min at 40 rpm.

The tablets of Tables 1-3A, 3B, 4, 24A, 24B and 25 were then formed using a Rotary press Kikusui VEL2, with 11 mm, WR (22.0R, 5.5 R) tooling, operated at a compression speed of 20 rpm and the compression force adjusted to produce tablets having a hardness of about NLT 100N.

Multiparticulate Capsule (MUPS) Formulations

In various aspects and embodiments, modified release compositions are provided as solid oral dosage forms in the form of a capsule comprising multiple coated particulates; the particulate component comprising (a) coated particulates of substantially enantiomerically pure (R)-amisulpride and (b) coated particulates of substantially enantiomerically pure (S)-amisulpride, where R and S amisulpride particulates are combined in the capsule in a ratio of R:S amisulpride between 65:35 to 90:10, between 80:20 to 88:12, or about 85:15 by weight of free base. In various aspects and embodiments, the extended release agent comprises the coating, which facilitates or provides for modified release of the API.

In various embodiments, the coating of the (R)-amisulpride and (S)-amisulpride particles is substantially the same, and in various embodiments, the coating of the (R)-amisulpride and (S)-amisulpride particles differs. In various embodiments, the particulates are coated with one or more polymer coatings comprising between about 8% and about 60%, between about 10% and about 45%, or between about 15% and about 30% by weight of the total particle weight.

It is to be understood that the weight percentage of the polymer coat can also be described as the weight of the polymer coating (e.g. polymer+plasticizer) as a percentage of the weight of the uncoated particles. Accordingly, in various embodiments modified release compositions are provided as solid oral dosage forms in the form of a capsule comprising multiple coated particulates; the particulate component comprising (a) coated particulates of substantially enantiomerically pure (R)-amisulpride and (b) coated particulates of substantially enantiomerically pure (S)-amisulpride, R and S amisulpride particulates combined in the capsule in a ratio of R:S amisulpride between 65:35 to 90:10, between 80:20 to 88:12, or a ratio of about 85:15 by weight of amisulpride free base. In various embodiments, the coating of the (R)-amisulpride and (S)-amisulpride is substantially the same, and in various embodiments, the coating of the (R)-amisulpride and (S)-amisulpride particles differs. In various embodiments, the particulates are coated with one or more polymer coatings comprising between about 10% and about 60%, between about 10% and about 45%, or between about 15% and about 35% by weight of the uncoated particle weight.

In various embodiments, the coated particulates of substantially enantiomerically pure (R)-amisulpride and substantially enantiomerically pure (S)-amisulpride are combined in the capsule in a ratio of R:S amisulpride between 65:35 to 90:10, between 80:20 to 88:12, or about 85:15 by weight of free base.

In various embodiments, the particulates comprise in addition to the API, a binder and optionally a lubricant excipient, the combined API, binder and lubricant particulates being coated with one or more polymers. In various embodiments, the API comprises between about 35% and about 65% of the total coated particle weight, the binder comprises between about 8% and about 20%, and in various embodiments between about 9% and about 15%, of the total coated particle weight, the lubricant excipient comprises between about 8% and about 20%, and in various embodiments between about 9% and about 15%, of the total coated particle weight, and the polymer coating between about 10% and about 45% by weight of the total particle weight.

In various embodiments, the particulates comprise in addition to the API, a binder and optionally a lubricant excipient, and the combined API, binder and lubricant particulates being coated with one or more polymers. In various embodiments, the API comprises between about 40% and about 85% of the total uncoated particle weight (and in various embodiments between about 65% and about 75% of the total uncoated particle weight), the binder comprises between about 8% and about 20%, and in various embodiments between about 9% and about 15%, of the total uncoated particle weight, the lubricant excipient comprises between about 8% and about 20%, and in various embodiments between about 9% and about 15%, of the total uncoated particle weight, and the polymer coating between about 10% and about 60% by weight of the uncoated particle weight, and in various embodiments between about 10% and about 45% by weight of the uncoated particle weight, and in various embodiments between about 15% and about 35% by weight of the uncoated particle weight.

In various embodiments, the ratio of the API to polymer coating is between about 1:0.5 and 1:0.6. In various embodiments, the ratio of the API to binder is between about 1:0.2 and 1:0.25. In various further embodiments, the ratio of the API to polymer coating is between about 1:0.5 and 1:0.6, and the ratio of the API to binder is between about 1:0.2 and 1:0.25.

In various embodiments, examples of binders include, but are not limited to, hydroxypropyl cellulose, hydroxypropyl methylcellulose, partially hydrolyzed polyvinyl alcohol, polyvinyl alcohol, methylcellulose, hydroxyethylcellulose, hydroxymethylcellulose, carboxymethylcellulose, polyvinylpyrrolidone, copolyvidone, polyethylene glycol, polyvinyl alcohol-acrylic acid-methyl methacrylate copolymer, vinyl acetate-vinylpyrrolidone copolymer, polyvinyl alcohol-polyethylene glycol-graft copolymer, pregelatinized starch, dextrin, dextran, pullulan, alginic acid, gelatin, pectin, and a mixture of one or more thereof. In various embodiments, one or more of hydroxypropyl cellulose and polyvinyl alcohol are used.

In various embodiments, examples of lubricant excipients include, but are not limited to, micronized talc, magnesium stearate, sodium stearyl fumarate, hydrated silicon dioxide, magnesium silicate, light anhydrous silicic acid, synthetic aluminum silicate, heavy anhydrous silicic acid, silicon dioxide, calcium stearate, aluminum stearate, potassium stearate, zinc stearate, yellow ferric oxide, red ferric oxide, and titanium oxide. In various embodiments, one or more of talc, magnesium stearate and sodium stearyl fumarate are used.

In various embodiments, the polymer coating comprises one or more water insoluble polymers and one or more plasticizers mixed with the one or more polymers. In various embodiments, examples of water insoluble polymers include, but are not limited to, ethylcellulose, acetyl cellulose, aminoalkylmethacrylate copolymer RS, ethyl acrylate, and vinyl acetate resin. In various embodiments, examples of plasticizers include, but are not limited to, triethyl citrate, polyethylene glycol, propylene glycol, polypropylene glycol, sorbitol sorbitan solution, triacetin, glycerin, glycerol fatty acid, silicon oil, acetyltriethyl citrate, diethyl phthalate, tributyl citrate, dibutyl phthalate, acetyltributyl citrate, dibutyl sebacate, glycerol triacetate, and acetylated monoglyceride. In various embodiments, one or more of ethylcellulose and aminoalkylmethacrylate copolymer RS are the polymers, and triethyl citrate is the plasticizer. In various embodiments, the polymer coating comprises a mixture of ethylcellulose and triethyl citrate where the weight ratio of ethylcellulose to triethyl citrate is in the range between about 3:1 to about 5:1 and in various embodiments about 4:1.

It is to be understood that in the present multiparticulate capsule formulations the R-amisulpride and the S-amisulpride containing particulates may be formulated and coated separately, and then sufficient portions of the R-amisulpride particulates and the S-amisulpride particulates are combined in a capsule to provide the desired amount of amisulpride mixture and ratio of R:S amisulpride. It is to be understood that if the percentage of amisulpride in a coated particulate differs between the R-amisulpride particulates and the S-amisulpride particulates (as may result from different uncoated particulate formulations and/or different amounts of polymer coating), then particulates are combined based on the weight of the amisulpride in the respective particulates.

Accordingly, it is to be understood that the absolute weights of the capsule formulations in Tables 10 and 11 are not indicative of the absolute weights of the various components in a final multiparticulate capsule comprising the desired amount of amisulpride and R:S ratio. However, the compositions of Tables 10 and 11 do provide the relative ratios of the various components in the respective particulates, R-amisulpride particulates in Table 10 and the S-amisulpride particulates in Table 11, of the particulate components of a multiparticulate capsule in various embodiments.

In various embodiments, the unequal mixture of R-amisulpride and S-amisulpride has an R-amisulpride to S-amisulpride ratio between 65:35 to 90:10, between 80:20 to 88:12, or about 85:15 by weight of free base.

In various embodiments, the modified release multiparticulate capsules have an R-amisulpride particulate relative component composition substantially in accord with that set forth in Table 10; that is, the weight ratios of the various components in the R-amisulpride particulates in the multiparticulate capsules are substantially in accord with the ratios (not absolute weights) set forth in Table 10. The absolute amounts of the components of the compositions of Table 10 are the amounts found in capsules made from the particulates, which were then dissolution tested (as described further below). Each lot so tested comprised the same amount of (R)-amisulpride and varying amounts of polymer coating.

In various embodiments, the present inventions provide modified release pharmaceutical multiparticulate capsules having an S-amisulpride particulate relative component composition substantially in accord with that set forth in Table 11; that is, the weight ratios of the various components in the S-amisulpride particulates in the multiparticulate capsules are substantially in accord with the ratios (not absolute weights) set forth in Table 11. The absolute amounts of the components of the compositions of Table 11 are the amounts found in capsules made from the particulates, which were then dissolution tested (as described further below). Each lot so tested comprised the same amount of (S)-amisulpride and varying amounts of polymer coating.

TABLE 10

Compositions R-Amisulpride Particulate Formulations

| | | Quantity (mg) | | |
|---|---|---|---|---|
| Component | Function | IR particles | Lot RC10 (10%) | Lot RC40 (40%) |
| (R)-amisulpride | API | 200 | 200 | 200 |
| Hydroxypropyl Cellulose | Binder | 44.0 | 44.0 | 44.0 |
| Micronized Talc | Lubricant | 44.4 | 44.4 | 44.4 |
| Ethylcellulose | Polymer in Polymer Coat | — | 23.3 | 93.0 |
| Triethyl Citrate | Plasticizer in Polymer Coat | — | 5.6 | 22.3 |
| Total Weight | | 288.4 | 317.2 | 403.8 |

TABLE 11

Compositions S-Amisulpride Particulate Formulations

| | | Quantity (mg) | | | | | | |
|---|---|---|---|---|---|---|---|---|
| Component | Function | IR particles | Lot SC10 (10%) | Lot SC20 (20%) | Lot SC30 (30%) | Lot SC40 (40%) | Lot SC50 (50%) | Lot SC60 (60%) |
| (S)-amisulpride | API | 200 | 200 | 200 | 200 | 200 | 200 | 200 |
| Hydroxypropyl Cellulose | Binder | 44.0 | 44.0 | 44.0 | 44.0 | 44.0 | 44.0 | 44.0 |
| Micronized Talc | Lubricant | 44.6 | 44.6 | 44.6 | 44.6 | 44.6 | 44.6 | 44.6 |
| Ethylcellulose | Polymer in Polymer Coat | — | 23.3 | 46.5 | 69.8 | 93.1 | 116.4 | 139.6 |
| Triethyl Citrate | Plasticizer in Polymer Coat | — | 5.6 | 11.2 | 16.8 | 22.3 | 27.9 | 33.5 |
| Total Weight | | 288.6 | 317.5 | 346.3 | 375.2 | 404.04 | 432.9 | 461.8 |

The particle size distributions for the particulates comprising the formulations of Tables 10 and 11 are shown in Tables 12 and 13, respectively. These particle size distributions were determined using a sieve analysis; the particulates being shifted through a stack of wire mesh sieves (conforming to BS 410 and ISP 3310-1 standards and with nominal aperture opening sizes as indicated in columns 1 of Tables 12 and 13) that are shaken to separate the particulates into discrete size ranges.

Figure 2A:
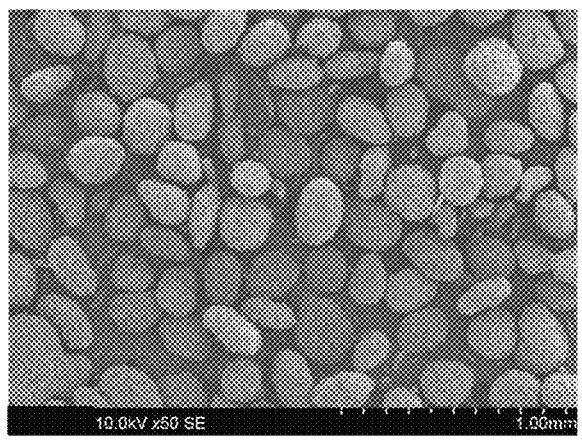
FIGS. 2A-2C present various scanning electron microscope (SEM) images of the particulates of Table 11; where
Figure 2B:
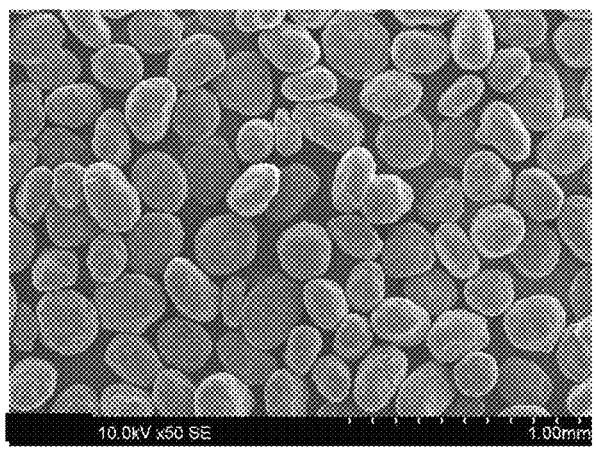
Figure 2C:
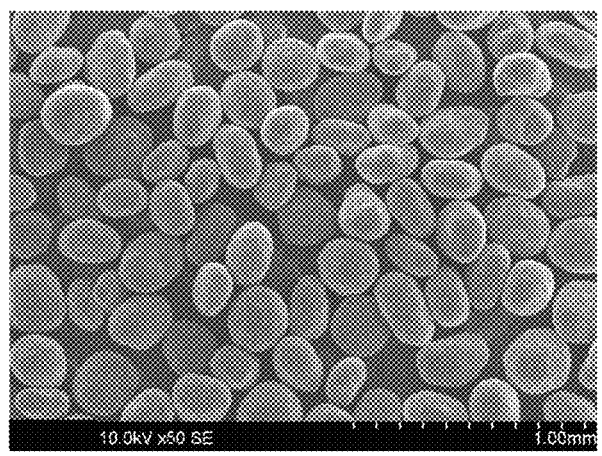

Scanning electron microscope (SEM) images of the particulates of Table 11 are shown, in FIGS. 2A-2C. SEM samples were sputter-coated with a Pt—Pd alloy using an ion sputtering system (Hitachi E1030). The SEM images were acquired using a Hitachi S-3400N scanning electron microscope.

TABLE 12

Particle Size Distribution (PSD) for Particulates in Formulations of Table 10 Fraction Percentage by Sieve Size

| Sieve size Microns | IR Particles | Lot RC40 (40%) |
|---|---|---|
| >500 | 0.25 | 0.0 |
| >355 | 0.49 | 1.7 |
| >250 | 0.82 | 22.0 |
| >212 | 24.96 | 35.0 |
| >180 | 33.96 | 17.4 |
| >125 | 27.33 | 21.3 |
| >90 | 2.86 | 2.4 |
| >63 | 1.64 | 0.3 |
| Base/<75 | 0.49 | 0.0 |

TABLE 13

Particle Size Distribution (PSD) for Particulates in Formulations of Table 11 Fraction Percentage by Sieve Size

| Sieve size Microns | IR Particles | Lot SC30 (30%) | Lot SC60 (60%) |
|---|---|---|---|
| >500 | 0.00 | 0.00 | 0.24 |
| >355 | 1.49 | 1.98 | 1.72 |
| >250 | 1.75 | 11.13 | 24.08 |
| >212 | 20.45 | 40.60 | 50.61 |
| >180 | 43.14 | 36.88 | 17.94 |
| >125 | 28.93 | 9.16 | 5.16 |
| >90 | 1.24 | 0.25 | 0.25 |
| >63 | 0.25 | 0.00 | 0.00 |
| Pass | 2.75 | 0.00 | 0.00 |
| D50 (μm) | 192.40 | 215.40 | 232.00 |

Figure 3A:
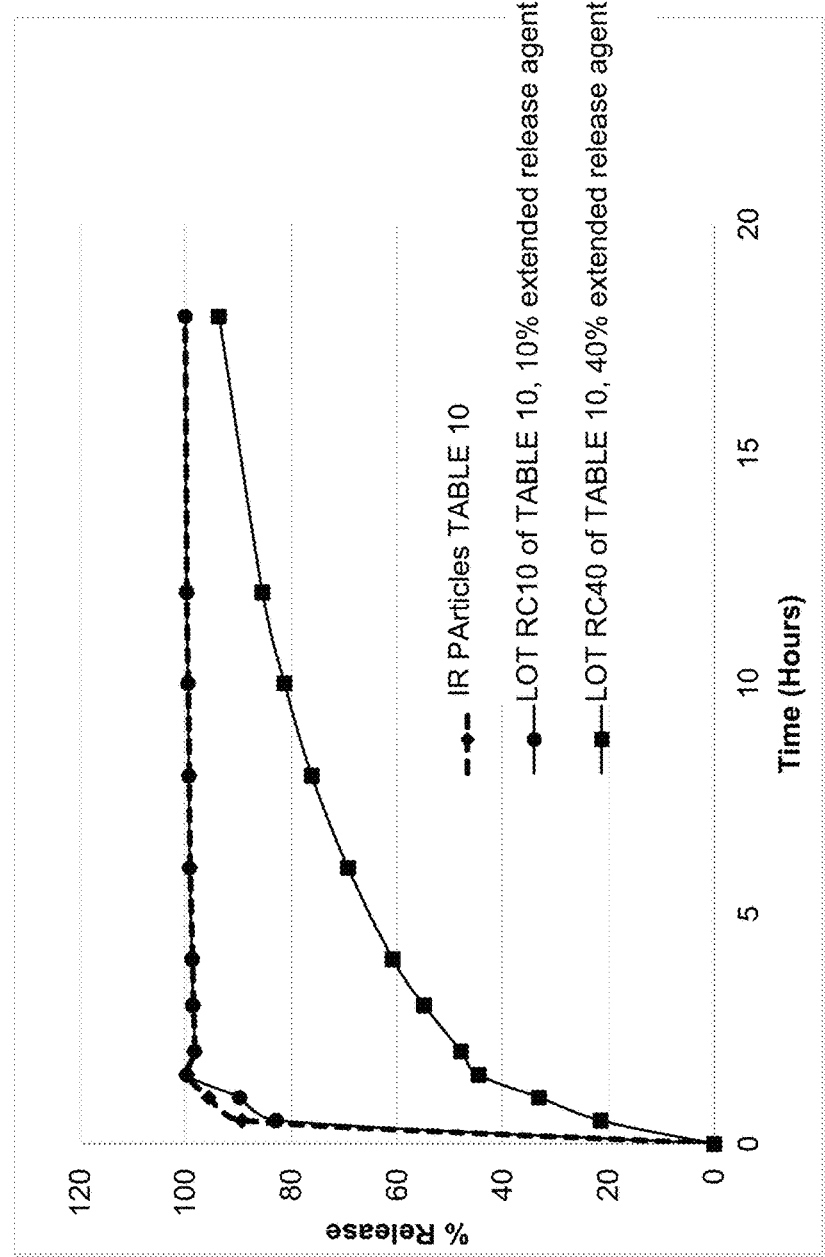
FIG. 3A presents various in vitro dissolution profiles for an immediate release (IR) formulation and various modified release pharmaceutical multiparticulate capsule (MUPS) formulations of Table 10.
Figure 3B:
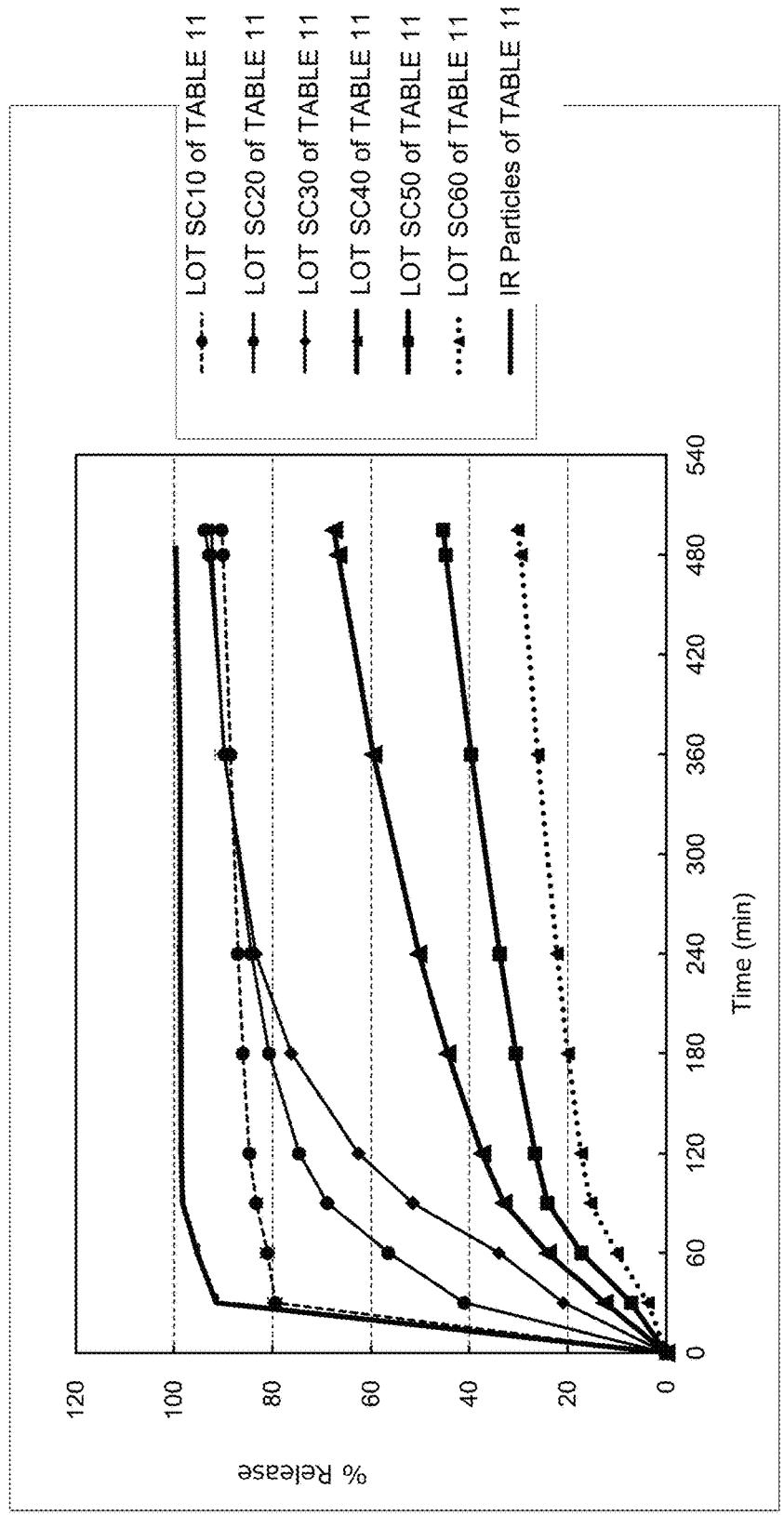
FIG. 3B presents various in vitro dissolution profiles for an immediate release (IR) formulation and various modified release pharmaceutical multiparticulate capsule (MUPS) formulations of Table 11.

The in vitro dissolution profiles of the formulations in FIGS. 3A and 3B were acquired using a paddle apparatus substantially in accord with that described by the United States Pharmacopeia Convention (USP) Apparatus 2 of Chapter 711 Dissolution; USP41-NF36 General Chapter <711> Dissolution. The apparatus was operated as described in Table 5 for the MR formulation dissolution data of FIGS. 3A and 3B. Amisulpride release was determined from 1.5 ml samples taken from the medium and analyzed using HPLC with a Kinetex Biphenyl, 4.6×100 mm, 2.6 μm (P/N: 00D-4622-E0) column and UV detector set to 280 nm at the time points indicated in the figures. The data plotted in FIGS. 3A and 3B is also provided, respectively, in Tables 14 and 15 below.

TABLE 14

Data of FIG. 3A (data is % API released vs Time)

| Time (hours) | IR Particles | Lot RC10 (10%) | Lot RC40 (40%) |
|---|---|---|---|
| 0 | 0 | 0 | 0 |
| 0.5 | 89.3 | 82.9 | 21.5 |
| 1 | 95.5 | 89.7 | 33.1 |
| 1.5 | 99.6 | 99.7 | 44.6 |
| 2 | 98.3 | 98.2 | 48.0 |
| 3 | 98.4 | 98.6 | 55.0 |
| 4 | 98.6 | 98.7 | 60.8 |
| 6 | 99.1 | 99.1 | 69.3 |
| 8 | 99.2 | 99.3 | 76.1 |
| 10 | 99.4 | 99.5 | 81.3 |
| 12 | 99.7 | 99.7 | 85.5 |
| 18 | 100.0 | 100.0 | 93.6 |

TABLE 15

Data of FIG 3B (data is % API released vs Time)

| Time (minutes) | IR Particles | Lot SC10 (10%) | Lot SC20 (20%) | Lot SC30 (30%) | Lot SC40 (40%) | Lot SC50 (50%) | Lot SC60 (60%) |
|---|---|---|---|---|---|---|---|
| 0 | 0 | 0 | 0 | 0 | 0 | 0 | 0 |
| 30 | 91.4 | 79.5 | 41 | 20.9 | 12.5 | 7.1 | 3.8 |
| 60 | 95.3 | 81.0 | 56.5 | 33.9 | 24.1 | 17.2 | 10.0 |
| 90 | 98.2 | 83.3 | 68.9 | 51.6 | 33 | 24.1 | 15.4 |
| 120 | 98.5 | 84.7 | 74.6 | 62.6 | 37.4 | 26.6 | 17.3 |
| 180 | 98.6 | 86.0 | 80.7 | 76.2 | 44.4 | 30.5 | 20 |
| 240 | 98.7 | 87.0 | 84.3 | 83.4 | 50.4 | 33.8 | 22.2 |
| 360 | 98.7 | 88.5 | 89.7 | 89.9 | 59.6 | 39.6 | 26.1 |
| 480 | 99.6 | 90.0 | 92.8 | 92.2 | 66.7 | 44.8 | 29.5 |
| 495 | | 90.3 | 93.8 | 92.3 | 67.6 | 45.3 | 30.2 |

In various embodiments, the modified release multiparticulate capsules have a composition substantially in accord with that set forth in Tables 16A and 16B. The capsules of Tables 16A and 16B each comprise 200 mg or 100 mg of (R)-amisulpride and (S)-amisulpride in the ratio R:S of 85:15, and varying amounts of polymer coating for the particulates. As described herein, the multiparticulate capsules are produced by combining appropriate amounts of polymer coated (R)-amisulpride particulates and polymer coated (S)-amisulpride particulates within a capsule.

TABLE 16A

Compositions Multiparticulate Capsules

| Component | Function | Lot C1A (10%) mg | Lot C1B (40%) mg | Lot C1C (40%) mg | Lot C1D (10%) mg |
|---|---|---|---|---|---|
| (R)-amisulpride | API | 170.0 | 170.0 | 85.0 | 85.0 |
| (S)-amisulpride | API | 30.0 | 30.0 | 15.0 | 15.0 |
| Hydroxypropyl Cellulose | Binder | 44.0 | 44.0 | 22.0 | 22.0 |
| Micronised Talc | Lubricant | 44.4 | 44.4 | 22.2 | 22.2 |
| Ethylcellulose | Polymer Coat | 23.2 | 93.0 | 46.5 | 11.6 |
| Triethyl Citrate | Polymer Coat | 5.5 | 22.3 | 11.2 | 2.8 |
| Total per Capsule | | 317.2 | 403.8 | 201.9 | 158.6 |
| Gelatin Capsules | Encapsulation | 1 unit | 1 unit | 1 unit | 1 unit |

TABLE 16B

| Component | Function | Lot C2A (22.5%) mg | Lot C2B (30%) mg |
|---|---|---|---|
| (R)-amisulpride | API | 170.0 | 170.0 |
| (S)-amisulpride | API | 30.0 | 30.0 |
| Hydroxypropyl Cellulose | Binder | 44.0 | 44.0 |
| Micronised Talc | Lubricant | 44.4 | 44.4 |
| Ethylcellulose | Polymer Coat | 52.5 | 69.9 |
| Triethyl Citrate | Polymer Coat | 12.4 | 16.6 |
| Total per Capsule | | 353.3 | 374.9 |
| Gelatin Capsules | Encapsulation | 1 unit | 1 unit |

Compositions Multiparticulate Capsules

TABLE 17

PSD for Particulates in Formulations of Lot C1B and C1C of Table 16A
Fraction Percentage by Sieve Size

| Sieve size Microns | R-amisulpride particles Lot C1B and C1C (40%) | S-amisulpride particles Lot C1B and C1C (40%) |
|---|---|---|
| >500 | 0.0 | 0.1 |
| >355 | 1.7 | 3.8 |
| >250 | 22.0 | 30.7 |
| >212 | 35.0 | 38.7 |
| >180 | 17.4 | 14.4 |
| >125 | 21.3 | 12.1 |
| >90 | 2.4 | 0.2 |
| >63 | 0.3 | 0.0 |
| Base/<75 | 0.0 | 0.0 |

The particle size distributions for the particulates comprising the formulations of Lot C1B and Lot C1C in Table 16A are shown in Table 17. These particle size distributions were determined using a sieve analysis; the particulates being shifted through a stack of wire mesh sieves (with nominal aperture opening sizes as indicated in column 1 of Table 17) that are shaken to separate the particulates into discrete size ranges.

Figure 4A:
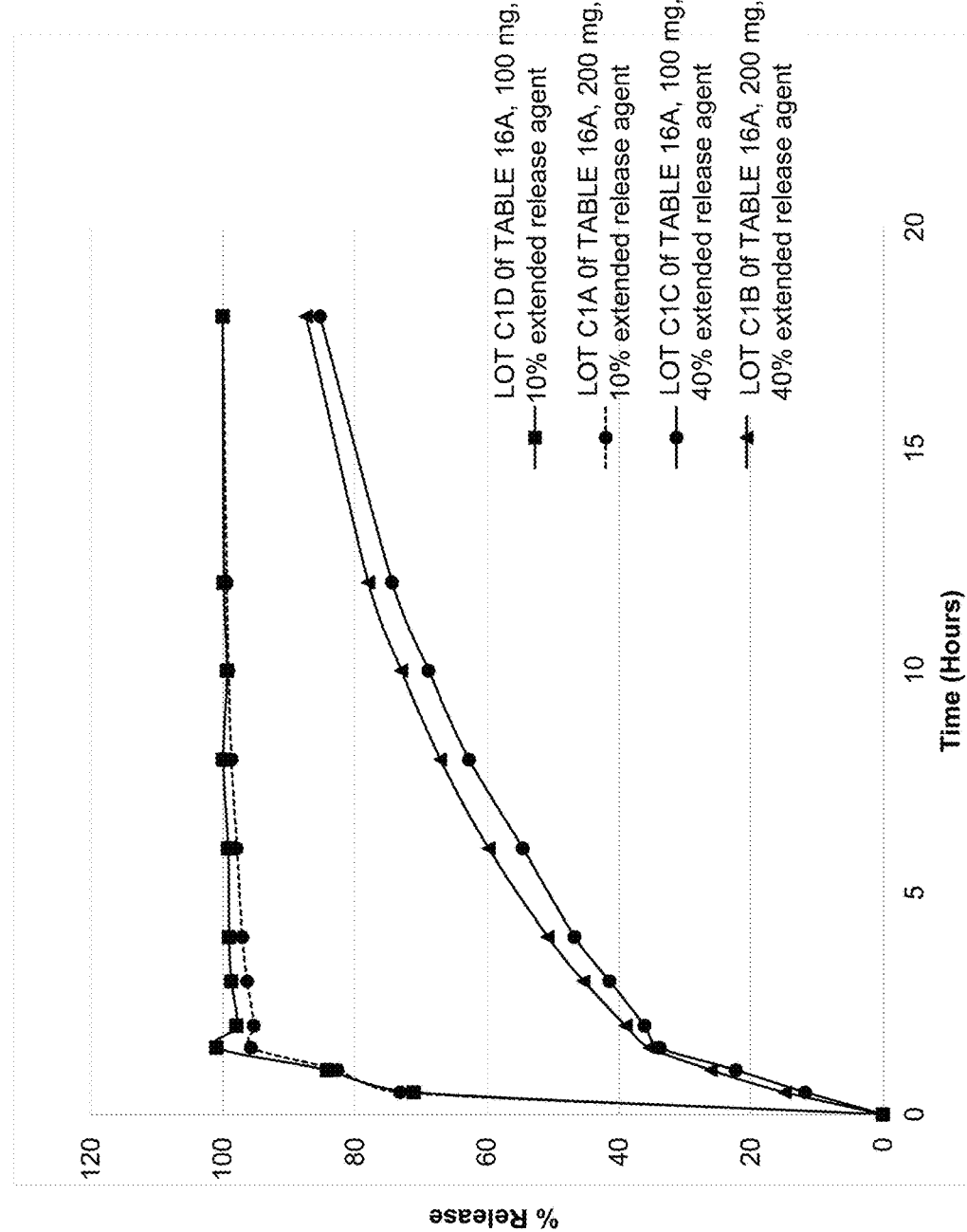
FIG. 4A presents various in vitro dissolution profiles for various modified release pharmaceutical multiparticulate capsule (MUPS) formulations of 85:15 (R:S-amisulpride) of Table 16A.
Figure 4B:
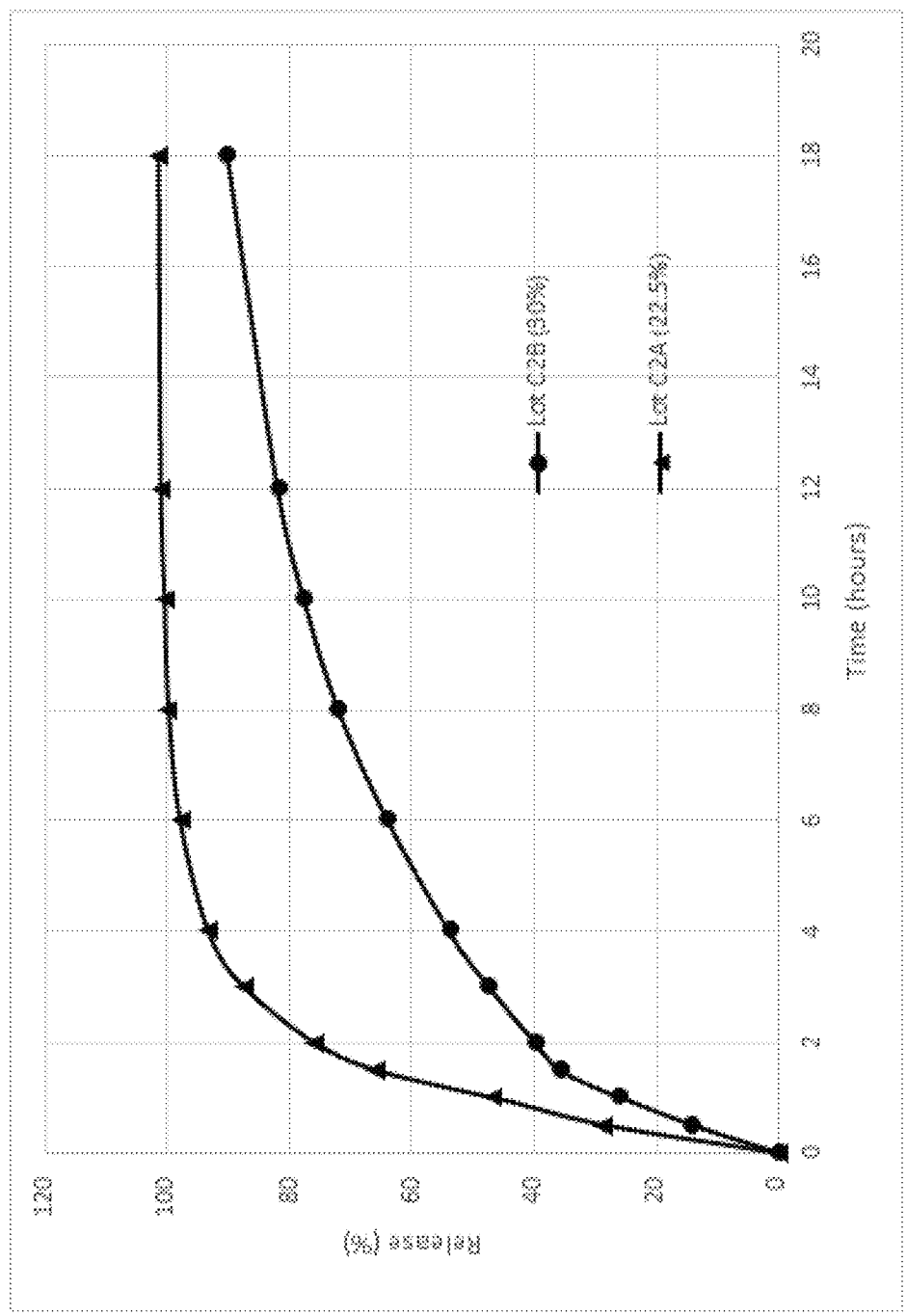
FIG. 4B presents various in vitro dissolution profiles for various modified release pharmaceutical multiparticulate capsule (MUPS) formulations of 85:15 (R:S-amisulpride) of Table 16B.

The in vitro dissolution profiles of the formulations in FIG. 4A and FIG. 4B were acquired using a paddle apparatus described by the United States Pharmacopeia Convention (USP) Apparatus 2 of Chapter 711 Dissolution; USP41-NF36 General Chapter <711> Dissolution. The apparatus was operated as described in Table 5 for the MR formulation dissolution data of FIGS. 4A and 4B. Amisulpride release was determined from 1.5 ml samples taken from the medium and analyzed using HPLC with a Kinetex Biphenyl, 4.6×100 mm, 2.6 µm (P/N: 00D-4622-E0) column and UV detector set to 280 nm at the time points indicated in the figures. The data plotted in FIGS. 4A and 4B is also provided, respectively, in Tables 18A and 18B below.

TABLE 18A

Data of FIG. 4A (data is % API released vs Time)

| Time (hours) | Lot C1D (100 mg, 10%) | Lot C1A (200 mg, 10%) | Lot C1C (100 mg, 40%) | Lot C1B (200 mg, 40%) |
|---|---|---|---|---|
| 0 | 0 | 0 | 0 | 0 |
| 0.5 | 71.2 | 73.2 | 11.8 | 14.9 |
| 1 | 84.2 | 82.7 | 22.3 | 26.1 |
| 1.5 | 100.9 | 95.7 | 33.8 | 35.4 |
| 2 | 97.9 | 95.3 | 36.2 | 39.0 |
| 3 | 98.7 | 96.3 | 41.4 | 45.4 |
| 4 | 99.0 | 97.1 | 46.7 | 50.8 |
| 6 | 99.2 | 97.8 | 54.5 | 59.7 |
| 8 | 99.9 | 98.7 | 62.7 | 67.1 |
| 10 | 99.3 | 99.1 | 68.9 | 73.0 |
| 12 | 99.8 | 99.4 | 74.4 | 78.0 |
| 18 | 100.0 | 100.0 | 85.3 | 87.4 |

TABLE 18B

Data of FIG. 4B (data is % API released vs Time)

| Time (hours) | Lot C2A (22.5%) | Lot C2B (30%) |
|---|---|---|
| 0 | 0 | 0 |
| 0.5 | 28.6 | 14.2 |
| 1 | 46.8 | 26.0 |
| 1.5 | 66.1 | 35.8 |
| 2 | 76.1 | 39.9 |
| 3 | 87.6 | 47.5 |
| 4 | 93.4 | 54.0 |
| 6 | 98.0 | 64.2 |
| 8 | 99.9 | 72.2 |
| 10 | 100.6 | 77.9 |
| 12 | 101.2 | 82.1 |
| 18 | 101.6 | 90.3 |

In various embodiments, the modified release multiparticulate capsule has a dissolution profile substantially in accord with that for Lot C1A in FIG. 4A, Lot C1B in FIG. 4A, Lot C1C in FIG. 4A, or Lot C1D in FIG. 4A when tested using a two-stage in vitro dissolution test substantially as set forth in Table 5 and the accompanying description.

In various embodiments, the modified release multiparticulate capsule has a dissolution profile substantially in accord with that for Lot C2A in FIG. 4B, or Lot C2B in FIG. 4B when tested using a two-stage in vitro dissolution test substantially as set forth in Table 5 and the accompanying description.

A variety of procedures can be used to make the modified release capsules described herein. For example, the (R)- amisulpride particulates of Table 10, the (S)-amisulpride particulates of Table 11, and the coated particulates of substantially enantiomerically pure (R)-amisulpride and coated particulates of substantially enantiomerically pure (S)-amisulpride used to make the modified release capsules of Tables 16A and 16B, were made as follows. The uncoated substantially enantiomerically pure (R)-amisulpride particulates and uncoated substantially enantiomerically pure (S)-amisulpride particulates were made separately using the same procedure; and coated separately to make modified release particulates using the same procedure.

The uncoated particulates were made by as follows. The active pharmaceutical ingredients ((R)-amisulpride and (S)-amisulpride) were separately delumped with a screen mill and the binder (hydroxypropyl cellulose) was separately delumped with a sieving shaker. The delumped active pharmaceutical particulates ingredients were each separately combined with the delumped hydroxypropyl cellulose and micronized talc (lubricant), blended and then granulated by spraying purified water in a wet high-shear granulator to make wet particulates, and wet particulates were then dried in a fluid bed granulator. The resultant dry particulates were sieved with sieving shaker to obtain the immediate release (IR) particulates. The resultant dry IR particulates were then coated (each enantiomer separately) to make the modified release (MR) particulates for each enantiomer.

More specifically, prior to mixing the active pharmaceutical ingredients ((R)-amisulpride and (S)-amisulpride) with the various excipients to form granules, the (R)-amisulpride and (S)-amisulpride are separately delumped. The delumping employed a Powrex (Quadro) Co mill QC-194S, configured with a round bar impeller and round holed screen having screen size 1.143 mm, and the impeller operated with a low rotating speed of 743 $min^{-1}$. The hydroxypropyl cellulose delumping employed an IIDA Sieving shaker (ES-65), with a 150 mmφ sieve, and sieve mesh sizes of 150 µm and 500 µM, with the shaking level rotating at 230 rpm and tapping at 130 rpm, and a total sieving time of 10 minutes.

Granulation was achieved using a Powrex FM-VG-05 (total capacity: 5 L) Granulator, configured with a blade of straight type 35° (rotating at 400 rpm), cross screws of 60 mm×3 plates, (rotating at 3000 rpm), seal air pressures of 20 NL/min (Blade), 10 NL/min (Cross screw), a two fluid nozzle spray gun (with spray gun nozzle size of 0.5 mm ID, length of nozzle tip to air cap of 0.5 mm and operated at a spray rate of 4 g/min, a spray air pressure of 0.08 MPa. It is to be understood that a temperature control jacket can be used and set as required for various steps in the process.

The procedure for granulation was as follows. The talc was added to the granulator container and blended for 1 minute. The sieved hydroxypropyl cellulose in propoer proportion was added to the delumped API ((R)-amisulpride or (S)-amisulpride) in a plastic bag and mixed shortly. The resultant mixture was added to the granulator container (containing talc) and blended for 3 minutes. The spray binder (purified water) was then started and sprayed in the following amounts and blended in the following eleven aliquots: aliquot 1 sprayed 50 g; aliquot 2 sprayed 50 g; aliquot 3 sprayed 25 g; aliquot 4 sprayed 0 g (blended for 5 min); aliquot 5 sprayed 15 g aliquot 6 sprayed 0 g (blended for 5 min); aliquot 7 sprayed 15 g; aliquot 8 sprayed 0 g (blended for 5 min); aliquot 9 sprayed 0 g (blended for 3 min); aliquot 10 sprayed 0 g (blended for 2 min); and aliquot 11 sprayed 0 g (blended for 2 min). After spraying, all granules in container including granules adhered on surface of container, blade, cross screw, and lid, were scraped off and the steps of spraying and blending for the 11 aliquots and scraping were repeated. As mentioned previously, it is to be understood that this process was carried out separately for each of the APIs ((R)-amisulpride and (S)-amisulpride), that is a given batch contained substantially only a single amisulpride enantiomer.

After granulation, the resulting particulates were dried using a Powrex FD-MP-01 (Total capacity: 0.6-3 L) operated with an inlet air flow of 0.79-0.91 $m^3$/min, and an inlet air temperature of 80° C. The wet particulates were added to the container and drying started. The drying was stopped when the outlet air temperature reached 40° C., and the particulates tested for loss of water; loss on drying (LOD) should be NMT 2.0%.

The dried particulates were then sieved (separately for each enantiomer) using an IIDA Sieving shaker (ES-65), with a 150 mmφ sieve, and sieve mesh sizes of 106 µm and 500 µm, with the shaking level rotating at 230 rpm and tapping at 130 rpm, and a total sieving time of 10 minutes. The resultant immediate release particulates were then coated to prepare the MR particulates.

Specifically, IR particulates of a single enantiomer were coated with a Powrex/FD-MP-01/SPC (Total capacity: 0.6-3 L) gas suspension/fluidized bed apparatus in 650 g batches configured with an inlet air flow of 0.77-0.94 $m^3$/min, a SPC pulse air pressure of 0.2 MPa, a two fluid nozzle spray gun (with spray gun nozzle size of 1.2 mm ID, length of nozzle tip to air cap of 2.0 mm and operated at a spray rate of 4 g/min, a spray air pressure of 0.2 MPa), and with preheating to provide an initial inlet temperature of 67° C. and outlet target temperature of 38° C., that exhibited a range of 36-40° C. After preheating, the IR particulates of a specific enantiomer were added to the container and granulation and spraying started. Coating amount was monitored (if necessary) by weight and the granulator was stopped when the sprayed amount reached the desired coating level. As mentioned previously, it is to understood that this process was carried out separately for each of the APIs ((R)-amisulpride and (S)-amisulpride), that is a given batch contained substantially only a single amisulpride enantiomer.

The coated particulates were then dried using a TABAI/ perfect oven PH-400 (a direct heating, static solid bed drier with tray and trucks) operated at 60° C., with metallic tray and a 1.5 cm thick particulate layer on the tray, and dried for 18 hours. Subsequent to drying, the particulates were sieved with a 500 µm sieve by hand.

(R)-(+)-amisulpride and (S)-(−)-amisulpride

The modified release formulations comprise unequal mixtures of (R)-(+)-amisulpride and (S)-(−)-amisulpride, or pharmaceutically acceptable salts thereof, where the amount of (R)-(+)-amisulpride is greater than the amount of (S)-(−)-amisulpride.

In various embodiments, the enantiomeric ratio of (R)-(+)-amisulpride to (S)-(−)-amisulpride, or pharmaceutically acceptable salts thereof, is in the range between about 65:35 to about 90:10 by weight of the free base, or about: 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, or 90:10, by weight of the free base. In various embodiments, the ratio of (R)-amisulpride to (S)-amisulpride, or pharmaceutically acceptable salts thereof, is 85:15 by weight. In various embodiments, the total combined amount of (R)-amisulpride and (S)-amisulpride in is about 50 mg, 75 mg, 100 mg, 150 mg, 200 mg, 300 mg, 400 mg, 500 mg, 600 mg, 700 mg, 750 mg, 800 mg, 900 mg, or 1000 mg. In various embodiments, once administered, or as administered over a treatment cycle, the total combined amount of (R)-(+)-amisulpride and (S)-(−)-amisulpride ranges from about 50-1000 mg or from about 200-750 mg.

In various embodiments, the ratio of (R)-(+)-amisulpride to (S)-(−)-amisulpride, or pharmaceutically acceptable salts thereof, is in a ratio effective to provide in a subject after administration: an occupancy of dopamine D2 receptors between about 20% and about 60%; and a suppression of time in rapid eye movement (REM) sleep is characterized, for example, by one or more of: (a) a decrease in REM sleep by an amount greater than about 10 minutes; (b) a latency to REM sleep by an amount greater than about 20 minutes, or (c) a decrease in total REM sleep time relative to total sleep time by an amount greater than about 5%.

In various embodiments, the total combined amount of (R)-amisulpride and (S)-amisulpride is sufficient to cause a suppression of the time in rapid eye movement (REM) sleep by an amount between about 15 minutes and about 60 minutes.

In various embodiments, the relative amounts of R and S amisulpride are chosen such that, upon release from the modified release pharmaceutical composition, the $D_2$ occupancy is about 20% to about 60%. Occupancies above about 65% are associated with adverse events. Considering adverse events, in some embodiments, the amount of S isomer in the composition should not exceed the amount necessary to achieve about 60% or about 50% $D_2$ occupancy upon release from the modified release pharmaceutical composition. In some embodiments, the amount of S-amisulpride should be the minimum to achieve about 20% to about 25% $D_2$ occupancy. In some embodiments, the amount of S-amisulpride should be the minimum to achieve about 25% to about 30% $D_2$ occupancy.

Dopamine $D_2$ receptor occupancy can be measured, for example, by D2 Positron Emission Tomography (PET) in human brain through the average occupancy observed in a group of humans of sufficient number to provide statistical significance of the result. Suppression of REM sleep can be measured, for example, by polysomnography (PSG) in human subjects through the average inhibition observed in a group of humans of sufficient number to provide statistical significance of the result.

In various embodiments, the amount of R-amisulpride administered, upon release from the modified release composition, should be sufficient to achieve a reduction on the time a patient spends in REM sleep time of at least about 10 minutes to about 45 minutes, about 15 minutes to 30 minutes, or about 18 minutes to about 31 minutes.

Dosing of (S)-(−)-amisulpride, upon release from the modified release composition, should be sufficient to achieve a $D_2$ occupancy level of between about 20% and about 60% to achieve the desired therapeutic effect with reduced adverse events. At levels above about 70% to about 75% the adverse events occur at an increasing frequency and severity. Higher dosing levels to achieve a greater $D_2$ occupancy can be used if the patient does not experience an unacceptable level of adverse events. Typical daily doses of (S)-(−)-amisulpride are from about 5 mg to about 150 mg, about 10 mg to about 150 mg, or about 15 mg to about 100 mg, or in various embodiments the daily dose is from about 20 mg to about 35 mg. All doses are as the free base. The doses may be administered in a single daily dose or in divided doses.

Typical daily doses of (R)-(+)-amisulpride free base are from about 50 mg to about 1000 mg, about 100 mg to about 600 mg, about 100 mg to about 300 mg, or about 130 mg to about 180 mg. All doses are as the free base. The doses may be administered in a single daily dose or in divided doses.

In various embodiments, the ratio of (R)-(+)-amisulpride to (S)-(−)-amisulpride, or pharmaceutically acceptable salts thereof, is in a ratio effective to provide in a subject after administration inhibition of dopamine $D_2$ activity and serotonin 5-$HT_7$ activity in said subject such that the ratio of the serotonin 5-$HT_7$ receptor inhibitory constant to the dopamine $D_2$ receptor inhibitory constant is in the range between about 2 to about 6, between about 3 to about 5, or about 4.

In various embodiments, the dopamine D2 receptor inhibitory constant is in the range between about 11 nM to about 20 nM and the serotonin 5-HT7 receptor inhibitory constant is in a range between about 40 nM to about 85 nM. In various embodiments, the dopamine D2 receptor inhibitory constant is in the range between about 15 nM to about 20 nM and the serotonin 5-HT7 receptor inhibitory constant is in a range between about 50 nM to about 80 nM. In various embodiments, the dopamine D2 receptor inhibitory constant is about 17 nM and the serotonin 5-HT7 receptor inhibitory constant is about 66 nM.

In various embodiments, where the ratio of (R)-amisulpride to (S)-amisulpride, or pharmaceutically acceptable salts thereof, is effective to provide in a subject after administration inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6, and in various embodiments between about 3 to about 5; the ratio of (R)-amisulpride to (S)-amisulpride, or pharmaceutically acceptable salts thereof, by weight is: about 80:20, about 81:19, about 82:18, about 83:17, about 84:16, about 85:15, about 86:14, about 87:13, about 88:12, about 89:11, or about 90:10; and in various embodiments about 85:15 by weight of the free base.

In various embodiments, the ratio of (R)-(+)-amisulpride to (S)-(−)-amisulpride over a treatment cycle is about 85:15 by weight, the treatment cycle is daily and the total amount of (R)-(+)-amisulpride and (S)-(−)-amisulpride is 200 mg or 400 mg over the treatment cycle.

In various embodiments, the total combined amount of (R)-amisulpride and (S)-amisulpride in a modified release pharmaceutical composition, once administered to a subject, or as administered to a subject over a treatment cycle, is sufficient to provide an occupancy of dopamine $D_2$ receptors between about 20% and about 60%; and a suppression of time in rapid eye movement (REM) sleep characterized, for example, by one or more of: (a) a decrease in REM sleep by an amount greater than about 10 minutes; (b) a latency to REM sleep by an amount greater than about 15 minutes, or (c) a decrease in total REM sleep time relative to total sleep time by an amount greater than about 5%.

In various embodiments, the ratio of (R)-amisulpride to (S)-amisulpride, or pharmaceutically acceptable salts thereof, is effective to provide an occupancy of dopamine $D_2$ receptors between about 30% and about 50%.

In various embodiments, the ratio of (R)-amisulpride to (S)-amisulpride, or pharmaceutically acceptable salts thereof, is effective to provide one or more of: (i) a decrease in REM sleep by an amount greater than about 10 minutes; (ii) a decrease in REM sleep by an amount greater than about 20 minutes; (iii) a decrease in REM sleep by an amount between about 15 minutes and about 45 minutes; and (iv) a decrease in REM sleep by an amount between about 15 minutes and about 30 minutes.

In various embodiments, the ratio of (R)-amisulpride to (S)-amisulpride, or pharmaceutically acceptable salts thereof, is effective to provide one or more of: (i) a decrease in total REM sleep time relative to total sleep time by an amount greater than about 5%; (ii) a decrease in total REM sleep time relative to total sleep time by an amount greater than about 6.5%; and (iii) a decrease in total REM sleep time relative to total sleep time by an amount greater than about 8%.

In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg, by weight of the free base.

In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg, by weight of the free base, and wherein the ratio of (R)-amisulpride to (S)-amisulpride, or pharmaceutically acceptable salts thereof, by weight is about: 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, or 90:10; and in various embodiments 85:15 by weight of the free base.

Methods of Treatment

The medicaments and modified release compositions can be used to treat, and/or used to manufacture a medicament to treat, a psychiatric disorder in a subject, a neurological disorder in a subject, or both a neurological disorder and a psychiatric disorder, the disorder including, but not limited to, one or more of a mood disorder, bipolar disorder (BPD), depression, bipolar depression, major depressive episodes associated with bipolar I disorder, major depressive disorder (MDD), as an adjunctive treatment of major depressive disorder; major depressive disorder with mixed features (MDD-MF), treatment resistant depression (TRD), schizophrenia, negative symptoms of schizophrenia, and schizoaffective disorder.

In various aspects and embodiments, there is provided a method of treating a psychiatric disorder in a subject comprising administering to the subject a modified release composition in a solid oral dosage form comprising amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients. In various embodiments, the one or more pharmaceutically acceptable excipients include one or more extended release agents. In various embodiments, the psychiatric disorder is bipolar disorder and/or depression associated with bipolar disorder. The ratio of (R)-(+)-amisulpride to (S)-(−)-amisulpride, or pharmaceutically acceptable salts thereof, may be in the range between about 65:35 to about 90:10, about 80:20 to about 88:12, or about 85:15 by weight of the free base; and one or more pharmaceutically acceptable excipients. In various embodiments, the one or more pharmaceutically acceptable excipients include one or more extended release agents.

In various embodiments of the method of treating:

(1) the modified release composition is administered in amounts between about 200 mg to about 400 mg per day of amisulpride by weight of free base as a solid oral dosage form, and in various embodiments once per day; and/or (2) the modified release composition when administered to a subject population provides a population average maximum QT interval prolongation over the time period of 12 hours after administration of: (a) less than about 0.45 milliseconds (ms) per 10 mg of amisulpride; (b) less than about 0.30 milliseconds (ms) per 10 mg of amisulpride; (c) less than about 0.20 milliseconds (ms) per 10 mg of amisulpride; (d) less than about 0.15 milliseconds (ms) per 10 mg of amisulpride; (e) less than about 0.10 milliseconds (ms) per 10 mg of amisulpride t; (f) less than about 0.05 milliseconds (ms) per 10 mg of amisulpride; or (g) less than about 0.02 milliseconds (ms) per 10 mg of amisulpride; and/or (3) the modified release composition when administered to a subject population provides a population average maximum QTcF interval prolongation over the time period of 12 hours after administration of: (a) less than about 10 milliseconds (ms); (b) less than about 9 milliseconds (ms); (c) less than about 8 milliseconds (ms); (d) less than about 7 milliseconds (ms); (e) less than about 6 milliseconds (ms); or (f) less than about 5 milliseconds (ms); and/or (4) the modified release composition when administered to a subject population provides a population average maximum QT interval prolongation over the time period of 12 hours after administration, that compared to a comparable immediate release formulation is: (a) at least about 75% less than that of said immediate release composition; (b) at least about 65% less than that of said immediate release composition; (c) at least about 60% less than that of said immediate release composition; (d) at least about 55% less than that of said immediate release composition; or (e) at least about 50% less than that of said immediate release composition; and/or (5) the modified release composition when administered to a subject population provides about 27 hours after said administration a population average occupancy of dopamine $D_2$ receptors between about 20% and about 60%; and/or (6) the modified release composition when administered to a subject population provides a population average occupancy of dopamine D2 receptors that, compared to an immediate release composition having the same total daily amount of amisulpride as the pharmaceutical composition, is (a) at least 85% of the dopamine D2 receptors occupancy of said immediate release composition; (b) at least 90% of the dopamine D2 receptors occupancy of said immediate release composition; or (c) at least 95% of the dopamine D2 receptors occupancy of said immediate release composition; and/or (7) the modified release composition when administered to a subject population provides, compared to an immediate release composition having the same total daily amount of amisulpride as the pharmaceutical composition, (A) a population average occupancy of dopamine D2 receptors at about 27 hours after administration that is at least 85% of the dopamine D2 receptors occupancy of said immediate release composition, (B) a blood plasma Cmax of amisulpride that is less than about 80% of the Cmax of said immediate release composition; and (C) a AUC from 0 to 24 hours after administration ($AUC_{0-24}$) of amisulpride that is (a) less than about 80% of the $AUC_{0-24}$ of said immediate release composition; and/or (8) the solid oral dosage form, when dissolution tested using a two-stage in vitro gastrointestinal simulation dissolution test described in Table 5, releases (a) less than about 40% of amisulpride after 1 hour, more than about 20% and less than about 60% of amisulpride agent after 3 hours, and more than about 30% and less than 100% of amisulpride after 6 hours; (b) less than about 30% of amisulpride after 1 hour, more than about 20% and less than about 60% of amisulpride after 3 hours, and more than about 30% and less than about 75% of amisulpride after 6 hours; (c) less than about 20% of amisulpride after 1 hour, more than about 20% and less than about 50% of amisulpride after 3 hours, and more than about 30% and less than about 75% of amisulpride after 6 hours; (d) more than about 30% and less than about 50% of amisulpride after 6 hours; (e) between about 30% and 75% of amisulpride after about 3 hours and more than about 75% of amisulpride after about 12 hours; or (f) more than about 75% of amisulpride after about 6 hours; and/or (9) the modified release composition, when administered to a subject population, is effective in minimizing fluctuations between Cmin and Cmax of amisulpride; and/or

(10) the modified release composition used in treating the psychiatric disorder is effective in minimizing the difference between Cmin and Cmax of amisulpride compared to the immediate release composition having the composition of Table 25 and the same total daily amount of amisulpride as the modified release pharmaceutical composition, wherein the value of Cmin is that at about 9 hours after administration; and/or

(11) the modified release composition used in treating the psychiatric disorder is effective in minimizing the difference between Cmin and Cmax of amisulpride compared to the immediate release composition having the composition of Table 25 and the same total daily amount of amisulpride as the modified release pharmaceutical composition, wherein the values of Cmax and Cmin are determined within about 9 hours after administration; and/or

(12) the modified release composition, when administered to a subject population, is effective in providing a ratio of Cmax/Cmin of amisulpride that is less than about 2, less than about 1.9, or less than about 1.8, wherein the value of Cmin is that at about 9 hours after administration, where in various embodiments the values of Cmax and Cmin are the population geometric mean values; and/or

(13) the modified release composition, when administered to a subject population, is effective in providing a population Cmax/Cmin ratio of amisulpride that is less than about 2, less than about 1.9, or less than about 1.8, wherein the values of Cmax and Cmin are determined within about 9 hours after administration, where in various embodiments the values of Cmax and Cmin are the population geometric mean values; and/or

(14) when the modified release composition is administered to a subject population (i) the area under the curve (AUC) of blood plasma concentration versus time of amisulpride from administration to Tmax ($AUC_{0-Tmax}$) is less than about 19%, less than about 18%, less than about 17%, less than about 16%, less than about 15%, less than about 14%, less than about 13%, or less than about 12% of the area under the curve from administration to 48 hours ($AUC_{0-48}$); and (ii) Tmax of amisulpride is between about 4 and about 6 hours after administration; and/or

(15) when the modified release composition is administered to a subject population (i) the area under the curve (AUC) of blood plasma concentration versus time of amisulpride from administration to Tmax ($AUC_{0-Tmax}$) is less than about 17%, less than about 16%, less than about 15%, less than about 14%, less than about 13%, or less than about 12% of the area under the curve from administration to "infinity" ($AUC_{0-INF}$), and (ii) Tmax of amisulpride is between about 4 and about 6 hours after administration; and/or

Figure 22A:
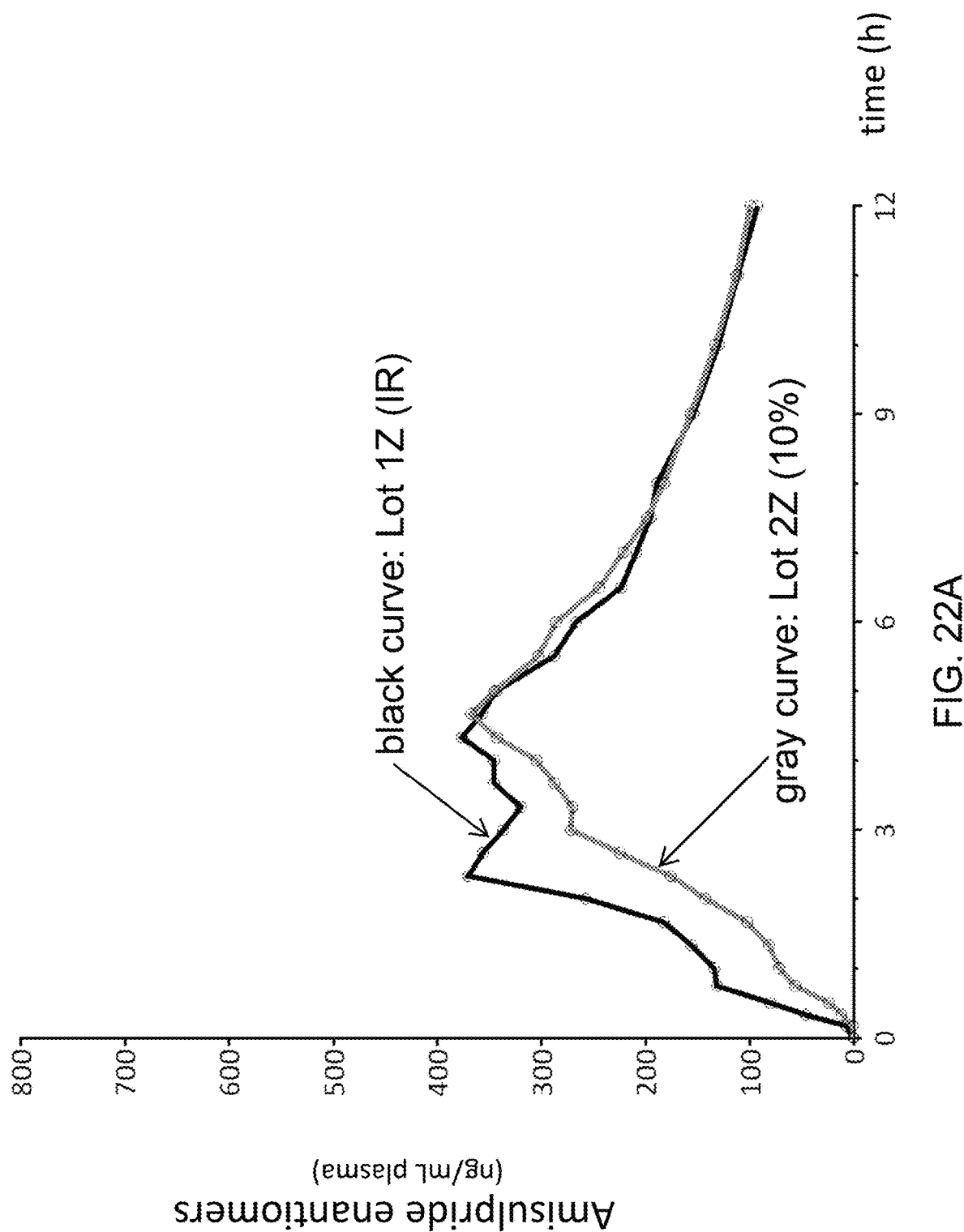
FIGS. 22A-FIG. 22K present data on the average blood plasma concentration over time from the human clinical studies of Example 7A for various modified releases pharmaceutical compositions compared to the immediate release formulation (Lot 1Z) used in the study.
Figure 22B:
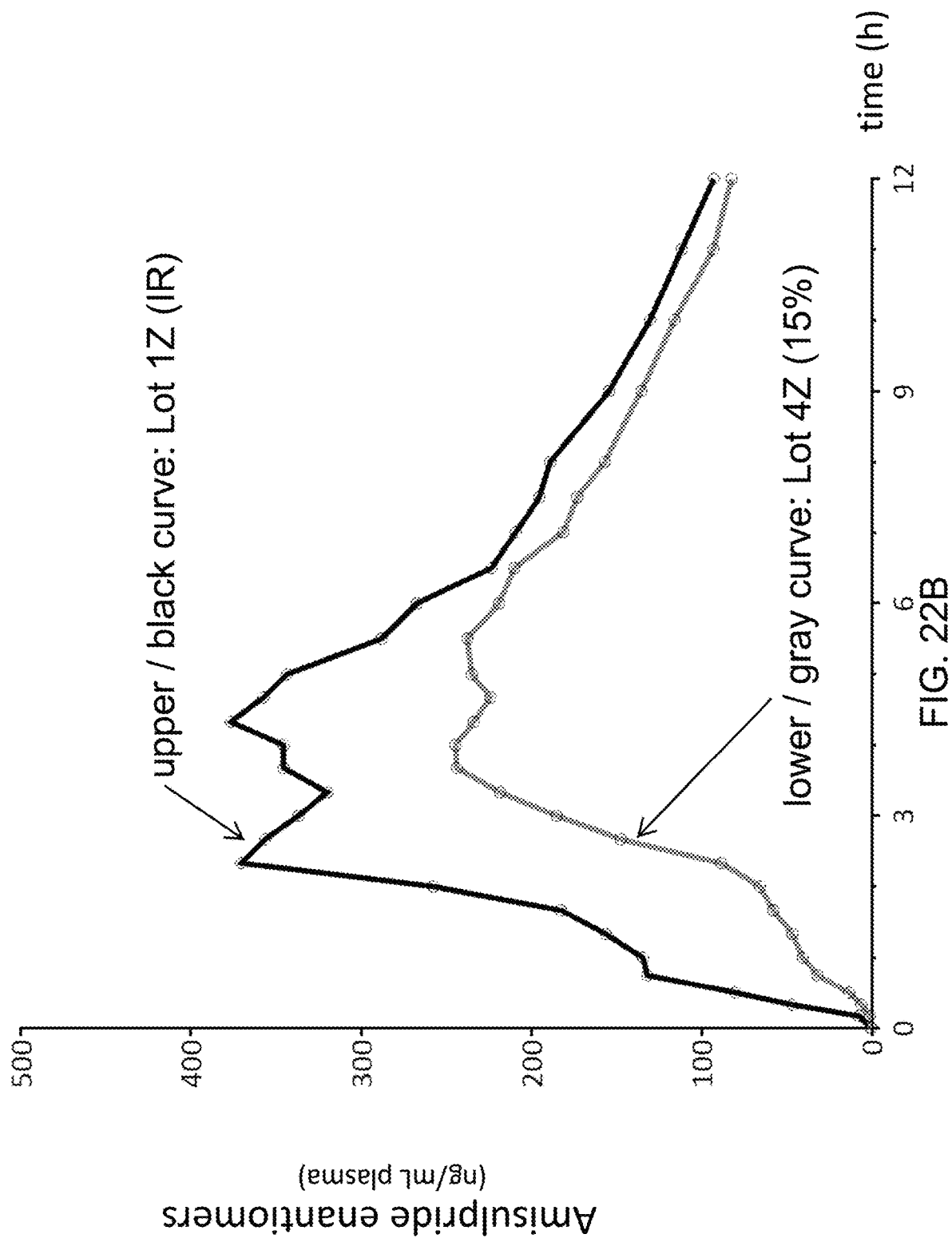
Figure 22C:
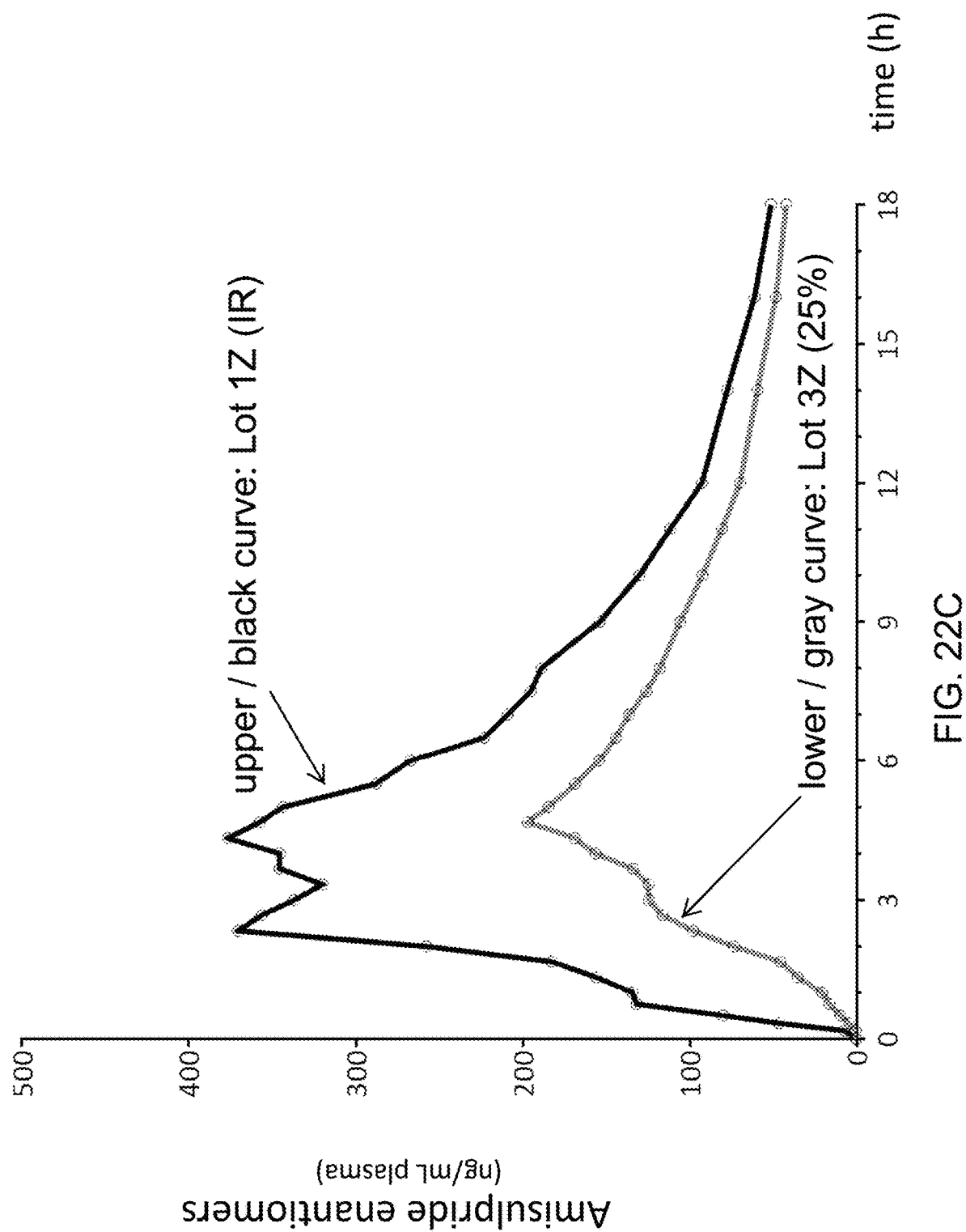
Figure 22D:
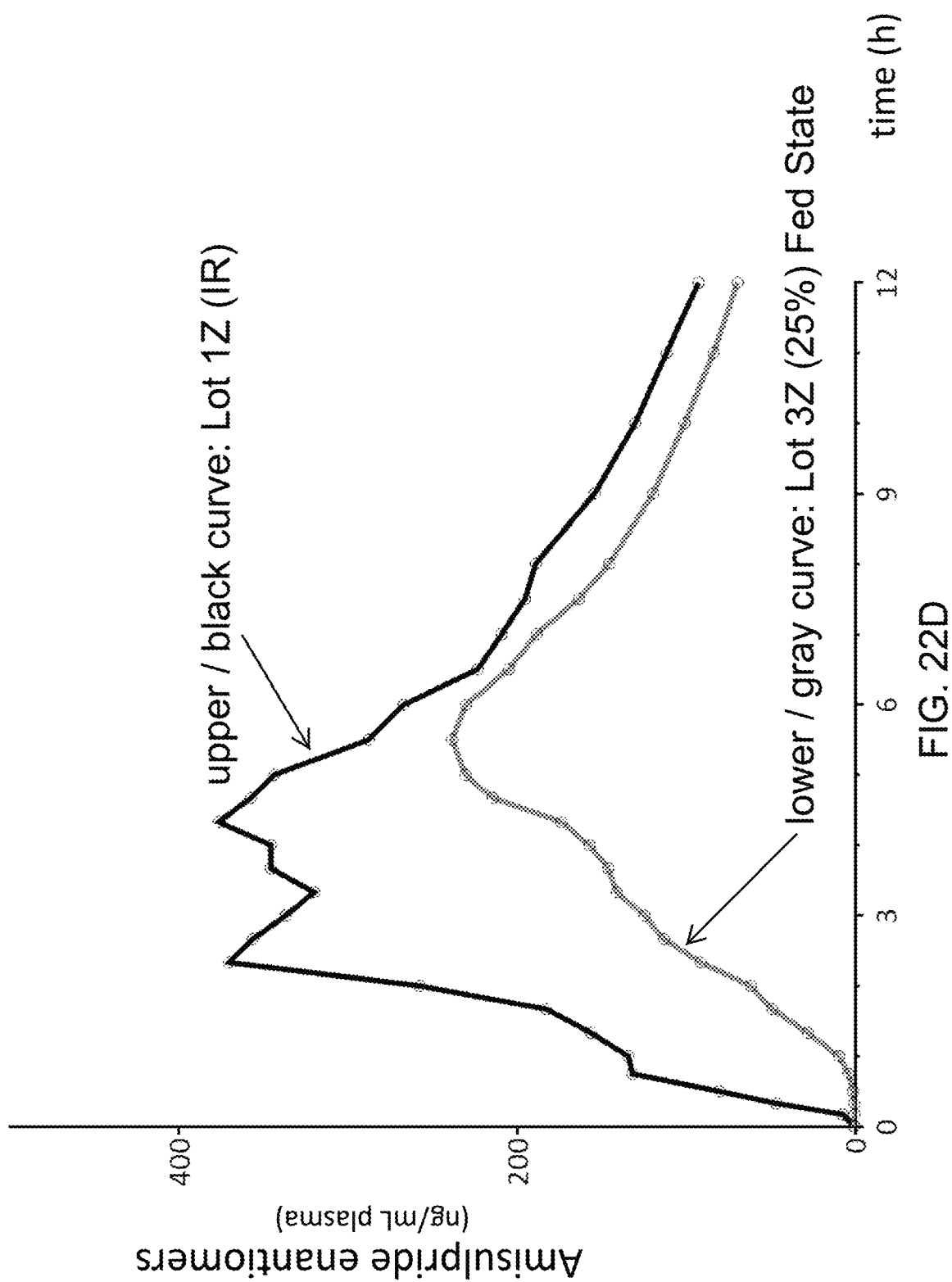
Figure 22E:
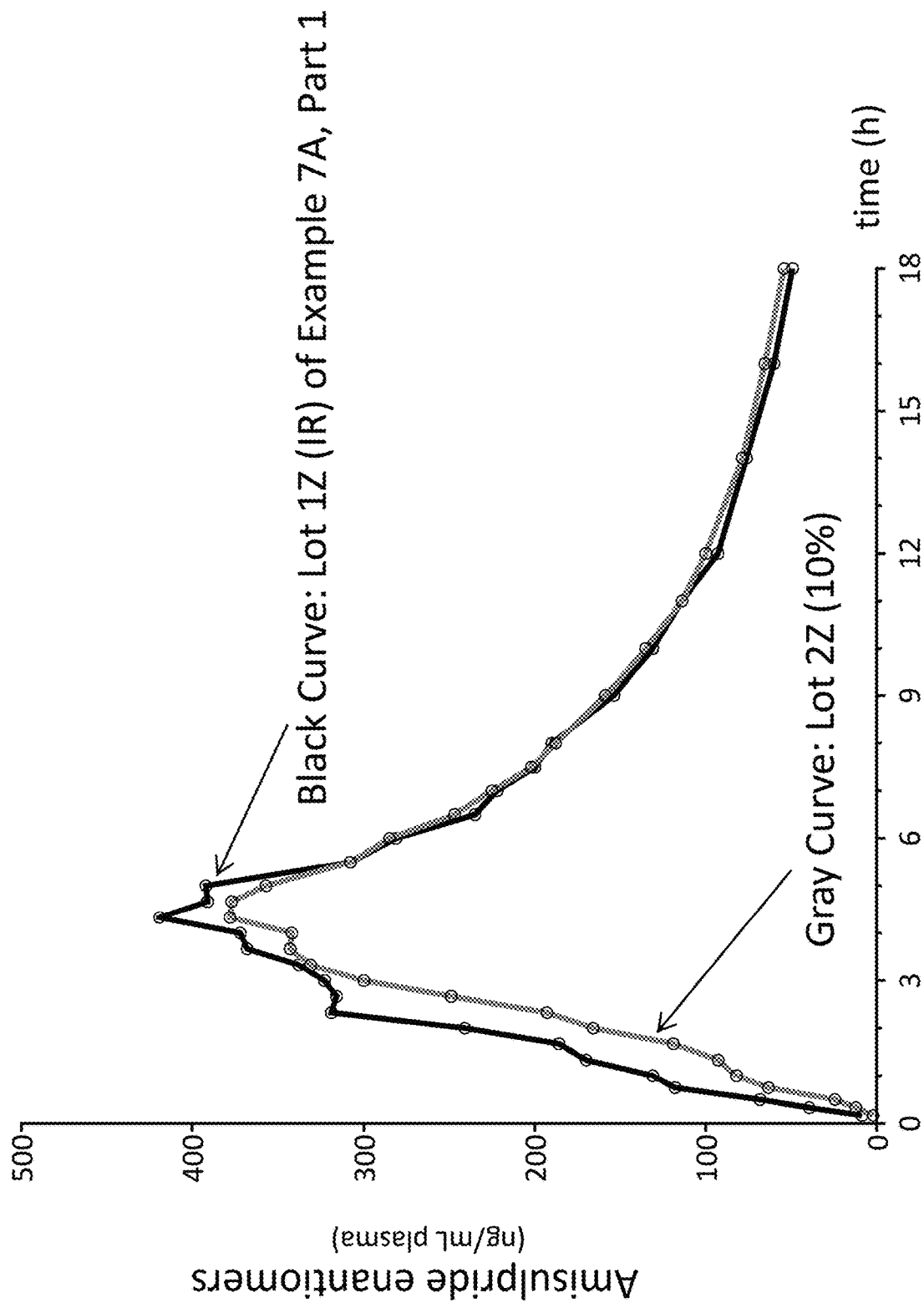
Figure 22F:
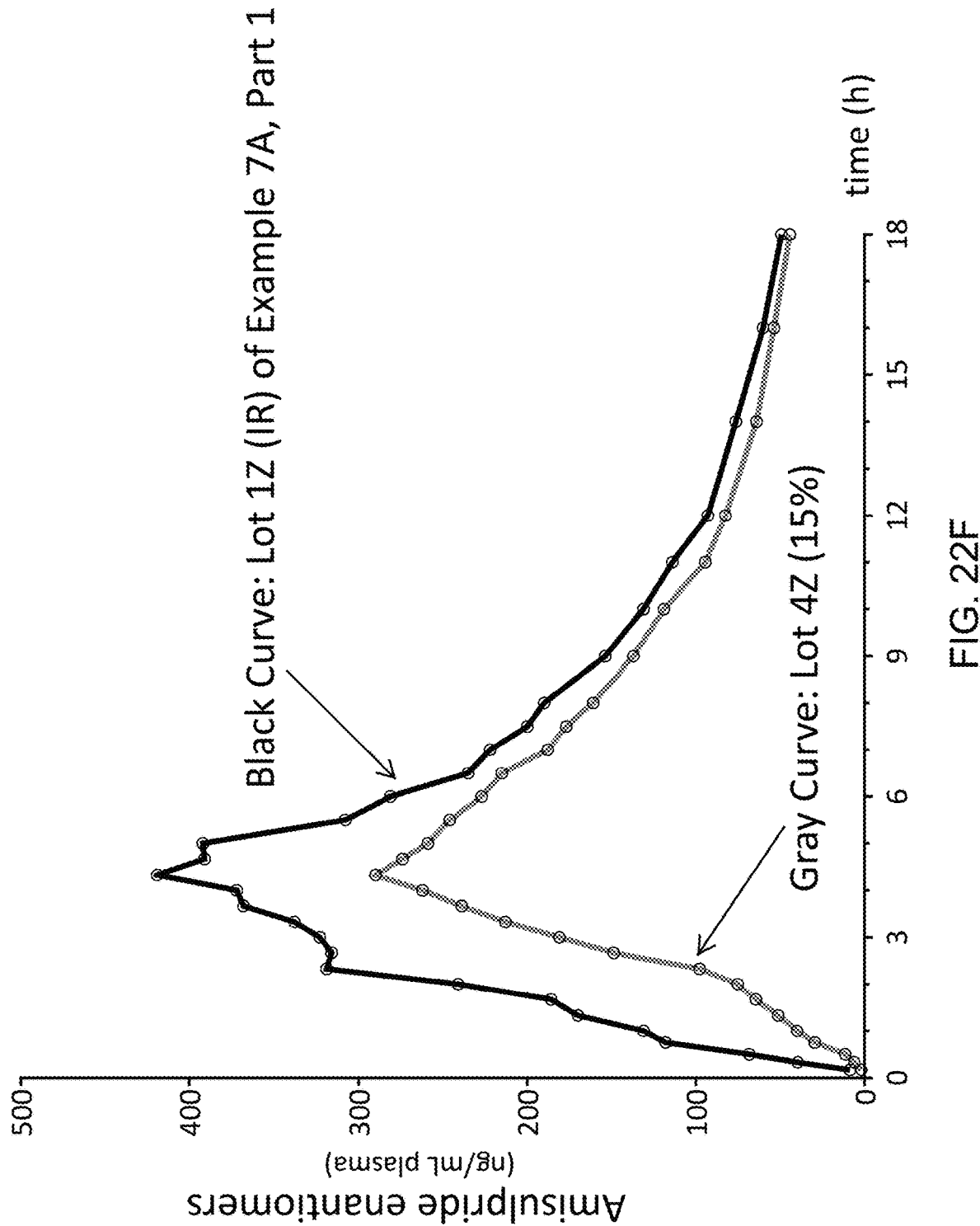
Figure 22G:
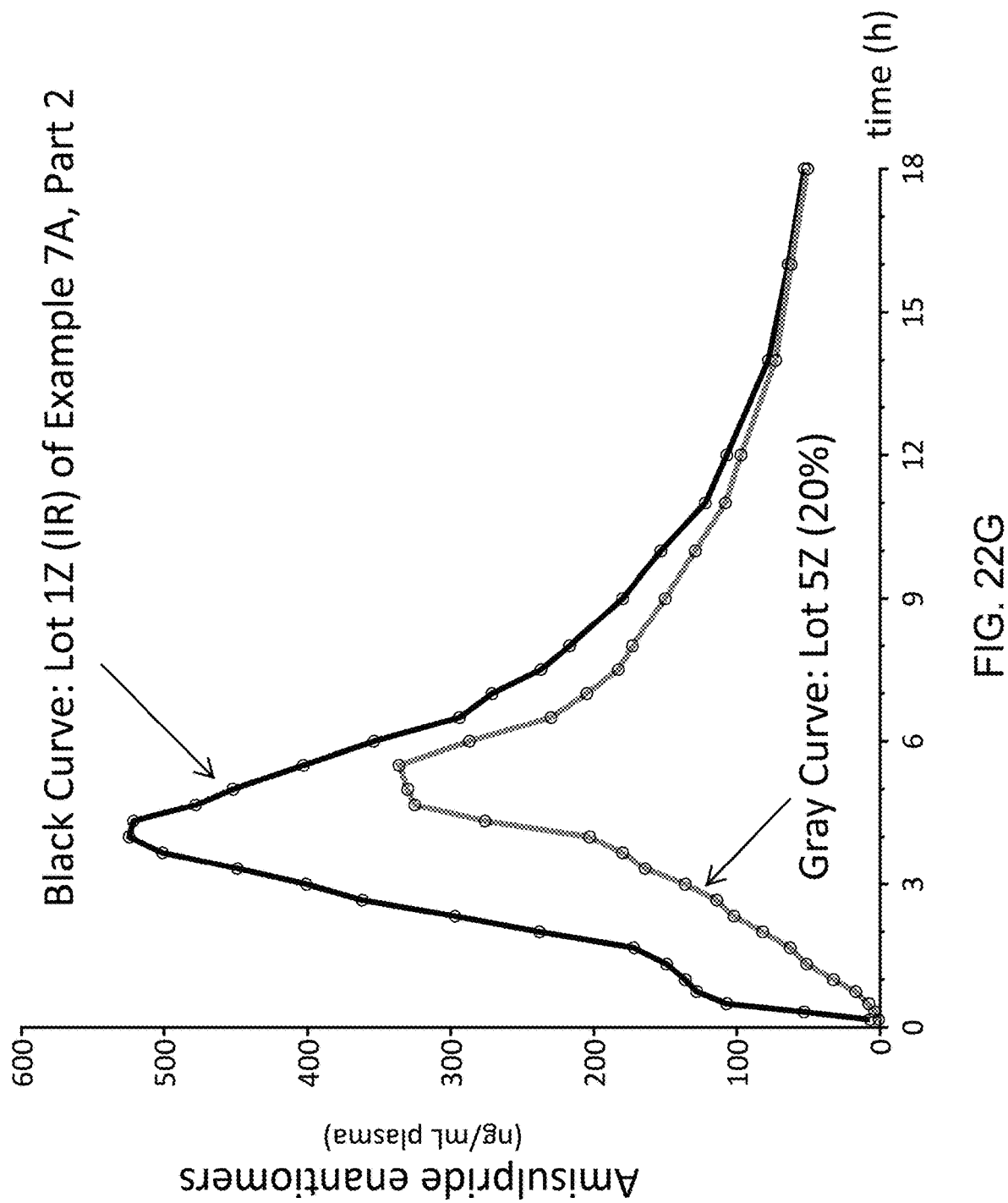
Figure 22H:
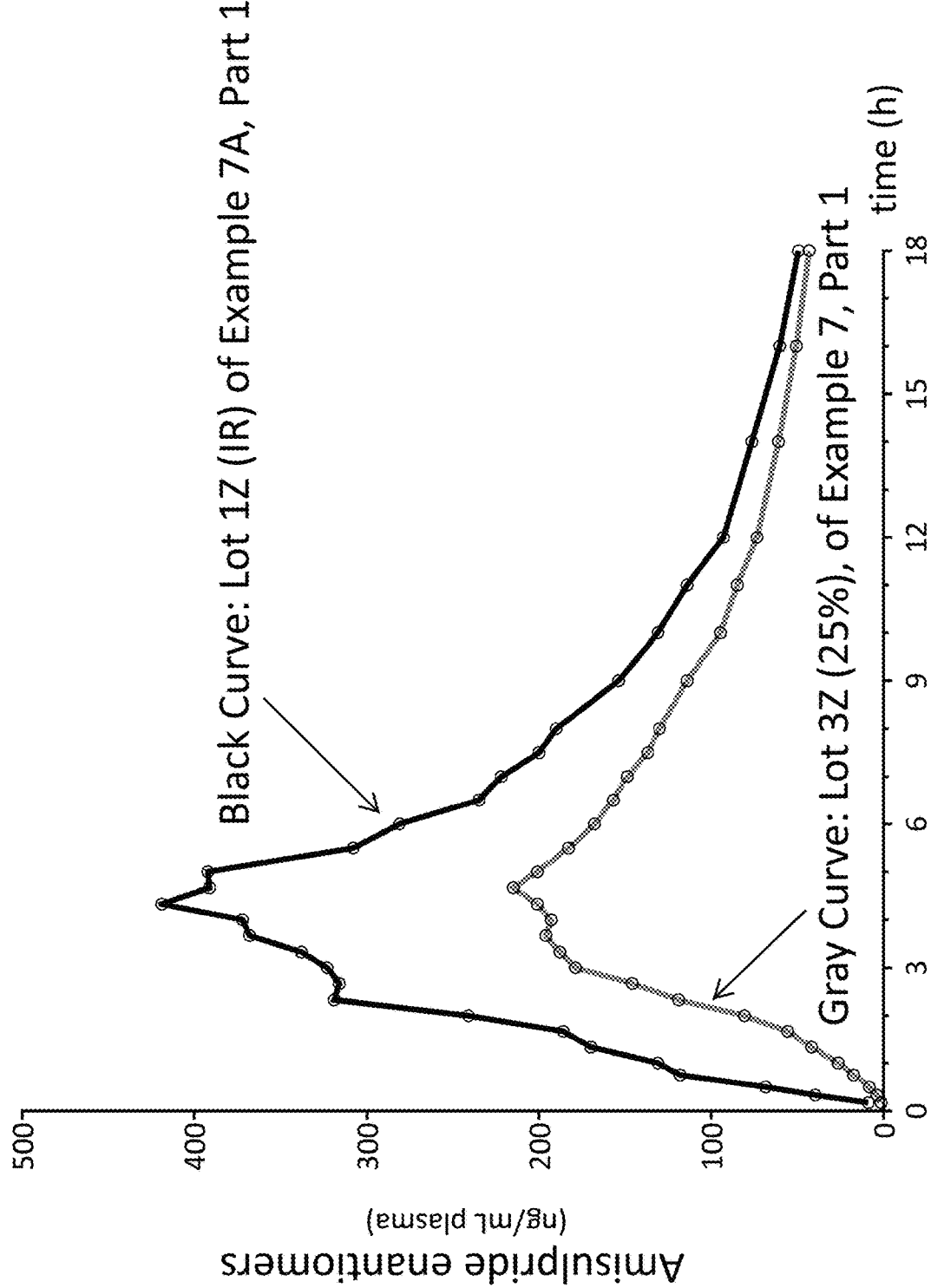
Figure 22I:
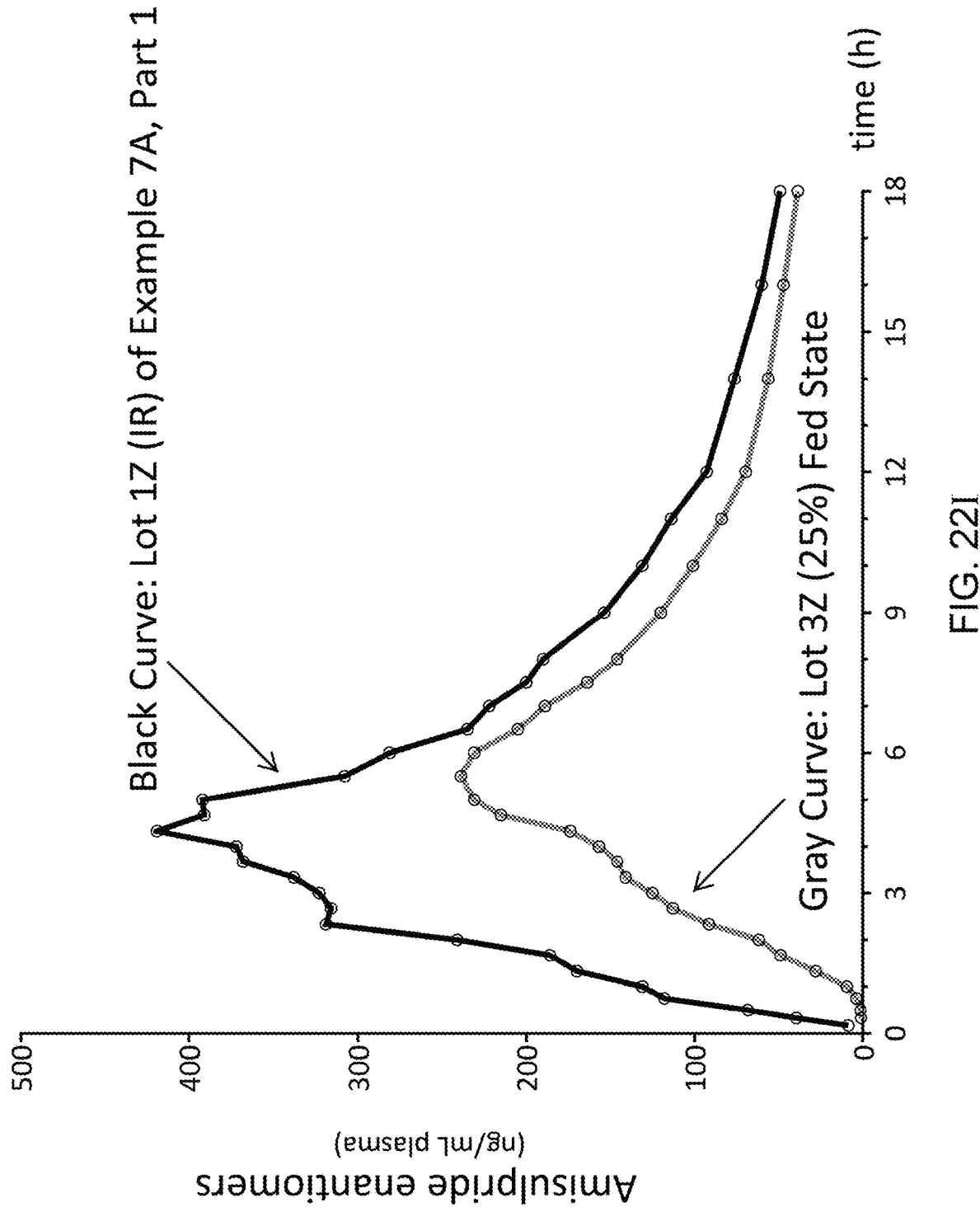
Figure 22J:
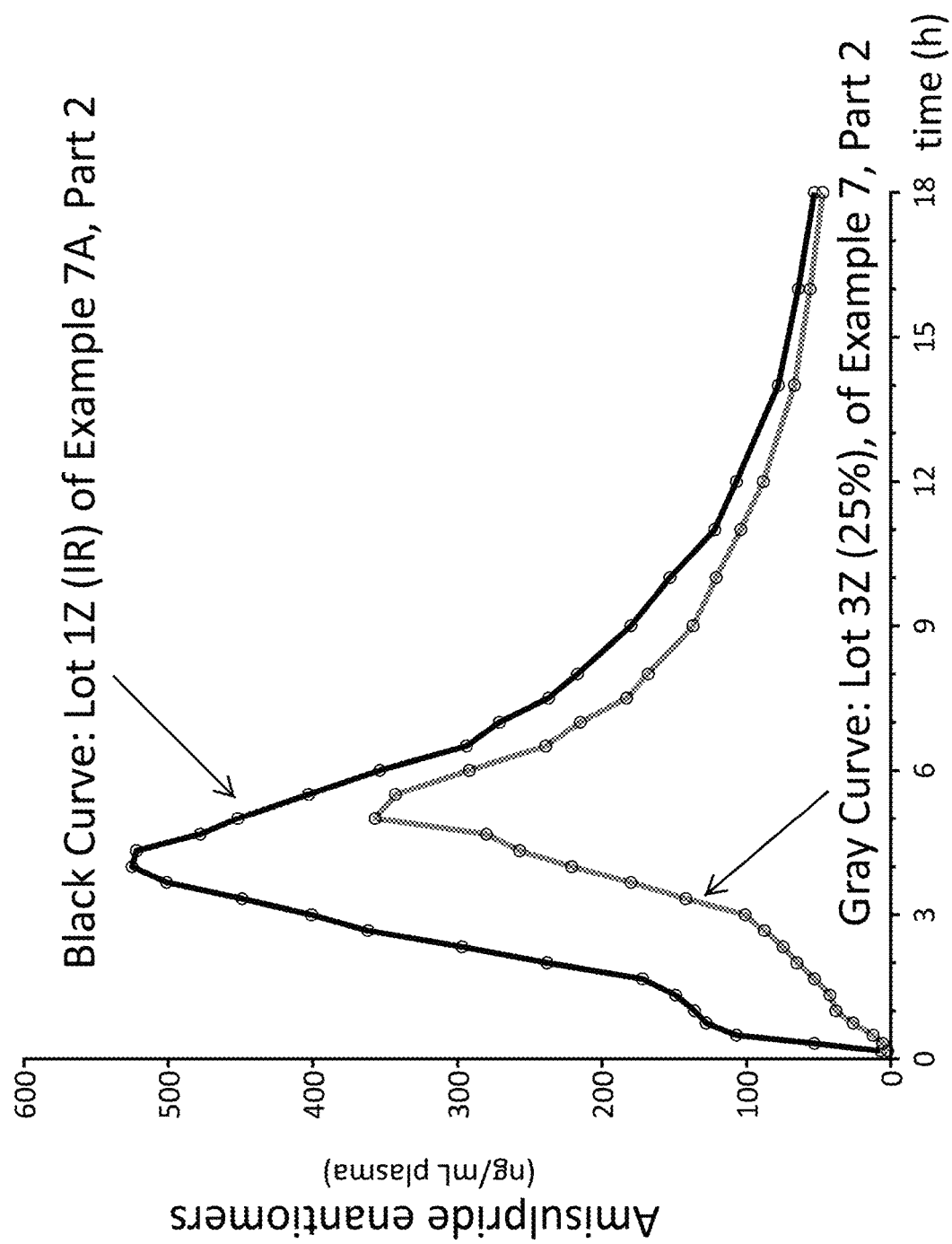

(16) the modified release composition when administered to a subject population provides a plasma concentration profile substantially the same as the profile of Lot 4Z in FIG. 22B, Lot 4Z in FIG. 22F, Lot 3Z in FIG. 22C, Lot 3Z in FIG. 22H, Lot 3Z in FIG. 22J, Lot 3Z with subjects in a fed state in FIG. 22I, Lot 3Z Fed State in FIG. 22D; and/or

Figure 22K:
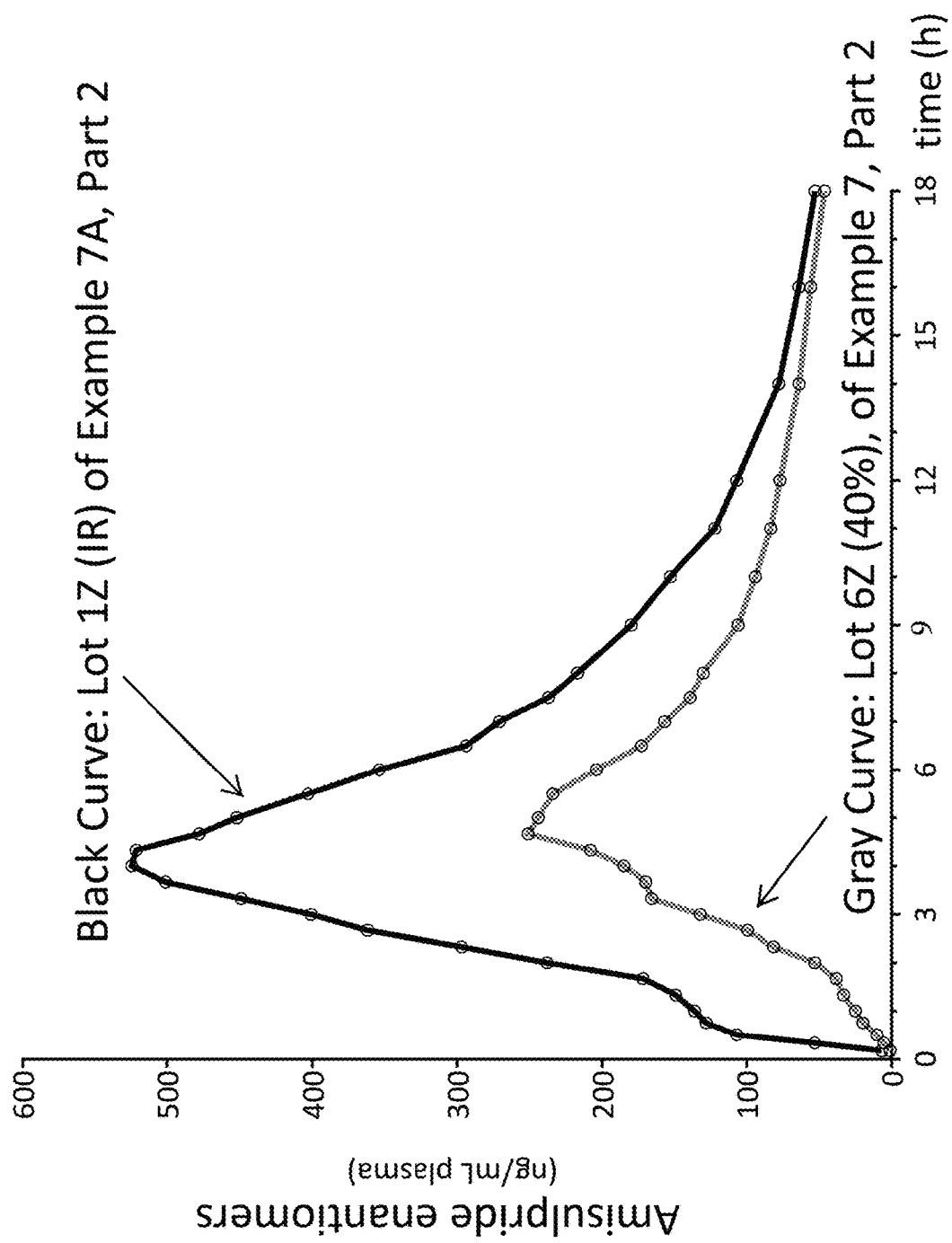

(17) the modified release composition when administered to a subject population provides a plasma concentration profile substantially the same as the profile of Lot 5Z in FIG. 22G, or Lot 6Z in FIG. 22K; and/or

(18) the modified release composition when administered to a subject population provides a blood plasma Cmax of amisulpride that is less than about 75%, 70%, 65%, 60%, 55%, or 50% of the Cmax achieved by the immediate release composition described in Table 25 and having the same total daily amount of amisulpride as in the modified release composition; and/or

(19) the modified release composition when administered to a subject population provides (i) when said administration is about 200 mg per day, provides a population geometric mean Cmax of (a) less than about 350 ng/mL; (b) less than about 300 ng/mL; or (c) less than about 250 ng/mL; and/or (ii) when said administration is about 400 mg per day, a population geometric mean Cmax of (a) less than about 500 ng/mL; (b) less than about 475 ng/mL; or (c) less than about 450 ng/mL; and/or

(20) the modified release composition comprises about 200 mg of total amisulpride and when administered to a subject population results in a maximum QT interval prolongation over the time period of 12 hours after administration of: (a) less than about 10 milliseconds (ms); (b) less than about 9 milliseconds (ms); (c) less than about 8 milliseconds (ms); (d) less than about 7 milliseconds (ms); (e) less than about 6 milliseconds (ms); or (f) less than about 5 milliseconds (ms); and/or

(21) the modified release composition comprises about 200 mg of total amisulpride and when administered to a subject population provides a QT interval prolongation at geometric mean Cmax that is: (a) less than about 10 milliseconds (ms); (b) less than about 9 milliseconds (ms); (c) less than about 8 milliseconds (ms); (d) less than about 7 milliseconds (ms); (e) less than about 6 milliseconds (ms); or (f) less than about 5 milliseconds (ms).

In various embodiments, the disorder is one or more of a mood disorder, bipolar disorder (BPD), depression, bipolar depression, major depressive disorder (MDD), as an adjunctive treatment of major depressive disorder, major depressive disorder with mixed features (MDD-MF), treatment resistant depression (TRD), schizophrenia, negative symptoms of schizophrenia, and schizoaffective disorder. In various embodiments, the provided are medicaments and methods for treatment of major depressive episodes associated with bipolar I disorder.

Treatment Cycle

It is to be understood that the modified release compositions can be administered over a treatment cycle as a single dosage unit form, comprising both (R)-amisulpride and the (S)-amisulpride enantiomers, in separate modified release dosage unit forms comprising only one of the amisulpride enantiomers, or a combination thereof. For example, in various embodiments, the (R)-amisulpride, or a pharmaceutically acceptable salt thereof, and the (S)-amisulpride, or a pharmaceutically acceptable salt thereof, are given separately during a treatment cycle.

In addition, it is to be understood that the administration of an amount of amisulpride over a treatment cycle may be provided in a multiple dosage regimen. For example, in various embodiments, a multiple dosage regimen comprises dosage with two or more modified release dosage unit forms substantially simultaneously; dosage with two or more modified release dosage unit forms sequentially; dosage with two or more modified release dosage unit forms within a period of time from one another, in various embodiments within 4 to 48 hours from one another; and combinations thereof.

For example, in various embodiments, the treatment cycle is two days, where the total S-enantiomer dosage amount is given once per treatment cycle (to, for example, maintain $D_2$ occupancy at therapeutic levels) and the total R-enantiomer dosage amount is given up to three times per day (e.g. up to six times per treatment cycle at roughly equally spaced intervals), in various embodiments in roughly equal dosage amounts per dose (to, for example, maintain desired plasma levels and have 5-HT7 effects throughout the day).

In various embodiments, the treatment cycle is daily and the administration occurs: (a) once per day; (b) twice per day; (c) thrice per day; or (d) four times per day. In various embodiments, the treatment cycle is every two days.

In various embodiments, the enantiomeric ratio of (R)-(+)-amisulpride to (S)-(−)-amisulpride, of the ratio portion of the modified release compositions, over a treatment cycle is about 85:15 by weight of the free base, the treatment cycle is daily and the total amount of (R)-(+)-amisulpride and (S)-(−)-amisulpride is about 200 mg over the treatment cycle. In various embodiments, the enantiomeric ratio of (R)-(+)-amisulpride to (S)-(−)-amisulpride over a treatment cycle is about 85:15 by weight of the free base, the treatment cycle is daily and the total amount of (R)-(+)-amisulpride and (S)-(−)-amisulpride is about 400 mg over the treatment cycle.

Polymorphs/Crystal Forms

It is to be understood, that in various embodiments that one or both of the enantiomeric amisulprides used in the various compositions, formulations, methods and medicaments is a crystalline form of the free base of the enantiomeric amisulpride of crystalline Forms A and Form A' as described in FIGS. 11A-11C and 12A-12D. In various embodiments, the (R)-(+)-amisulpride is crystalline (R)-(+)-amisulpride of crystal Form A; the (S)-(−)-amisulpride is crystalline (S)-(−)-amisulpride of crystal Form A', or both.

In various embodiments the enantiomeric amisulpride is provided in one or more of high polymorph purity, chiral purity, and chemical purity.

In various embodiments, the (R)-(+)-amisulpride is crystalline (R)-(+)-amisulpride of crystal Form A and has greater than about 95% chemical purity; the (S)-(−)-amisulpride is crystalline (S)-(−)-amisulpride of crystal Form A' and has greater than about 95% chemical purity, or the (R)-(+)-amisulpride is crystalline (R)-(+)-amisulpride of crystal Form A having a greater than about 95% chemical purity and the (S)-(−)-amisulpride is crystalline (S)-(−)-amisulpride of crystal Form A' having greater than about 95% chemical purity.

In various embodiments, crystalline forms of the present inventions have several advantageous physical properties. For example, in contrast to (S)-amisulpride D-tartrate crystalline forms, the (R)-amisulpride Form A and (S)-amisulpride Form A' crystalline forms are substantially non-hygroscopic, exhibiting less than a 0.5% maximum mass change in water sorption isotherms, at 25° C. scanned over 0 to 95% relative humidity, as measured by dynamic vapor sorption (DVS), whereas crystalline (S)-amisulpride D-tartrate was found to be highly hygroscopic, exhibiting a 52±9% (n=4, σ=18.25) maximum mass change in water sorption isotherms, at 25° C. scanned over 0 to 95% relative humidity, as measured by DVS.

The abbreviation "DSC" refers to differential scanning calorimetry, the abbreviation XRPD refers to x-ray powder diffraction, the abbreviation NMR refers to nuclear magnetic resonance, the abbreviation DVS refers to, dynamic vapor sorption, the abbreviation HPLC refers to high performance liquid chromatography, and the abbreviation GC refers to gas chromatography. The abbreviations (R)-(+)-amisulpride and (R)-amisulpride refer to R-4-Amino-N-[(1-ethyl-2-pyrrolidinyl)methyl]-5-(ethylsulfonyl)-2-methoxybenzamide. The abbreviations (S)-(−)-amisulpride and (S)-amisulpride refer to S-4-Amino-N-[(1-ethyl-2-pyrrolidinyl)methyl]-5-(ethylsulfonyl)-2-methoxybenzamide.

As used herein the term "polymorph purity" refers to the weight % that is the specified polymorph form. For example, when a crystalline (R)-amisulpride Form A is characterized as having greater than 95% polymorph purity, that means that greater than 95% by weight of the substance is crystalline (R)-amisulpride of Form A and less than 5% by weight of any other polymorph or amorphous form of (R)-amisulpride.

As used herein the terms "chiral purity" and "enantiomeric purity" are used interchangeably and refers to the weight % that is the specified enantiomer. For example, when a (R)-amisulpride containing substance (such as a compound or crystal) is characterized as having greater than 90% chiral purity, that means that greater than 95% by weight of the amisulpride in the substance is the (R)-amisulpride and less than 5% by weight is in any other enantiomeric form of amisulpride.

As used herein the term "chemical purity" refers to the weight % that is the specified chemical entity, including specified polymorph form. For example, when a crystalline amisulpride Form A is characterized as having greater than 95% chemical purity, that means that greater than 95% by weight of the substance is crystalline amisulpride Form A and less than 5% by weight of other compound including other polymorphs.

For example, when a crystalline (R)-amisulpride Form A is characterized as having greater than 99% chemical purity and greater than 97% chiral purity, that means greater than 97% by weight of the substance is of enantiomeric form (R)-amisulpride Form A and less than 3% by weight of any other amisulpride enantiomer, and that greater than 99% by weight of the substance is amisulpride and less than 1% by weight of other compounds. For example, when a crystalline (R)-amisulpride Form A is characterized as having greater than 99% chemical purity, greater than 97% chiral purity and greater than 95% polymorph purity, that means that greater than 95% by weight of the substance is crystalline (R)-amisulpride of Form A and less than 5% by weight of any other polymorph or amorphous form of (R)-amisulpride, greater than 97% by weight of the substance is of enantiomeric form (R)-amisulpride and less than 3% by weight of any other amisulpride enantiomer, and that greater than 99% by weight of the substance is amisulpride and less than 1% by weight of other compounds.

Chemical purity may be characterized using a number of conventional analytical techniques, including but not limited to high performance liquid chromatography (HPLC) and gas chromatography (GC). Chiral purity (also known as enantiomeric purity) may be characterized using a number of conventional analytical techniques, including but not limited to chiral high performance liquid chromatography (HPLC). Water content may be characterized using a number of conventional analytical techniques, including but not limited to coulometric titration.

For example, in various embodiments, crystalline (R)-amisulpride of Form A, crystalline (S)-amisulpride of Form A', or both, are provided as active ingredients that have a greater than about 90% polymorph purity, greater than about 95% polymorph purity, greater than about 97% polymorph purity, greater than about 99% polymorph purity, greater than about 99.5% polymorph purity, greater than about 99.7% polymorph purity, or greater than about 99.9% polymorph purity.

For example, in various embodiments, crystalline (R)-amisulpride of Form A, crystalline (S)-amisulpride of Form A', or both, are provided as active ingredients that have a greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, crystalline (R)-amisulpride of Form A, crystalline (S)-amisulpride of Form A', or both, are provided that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents.

Disorders

The Diagnostic and Statistical Manual of Mental Disorders, Fifth Ed., hereinafter, the "DSM-5"), published by the American Psychiatric Association in 2013, and is incorporated herein by reference, provides a standard diagnostic system upon which persons of skill rely for diagnosis of various diseases and disorders.

In various aspects, the disease or disorder which the medicaments and methods treat comprises one or more of a psychiatric disorder; mood disorder; depressive disorder; bipolar disorder; bipolar depression (e.g. major depressive episodes associated with bipolar I disorder), schizophrenia; schizoaffective disorder; anxiety disorder; obsessive-compulsive disorder; behavior disturbances associated with a neurocognitive disorder; conduct disorder; neurological disorder; medication-induced movement disorder; and motor disorder.

In various embodiments, the neurological or psychiatric disease or disorder is one or more of a mood disorder, bipolar disorder (BPD), depression, bipolar depression, major depressive episodes associated with bipolar I disorder, major depressive disorder (MDD), as an adjunctive treatment of major depressive disorder, major depressive disorder with mixed features (MDD-MF), treatment resistant depression (TRD), schizophrenia, negative symptoms of schizophrenia, treatment resistant depression (TRD) and schizoaffective disorder.

In various embodiments, the neurological or psychiatric disease or disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (e.g., phencyclidine, ketamine and other dissociative anesthetics, amphetamine and other psychostimulants and cocaine) psychotic disorder, psychosis disorder, psychosis associated with affective disorders, brief reactive psychosis, schizoaffective psychosis, "schizophrenia-spectrum" disorders such as schizoid or schizotypal personality disorders, or illnesses with associated psychosis (such as major depression, manic depressive (bipolar) disorder, Alzheimer's disease and post-traumatic stress syndrome), including both positive, negative, and cognitive symptoms of schizophrenia and other psychoses; anxiety disorders including acute stress disorder, agoraphobia, generalized anxiety disorder, obsessive-compulsive disorder and related disorders including body dysmorphic disorder, hoarding disorder, trichotillomania, and excoriation disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, *Cannabis*, cocaine, hallucinogens, inhalants, nicotine, opioids, phencyclidine, sedatives, hypnotics or anxiolytics); eating disorders such as obesity, bulimia nervosa, pica and compulsive eating disorders; bipolar disorders, including, bipolar depression, bipolar I disorder, bipolar II disorder, cyclothymic disorder, substance/medication-induced bipolar and related disorders, bipolar and related disorder due to another medical condition, other specified bipolar and related disorder, and unspecified bipolar and related disorders, depressive disorders including, but not limited to, unipolar depression, seasonal depression and post-partum depression, atypical depression, catatonic depression, elderly depression, endogenous depression, melancholic depression, perinatal depression, situational depression, chronic depression, bipolar depression, major depressive disorder (MDD), as an adjunctive treatment MDD, major depressive disorder with anxious distress, MDD with mixed features (MDD-MF), MDD with melancholic features, MDD with atypical features, MDD with mood-congruent psychotic features, MDD with mood-incongruent psychotic features, MDD with catatonia, with peripartum onset, MDD with seasonal pattern, treatment resistant depression (TRD), and persistent depressive disorder (dysthymia), and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders; and sleep disorders including insomnia, disturbed sleep, jet lag, hypersomnia, cataplexy, sleep apnea, obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

Psychiatric disorders are pathological conditions of the brain characterized by identifiable symptoms that result in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity. Mood disorders are a type of psychiatric disorder often defined as a group of heterogeneous, typically recurrent illnesses including unipolar (depressive) and bipolar (manic-depressive) disorders characterized by pervasive mood disturbances, psychomotor dysfunction, and vegetative symptoms. Suicide, the most serious complication in patients with mood disorders, is the cause of death in 15 to 25% of untreated patients with mood disorders; unrecognized or inadequately treated depression contributes to 50 to 70% of all completed suicides.

The term "mood disorder" as used herein includes depression, major depression, major depressive disorder, mild depression, severe depression without psychosis, severe depression with psychosis, melancholia (formerly endogenous depression), atypical depression, dysthymic disorder, manic depression, bipolar disorder, bipolar depression (e.g. major depressive episodes associated with bipolar I disorder), bipolar I disorder, bipolar II disorder, bipolar III disorder, cyclothymic disorder, and chronic hypomania.

In various embodiments, the neurological or psychiatric disease or disorder is a bipolar disorder. Bipolar disorders (including both bipolar I and bipolar II) are serious psychiatric disorders that have a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although patients spend considerable more time in the depressive state. Other related conditions include cyclothymic disorder.

In bipolar I disorder, full-fledged manic and major depressive episodes alternate. Bipolar I disorder commonly begins with depression and is characterized by at least one manic or excited period during its course. The depressive phase can be an immediate prelude or aftermath of mania, or depression and mania can be separated by months or years.

In bipolar II disorder, depressive episodes alternate with hypomanias (relatively mild, nonpsychotic periods of usually <1 week). During the hypomanic period, mood brightens, the need for sleep decreases, and psychomotor activity accelerates beyond the patient's usual level. Often, the switch is induced by circadian factors (e.g., going to bed depressed and waking early in the morning in a hypomanic state). Hypersomnia and overeating are characteristic and may recur seasonally (e.g., in autumn or winter); insomnia and poor appetite occur during the depressive phase. For some persons, hypomanic periods are adaptive because they are associated with high energy, confidence, and supernormal social functioning. Many patients who experience pleasant elevation of mood, usually at the end of a depression, do not report it unless specifically questioned.

Patients with major depressive episodes and a family history of bipolar disorders often exhibit subtle hypomanic tendencies; their temperament is termed hyperthymic (i.e., driven, ambitious, and achievement-oriented).

In cyclothymic disorder, less severe hypomanic and mini-depressive periods follow an irregular course, with each period lasting a few days. Cyclothymic disorder is commonly a precursor of bipolar II disorder. But it can also occur as extreme moodiness without being complicated by major mood disorders. In such cases, brief cycles of retarded depression accompanied by low self-confidence and increased sleep alternate with elation or increased enthusiasm and shortened sleep. In another form, low-grade depressive features predominate; the bipolar tendency is shown primarily by how easily elation or irritability is induced by antidepressants. In chronic hypomania, a form rarely seen clinically, elated periods predominate, with habitual reduction of sleep to <6 hours. Persons with this form are constantly overcheerful, self-assured, overenergetic, full of plans, improvident, overinvolved, and meddlesome; they rush off with restless impulses and accost people.

Accordingly, in various embodiments, the neurological or psychiatric disease or disorder is one or more of bipolar I disorder, bipolar II disorder, cyclothymic disorder, other specified bipolar and related disorder, or unspecified bipolar and related disorder, and bipolar I disorder or bipolar II disorder with the specifiers of anxious distress, with mixed features, with rapid cycling, with melancholic features, with atypical features, with mood-congruent psychotic features, with mood incongruent psychotic features, with catatonia, with peripartum onset, and/or with seasonal pattern. A relatively recent article by Hu et al [*Prim Care Companion CNS Disord.* 2014; 16(2): PCC.13r01599] highlights that bipolar disorder, while commonly encountered in the primary care setting, is often misdiagnosed or undiagnosed. The DSM-5 attempts to capture the large proportion of patients with subsyndromal mixed symptoms with the inclusion of the mixed specifier.

In various embodiments, the neurological or psychiatric disease or disorder is a depressive disorder. Depressive disorders include, but are not limited to, depressive disorders including, but not limited to, unipolar depression, seasonal depression and post-partum depression, atypical depression, catatonic depression, elderly depression, endogenous depression, melancholic depression, perinatal depression, situational depression, chronic depression, bipolar depression (e.g., major depressive episodes associated with bipolar I disorder), major depressive disorder (MDD), major depressive disorder with mixed features (MDD-MF), treatment resistant depression (TRD), and dysthymia, and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders.

Depression is an affective disorder, the pathogenesis of which cannot be explained by any single cause or theory. Unfortunately, treatment options for depressed patients who have suboptimal clinical responses to therapy with an antidepressant are limited. Approximately thirty percent (30%) of patients initiating antidepressant therapy show suboptimal or delayed clinical responses to the first-line antidepressant agents that are commonly used to treat depression.

Typically, if a patient exhibits suboptimal or delayed clinical response after several weeks of therapy with an antidepressant, the clinician's initial approach is to increase the dose of the antidepressant. If the patient's response remains unsatisfactory after increasing the dose, the most common approaches that many clinicians will pursue are: a) switching to another antidepressant; or b) adding a second antidepressant; or c) attempting an augmentation therapy by administering agents such as lithium carbonate, thyroid hormone (triiodothyronine), psychostimulants, modafinil, atypical antipsychotics, buspirone, or pindolol.

In its full syndromal expression, clinical depression manifests as major depressive disorder, with episodic course and varying degrees of residual manifestations between episodes. The mood is typically depressed, irritable, and/or anxious. The patient may appear miserable, with furrowed brows, downturned corners of the mouth, slumped posture, poor eye contact, and monosyllabic (or absent) speech. The morbid mood may be accompanied by preoccupation with guilt, self-denigrating ideas, decreased ability to concentrate, indecisiveness, diminished interest in usual activities, social withdrawal, helplessness, hopelessness, and recurrent thoughts of death and suicide. Sleep disorders are common. In some, the morbid mood is so deep that tears dry up; the patient complains of an inability to experience usual emotions—including grief, joy, and pleasure—and of a feeling that the world has become colorless, lifeless, and dead.

Melancholia (formerly endogenous depression) is characterized by marked psychomotor slowing (of thinking and activity) or agitation (e.g., restlessness, wringing of the hands, pressure of speech), weight loss, irrational guilt, and loss of the capacity to experience pleasure. Mood and activity vary diurnally, with a nadir in the morning. Most melancholic patients complain of difficulty falling asleep, multiple arousals, and insomnia in the middle of the night or early morning. Sexual desire is often diminished or lost. Amenorrhea can occur. Anorexia and weight loss may lead to emaciation and secondary disturbances in electrolyte balance.

In atypical depression, reverse vegetative features dominate the clinical presentation; they include anxious-phobic symptoms, evening worsening, initial insomnia, hypersomnia that often extends into the day, and hyperphagia with weight gain. Unlike patients with melancholia, those with atypical depression show mood brightening to potentially positive events but often crash into a paralyzing depression with the slightest adversity. Atypical depressive and bipolar II disorders overlap considerably.

In dysthymic disorder, depressive symptoms typically begin insidiously in childhood or adolescence and pursue an intermittent or low-grade course over many years or decades; major depressive episodes may complicate it (double depression). In pure dysthymia, depressive manifestations occur at a subthreshold level and overlap considerably with those of a depressive temperament: habitually gloomy, pessimistic, humorless, or incapable of fun; passive and lethargic; introverted; skeptical, hypercritical, or complaining; self-critical, self-reproaching, and self-derogatory; and preoccupied with inadequacy, failure, and negative events.

Thorough evaluation of many persons with depression reveals bipolar traits, and as many as one in five patients with a depressive disorder also develops frank hypomania or mania. Most switches from unipolar to bipolar disorder occur within 5 years of the onset of depressive manifestations. Predictors of a switch include early onset of depression (<25 years old), postpartum depression, frequent episodes of depression, quick brightening of mood with somatic treatments (e.g., antidepressants, phototherapy, sleep deprivation, electroconvulsive therapy), and a family history of mood disorders for three consecutive generations.

Between episodes, patients with bipolar disorder exhibit depressive moodiness and sometimes high-energy activity; disruption in developmental and social functioning in bipolar depression is more common than in unipolar disorder. In bipolar disorder, depression episodes are shorter (3 to 6 months), age of onset is younger, onset of episodes is more abrupt, and cycles (time from onset of one episode to that of the next) are shorter than in unipolar disorder. Cyclicity is particularly accentuated in rapid-cycling forms of bipolar disorder (usually defined as >=4 episodes/year). In addition depressive episodes in bipolar disorder are a difficult component of BPD to treat. For example, psychiatrists indicate that about 25% of patients across all bipolar disorders are refractory during a manic episode, while about 70% are refractory during a depressive episode.

Accordingly, in various embodiments, the neurological or psychiatric disease or disorder is one or more of bipolar depression, major depressive episodes associated with bipolar I disorder, major depressive disorder (MDD), persistent depressive disorder (Dysthymia), premenstrual dysphoric disorder (PMDD), major depressive disorder with mixed features (MDD-MF), depressive disorder due to another medical condition, other specified depressive disorder, unspecified depressive disorder, or treatment resistant depression (TRD), and MDD with the specifiers of anxious distress, with mixed features, with melancholic features, with atypical features, with mood-congruent psychotic features, with mood-incongruent psychotic features, with catatonia, with peripartum onset, and/or with seasonal pattern, and seasonal affective disorder.

It is to be understood that TRD is a term used in clinical psychiatry to describe cases of major depressive disorder (MDD) that do not respond adequately to appropriate courses of adequate dose and duration of at least two antidepressants.

In various embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In various embodiments, it is believed that the compositions and methods of the present inventions do not increase the risk of suicidal thinking and/or behavior in children, adolescents and/or young adults with a depressive disorder, e.g., with MDD. In various embodiments, the present inventions provide medicaments for and provide methods of treating one or more symptoms of a depressive disorder (e.g., MDD) in children, adolescents and/or young adults without increasing the risk of suicidal thinking and/or behavior.

In various embodiments, the neurological or psychiatric disease or disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making.

Accordingly, in various embodiments, the neurological or psychiatric disease or disorder is one or more of schizotypal (personality) disorder, delusional disorder, brief psychotic disorder, schizophreniform disorder, schizophrenia, schizoaffective disorder, substance/medication-induced psychotic disorder, psychotic disorder due to another medical condition, other specified schizophrenia spectrum and other psychotic disorder, unspecified schizophrenia spectrum, and other psychotic disorder.

It is to be understood that schizoaffective disorder includes a condition that includes aspects of both schizophrenia and a mood disorder, such as, for example, a major depressive disorder, a bipolar disorder, major depressive episodes associated with a bipolar disorder, etc.

In various embodiments, the neurological or psychiatric disease or disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

In various embodiments, the neurological or psychiatric disease or disorder is a sleep disorder including those sleep disorders which are produced by psychiatric conditions, including, but not limited to, insomnia, disturbed sleep, jet lag, hypersomnia, cataplexy, sleep related disorder (e.g., sleep apnea, insomnia, narcolepsy, cataplexy), obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

In various embodiments, the present inventions provide medicaments for and provide methods of suppressing rapid eye movement (REM) during both sleep and daytime equivalent.

In various embodiments, the present inventions provide medicaments for and provide methods of suppressing or eliminating pathological or excessive REM during the night or daytime equivalent.

In various embodiments, the neurological and/or psychiatric disease or disorders are obsessive-compulsive disorder and related disorders (e.g., body dysmorphic disorder, hoarding disorder, trichotillomania, excoriation disorder).

In various embodiments, the neurological and/or psychiatric diseases or disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

In various embodiments, the compositions, formulations, methods and medicaments may be used in combination with other therapies. Suitable therapies include, but are not limited to, psychotherapy, cognitive behavioral therapy, electroconvulsive therapy, transcranial magnetic stimulation, vagus nerve stimulation, and deep-brain stimulation.

Aspects, embodiments, and features may be further understood from the following examples, which should not be construed as limiting the scope of the inventions. Example 1 presents in vitro data, Examples 2 and 3 animal study data, and Examples 4-7 present human clinical data.

Example 1: In Vitro Assays of Dopamine D2 and Serotonin 5-HT7 Affinities

Amisulpride enantiomers and racemic amisulpride were tested for affinity to Dopamine $D_2$s receptors recombinantly expressed in human Chinese Hamster Ovary (CHO) cells by radioligand binding techniques (Eurofins Panlabs, Inc.). The receptors' $B_{max}$ value was 1.6 pmole/mg protein. The radioligand was [3H] Spiperone at 0.16 nM concentration with 0.090 nM dissociation constant (Kd, historical value under identical laboratory conditions). The incubation buffer was 50 mM Tris-HCl, pH 7.4, 1.4 mM ascorbic acid, 0.001% BSA, and 150 mM NaCl. The amisulpride compound under study (e.g., enantiomeric amisulprides and racemic amisulpride) was dissolved in dimethyl sulfoxide (DMSO) and added to the assay wells for a 1% final concentration. Percent inhibition values of specific binding by amisulpride enantiomers and racemic amisulpride were generated with 12 serial dilutions from 10 micromolar down to 3 nM final concentrations. Each concentration was tested in duplicate. Amisulpride enantiomer affinities and racemic amisulpride affinities for dopamine D2 receptors are based on the average of 3 independent experiments. Affinities were calculated with the Cheng-Prusoff equation and the observed IC50 of the tested compound, the concentration of radioligand employed in the assay, and the historical value for the Kd of the ligand (obtained experimentally).

Amisulpride enantiomers and racemic amisulpride were tested for affinity to Serotonin 5-$HT_7$ receptors recombinantly expressed in human CHO-K1 cells by radioligand binding techniques (Eurofins Panlabs, Inc.). The receptors' $B_{max}$ value was 0.95 pmole/mg protein. The radioligand is [3H]Lysergic acid diethylamide (LSD) at 5.5 nM concentration with 7.40 nM dissociation constant (Kd, historical value under identical laboratory conditions). The incubation buffer was 50 mM Tris-HCl, pH 7.4, 10 mM $MgCl_2$, 0.5 mM EDTA. The amisulpride compound under study (e.g., enantiomeric amisulprides and racemic amisulpride) was dissolved in DMSO and added to the assay wells for a 1% final concentration. Percent inhibition values of specific binding by amisulpride enantiomers and racemic amisulpride were generated with 12 serial dilutions from 10 micromolar down to 3 nM final concentrations. Each concentration was tested in duplicate. Amisulpride enantiomer affinities and racemic amisulpride affinities for serotonin 5-HT7 receptors are based on the average of 3 independent experiments. Affinities were calculated with the Cheng-Prusoff equation and the observed IC50 of the tested compound, the concentration of radioligand employed in the assay, and the historical value for the Kd of the ligand (obtained experimentally).

Percent inhibition of specific binding was determined as a function of test drug concentration (i.e., (R)-amisulpride (S)-amisulpride, and racemic amisulpride). It was discovered that there are distinct pharmacological activities with the potential for combined clinical benefit which reside in opposite enantiomers.

Figure 5B:
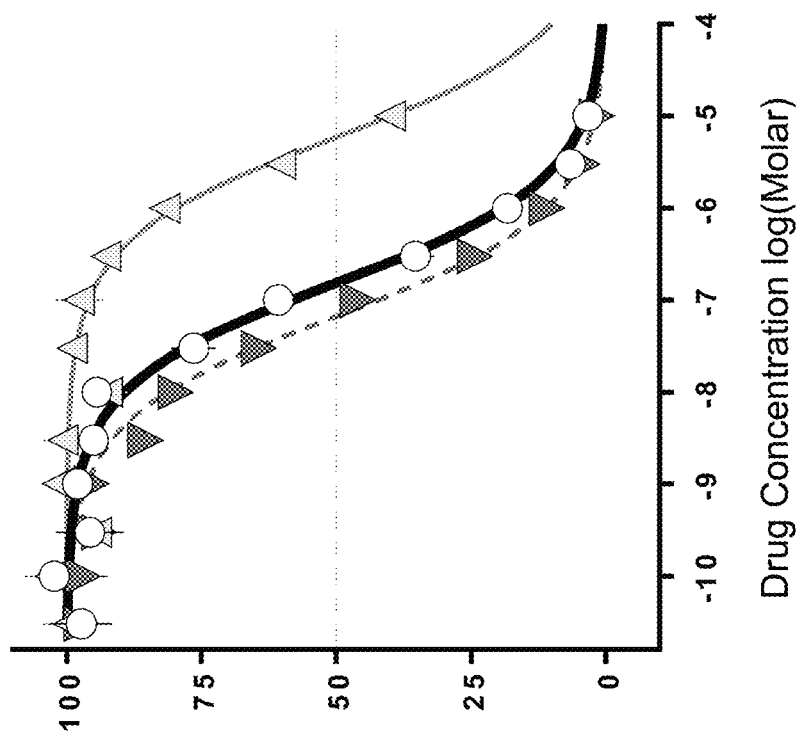
FIGS. 5A-5C present various analytical in vitro data for the inhibition of radioligand binding activity by racemic amisulpride, (R)-amisulpride, and (S)-amisulpride, and various mixtures of (R)-amisulpride and (S)-amisulpride; where
Figure 5A:
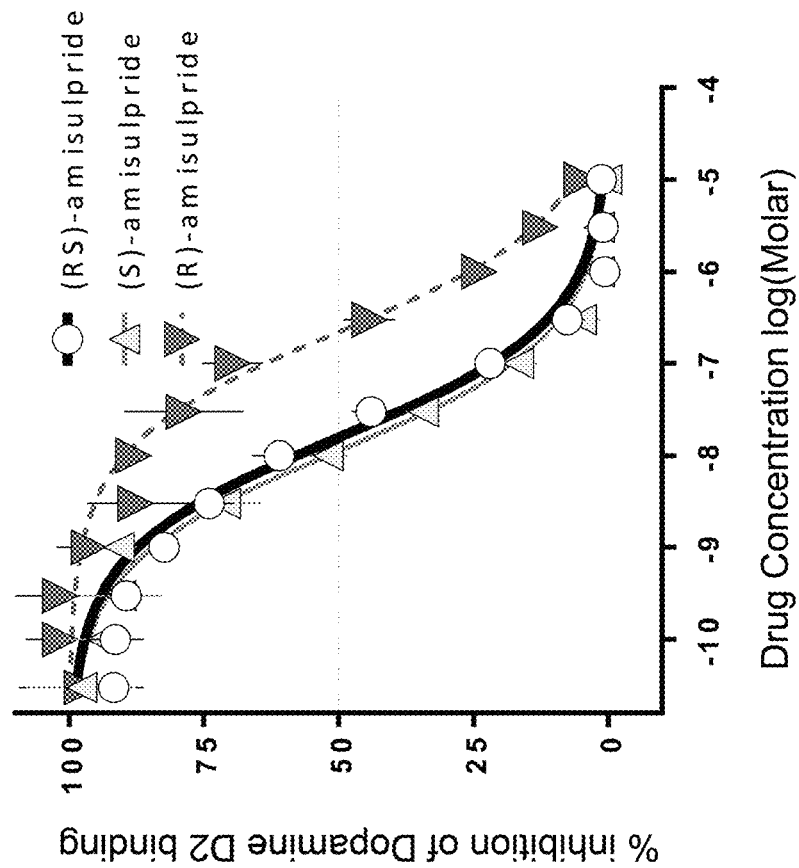

Referring to FIG. 5A, depicted is the data on the % inhibition of dopamine D2 binding of Example 1 for (R)-amisulpride (downward triangle), (S)-amisulpride (upward triangle), and racemic amisulpride (circle). The vertical bars represent ±1 standard deviation from the 3 independent determinations. FIG. 5A illustrates that the (S)-enantiomer is the more potent enantiomer for dopamine $D_2$ receptors.

Referring to FIG. 5B, depicted is the data on the % inhibition of serotonin 5-HT7 binding of Example 1 for (R)-amisulpride (downward triangle), (S)-amisulpride (upward triangle), and racemic amisulpride (circle). The vertical bars represent ±1 standard deviation from the 3 independent determinations. FIG. 5B illustrates that the (R)-enantiomer is more potent in inhibiting binding to serotonin $5\text{-}HT_7$ receptors.

Table 19 summarizes inhibitor constant (Ki) values in nM determined in vitro by radioligand binding and compares racemic amisulpride to a mixture of of (R)-(+)-amisulpride and (S)-(−)-amisulpride of about 85:15 by weight. Human dopamine $D_2$ receptors or human serotonin $5\text{-}HT_7$ receptors were expressed in CHO cells or CHO-K1 cells, respectively. Standard error of the mean is presented based on multiple, independent determinations.

TABLE 19

|  | Racemic (50:50) | (R)-amisulpride:(S)-amisulpride (85:15) |
|---|---|---|
| Dopamine $D_2$ | 7.1 ± 0.26 | 17 ± 0.62 |
| Serotonin 5-$HT_7$ | 89 ± 2 | 66 ± 16 |
| 5-$HT_7/D_2$ | 13 | 4 |

Example 1 shows that the (R)-enantiomer is highly stereoselective for serotonin 5-HT7 receptors such that the 5-HT7 antagonism of amisulpride resides almost exclusively in the (R)-enantiomer and that the (S)-enantiomer is highly stereoselective for dopamine D2 receptors such that the D2 antagonism of racemic amisulpride resides predominantly in the (S)-enantiomer. Referring to again to FIG. 5A, the D2 antagonism of (S)-amisulpride was determined to be about 20 fold that of the (R)-amisulpride, and referring to again to FIG. 5B, the 5-HT7 antagonism of (R)-amisulpride was determined to be about 300 fold that of the (S)-amisulpride.

Figure 5C:
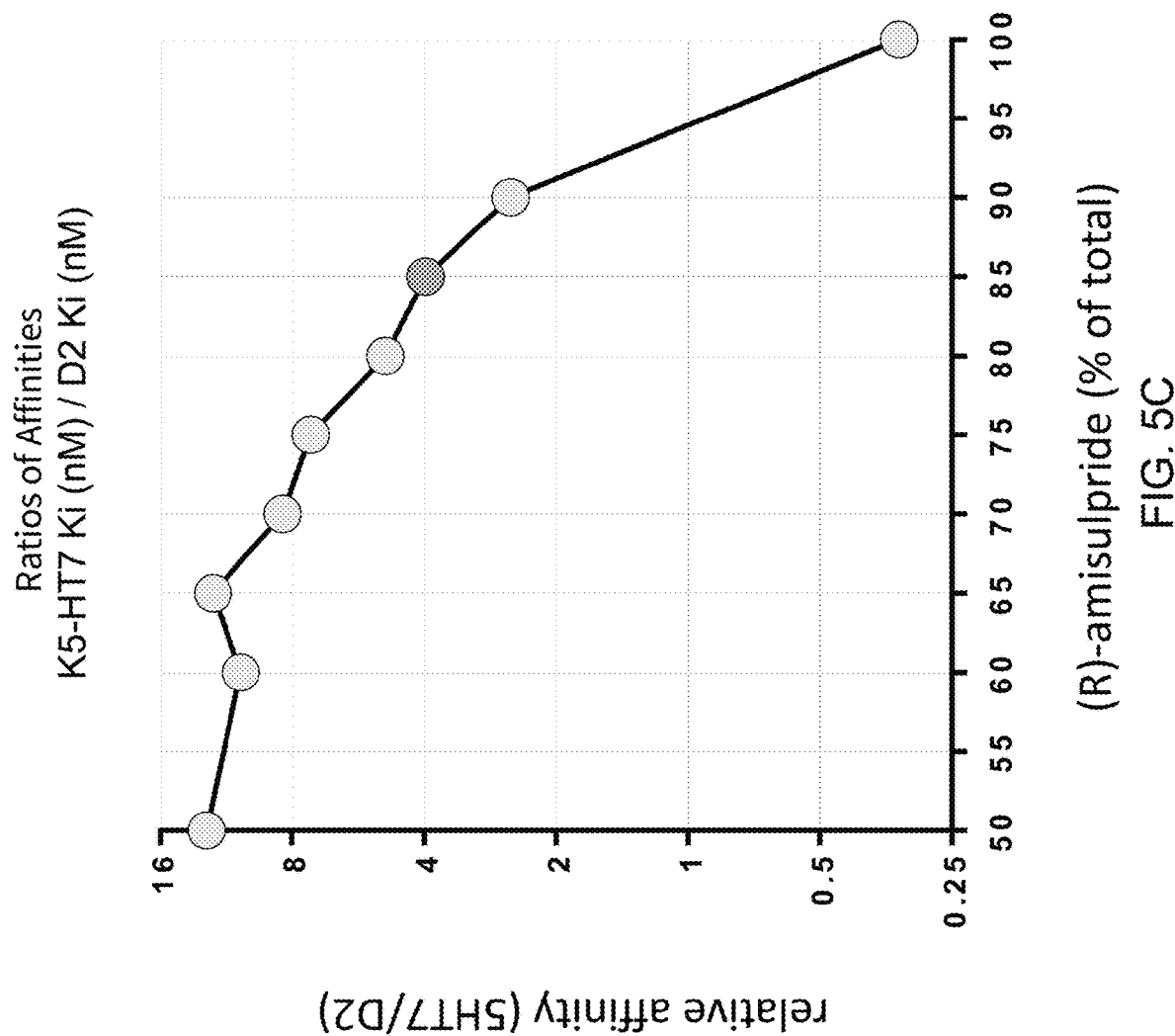

Referring to FIG. 5C, depicted is the data on relative receptor affinity (5-HT7: D2) for various mixtures of (R)-amisulpride and (S)-amisulpride, determined in accordance with the procedures of Example 1, where the x-axis indicates the percentage of the tested drug that was (R)-amisulpride, the remainder percentage being (S)-amisulpride. Table 20 lists for various weight ratios (R)-amisulpride to (S)-amisulpride (first column), from the (S)-enantiomer alone (0:100 ratio) to (R)-enantiomer alone (100:0 ratio), the Ki values (average±1 standard deviation) in nM for n=3 independent determinations, for dopamine D2 (second column) and serotonin 5-HT7 (third column), and the ratio of 5-HT7 to D2 Ki values (fourth column and plotted in FIG. 5C).

TABLE 20

Ki Values for Enantiomeric Amisulpride and Mixtures of Amisulpride Enantiomers

| Ratio R:S | in vitro Ki values | | Ratio 5-HT7/D2 |
|---|---|---|---|
| | D2 Ki (nM) | 5-HT7 (nM) | |
| 0:100 | 4.43 ± 0.70 | 1,860 ± 260 | 420 |
| 50:50 | 7.10 ± 0.26 | 89 ± 2 | 13 |
| 60:40 | 7.51 ± 0.57 | 79 ± 4 | 11 |
| 65:35 | 6.50 ± 0.64 | 79 ± 9 | 12 |
| 70:30 | 8.54 ± 1.61 | 72 ± 4 | 8 |
| 75:25 | 8.16 ± 0.17 | 59 ± 6 | 7 |
| 80:20 | 12 ± 0.73 | 59 ± 10 | 5 |
| 85:15 | 16 ± 0.62 | 66 ± 16 | 4 |
| 90:10 | 18.9 ± 0.95 | 48 ± 8 | 3 |
| 100:0 | 140 ± 31 | 47 ± 4 | 0.3 |

Examples 2, 3A, and 3B: Animal Studies

A series of animal studies were performed on rats with various doses of (R)-amisulpride.

Example 2: Forced Swim Test

The Forced Swim test (FST) is an indicator of the antidepressant-like activity of a test compound. The rat will swim before "giving up" and becoming immobile. A compound with antidepressant-like activity will decrease the time the rat is immobile.

The animals (n=90) were divided into five groups. Animals in four groups were treated with one of the three doses of (R)-amisulpride or imipramine (control), whereas those in the other group received only vehicle (M phosphoric acid+ 0.1 M NaOH (pH6-7)). In the training session, each animal was gently placed into the plastic cylinder containing 5.8 L of water set at 25±1° C. Fifteen minutes after the beginning of the training session, the animal was removed from the water. The dosing solutions were administered 15 minutes after finishing of the training.

Prior to the swim test, animals were intraperitoneally administered vehicle (1 ml/kg), imipramine (10 mg/kg) or (R)-amisulpride (0.15, 0.5 and 1.5 mg/kg) at 24 hours, 5 hours and 1 hour prior to the swim test. The swim test was performed for 5 minutes in the same manner as the training session. In the swim test, the behavior of each animal was horizontally recorded using a video camera. After the swim test, animals were immediately sacrificed by inhalation of carbon dioxide.

The swim movies were handled in a blind manner to ensure that the person who measured the immobility time had no information on the treatment. An animal was judged to be immobile whenever it remained floating in the water without moving its body or forepaws except for the slight movement to maintain its posture. The total time for which the animal remained immobile was defined as the immobility time. An observer blinded to the doses measured the immobility times. The immobility time of each animal was measured to one decimal place and rounded to a whole number. Immobility time was expressed in units of seconds. In each series the means of immobility time were calculated and rounded to a whole number using. The mean and standard error (SE) for each group were calculated using the data obtained from three experimental series and rounded to a whole number. All results are represented as the mean±SE.

The data of imipramine were analyzed using t-test with a two-sided significance level of 5% ($p<0.05$). In the case imipramine significantly decrease the immobility time compared to control, the data of (R)-amisulpride were then analyzed parametrically using Dunnett's multiple comparison test with a two-sided significance level of 5% ($p<0.05$). The data is presented in FIG. 6.

Figure 6:
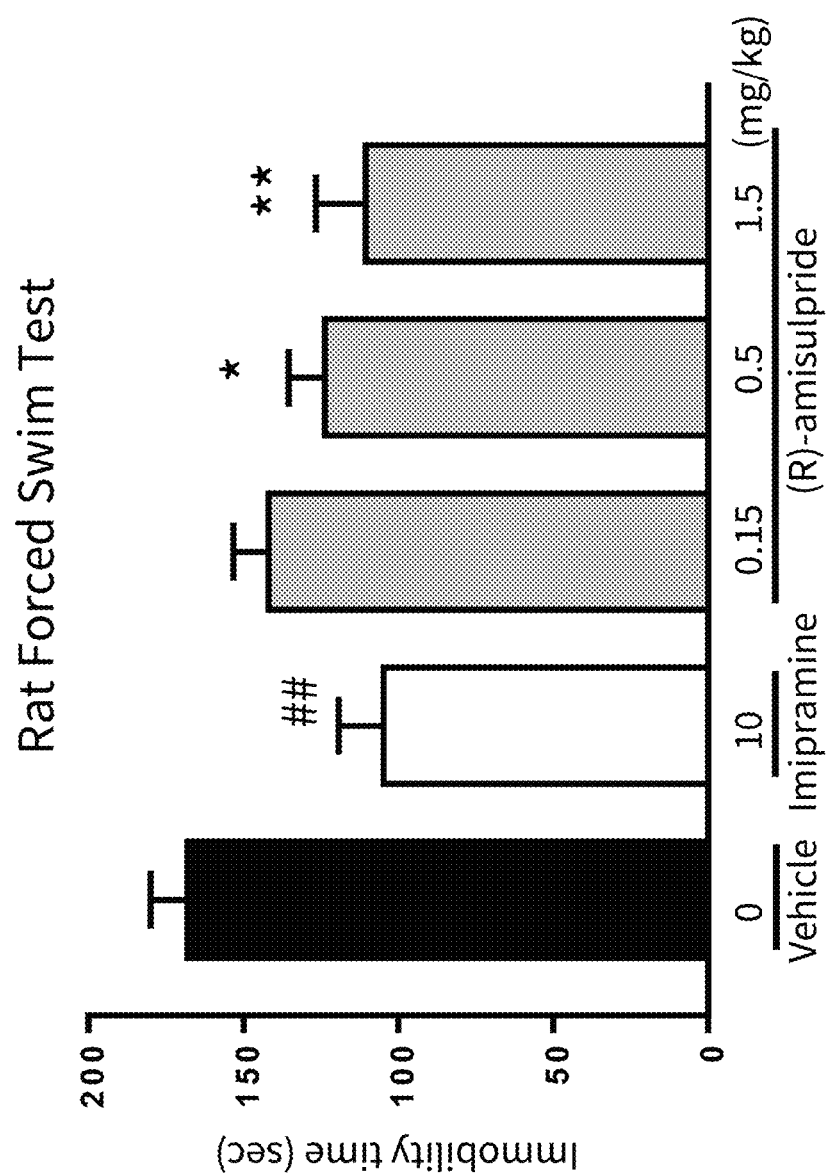
FIG. 6 presents analytical data on the in vivo effects of (R)-amisulpride in a Rat Forced Swim Test, compared to vehicle and imipramine.

Referring to FIG. 6, data is presented for vehicle, imipramine (comparator), and 0.15, 0.5 and 1.5 mg/kg of (R)-amisulpride. The immobility time values are mean±standard error of the mean (SEM). The symbol ## indicates a p-value of $p<0.01$ vs. vehicle (determined using a two-sided t-test); * indicates a p-value of $p<0.05$ and ** indicates a p-value of $p<0.01$ vs. vehicle (determined using a parametric two-sided Dunnett's multiple comparison test).

The immobility time of animals in the vehicle-treated group was 168±12 sec. Imipramine of 10 mg/kg shortened the immobility time by more than 20% in all series and the immobility time average was 105±15 sec, which was significantly shorter than the average of vehicle-treated group. Animals treated with (R)-amisulpride at doses of 0.15, 0.5, and 1.5 mg/kg had immobility times of 142±11, 124±12 and 111±16 sec, respectively. (R)-amisulpride significantly decreased the immobility time at 0.5 and 1.5 mg/kg comparable to imipramine) indicative of antidepressant-like activity for (R)-amisulpride.

Example 3A: Sleep Study of (R)-Amisulpride

In rodents, 5-HT7 receptor blockade has been shown to be effective in models of depression and to increase the latency to REM sleep and decrease REM duration.

In this study, the effect of (R)-amisulpride on sleep architecture in freely moving rats in the light phase was evaluated. Rapid eye movement (REM) sleep time, non-rapid eye movement (NREM) sleep time, WAKE time were measured using electroencephalogram (EEG) and electromyogram (EMG) recordings. (R)-amisulpride (10, 30, 100 mg/kg, p.o.) was administered 10 min before the beginning of recording, during the light phase. EEG and EMG recordings were made for 6 hr starting at the beginning of the light phase. Vehicle (0.05 N HCl/0.5% Methyl Cellulose 400 solution) or dosing suspensions were orally administered 10 min before the beginning of light phase. The volume of administration was 5 mL/kg. The order of drug treatment varied pseudo-randomly and at least 1 week was allowed between the experiments for individual animals.

A radio transmitter (TL11M2-F40-EET; Data Science International, New Brighton, Minn., USA) was implanted subcutaneously in the back of anesthetized animals, and a pair of electrode wires was stereotaxically implanted into the skull in the following locations: one in the frontoparietal (2 mm anterior to the bregma and 2 mm left to the midline), and the other in parietal (5 mm posterior to the bregma and 2 mm right to the midline) areas. The EEG electrodes were fixed using dental cement. Electromyograms (EMG) were recorded from the dorsal neck muscle. The animals, then, were allowed at least 1 week recovery in individual plastic cages before EEG/EMG recording. EEG/EMG were recorded in the home cages in a soundproof box using Dataquest A.R.T. software (Data Science International, New Brighton, Minn., USA) at a sampling rate of 500 Hz.

Sleep stage analysis was conducted off-line using Sleepsign software (KISSEI COMTEC CO., LTD, Nagano, Japan). Electrographic activity of 10-sec epochs were analyzed and each epoch was automatically assigned as WAKE, REM, and NREM based on the waveforms of EEG and EMG according to the following definitions: WAKE was defined as a condition in which EMG exceeded the individual threshold, NREM was defined as a condition in which the power of delta waves (0.5-4 Hz) exceeded the individual threshold with no EMG activity, and REM was defined as a condition in which the power of theta waves (4-8 Hz) exceeded 40% of the total power of frequencies between 0.5 and 80 Hz in the presence of no EMG activity. The duration of each REM, WAKE, and NREM periods were calculated by summing time spent in each condition during sleep every 2 hours.

Figures 7A, 7B:
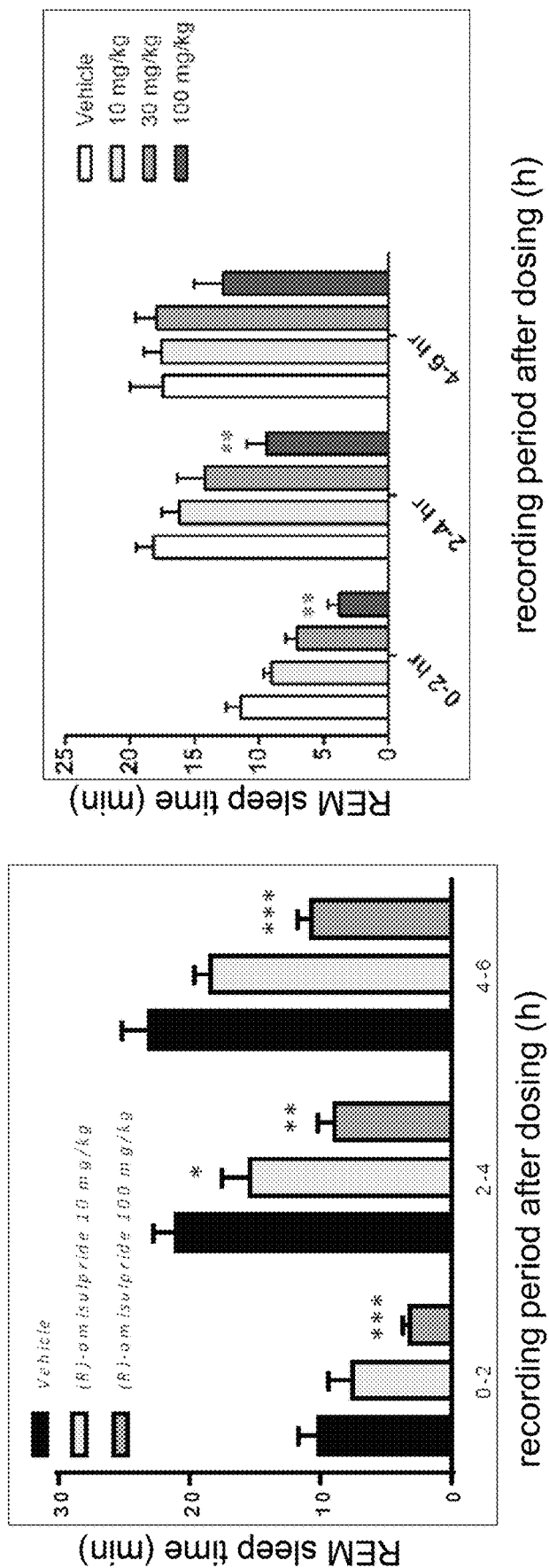
FIGS. 7A and 7B present analytical data on the in vivo effects of (R)-amisulpride on suppression of REM sleep time in rats.

Referring to FIGS. 7A (n=6) and 7B (n=7), data is presented for vehicle and 10 mg/kg, 30 mg/kg and 100 mg/kg of (R)-amisulpride. The y-axis represents the time in minutes that REM sleep was suppressed and these values are mean±standard error of the mean (SEM). The symbol * indicates a p-value of $p<0.05$,  indicates a p-value of $p<0.01$; and * indicates a p-value of $p<0.001$; (determined using a two-way ANOVA followed by post-hoc parametric Dunnett multiple comparison test).

All data are expressed as means±S.E.M. REM sleep, NREM sleep time, and WAKE time each of sequential 2-hr periods were compared statistically using a repeated measures two-way ANOVA, followed by post-hoc Dunnett tests. All statistical analyses were performed using GraphPad Prism 6 software (GraphPad Software, Inc., CA, USA, ver. 6.03J).

It was determined that (R)-amisulpride (10, 30, 100 mg/kg, p.o.) treatment reduced REM sleep duration in dose-dependent manner in freely moving rat, with significant reductions in REM sleep duration following 100 mg/kg in the 0-2 hr and 2-4 hr periods (time after administration). There was no observed effect of (R)-amisulpride on NREM sleep time and WAKE time.

Example 3B: Sleep Study of 85:15 (R:S-Amisulpride) and Racemic Amisulpride

In rodents, 5-HT7 receptor blockade has been shown to be effective in models of depression and to increase the latency to REM sleep and decrease REM duration.

In this study, the effect of 85:15 (R:S-amisulpride) and racemic amisulpride on sleep architecture in freely moving rats in the light phase was evaluated. Groups in this study were as follows. Test compound was administered to rats in a cross-over design.

| Group No. | Fixed ratio amisulpride | Total dose (R/S dose) (mg/kg) | Number of animals |
|---|---|---|---|
| 1 | Vehicle (*) | | |
| 2 | R/S = 50/50 | 30 (15/15) | |
| 3 | R/S = 85/15 | 30 (25.5/4.5) | |
| 4 | R/S = 50/50 | 100 (50/50) | |
| 5 | R/S = 85/15 | 100 (85/15) | |

(*) 0.05N HCl/0.5% MC treatment

Vehicle or fixed ratio amisulpride dosing solutions were orally administered 10 min before the beginning of light phase (light phase: 10:00 AM to 10:00 PM). The individual dosing volume was 4 mL/kg. The individual dosing volume was calculated based on the animals' body weight measured on each experimental day. At least 1-week wash-out period after each treatment was provided.

| Animal | Treatments (R/S ratio; Dose mg/kg) | | | | |
|---|---|---|---|---|---|
| No. | 1st | 2nd | 3rd | 4th | 5th |
| Rat 1 | Vehicle | 50/50; 100 | 85/15; 100 | 50/50; 30 | 85/15; 30 |
| Rat 2 | 50/50; 100 | Vehicle | 85/15; 100 | 50/50; 30 | 85/15; 30 |
| Rat 3 | Vehicle | 50/50; 100 | 85/15; 100 | 50/50; 30 | 85/15; 30 |
| Rat 4 | 50/50; 100 | Vehicle | 85/15; 100 | 50/50; 30 | 85/15; 30 |
| Rat 5 | Vehicle | 50/50; 100 | 85/15; 100 | 50/50; 30 | 85/15; 30 |
| Rat 6 | Vehicle | 50/50; 100 | 85/15; 100 | 50/50; 30 | 85/15; 30 |
| Rat 7 | 50/50; 100 | Vehicle | 85/15; 100 | 50/50; 30 | 85/15; 30 |

The R-amisulpride and S-amisulpride were separately weighed. The vehicle (0.05 N HCl/0.5% MC solution) was then added to prepare each solution with a concentration of 25 mg/mL (100 mg/kg dosing solution) or 7.5 mg/mL (30 mg/kg dosing solution). Fixed-ratio amisulpride (R/S=85/15 or 50/50) solution (i.e. a dosing formulation) was prepared by mixing R-amisulpride and S-amisulpride solution.

A radio transmitter was implanted intraperitoneally in each anesthetized animal (sodium pentobarbital, 32.4 mg/kg, i.p. and medetomidine hydrochloride, 0.5 mg/kg, i.p.). A pair of electrode wires was stereotaxically implanted into the skull in the following locations: one in the fronto-parietal (2 mm anterior to the bregma and 2 mm left to the midline), and the other in parietal (5 mm posterior to the bregma and 2 mm right to the midline) areas. The electroencephalogram (EEG) electrodes were fixed using dental cement. Electromyograms (EMG) were recorded from the dorsal neck muscle. The animals were allowed at least 2 weeks recovery in individual plastic cages before EEG/EMG recording. EEG/EMG was recorded in the home cages in a soundproof box using Dataquest A.R.T. software (Data Science International, New Brighton, Minn., USA) at a sampling rate of 500 Hz.

Sleep stage analysis was conducted off-line using Sleepsign software (KISSEI COMTEC CO., LTD, Japan). Electrographic activity of 10-sec epochs were analyzed and each epoch was automatically assigned as WAKE, REM, and NREM based on the waveforms of EEG and EMG according to the following definitions: WAKE was defined as a condition in which EMG exceeded the individual threshold, NREM was defined as a condition in which the power of delta waves (0.5-4 Hz) exceeded the individual threshold with no EMG activity, and REM was defined as a condition in which the power of theta waves (4-8 Hz) exceeded 40% of the total power of frequencies between 0.5 and 80 Hz in the presence of no EMG activity. Based on the previous study which demonstrated that R-amisulpride was active 0 to 4 hours after administration (1), durations of REM sleep, NREM sleep, and WAKE were calculated using the data from the first 4 hours after treatment.

All data were expressed as a mean±SEM. Difference between 85/15 and 50/50 amisulpride at each dose in each sleep architecture (i.e. REM sleep duration, NREM sleep duration, and WAKE duration) during the first 4 hours after administration were assessed by a repeated measures one-way ANOVA, followed by post-hoc Bonferroni multiple comparison test. All statistical analyses were performed using GraphPad Prism 6 software (GraphPad Software, Inc., CA, USA, ver. 6.03J). P values less than 0.05 were considered to be statistically significant.

Figure 7C:
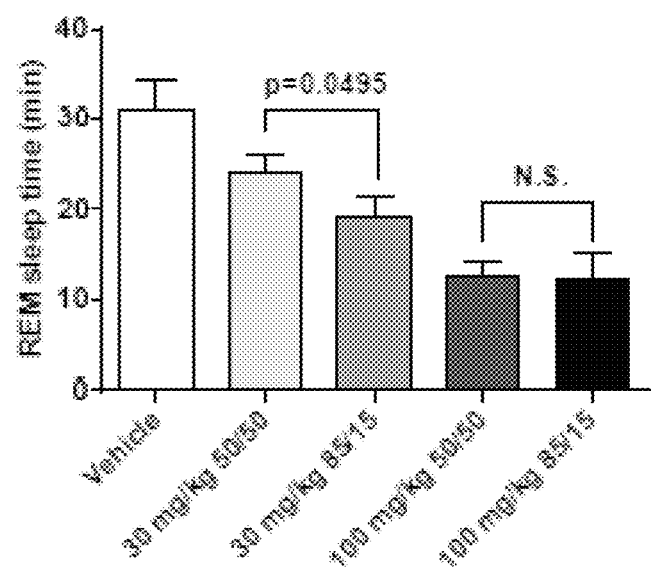
FIGS. 7C, 7D, and 7E present analytical data on the in vivo effects of 85:15 ratio (R:S-amisulpride) and racemic amisulpride (50:50 R:S-amisulpride) on suppression of REM sleep time in rats.
Figure 7D:
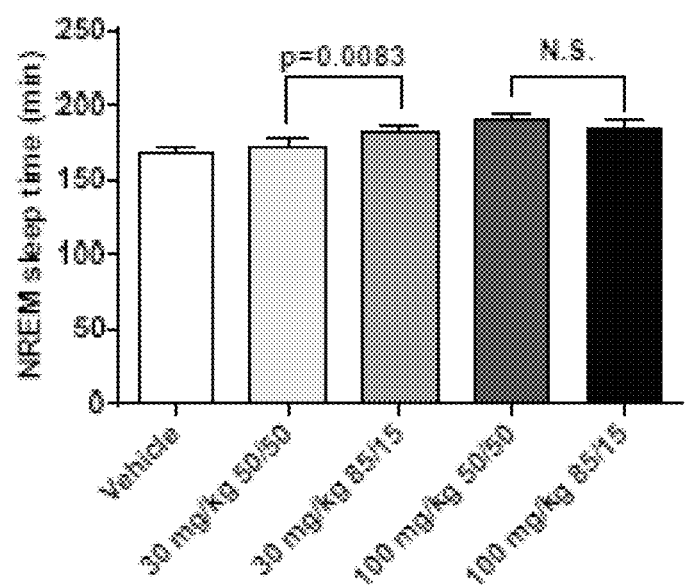
Figure 7E:
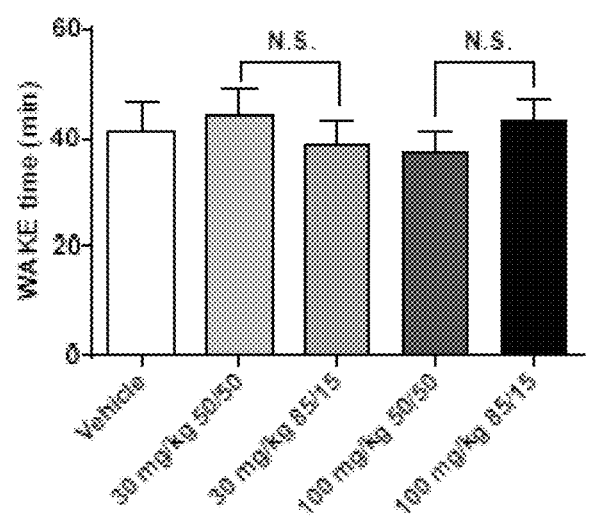

FIG. 7C presents data comparing vehicle to 30 mg/kg and 100 mg/kg of 85:15 ratio (R:S-amisulpride) and racemic amisulpride in REM sleep time (min). FIG. 7D presents data comparing vehicle to 30 mg/kg and 100 mg/kg of 85:15 ratio (R:S-amisulpride) and racemic amisulpride in NREM sleep time (min). FIG. 7E presents data comparing vehicle to 30 mg/kg and 100 mg/kg of 85:15 ratio (R:S-amisulpride) and racemic amisulpride in WAKE time (min).

Results show that at total 30 mg/kg dose of amisulpride, the fixed ratio (R/S=85/15) demonstrated greater REM sleep time reduction (p=0.0495) and NREM sleep time increase (p=0.0083), compared to racemate (R/S=50/50). These differences in REM and NREM sleep times were not observed at total 100 mg/kg dose of amisulpride. There was no difference between 85/15 and 50/50 in WAKE time at any doses tested in this study. The intensity of REM sleep suppression appeared to be dose-dependent on the amount of R-amisulpride in the total dose. Indeed, each treatment, 30 mg/kg (50/50), 30 mg/kg (85/15), 100 mg/kg (50/50), and 100 mg/kg (85/15) contained 15, 25.5, 50, and 85 mg/kg of R-amisulpride, respectively. Greater REM sleep reduction was observed in the treatment group administered higher doses of R-amisulpride. The effect of R-amisulpride on REM sleep suppression was saturated at higher doses (i.e. ≥50 mg/kg of R-amisulpride). Similar effects were also observed in the NREM sleep time.

In conclusion, the fixed ratio (R/S=85/15) amisulpride exhibits greater REM sleep time reduction and NREM sleep time increase than those of racemate (R/S=50/50) in freely moving rats.

Examples 4-7A and 7B Human Studies

A series of human clinical studies were performed with various doses of (R)-amisulpride, (S)-amisulpride, and an 85:15 ratio by weight percentage (w/w %) mixture of (R)-amisulpride to (S)-amisulpride.

Example 4: Dopamine $D_2$ Receptor Occupancy PET Study

In these human clinical studies, each of the enantiomers is administered to healthy human subjects in single doses to determine the maximum tolerated doses.

The minimum dose of (S)-amisulpride able to occupy Dopamine $D_2$ receptors in the brain at a clinically significant threshold for effect was determined by administering single doses of (S)-amisulpride to healthy human volunteers participating in a Positron Emission Tomography (PET) clinical study. The set-point for minimum effective dose of (S)-amisulpride was the lowest dose level able to bind approximately one quarter to one third of brain Dopamine $D_2$ receptors in volunteers.

Dopamine $D_2$ occupancy of (S)-amisulpride following single oral administration was performed in normal healthy volunteers using Positron Emission Tomography (PET) together with a highly selective $D_2$ PET radiotracer. Subjects were enrolled into the study with the aim of having a narrow (<2-fold) prediction interval for $RO_{50}$ (the dose required for 50% D2 receptor occupancy). On day −1 (prior to dose administration), baseline PET scans (90 minutes) were performed for each subject and served as a control. On day 1, (S)-amisulpride was orally administered as a 10 ml oral solution prepared at the clinical site pharmacy. The oral solution is a citrate buffer solution at pH 4.5 containing citric acid monohydrate, trisodium citrate dihydrate and water. The concentration can be determined from the amount of (S)-amisulpride and total volume. Dosages of 25 mg, 45 mg, 100 mg and 200 mg were used. The selective $D_2$ PET tracer (11C PHNO) was then administered intravenously prior to PET scans post-dose. At a predetermined time after PET tracer administration, post-dose PET scans (90 minute) were initiated and conducted at approximately 3, 8, and 27 hours post-dose. Plasma samples were collected throughout the course of the PET scan session and were analyzed for (S)-amisulpride levels. The plasma concentrations peaked in a 3 hour time frame and declined several-fold to near baseline levels over the 27 hour time interval. The elimination of (S)-amisulpride was consistent with the biphasic elimination half-life reported for amisulpride, which is characterized by an initial elimination phase of 2 to 5 hours and a terminal plasma half-life of approximately 12 hours. (A. J. Coukell et al, CNS Drugs 6(3), 237-256 (1996))

A Simplified Reference Tissue Model (SRTM) analysis with the caudate and putamen serving as the regions of interest (ROI) and cerebellum as the reference region was employed for estimating $D_2$ occupancy. To more accurately determine the relationship between $D_2$ occupancy and doses of S-amisulpride, the observed $D_2$ occupancy for each dose/subject was plotted against the derived plasma concentration to determine the dose levels associated with occupancies between 30% and 50% of brain Dopamine $D_2$ receptors.

Figure 8:
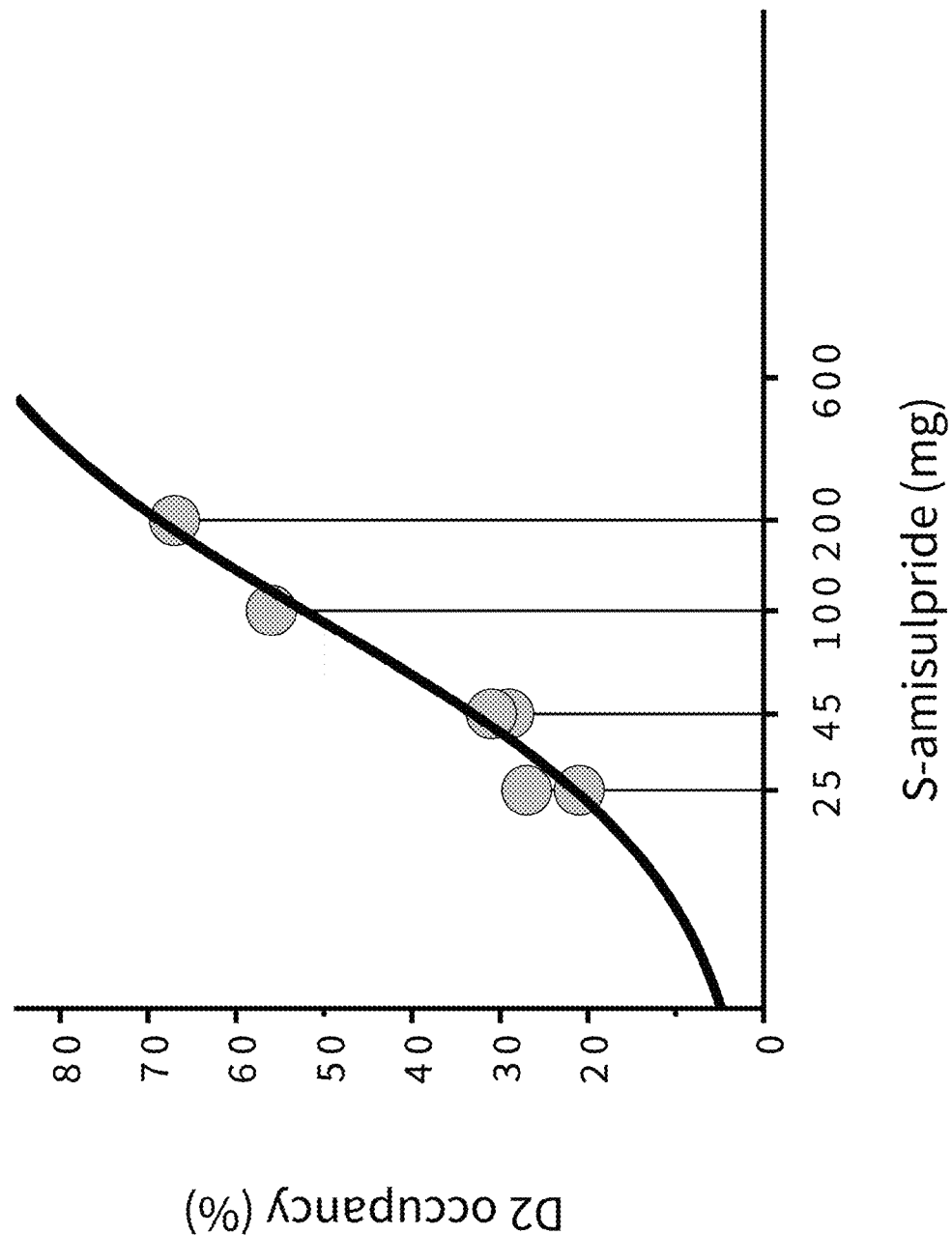
FIG. 8 presents analytical data from human clinical studies on the effects of (S)-amisulpride binding to dopamine D2 receptors in the brain of human volunteers using PET imaging.

FIG. 8 presents analytical data from the human clinical studies (n=6) on the effects of (S)-amisulpride binding to dopamine D2 receptors. The PET scans were conducted 27 hours post-dose, and the amount of (S)-amisulpride resulting in 50% occupancy ($RO_{50}$) was determined to be 92 mg with a ±95% confidence interval of 72 mg to 124 mg.

It was unexpectedly discovered that given the declining plasma concentrations, stable D2 brain occupancies were nevertheless observed out to 27 hours. In comparison, another rapidly eliminated D2 antagonist, quetiapine, has an elimination half-life of about 7 hours and a D2 occupancy trough associated with the plasma concentration trough. (C. L. Delaney and C. B. Nemeroff, Clin. Pharmokinetics, 40 (7), 509-522 (2001); D. C. Mamo et al., J. Clin. Psychiatry, 69:1, 81-86 (2008)). Thus, it was surprisingly discovered that after 27 hours (over two full half-lives) the brain D2 occupancy in the study (Example 6 of the human studies) for subjects administered an 85:15 mixture ((R)-amisulpride:(S)-amisulpride) was still as high as it was at 8 hours post dose.

Example 5: REM Suppression Study

The minimum dose of (R)-amisulpride able to significantly suppress Rapid Eye Movement (REM) sleep in healthy volunteers to a clinically significant effect was determined by administering (R)-amisulpride, as a 20 ml oral solution prepared at the clinical site pharmacy, to volunteers participating in a polysomnography (PSG) clinical study. The oral solution is a citrate buffer solution at pH 4.5 containing citric acid monohydrate, trisodium citrate dihydrate and water. The concentration can be determined from the amount of (S)-amisulpride and total volume. REM suppression was the biomarker used to determine clinically-significant levels of 5-$HT_7$ antagonism and its pharmacodynamics. REM suppression was assessed by total time in minutes spent in REM sleep and by the latency in minutes to REM sleep. It was determined that an example minimum effective dose of (R)-amisulpride was the dose able to inhibit REM sleep by more than about 10 minutes. REM suppression in human volunteers is an established translational biomarker useful to identify doses for antidepressant effects in patients.

The dose of (R)-amisulpride able to suppress Rapid Eye Movement (REM) sleep in humans was identified in healthy subjects in a single-blind, placebo-controlled, randomized, 2-stage, 2-way crossover in-clinic polysomnography (PSG) study of a single oral dose of (R)-amisulpride. Subjects receive a single dose of either (R)-amisulpride or placebo on each of 2 sequential nights, subjects received drug on one night or the other of the two sequential nights. Two dose-levels of (R)-amisulpride (either 340 mg or 600 mg) were administered in the 2 different stages of the clinical study. The primary endpoint was REM sleep suppression as determined at post dose time points in the measures of latency to REM sleep, REM sleep time in minutes, and percent decrease in REM sleep time relative to total sleep time.

Figure 9:
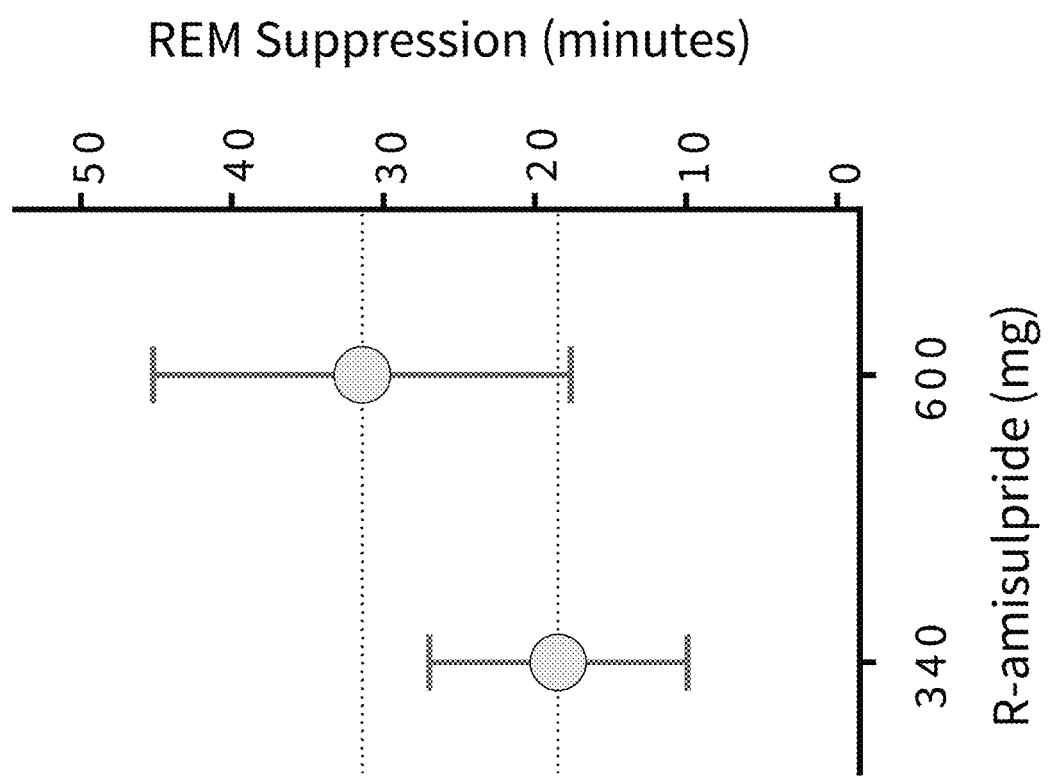
FIG. 9 presents analytical data from human clinical studies on the effects of (R)-amisulpride in suppressing REM sleep in human volunteers using PSG to record sleep stages.

FIG. 9 presents analytical data from the human clinical studies (n=33) on the effects of (R)-amisulpride in suppressing REM sleep. The REM suppression time value is the Least Square Mean differences from placebo, and the error bars represent the 90% confidence interval (CI). Tables 21-23 present data from this study.

The results presented in Tables 21-23 were determined from an analysis of the date based on a linear mixed model with terms for treatment, period, and treatment sequence as fixed effects, respective baseline PSG value as a continuous covariate, and treatment-by-baseline PSG interaction, and subject nested within sequence as a random effect, the Kenward and Roger correction for the degrees of freedom and an unstructured covariance structure to model the intra-subject correlation. The abbreviations used in Tables 21-23 are as follows: PSG=polysomnography; CI=confidence interval; LS=least-squares; REM=rapid eye movement; SE=standard error.

TABLE 21

REM Suppression and % Decrease in REM Sleep Time

| Primary PSG Endpoint (unit) | Treatment | n | LS Mean (SE) | 90% CI | (R)-amisulpride v Placebo LS Mean Difference (SE) | 90% CI |
|---|---|---|---|---|---|---|
| REM Time (Minutes) | Placebo | 13 | 107.98 (5.65) | (98.23, 117.72) | −31.39 (7.99) | (−45.17, −17.61) |
| | (R)-amisulpride 600 mg | 13 | 76.59 (5.65) | (66.85, 86.33) | | |
| REM Time (Minutes) | Placebo | 20 | 110.05 (4.69) | (102.08, 118.02) | −18.45 (4.91) | (−26.99, −9.91) |
| | (R)-amisulpride 340 mg | 20 | 91.60 (4.69) | (83.63, 99.57) | | |

TABLE 22

% Decrease in REM Sleep Time

| Primary PSG Endpoint (unit) | Treatment | n | LS Mean (SE) | 90% CI | (R)-amisulpride v Placebo LS Mean Difference (SE) | 90% CI |
|---|---|---|---|---|---|---|
| REM Percent (%) | Placebo | 13 | 24.30 (1.14) | (22.33, 26.27) | −6.24 (1.45) | (−8.87, −3.61) |
|  | (R)-amisulpride 600 mg | 13 | 18.06 (1.14) | (16.09, 20.03) |  |  |
| REM Percent (%) | Placebo | 20 | 25.69 (0.92) | (24.13, 27.25) | −4.15 (1.09) | (−6.04, −2.25) |
|  | (R)-amisulpride 340 mg | 20 | 21.55 (0.92) | (19.98, 23.11) |  |  |

TABLE 23

Latency to REM Sleep

| Primary PSG Endpoint (unit) | Treatment | n | LS Mean (SE) | 90% CI | (R)-amisulpride v Placebo LS Mean Difference (SE) | 90% CI |
|---|---|---|---|---|---|---|
| Latency to REM Sleep (Minutes) | Placebo | 13 | 89.06 (7.71) | (75.72, 102.40) | 20.30 (9.39) | (3.28, 37.31) |
|  | (R)-amisulpride 600 mg | 13 | 109.35 (7.71) | (96.01, 122.69) |  |  |
| Latency to REM Sleep (Minutes) | Placebo | 20 | 77.03 (9.42) | (61.01, 93.04) | 28.23 (9.82) | (11.15, 45.30) |
|  | (R)-amisulpride 340 mg | 20 | 105.25 (9.42) | (89.23, 121.27) |  |  |

A single oral dose of 340 mg (R)-amisulpride was observed to result in a decrease in the time spent in REM sleep of 10-27 minutes, reducing the portion of the night spent in REM by 2-6 percentage points, and increasing the latency to first REM by 11 to 45 minutes (ranges are for 90% confidence intervals).

A single oral dose of 600 mg (R)-amisulpride was observed to result in a decrease in the time spent in REM sleep of 18-45 minutes, reducing the portion of the night spent in REM by 4-9 percentage points, and increasing the latency to first REM by 3 to 37 minutes (ranges are for 90% confidence intervals). Further, R-amisulpride was well tolerated in this study. Of the 13 subjects dosed with 600 mg R-amisulpride, 3 subjects reported adverse events. Vital signs and ECGs were normal.

The human clinical trials of Examples 4 and 5 identified distinct pharmacological effects between the R- and S-enantiomers of amisulpride. The dose-occupancy relationship of S-amisulpride identified minimal effective doses of 25 mg to 100 mg for levels of D2 occupancies between 20% to 50%. Additionally, a single dose of R-amisulpride (600 mg) was sufficient to produce clinically meaningful and statistically significant suppression of REM sleep, indicating serotonergic (5-HT7) antagonism for R-amisulpride in humans.

Example 6: Dopamine $D_2$ Receptor Occupancy Study 85:15, R:S Mixture

In these human clinical studies, single oral doses of a fixed ratio composition of (R)-amisulpride to (S)-amisulpride of 85:15 by weight were administered to healthy volunteers at total composition amounts of: 200 mg (170 mg R-amisulpride:30 mg S-amisulpride); 300 mg (255 mg R-amisulpride:45 mg S-amisulpride); 400 mg (340 mg R-amisulpride:60 mg S-amisulpride); 600 mg (510 mg R-amisulpride:90 mg S-amisulpride); and 700 mg (595 mg R-amisulpride:105 mg S-amisulpride). Doses were administer4ed as a 20 mL oral solution in citrate buffer.

Dopamine D2 occupancy was measured by using Positron Emission Tomography (PET) together with a highly selective D2 and PET radiotracer 11C—PHNO. PET scans were performed prior to and post dosing. Dopamine D2 receptor occupancy was calculated for each postdose PET scan via regional estimate of the binding potential relative to the nondisplaceable component (BPND). These estimates were derived using the simplified reference tissue model (SRTM) with the cerebellum serving as the reference region. Brain regions of interest that were considered include the D2-rich regions such as caudate and putamen. Identification of brain regions was performed using co-registration of PET images with each subject's high-resolution T1-weighted MRI (structural brain) scan.

The primary endpoint of this study was to determine the relationship between the dose (total mg) of the fixed ratio composition and its occupancy of brain dopamine D2 receptors in healthy subjects using PET.

Figure 10A:
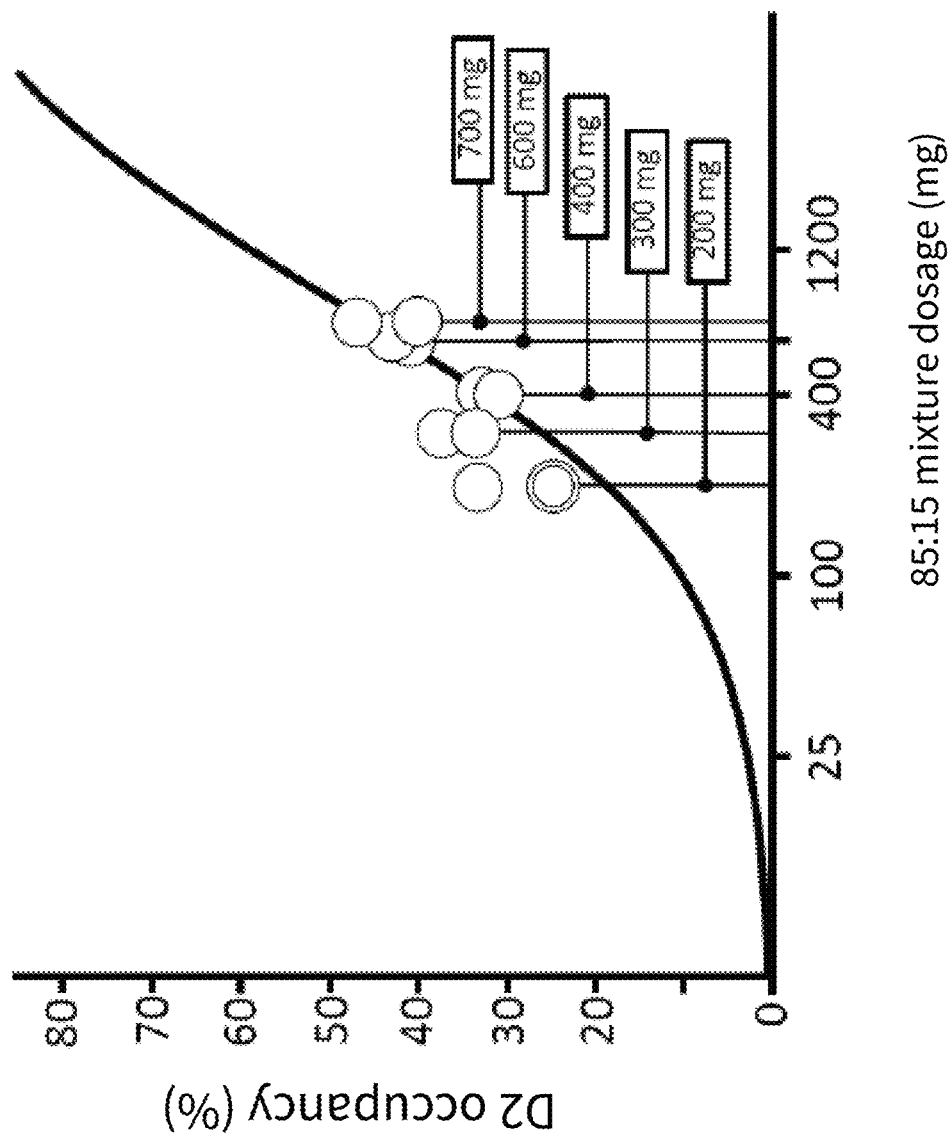
FIGS. 10A, 10B and 10C present analytical data on the effects of mixtures of amisulpride; where

FIG. 10A presents data from the human clinical study (n=11) on the binding to dopamine $D_2$ receptors of the 85:15 ratio by weight percentage (w/w %) composition of (R)-amisulpride to (S)-amisulpride.

The human clinical trials of Examples 4-6 determined that increasing the ratio of (R)-amisulpride relative to (S)-amisulpride changes the pharmacology of the unequal enantiomeric mixtures of amisulpride. Increasing the ratio of (R)-amisulpride relative to (S)-amisulpride changed the balance of clinically-meaningful pharmacological activities from a dopamine $D_2$ receptor-dominating compound (the racemate) into a 5-$HT_7$ pharmacodynamic-preferring composition.

The human clinical trials of Examples 5 and 6 unexpectedly discovered that given the declining plasma concentrations, stable D2 brain occupancies were nevertheless observed out to 27 hours. In comparison, another rapidly eliminated D2 antagonist, quetiapine, has an elimination half-life of about 7 hours and a D2 occupancy trough associated with the plasma concentration trough. (C. L. Delaney and C. B. Nemeroff, Clin. Pharmokinetics, 40 (7), 509-522 (2001); D. C. Mamo et al., J. Clin. Psychiatry, 69:1, 81-86 (2008)). Thus, it was surprisingly discovered that after 27 hours (over two full half-lives) the brain D2 occupancy in the study for subjects administered an 85:15 mixture ((R)-amisulpride:(S)-amisulpride) was still as high as it was at 8 hours post dose.

The human clinical trials of Examples 4 and 5 also determined that the 85:15 fixed ratio composition of (R)-amisulpride to (S)-amisulpride provided the highest ratio of overlap of 5-HT7 effect (required to sustain a decrease in the amount of REM sleep between about 20 to about 45 minutes, a latency to REM sleep of about 15 minutes, and a decrease in total REM sleep time relative to total sleep time of about 5%) with a D2 occupancy in the range between about 30% to about 50%.

Figure 10B:
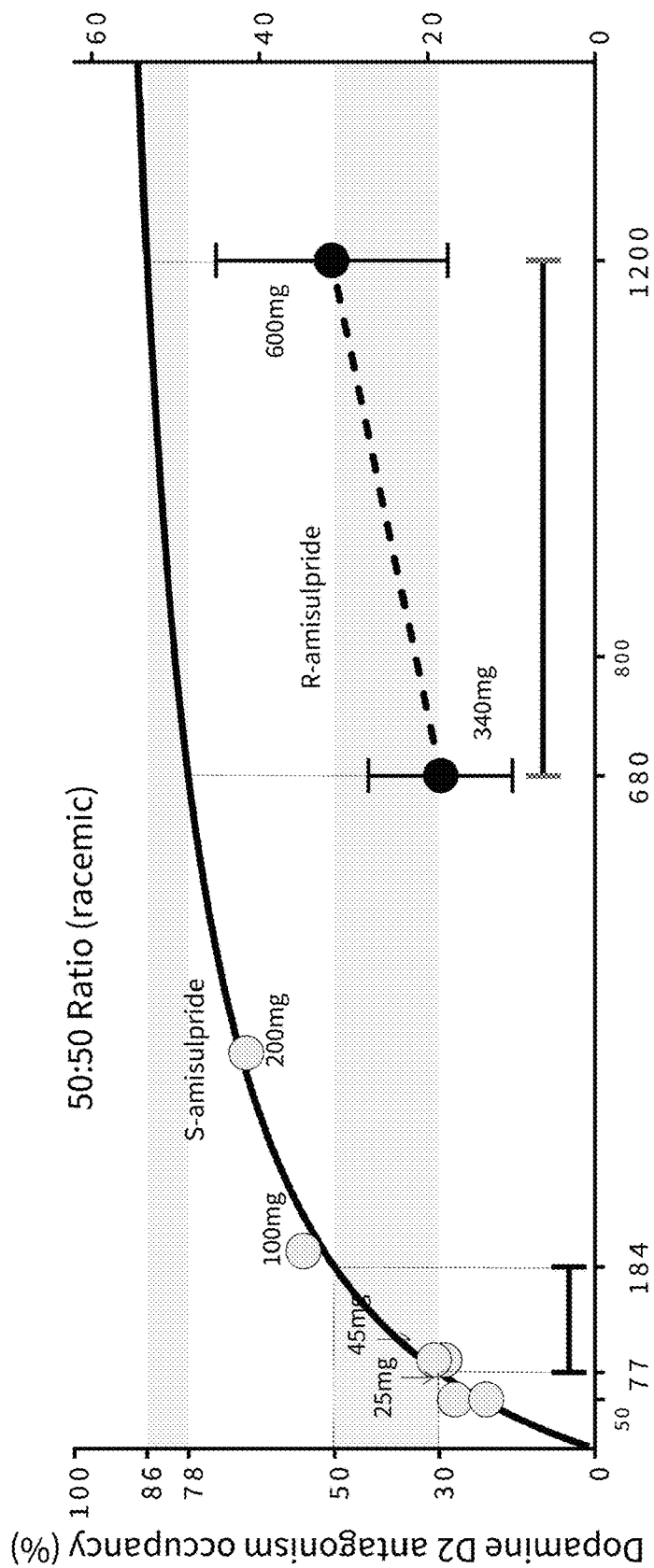
Figure 10C:
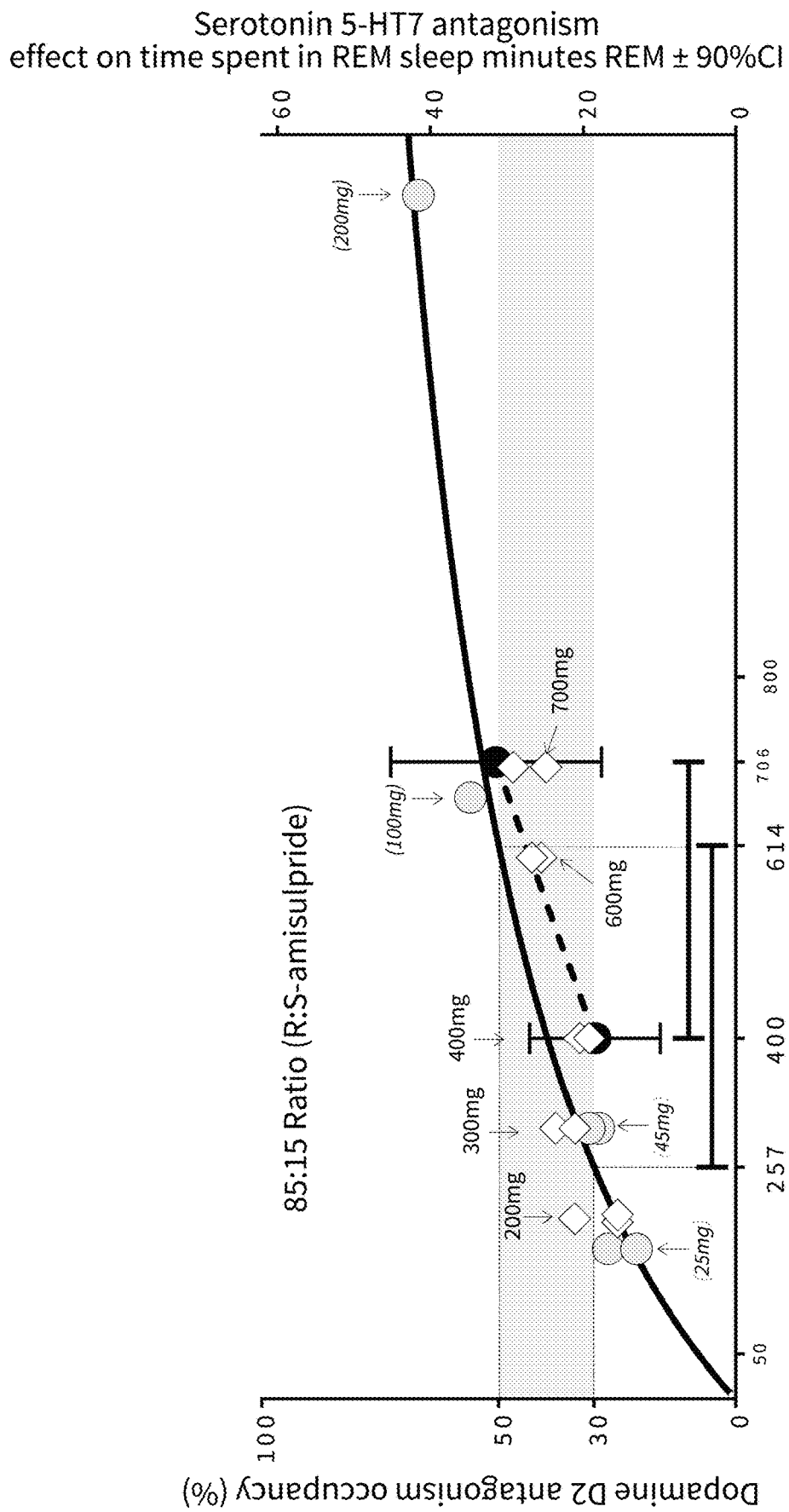

FIGS. 10B and 10C summarize data from Examples 4-6 and illustrates the substantial overlap of the 5-$HT_7$ effect with 30% to 50% D2 receptor occupancy that may be achieved with administration of an 85:15 ratio by weight percentage (w/w %) mixture of (R)-amisulpride to (S)-amisulpride. FIG. 10B presents data on a racemic (50:50 ratio by weight percentage mixture of (R)-amisulpride to (S)-amisulpride) and FIG. 10C presents data on an 85:15 ratio by weight percentage mixture of (R)-amisulpride to (S)-amisulpride.

FIG. 10B illustrates that the desired therapeutic effect attributable to serotonin 5-HT7 antagonism cannot be achieved with a racemic mixture without also resulting in D2 occupancy levels associate with EPS side effects. For example, even for lower 5-HT7 antagonism effects (e.g., decrease in the amount of REM sleep by about 20) the D2 occupancy is about 78%, a level strongly associated with EPS related side effects. Accordingly, racemic amisulpride cannot provide the antidepressant effect of (R)-(+)-amisulpride discovered by the present inventors at dosages that also have less than about 60% D2 receptor occupancy. Correspondingly, dosages of racemic amisulpride that provide less than about 60% D2 receptor occupancy cannot provide sufficient serotonergic antagonism to provide the discovered antidepressant effect of (R)-(+)-amisulpride.

FIG. 10C illustrates a R:S enantiomeric ratio (85:15) therapeutic agent that provides both a desirable D2 dopamine effect at D2 occupancy levels not generally associated with EPS side effects and a desirable serotonergic antagonism that provides the discovered antidepressant effect of (R)-(+)-amisulpride. In various embodiments, the present inventors have discovered that between about 200 mg and about 700 mg of total amisulpride, in a R:S ratio of 85:15 by weight, can provide a therapeutic D2 dopamine effect and a therapeutic serotonergic antagonism whilst decreasing and/or eliminating negative side effects generally associated with high D2 occupancy.

Figure 19A:
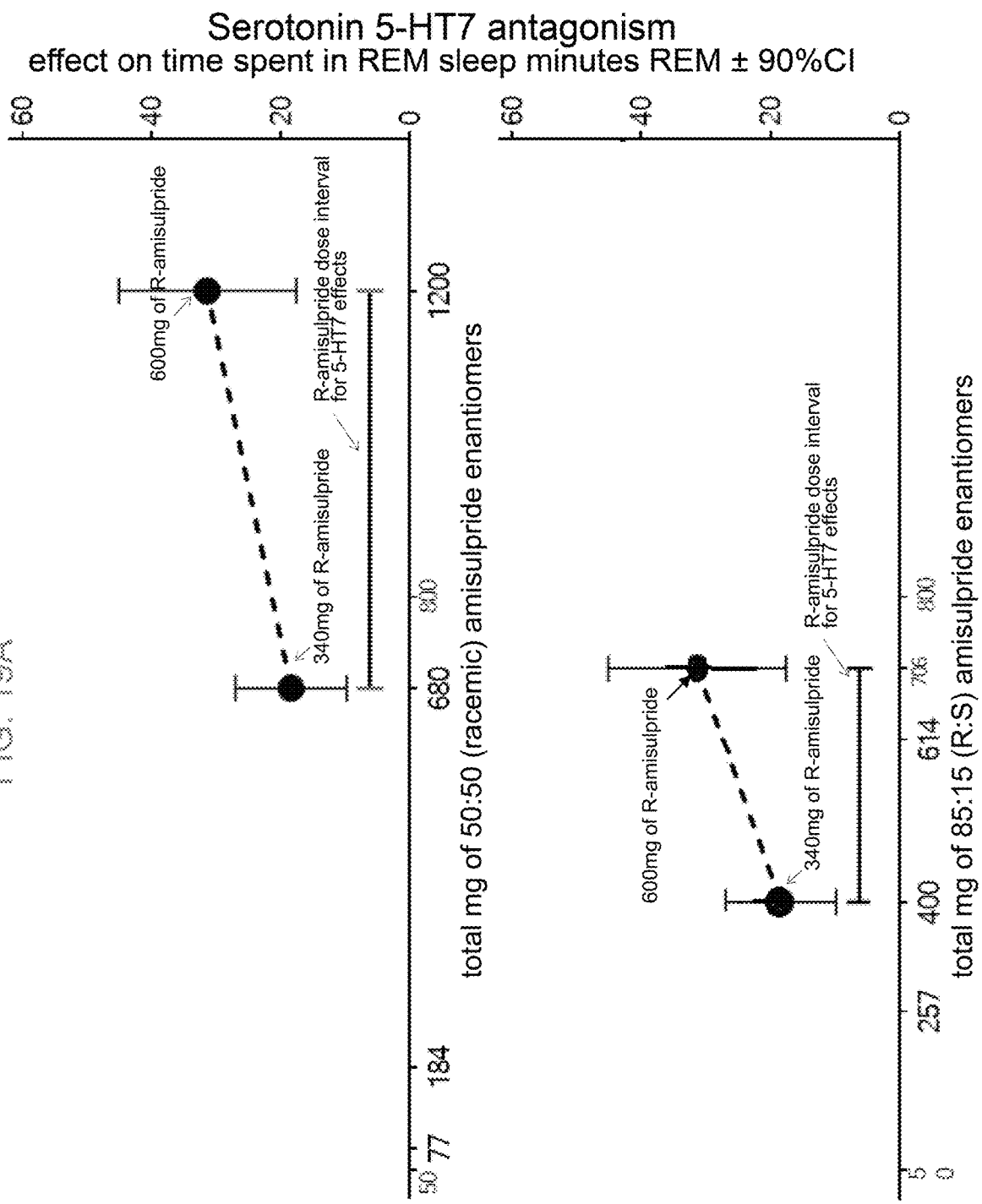
Figure 19C:
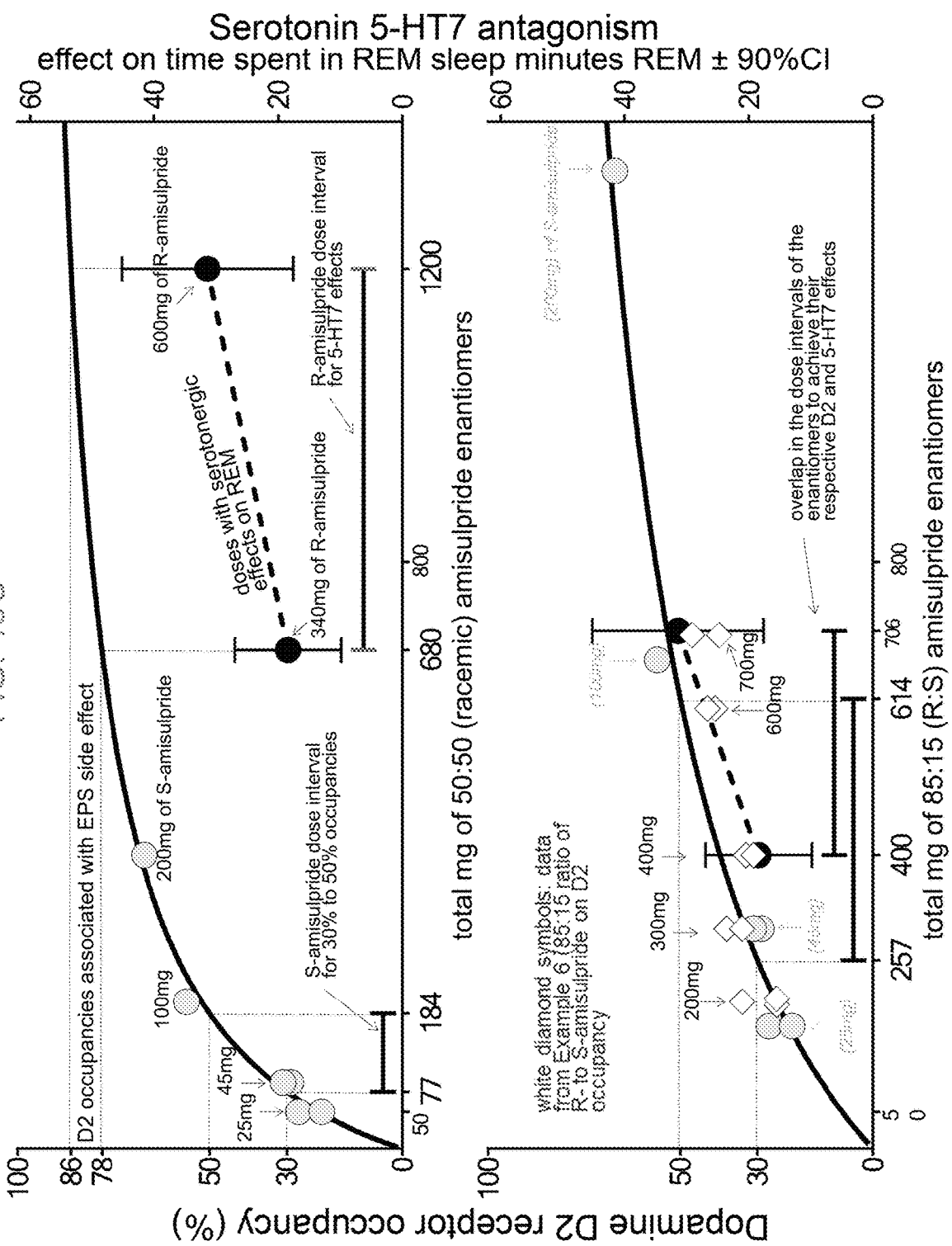

From another perspective, FIGS. 19A, 19B, and 19C present analytical data on the effects of mixtures of amisulpride.

FIG. 19A presents data from human clinical studies on the effects of (R)-amisulpride (dark circles) on 5-$HT_7$ (decrease in the amount of REM sleep minutes) from Example 5, where the x-axis in the top graph is 50:50 racemic amisulpride, and the x-axis in the bottom graph is 85:15 ratio by weight percentage (w/w %) of R:S-amisulpride. The mg designations indicate the amount of the indicted enantiomer in the racemic mixture (top graph) and in the 85:15 ratio of R:S amisulpride. The amount of total amisulpride is reduced by changing the mixture of R:S amisulpride. For example, in a racemic mixture, it would require 680 mg of amisulpride in order to administer 340 mg of (R)-amisulpride. In contrast, in an 85:15 ratio of R:S, 400 mg of amisulpride would provide 340 mg of (R)-amisulpride.

FIG. 19B presents data from human clinical studies on the binding to dopamine D2 receptors of (S)-amisulpride and an 85:15 ratio by weight percentage (w/w %) of (R)-amisulpride to (S)-amisulpride. The x-axis in the top graph is 50:50 racemic amisulpride. The mg designations indicate the amount of the indicted enantiomer in the racemic mixture (top graph). The top graph shows the effect of (S)-amisulpride (grey circles) has on D2 occupancy based on data from Example 4. In the top graph, about 30-50% of $D_2$ occupancy is associated with about 77-184 mg of racemic amisulpride, which corresponds to about 39-92 mg of (S)-amisulpride and about 39-92 mg of (R)-amisulpride. The x-axis in the bottom graph is 85:15 ratio of (R)-amisulpride to (S)-amisulpride. The mg designations indicate the amount of the indicted enantiomer in the 85:15 ratio of R:S-amisulpride (bottom graph). The bottom graph shows the effects of (S)-amisulpride (grey circles) and 85:15 ratio (white diamonds) have on D2 occupancy based on data from Example 4 and Example 6, respectively. The bottom graph shows that about 30-50% of D2 occupancy is associated with about 257-614 mg of 85:15 ratio of R:S-amisulpride, which corresponds to about 39-92 mg of (S)-amisulpride and about 218-522 mg of (R)-amisulpride. As readily apparent, the ratio of 85:15 R:S amisulpride provides a greater amount of R enantiomer than S enantiomer.

FIG. 19C illustrates the substantial overlap of the 5-$HT_7$ effect with 30% to 50% D2 receptor occupancy that can be achieved with administration of an 85:15 ratio of (R)-amisulpride to (S)-amisulpride. The x-axis in the top graph is the total amount of racemic amisulpride. The mg designations indicate the amount of the indicted enantiomer in the racemic mixture. The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-$HT_7$. The x-axis in the bottom graph is the total amount of 85:15 ratio R:S amisulpride. The mg designations indicate the amount of the indicted enantiomer in the 85:15 ratio mixture (bottom graph). The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-$HT_7$. The white diamonds are data for the 85:15 ratio R:S amisulpride from Example 6 (D2 occupancy).

As can be seen in FIG. 19C top graph, about 30-50% of $D_2$ occupancy is associated with about 77-184 mg of racemic amisulpride, which corresponds to about 39-92 mg of (S)-amisulpride and about 39-92 mg of (R)-amisulpride (top graph). However, about 39-92 mg of (R)-amisulpride is not enough to achieve sufficient $5$-$HT_7$ effect associated with the discovered antidepressant activity. As shown on the dotted line and solid black circles, 340 mg of (R)-amisulpride provides a decrease in REM sleep by about 20 minutes. 340 mg of (R)-amisulpride projected onto the curve of racemic amisulpride (solid line) shows that the $D_2$ occupancy is 78%, which is in the range that is associated with side effects. Similarly, as shown on the dotted line and solid black circles, 600 mg of (R)-amisulpride provides a decrease in REM sleep by about 30 minutes. 600 mg of (R)-amisulpride projected onto the curve of racemic amisulpride (solid line) shows that the D2 occupancy is 86%, which above the occupancy level associated with significant dopamine D2 receptor occupancy side effects.

Also, as shown in FIG. 19C bottom graph, about 275-614 mg of amisulpride (85:15 ratio of R:S) provides about 30-50% $D_2$ antagonism. The amount of about 257-614 mg (85:15 ratio of R:S) corresponds to about 39-92 mg (S)-amisulpride and about 218-522 mg (R)-amisulpride. The ratio of 85:15 R:S amisulpride provides a greater amount of R enantiomer than the S enantiomer. This in turn allows for administration of greater amount of (R)-amisulpride than (S)-amisulpride in order to avoid side effects associated with $D_2$ occupancy while, as the inventors have discovered, still providing sufficient 5-HT7 effect. A racemic mixture of amisulpride does not and cannot provide this unequal amount of (R) and (S)-amisulpride. The inventors have thus discovered that the ratio of 85:15 R:S amisulpride provides a substantial overlap in the dose intervals of the two enantiomers that achieves their respective D2 and 5-HT7 effects.

Example 7A: Human Clinical Studies (PK and QT Interval)

In Part 1 of these human clinical studies, single solid oral doses of a fixed ratio composition of (R)-amisulpride to (S)-amisulpride of 85:15 by weight were administered to healthy volunteers at total composition amounts of 200 mg (170 mg R-amisulpride:30 mg S-amisulpride). Three formulations were studied, an IR formulation and three MR matrix tablet formulations, as set forth in Table 24A. Each human volunteer was dosed with various formulations with a 7-day wash out period between formulation switch. The effects of each formulation on a subject were monitored for 48 hours.

In Part 2 of these human clinical studies, single solid oral doses of a fixed ratio composition of (R)-amisulpride to (S)-amisulpride of 85:15 by weight were administered to healthy volunteers at total composition amounts of 200 mg (170 mg R-amisulpride:30 mg S-amisulpride). Four formulations were studied, an IR formulation and two MR matrix tablet formulations, as set forth in Table 24B, and the formulation of Lot 3Z set forth in Table 24A. Each human volunteer was dosed with various formulations with a 7-day wash out period between formulation switch. The effects of each formulation on a subject were monitored for 48 hours.

In both Part 1 and Part 2, blood plasma concentrations of total amisulpride (R and S enantiomers combined) were measured 3 hours pre-dose (±15 minutes), within 15 minutes of dosing, at the following time intervals post-dose (±5 minutes): 10, 20, 30, 45 60, 80, 100, 120, 140, 160, 180, 200, 220, 240, 260, 280 minutes; 24 hours post-dose (±15 minutes); 27 hours post-dose (±15 minutes), and 48 hours post-dose (±15 minutes).

TABLE 24A

Compositions MR Tablets Example 7A

| | Component | Function | Lot 2Z (10%) mg/tab | Lot 3Z (25%) mg/tab | Lot 4Z (15%) mg/tab |
|---|---|---|---|---|---|
| Intra-granular component | (R)-amisulpride | API | 170 | 170 | 170 |
| | (S)-amisulpride | API | 30 | 30 | 30 |
| | D-Mannitol*[1] | Filler | 29.5 | 29.5 | 29.5 |
| | Pregelatinized starch | Filler | 29.5 | 29.5 | 29.5 |
| | Polyvinyl alcohol | Binder | 5.5 | 5.5 | 5.5 |
| | Purified water*[2] (binder solvent) | Solvent | 72 | 72 | 72 |
| | Subtotal (granule component)*[5] | | 264.5 | 264.5 | 264.5 |
| Extra-granular component | Hypromellose*[3] | Extended release agent | 50.0 | 125.0 | 75.0 |
| | D-Mannitol*[4] | Filler | 178.0 | 103.0 | 153.0 |
| | Magnesium stearate | Lubricant | 7.5 | 7.5 | 7.5 |
| | Total tablet weight (mg) | | 500 | 500 | 500 |

*[1]Crystalline powder, Pearlitol 50C (Roquette)
*[2]Water is removed during processing.
*[3]Metolose SR 90SH-100SR (Shin Etsu)
*[4]Spray dried powder, Pearlitol 100SD (Roquette)
*[5]After water removed during processing

TABLE 24B

Compositions MR Tablets Example 7A Part 2 only

| | Component | Function | Lot 5Z (20%) mg/tab | Lot 6Z (40%) mg/tab |
|---|---|---|---|---|
| Intra-granular component | (R)-amisulpride | API | 170 | 170 |
| | (S)-amisulpride | API | 30 | 30 |
| | D-Mannitol*[1] | Filler | 29.5 | 29.5 |
| | Pregelatinized starch | Filler | 29.5 | 29.5 |
| | Polyvinyl alcohol | Binder | 5.5 | 5.5 |
| | Purified water*[2] (binder solvent) | Solvent | 72 | 72 |
| | Subtotal (granule component)*[5] | | 264.5 | 264.5 |
| Extra-granular | Hypromellose*[3] | Extended release agent | 100.0 | 200.0 |

TABLE 24B-continued

Compositions MR Tablets Example 7A Part 2 only

| Component | | Function | Lot 5Z (20%) mg/tab | Lot 6Z (40%) mg/tab |
|---|---|---|---|---|
| component | D-Mannitol*[4] | Filler | 128.0 | 28.0 |
| | Magnesium stearate | Lubricant | 7.5 | 7.5 |
| Total tablet weight | | | 500 | 500 |

*[1]Crystalline powder, Pearlitol 50C (Roquette)
*[2]Water is removed during processing.
*[3]Metolose SR 90SH-100SR (Shin Etsu)
*[4]Spray dried powder, Pearlitol 100SD (Roquette)
*[5]Water is removed during processing

TABLE 25

Composition IR Tablet (Lot 1Z) Example 7A Part 1 and Part 2

| Component | Function | Quantity (mg/tablet) |
|---|---|---|
| Core Tablet | | |
| (R)-amisulpride | API | 170.0 |
| (S)-amisulpride | API | 30.0 |
| D-Mannitol | Filler | 167.5 |
| Partly pregelatinized starch | Filler | 100.0 |
| Partially hydrolyzed polyvinyl alcohol | Binder | 10.0 |
| Purified water*[2] | Granulation Solvent | q.s. |
| Croscarmellose sodium | Disintegrant | 15.0 |
| Magnesium stearate | Lubricant | 7.5 |
| Weight of Core tablet | | 500.0 |
| Film Coat Suspension | | |
| Hypromellose | Coating agent | 3.78 |
| Macrogol 400 | Coating agent | 0.38 |
| Titanium oxide | Coating agent | 1.89 |
| Talc | Coating agent | 1.36 |
| Yellow ferric oxide | Coloring agent | 0.11 |
| Red ferric oxide | Coloring agent | 0.05 |
| Purified water | Coating solvent | q.s. |
| Carnauba wax | Polishing agent | 0.01 |
| Total Weight | | 507.58 | q.s. means quantum sufficiat (as much as necessary)

FIGS. 22A-22D present data on the average blood plasma concentrations of total amisulpride (R and S enantiomers combined) as a function of time for twelve subjects (n=12) in Part 1 of this study. TABLE 26A lists the data plotted in FIGS. 22A-22D and also provides the standard deviation ($\sigma$) of the average. FIGS. 22A-22D present data for subjects who were successfully administered all of the formulations of Part 1 of Example 7A (n=12) that is for subjects who each administered Lot 1Z, Lot 2Z, Lot 4Z, Lot 3Z, and Lot 3Z fed state.

FIGS. 22E-22K present data on the average blood plasma concentrations of total amisulpride (R and S enantiomers combined) as a function of time for subjects in Part 1 and Part 2 of this example. The data presented for the subjects of Part 1 differs from that presented in FIGS. 22A-22D in that data for all subjects is presented in FIGS. 22E, 22F, 22H and 22I. FIGS. 22Gm 22J and 22K present data on subjects in Part 2 of this study. Eighteen subjects were administered Lot 5Z (n=18 for most time points), and seventeen subjects were administered Lot 6Z (n=17 for most time points) in Part 2 of this study. Tables 26B and 26C list the data plotted in FIGS. 22E-22K and also provides the standard deviation ($\sigma$) of the average.

TABLE 26A

Average Blood Plasma Concentration of Amisulpride (ng/mL) and Standard Deviation ($\sigma$) (n = 12) of data plotted in FIGS. 22A-22D

| Time (hours) | Lot 1Z (IR) [ng/mL] | $\sigma$ | Lot 2Z (10%) [ng/mL] | $\sigma$ | Lot 4Z (15%) [ng/mL] | $\sigma$ | Lot 3Z (25%) [ng/mL] | $\sigma$ | Lot 3Z (25%) Fed State [ng/mL] | $\sigma$ |
|---|---|---|---|---|---|---|---|---|---|---|
| 0 | 0.53 | 0.10 | 0.53 | 0.10 | 0.50 | 0.00 | 0.50 | 0.00 | 0.50 | 0.00 |
| 0.17 | 7.64 | 9.86 | 1.03 | 0.92 | 1.35 | 1.49 | 0.83 | 0.70 | 0.50 | 0.00 |
| 0.33 | 46.82 | 40.56 | 12.28 | 26.25 | 6.23 | 5.01 | 4.62 | 6.08 | 0.63 | 0.33 |
| 0.5 | 80.46 | 55.85 | 24.60 | 38.51 | 13.40 | 11.45 | 10.10 | 9.18 | 1.32 | 1.46 |
| 0.75 | 132.02 | 72.99 | 56.75 | 38.66 | 32.19 | 19.96 | 16.73 | 11.38 | 4.13 | 4.59 |
| 1 | 134.57 | 67.22 | 72.33 | 38.40 | 40.79 | 22.74 | 20.97 | 9.27 | 9.77 | 10.65 |
| 1.33 | 156.44 | 121.71 | 81.96 | 44.44 | 46.82 | 30.52 | 35.74 | 13.64 | 28.19 | 40.00 |
| 1.67 | 182.95 | 162.32 | 102.82 | 62.52 | 58.02 | 37.32 | 45.98 | 23.33 | 49.30 | 73.57 |
| 2 | 257.93 | 254.93 | 143.33 | 125.72 | 66.08 | 41.41 | 73.88 | 58.22 | 61.97 | 70.94 |
| 2.33 | 370.72 | 391.80 | 176.38 | 180.37 | 88.71 | 60.61 | 98.21 | 85.95 | 91.63 | 103.76 |
| 2.67 | 356.56 | 318.41 | 224.82 | 259.16 | 147.55 | 158.90 | 116.45 | 98.53 | 113.34 | 124.23 |
| 3 | 337.22 | 252.92 | 272.19 | 346.48 | 185.52 | 176.82 | 124.83 | 93.35 | 124.95 | 101.15 |
| 3.33 | 320.33 | 185.11 | 271.03 | 288.35 | 218.63 | 219.97 | 124.75 | 73.57 | 141.30 | 129.53 |
| 3.67 | 345.92 | 177.01 | 288.08 | 247.01 | 243.91 | 206.05 | 134.04 | 66.44 | 146.42 | 128.12 |
| 4 | 345.92 | 148.68 | 305.14 | 234.27 | 244.77 | 172.26 | 156.81 | 86.32 | 157.43 | 106.42 |
| 4.33 | 376.75 | 180.40 | 343.17 | 214.91 | 234.06 | 111.57 | 169.28 | 92.11 | 174.15 | 116.29 |
| 4.67 | 357.75 | 179.05 | 368.17 | 170.25 | 224.25 | 90.07 | 197.43 | 86.48 | 214.65 | 112.30 |
| 5 | 343.92 | 132.76 | 345.58 | 149.74 | 235.25 | 87.69 | 184.88 | 96.64 | 230.76 | 99.92 |
| 5.5 | 288.08 | 87.67 | 303.58 | 137.95 | 237.79 | 133.68 | 169.12 | 79.79 | 238.75 | 83.73 |
| 6 | 267.50 | 86.62 | 286.50 | 149.56 | 219.28 | 127.58 | 154.79 | 67.05 | 230.50 | 70.59 |
| 6.5 | 223.67 | 67.02 | 245.50 | 115.15 | 210.17 | 119.65 | 144.68 | 64.10 | 205.20 | 56.65 |
| 7 | 209.33 | 69.27 | 221.63 | 93.77 | 181.59 | 80.57 | 136.45 | 57.70 | 188.71 | 53.94 |
| 7.5 | 195.58 | 66.44 | 198.83 | 77.97 | 173.44 | 73.53 | 126.19 | 52.11 | 163.64 | 50.69 |
| 8 | 189.25 | 81.10 | 182.48 | 72.36 | 156.98 | 64.91 | 118.13 | 46.18 | 145.83 | 46.48 |
| 9 | 154.33 | 57.16 | 156.95 | 64.70 | 135.54 | 63.07 | 105.87 | 43.95 | 119.80 | 38.25 |

TABLE 26A-continued

Average Blood Plasma Concentration of Amisulpride (ng/mL) and Standard Deviation (σ)
(n = 12) of data plotted in FIGS. 22A-22D

| Time | Lot 1Z (IR) | | Lot 2Z (10%) | | Lot 4Z (15%) | | Lot 3Z (25%) | | Lot 3Z (25%) Fed State | |
|---|---|---|---|---|---|---|---|---|---|---|
| (hours) | [ng/mL] | σ | [ng/mL] | σ | [ng/mL] | σ | [ng/mL] | σ | [ng/mL] | σ |
| 10 | 130.31 | 45.56 | 133.57 | 58.64 | 116.03 | 53.70 | 92.68 | 36.34 | 101.15 | 32.23 |
| 11 | 111.89 | 49.19 | 113.67 | 50.63 | 93.29 | 39.68 | 81.10 | 33.98 | 84.08 | 27.58 |
| 12 | 92.99 | 33.61 | 99.89 | 42.28 | 82.59 | 33.74 | 70.23 | 26.78 | 69.77 | 20.65 |
| 14 | 77.87 | 26.09 | 77.50 | 29.25 | 64.01 | 23.95 | 59.75 | 21.41 | 56.53 | 16.30 |
| 16 | 61.58 | 19.88 | 64.99 | 26.08 | 54.32 | 19.12 | 48.86 | 16.62 | 47.40 | 14.09 |
| 18 | 51.79 | 17.94 | 54.04 | 21.65 | 45.04 | 15.39 | 42.49 | 15.15 | 38.95 | 12.08 |
| 20 | 43.29 | 16.05 | 47.29 | 19.19 | 40.89 | 13.89 | 38.72 | 13.60 | 33.93 | 10.15 |
| 22 | 36.06 | 11.99 | 39.46 | 16.22 | 35.37 | 11.33 | 35.62 | 13.45 | 30.58 | 9.08 |
| 24 | 31.17 | 9.84 | 34.82 | 13.23 | 31.39 | 9.82 | 32.02 | 12.60 | 28.62 | 8.57 |
| 27 | 26.68 | 8.44 | 30.03 | 11.23 | 25.08 | 8.20 | 28.67 | 12.45 | 23.72 | 7.42 |
| 48 | 8.76 | 5.07 | 10.93 | 5.61 | 10.62 | 5.38 | 11.54 | 7.24 | 10.17 | 5.84 |

TABLE 26B

Average Blood Plasma Concentration of Amisulpride (ng/mL) and Standard Deviation (σ) of
data plotted in FIGS. 22E, 22F, 22H, and 22I

| Time | Lot 1Z (IR) | | Lot 2Z (10%) | | Lot 4Z (15%) | | Lot 3Z (25%) | | Lot 3Z (25%) Fed State | |
|---|---|---|---|---|---|---|---|---|---|---|
| (hours) | [ng/mL] | σ | [ng/mL] | σ | [ng/mL] | σ | [ng/mL] | σ | [ng/mL] | σ |
| 0 | 0.84 | NC | 0.85 | NC | NC | NC | NC | NC | NC | NC |
| 0.17 | 9.01 | 9.63 | 2.33 | 3.1 | 1.95 | 1.75 | 1.41 | 0.96 | NC | NC |
| 0.33 | 39.8 | 37.7 | 12.5 | 24 | 6.26 | 4.98 | 3.95 | 5.56 | 1.29 | 0.389 |
| 0.5 | 68.6 | 54.5 | 24.7 | 35.3 | 11.8 | 11.3 | 8.39 | 8.48 | 1.6 | 1.61 |
| 0.75 | 118 | 75.8 | 63.5 | 46.5 | 29.6 | 19.8 | 17.5 | 12.8 | 4.13 | 4.59 |
| 1 | 131 | 61.8 | 82.1 | 48.2 | 40.2 | 23.6 | 26.4 | 21.5 | 9.77 | 10.6 |
| 1.33 | 170 | 114 | 92.8 | 46.4 | 51.4 | 35.6 | 41.9 | 27.6 | 28.2 | 40 |
| 1.67 | 186 | 143 | 119 | 67.6 | 64.7 | 39.9 | 55.8 | 39.4 | 49.3 | 73.6 |
| 2 | 241 | 219 | 166 | 127 | 75.4 | 45.4 | 80.8 | 58.4 | 62 | 70.9 |
| 2.33 | 319 | 338 | 193 | 165 | 97.9 | 60.7 | 119 | 97.8 | 91.6 | 104 |
| 2.67 | 316 | 279 | 249 | 240 | 149 | 146 | 146 | 124 | 113 | 124 |
| 3 | 323 | 241 | 300 | 324 | 181 | 163 | 179 | 205 | 125 | 101 |
| 3.33 | 338 | 231 | 331 | 329 | 213 | 203 | 188 | 215 | 141 | 130 |
| 3.67 | 368 | 215 | 343 | 277 | 239 | 190 | 196 | 203 | 146 | 128 |
| 4 | 372 | 187 | 342 | 234 | 262 | 176 | 193 | 150 | 157 | 106 |
| 4.33 | 419 | 249 | 378 | 224 | 290 | 227 | 201 | 130 | 174 | 116 |
| 4.67 | 391 | 207 | 377 | 161 | 274 | 196 | 215 | 109 | 215 | 112 |
| 5 | 392 | 199 | 357 | 147 | 259 | 116 | 201 | 111 | 231 | 99.9 |
| 5.5 | 308 | 111 | 308 | 131 | 246 | 126 | 183 | 92.5 | 239 | 83.7 |
| 6 | 281 | 97.1 | 285 | 137 | 227 | 120 | 168 | 81.2 | 231 | 70.6 |
| 6.5 | 235 | 72 | 247 | 113 | 215 | 111 | 157 | 73.2 | 205 | 56.6 |
| 7 | 222 | 73.3 | 225 | 92.3 | 188 | 76.5 | 149 | 66.5 | 189 | 53.9 |
| 7.5 | 200 | 67.6 | 202 | 74.7 | 177 | 68.4 | 137 | 60.5 | 164 | 50.7 |
| 8 | 190 | 78.2 | 188 | 72.6 | 161 | 60.6 | 130 | 57.6 | 146 | 46.5 |
| 9 | 154 | 55.5 | 159 | 62.8 | 137 | 58.2 | 114 | 49.4 | 120 | 38.3 |
| 10 | 131 | 44.8 | 135 | 56.4 | 119 | 49.8 | 94.6 | 36.1 | 101 | 32.2 |
| 11 | 114 | 46.1 | 114 | 48.6 | 94.5 | 36.6 | 84.9 | 35.6 | 84.1 | 27.6 |
| 12 | 93 | 32.7 | 100 | 41.9 | 82.6 | 31.1 | 73.5 | 28.7 | 69.8 | 20.6 |
| 14 | 76.5 | 25.9 | 78.8 | 30.7 | 64.2 | 22 | 61.1 | 21.6 | 56.5 | 16.3 |
| 16 | 60.4 | 19.7 | 65.6 | 26.3 | 53.9 | 17.7 | 50.8 | 18.3 | 47.4 | 14.1 |
| 18 | 49.5 | 17.5 | 54.5 | 22.1 | 44.5 | 14.2 | 43.3 | 15.3 | 39 | 12.1 |
| 20 | 41.3 | 15.6 | 47.7 | 18.8 | 40.5 | 12.9 | 39.2 | 13.7 | 33.9 | 10.2 |
| 22 | 35.7 | 12.2 | 39.5 | 15.8 | 34.9 | 10.6 | 35.4 | 13.1 | 30.6 | 9.08 |
| 24 | 31.3 | 10.1 | 34.8 | 13.1 | 30.8 | 9.23 | 32.5 | 12.5 | 28.6 | 8.57 |
| 27 | 25.7 | 8.28 | 29.9 | 11.8 | 24.7 | 7.8 | 28.9 | 12.6 | 23.7 | 7.42 |
| 48 | 9.12 | 4.98 | 10.7 | 5.2 | 10.6 | 5.05 | 11.6 | 6.89 | 10.2 | 5.84 |

NC = not calculated

TABLE 26C

Average Blood Plasma Concentration of Amisulpride (ng/mL) and Standard Deviation (σ) of data plotted in FIGS. 22G, 22J and 22K

| Time | Lot 1Z (IR) Part 2 | | Lot 3Z (25%) Part 2 | | Lot 5Z (20%) Part 2 | | Lot 6Z (40%) Part 2 | |
|---|---|---|---|---|---|---|---|---|
| (hours) | [ng/mL] | σ | [ng/mL] | σ | [ng/mL] | σ | [ng/mL] | σ |
| 0 | NC | NC | NC | NC | NC | NC | NC | NC |
| 0.17 | 7.01 | 14 | 2.18 | 2.88 | 0.87 | 0.53 | 1.18 | 0.52 |
| 0.33 | 53.3 | 57.1 | 5.75 | 7.06 | 3.97 | 3.44 | 5.42 | 4.81 |
| 0.5 | 107 | 123 | 12.4 | 12.7 | 7.86 | 5.72 | 10.2 | 6.85 |
| 0.75 | 128 | 98.9 | 26.3 | 16.5 | 17 | 14 | 20 | 12.8 |
| 1 | 136 | 84.9 | 38.2 | 23.8 | 32.5 | 23.2 | 25.2 | 16.4 |
| 1.33 | 149 | 74.6 | 42.4 | 27.1 | 51.4 | 32.4 | 33.4 | 19.7 |
| 1.67 | 172 | 82.1 | 53 | 29.1 | 62.9 | 44.4 | 38.6 | 22.5 |
| 2 | 238 | 176 | 65.3 | 29.7 | 82 | 50.9 | 53.2 | 37 |
| 2.33 | 297 | 236 | 74.7 | 25.5 | 102 | 64.3 | 81.8 | 79.4 |
| 2.67 | 362 | 340 | 87.7 | 30.7 | 114 | 75.5 | 99.5 | 87.2 |
| 3 | 401 | 330 | 101 | 54.5 | 136 | 93.8 | 132 | 134 |
| 3.33 | 449 | 276 | 142 | 111 | 164 | 115 | 166 | 169 |
| 3.67 | 501 | 280 | 180 | 135 | 180 | 108 | 170 | 157 |
| 4 | 525 | 294 | 221 | 150 | 203 | 109 | 185 | 164 |
| 4.33 | 522 | 261 | 257 | 143 | 276 | 181 | 208 | 136 |
| 4.67 | 478 | 228 | 280 | 153 | 325 | 216 | 251 | 170 |
| 5 | 452 | 199 | 357 | 209 | 330 | 189 | 244 | 178 |
| 5.5 | 403 | 203 | 343 | 228 | 336 | 228 | 234 | 130 |
| 6 | 354 | 163 | 292 | 200 | 287 | 183 | 204 | 111 |
| 6.5 | 294 | 123 | 239 | 130 | 230 | 127 | 173 | 87 |
| 7 | 271 | 109 | 215 | 111 | 205 | 109 | 157 | 72.7 |
| 7.5 | 237 | 84.3 | 183 | 96 | 183 | 90 | 139 | 63.7 |
| 8 | 217 | 83.8 | 168 | 85.9 | 173 | 78.9 | 130 | 53.3 |
| 9 | 180 | 66.8 | 137 | 62.7 | 150 | 63.4 | 106 | 41.9 |
| 10 | 153 | 55.3 | 121 | 53.4 | 129 | 55 | 94.2 | 41.5 |
| 11 | 122 | 46.1 | 104 | 42.1 | 108 | 42.6 | 83.5 | 33.5 |
| 12 | 107 | 39.5 | 88.4 | 37 | 97.3 | 41.7 | 77.2 | 34.8 |
| 14 | 78 | 22.7 | 66.9 | 28.8 | 73.1 | 31.4 | 64 | 28.3 |
| 16 | 64.2 | 25.7 | 56 | 24.5 | 62.3 | 27.9 | 56.1 | 23.1 |
| 18 | 53.1 | 14.2 | 47.3 | 19.2 | 50.7 | 20.7 | 46.6 | 20.2 |
| 20 | 46.1 | 18.1 | 41 | 15.8 | 44.6 | 18.7 | 42.1 | 19.5 |
| 22 | 39.9 | 15.4 | 36.8 | 14.4 | 38.4 | 15.4 | 38.7 | 18.7 |
| 24 | 35.9 | 15.2 | 33 | 13.3 | 34.9 | 14.3 | 36.8 | 19.4 |
| 27 | 29.9 | 12.1 | 28.3 | 11.7 | 29.8 | 12.2 | 35 | 17.4 |
| 48 | 9.91 | 5.01 | 10.7 | 4.93 | 12.2 | 7.38 | 12.9 | 7.11 |

NC = not calculated

FIGS. 20A-20B present, respectively, the geometric mean of Cmax and AUC for the subjects of Part 1 of this study. The error bars in FIGS. 20A-20B represent the 95% confidence intervals. FIGS. 20A-20B present data for subjects who were successfully administered all of the formulations of Part 1 of Example 7A (n=12) that is for subjects who each administered Lot 1Z, Lot 2Z, Lot 4Z, Lot 3Z, and Lot 3Z fed state. Table 27A presents the data plotted in FIGS. 20A-20B. The data in Table 27A presents the geometric mean of the subjects' Cmax and AUC, the lower 95% confidence interval (L CI) and upper 95% confidence interval (U CI).

Figures 20C, 20D:
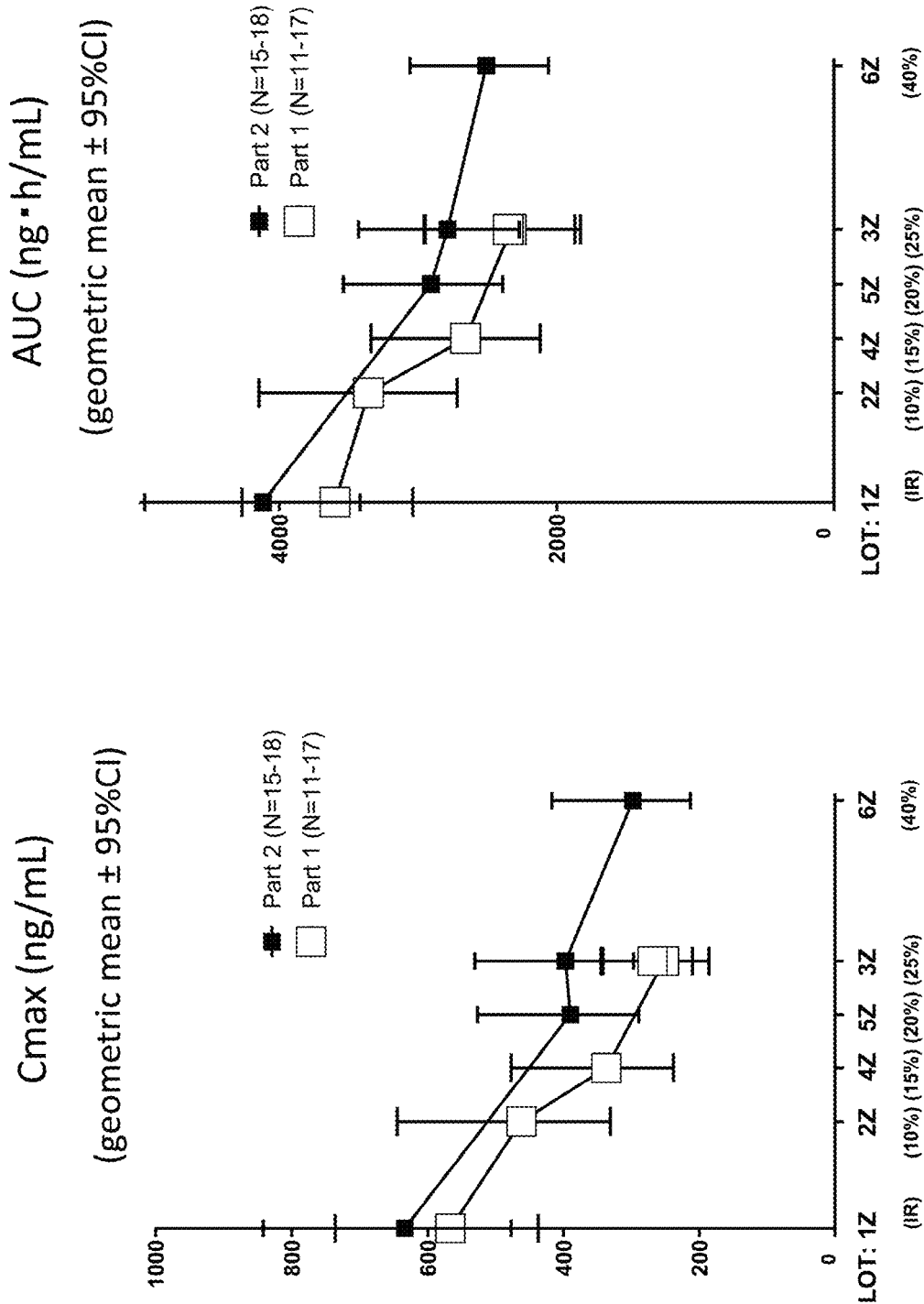
FIGS. 20C and 20D present, respectively, the geometric mean of Cmax and AUC for the subjects of Example 7A Part 1 (open squares) and Part 2 (filled squares), the error bars represent the 95% confidence intervals. Two squares are shown for Lot 3Z in FIGS. 20C and 20D, one square presenting data for Lot 3Z administered in the fed state, and the other for Lot 3Z administered in a fasted state, see Table 27B.

FIGS. 20C-20D present, respectively, the geometric mean of Cmax and AUC for the subjects of Part 2 of this study (filled squares) compared to the subjects of Part 1 (open squares). The error bars in FIGS. 20C-20D represent the 95% confidence intervals.

Tables 27B and 27C present the data plotted in FIGS. 20C-20D. The data in Tables 27B and 27C presents the geometric mean of the subjects' Cmax and AUC, the lower 95% confidence interval (L CI), upper 95% confidence interval (U CI), and coefficient of variation (CV %). Table 27B presents data for subjects of Part 1 of this study for all subjects administered the respective formulation. Table 27C presents data for subjects of Part 2 of this study for all subjects administered the respective formulation.

Figure 21C:
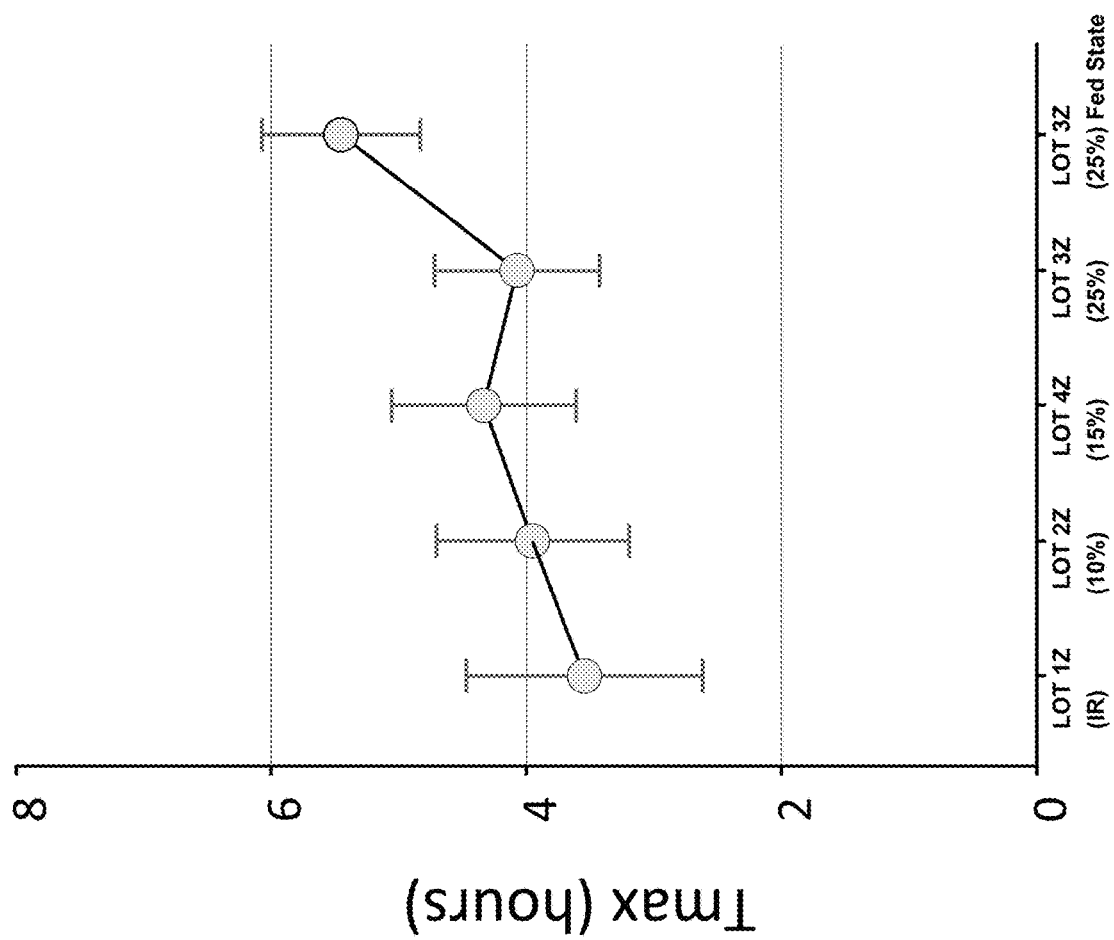
FIG. 21C presents geometric mean Tmax data for the subjects of the study of Example 7A, Part 1, the error bars represent the ±95% confidence intervals.

FIGS. 21A-21B present, respectively, average Cmax and AUC for the subjects of Part 1 of this study where the values for Cmax and AUC have been normalized for each subject to the Cmax and AUC value of that subject when administered the IR tablet, i.e. a tablet having a composition substantially similar to that of Lot 1Z. FIG. 21C presents average Tmax data for the subjects of Part 1 of this study. The error bars in FIGS. 21A-21C represent the 95% confidence intervals. FIGS. 21A-21C present data for subjects who were successfully administered all of the formulations of Part 1 of Example 7A (n=12) that is for subjects who each administered Lot 1Z, Lot 2Z, Lot 4Z, Lot 3Z, and Lot 3Z fed state.

Figures 21D, 21E:
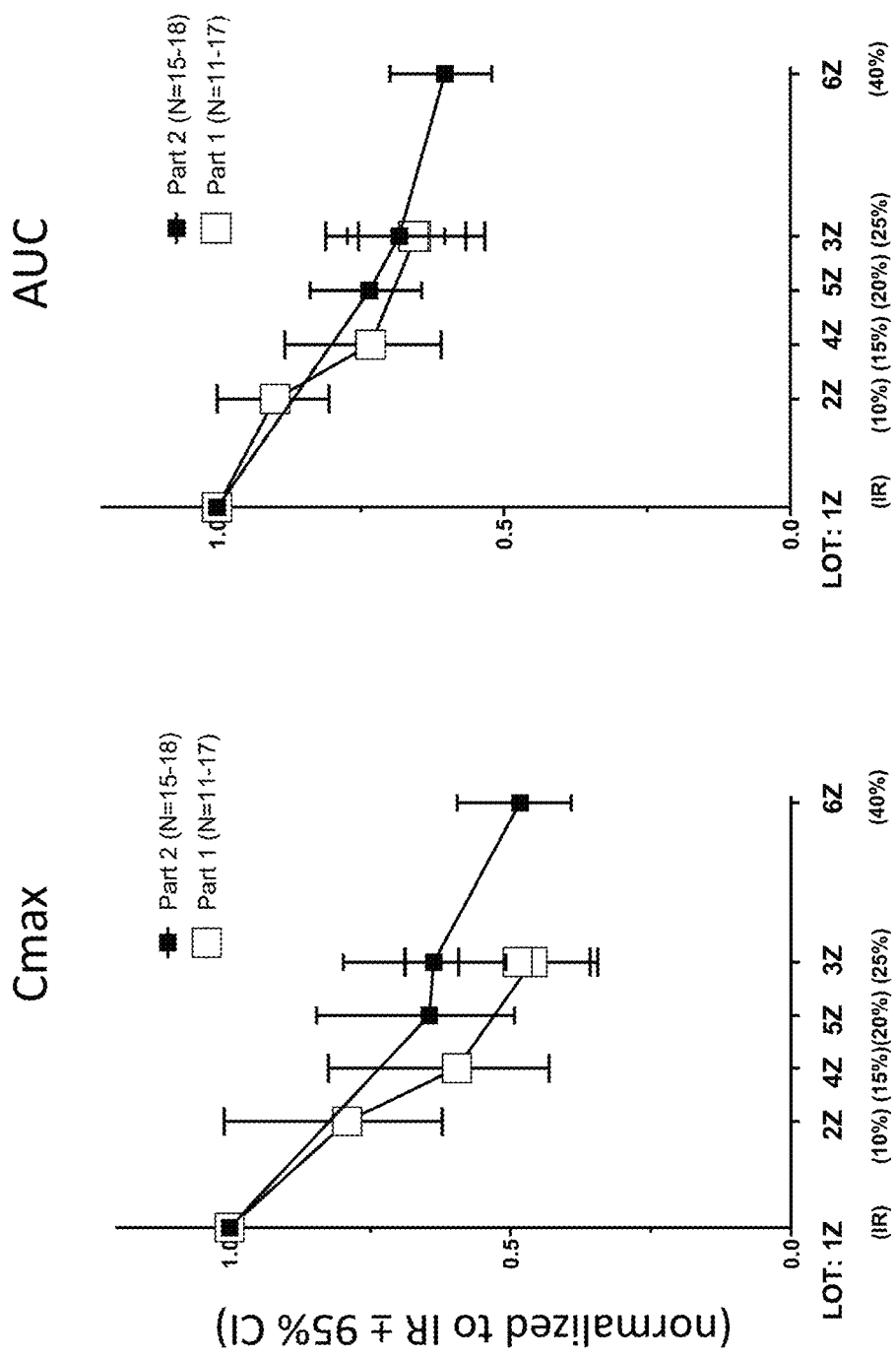
FIGS. 21D and 21E present, respectively, geometric mean Cmax and AUC for the subjects of the study of Example 7A, Part 1 (open squares) and Part 2 (filled squares), the error bars represent the ±95% confidence intervals.
Figure 21F:
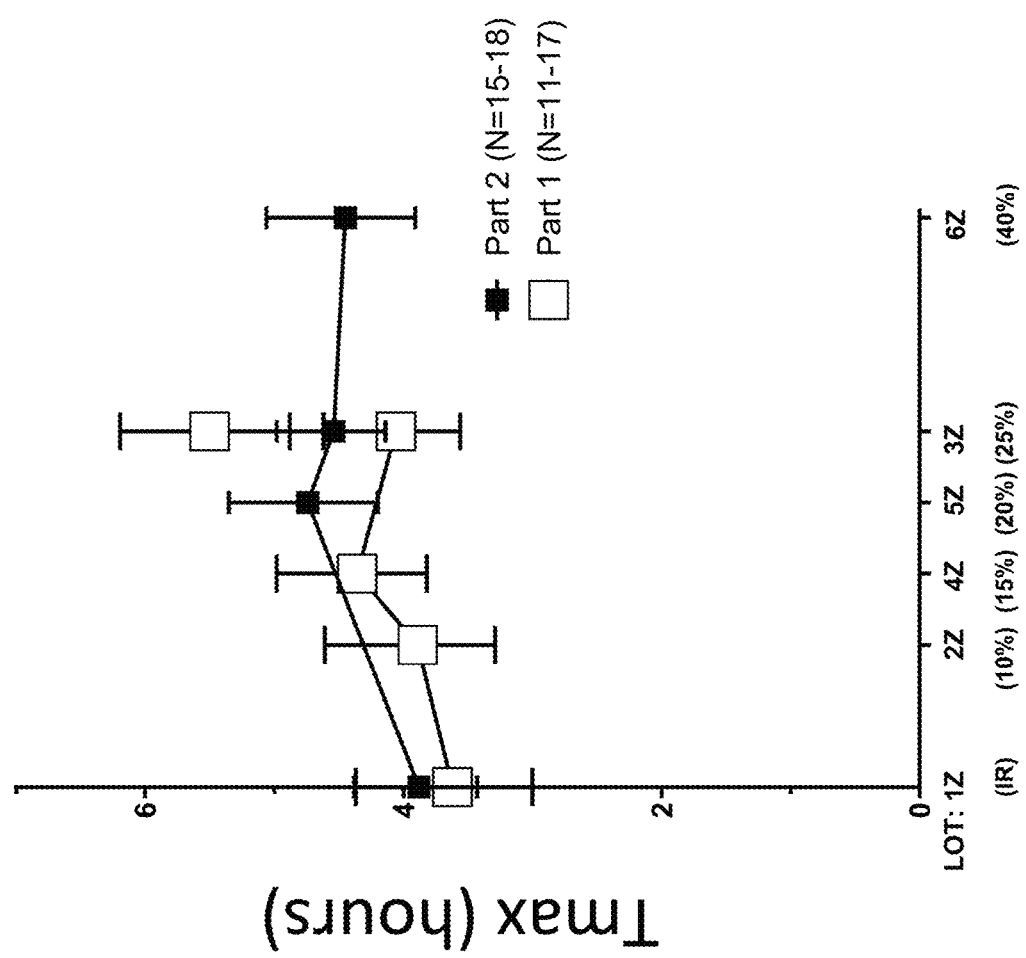
FIG. 21F presents geometric mean Tmax data for the subjects of the study of Example 7A, Part 1 (open squares) and Part 2 (filled squares), the error bars represent the ±95% confidence intervals. Two squares are shown for Lot 3Z in FIG. 21F, the upper square presenting data for Lot 3Z administered in the fed state, and the lower square Lot 3Z administered in a fasted state.

FIGS. 21D-21E present, respectively, geometric mean Cmax and AUC for the subjects of Part 2 of this study (filled squares) compared to the subjects of Part 1 (open squares) where the values for Cmax and AUC have been normalized for each subject to the Cmax and AUC value of that subject when administered the IR tablet, i.e. a tablet having a composition substantially similar to that of Lot 1Z. FIG. 21F presents geometric mean Tmax data for the subjects of Part 2 of this study (filled squares) compared to the subjects of Part 1 (open squares). The error bars in FIGS. 21D-21F represent the 95% confidence intervals.

Table 28A presents the data plotted in FIGS. 21A-21B, Table 29A presents Cmax and AUC data on individual subjects in Part 1 of this study, and Table 30A presents Tmax data on individual subjects in Part 1 of this study. The data in Table 28A presents the normalized average of the subjects' Cmax and AUC where an individual subject's Cmax and AUC was normalized to their IR value, the standard deviation, and the lower 95% confidence interval (L CI) and upper 95% confidence interval (U CI).

Tables 28B and 28C present the data plotted in FIGS. 21D-21E, Table 29B presents Cmax and AUC data on individual subjects in Part 2 of this study, and Table 30B presents Tmax data on individual subjects in Part 2 of this study.

The data in Table 28B presents the normalized average of the subjects' Cmax and AUC for all subjects administered the respective formulation in Part 1 of this study where an individual subject's Cmax and AUC was normalized to their IR value, the lower 95% confidence interval (L CI) and upper 95% confidence interval (U CI).

The data in Table 28C presents the normalized average of the subjects' Cmax and AUC for all subjects administered the respective formulation in Part 2 of this study where an individual subject's Cmax and AUC was normalized to their IR value, the lower 95% confidence interval (L CI) and upper 95% confidence interval (U CI).

Table 31A presents data on the ratio of the total amisulpride AUC from administration to Tmax ($AUC_{0-Tmax}$) to total amisulpride AUC from administration to infinity ($AUC_{0-INF}$), on individual subjects in Part 1 of this study and the average ratio (±the 95% confidence interval for the average) for various compositions. The AUC is given in units of hr*ng/mL.

Table 31B presents data on the ratio of the total amisulpride AUC from administration to Tmax ($AUC_{0-Tmax}$) to total amisulpride AUC from administration to 48 hours ($AUC_{0-48}$) on individual subjects in Part 1 of this study and the average ratio (±the 95% confidence interval for the average) for various compositions. The AUC is given in units of hr*ng/mL.

Table 31C presents data on the ratio of the total amisulpride AUC from administration to Tmax ($AUC_{0-Tmax}$) to total amisulpride AUC from administration to 48 hours ($AUC_{0-48}$) on individual subjects in Part 2 of this study and the average ratio (±the 95% confidence interval for the average) for various compositions. The AUC is given in units of hr*ng/mL.

In Parts 1 and 2 of this study, the pharmacokinetics of an immediate release formulation (Lot 1Z) was compared with that of various modified release formulations in subjects following oral administration. The Cmax observed in Part 1 following administration of the modified release formulation of Lot 3Z (geometric mean=238 ng/mL) is reduced relative to the Cmax value observed for the immediate release formulation (geometric mean=567 ng/mL). In this study, the Cmax observed following administration of the modified release formulation of Lot 3Z is approximately 50% of the Cmax observed following administration of the immediate release formulation of Lot 1Z. The reduction in Cmax observed with the modified release formulation Lot 3Z is accompanied by a decrease in bioavailability. AUC decreased to approximately 60% of that of the IR formulation. When administered in a fed state, the modified release formulation of Lot 3Z maintained similar Cmax and AUC values, but had a longer Tmax compared to the immediate release formulation of Lot 1Z.

It was observed in Part 2 that following administration of the modified release formulation of Lot 5Z the maximum concentration of total amisulpride was reached at between 2.33 and 7 hours post dose (median 4.84 h), after which concentrations followed a biphasic or triphasic decline, remaining quantifiable up to the final sampling time point of 48 hours post-dose in all subjects. Elimination of the modified release formulation of Lot 5Z had a geometric mean half-life of 15-15.5 hours. The modified release formulation of Lot 5Z resulted in an approximate 33-37% reduction in Cmax and an approximate 24-28% reduction in AUC(0-48), compared to an immediate release formulation (Lot 1Z) at the same dose level. Elimination half-life was relatively unchanged with respect to the immediate release (IR) formulation, a small increase of approximately 2.5 hours was observed. Variability of all parameters was similar between the IR formulation and the modified release formulation of Lot 5Z.

It was observed that following administration of the modified release formulation of Lot 6Z maximum concentration of total amisulpride wad reached at between 2.33 and 6 hours post dose (median 4.67 h), after which concentrations followed a biphasic or triphasic decline, remaining quantifiable up to the final sampling time point of 48 hours post-dose in all subjects. Elimination of the modified release formulation of Lot 6Z had a geometric mean half-life of 15.9-16.1 hours. The modified release formulation of Lot 6Z resulted in an approximate 51-54% reduction in Cmax and an approximate 38-42% reduction in AUC(0-48), compared an immediate release formulation (Lot 1Z) at the same dose level. Elimination half-life was relatively unchanged with respect to the immediate release (IR) formulation with a small increase of approximately 3.5 hours. Variability of AUC parameters was similar between the IR tablet and the modified release formulation of Lot 6Z, however variability was slightly increased for Cmax.

In this study the "fed state" was achieved by providing a breakfast consumed over a maximum period of 25 min, with dosing occurring 30 min after the start of breakfast. Subjects were encouraged to eat their meal evenly over the 25 min period, and must have completed 90% of meal in order to be dosed.

TABLE 27A

Cmax (ng/mL) and AUC (ng*h/mL) for Various Compositions in Part 1

| Parameter | Lot 1Z IR | Lot 2Z (10%) | Lot 4Z (15%) | Lot 3Z (25%) | Lot3Z (25%) Fed State |
|---|---|---|---|---|---|
| Cmax | 567 | 424 | 297 | 238 | 269 |
| L CI | 411 | 275 | 206 | 176 | 210 |
| U CI | 780 | 652 | 429 | 210 | 345 |
| AUC | 3811 | 3426 | 2715 | 2478 | 2615 |
| L CI | 3157 | 2594 | 2033 | 1831 | 2027 |
| U CI | 4600 | 4525 | 3627 | 3353 | 3374 |

TABLE 27B

Cmax (ng/mL) and AUC (ng*h/mL) for Various Compositions in Part 1 (all subjects)

| Parameter | Lot 1Z IR | Lot 2Z (10%) | Lot 4Z (15%) | Lot 3Z (25%) | Lot 3Z (25%) Fed State |
|---|---|---|---|---|---|
| Cmax | 567 | 462 | 337 | 252 | 269 |
| L CI | 437 | 331 | 238 | 186 | 210 |
| U CI | 736 | 645 | 477 | 342 | 345 |
| CV % | 54.1 | 66.0 | 65.9 | 62.0 | 38.0 |
| AUC | 3600 | 3360 | 2660 | 2330 | 2350 |
| L CI | 3040 | 2720 | 2120 | 1830 | 1870 |
| U CI | 4270 | 4150 | 3340 | 2960 | 2950 |
| CV % | 33.9 | 39.7 | 41.1 | 47.7 | 34.8 |

TABLE 27C

Cmax (ng/mL) and AUC (ng*h/mL) for Various Compositions in Part 2

| Parameter | Lot 1Z IR | Lot 5Z (20%) | Lot 3Z (25%) | Lot 6Z (40%) |
|---|---|---|---|---|
| Cmax | 634 | 390 | 397 | 298 |
| L CI | 477 | 289 | 297 | 213 |
| U CI | 842 | 527 | 531 | 417 |
| CV % | 57.3 | 66.5 | 56.4 | 72.8 |
| AUC $_{(0-48)}$ | 4120 | 2910 | 2790 | 2510 |
| L CI | 3420 | 2390 | 2270 | 2060 |
| U CI | 4970 | 3540 | 3430 | 3060 |
| CV % | 36.3 | 41.2 | 38.4 | 39.9 |

TABLE 28A

Normalized Cmax and AUC for Various Compositions in Part 1 (subjects who were successfully administered all of the formulations of Part 1 of Example 7A (n = 12))

| Parameter | Lot 1Z IR | Lot 2Z (10%) | Lot 4Z (15%) | Lot 3Z (25%) | Lot 3Z (25%) Fed State |
|---|---|---|---|---|---|
| Cmax | 1 | 0.781 | 0.595 | 0.453 | 0.556 |
| SD | n/a | 0.230 | 0.363 | 0.169 | 0.375 |
| L CI | n/a | 0.626 | 0.351 | 0.339 | 0.304 |
| U CI | n/a | 0.936 | 0.839 | 0.566 | 0.808 |
| AUC | 1 | 0.893 | 0.713 | 0.631 | 0.686 |
| SD | n/a | 0.148 | 0.234 | 0.186 | 0.268 |
| L CI | n/a | 0.794 | 0.556 | 0.506 | 0.506 |
| U CI | n/a | 0.992 | 0.870 | 0.756 | 0.866 |

TABLE 28B

Normalized Cmax and AUC for Various Compositions in Part 1 (all subjects)

| Parameter | Lot 1Z IR | Lot 2Z (10%) | Lot 4Z (15%) | Lot 3Z (25%) | Lot 3Z (25%) Fed State |
|---|---|---|---|---|---|
| Cmax | 1 | 0.791 | 0.596 | 0.461 | 0.487 |
| L CI | n/a | 0.622 | 0.431 | 0.358 | 0.345 |
| U CI | n/a | 1.01 | 0.824 | 0.593 | 0.688 |
| AUC | 1 | 0.899 | 0.733 | 0.654 | 0.658 |
| L CI | n/a | 0.805 | 0.610 | 0.567 | 0.533 |
| U CI | n/a | 1.00 | 0.882 | 0.754 | 0.811 |

TABLE 28C

Normalized Cmax and AUC for Various Compositions in Part 2

| Parameter | Lot 1Z IR | Lot 5Z (20%) | Lot 3Z (25%) | Lot 6Z (40%) |
|---|---|---|---|---|
| Cmax | 1 | 0.645 | 0.637 | 0.483 |
| L CI | n/a | 0.493 | 0.508 | 0.392 |
| U CI | n/a | 0.845 | 0.798 | 0.595 |
| AUC | 1 | 0.735 | 0.683 | 0.603 |
| L CI | n/a | 0.644 | 0.603 | 0.521 |
| U CI | n/a | 0.838 | 0.773 | 0.699 |

TABLE 29A

Cmax and AUC by Subject for Various Compositions in Part 1

| Subject | Lot 2Z (10%) Cmax | Lot 2Z (10%) AUC | Lot 4Z (15%) Cmax | Lot 4Z (15%) AUC | Lot 3Z (25%) Cmax | Lot 3Z (25%) AUC | Lot 3Z (25%) Fed State Cmax | Lot 3Z (25%) Fed State AUC | Lot 1Z IR Cmax | Lot 1Z IR AUC |
|---|---|---|---|---|---|---|---|---|---|---|
| 1 | 230 | 2015 | 125 | 1388 | 85.8 | 982 | 134 | 1364 | 424 | 2699 |
| 2 | 417 | 3050 | 262 | 2930 | 270 | 2820 | NC | NC | 494 | 3580 |
| 5 | 406 | 3300 | 992 | 3600 | 330 | 3390 | NC | NC | 1110 | 4760 |
| 6 | 1080 | 5470 | NC | NC | 936 | 5190 | NC | NC | 933 | 5660 |
| 7 | 1260 | 5568 | 634 | 3583 | 305 | 2613 | 252 | 2821 | 1200 | 5280 |
| 8 | NC | NC | NC | NC | NC | NC | NC | NC | 813 | 4390 |
| 12 | 652 | 4162 | 589 | 4005 | 246 | 2640 | 206 | 2293 | 325 | 2933 |
| 13 | 212 | 2366 | 232 | 1990 | 158 | 1615 | 243 | 2169 | 402 | 2907 |
| 16 | 525 | 3735 | 778 | 4306 | 242 | 2792 | 311 | 2975 | 497 | 3348 |
| 17 | 165 | 2292 | 188 | 3362 | 164 | 3841 | 379 | 4076 | 240 | 3182 |
| 18 | 590 | 4564 | 375 | 3214 | 366 | 3267 | 304 | 2050 | 658 | 4494 |
| 20 | 538 | 3112 | 301 | 3128 | 342 | 2923 | 529 | 4137 | 1070 | 4291 |
| 21 | NC | NC | NC | NC | 93 | 1090 | NC | NC | 248 | 1740 |
| 22 | 789 | 5358 | 334 | 3299 | 241 | 3096 | 191 | 2466 | 861 | 5031 |
| 23 | 229 | 1908 | 161 | 1125 | 270 | 1334 | 199 | 1421 | 458 | 2435 |
| 25 | 392 | 5390 | 325 | 3750 | 257 | 3439 | 309 | 2654 | 429 | 4796 |
| 26 | 664 | 4296 | 300 | 2952 | 408 | 3579 | 296 | 3396 | 665 | 4925 |

NC = not calculated

TABLE 29B

Cmax and AUC by Subject for Various Compositions in Part 2

| Subject | Lot 5Z (20%) Cmax | Lot 5Z (20%) AUC | Lot 3Z (25%) Cmax | Lot 3Z (25%) AUC | Lot 6Z (40%) Cmax | Lot 6Z (40%) AUC | Lot 1Z (IR) Cmax | Lot 1Z (IR) AUC |
|---|---|---|---|---|---|---|---|---|
| 78 | 454 | 2210 | 459 | 1920 | 356 | 1520 | 1070 | 3920 |
| 79 | 562 | 3910 | 257 | 2440 | 121 | 1660 | 386 | 3470 |
| 80 | 870 | 5450 | 442 | 3690 | 560 | 3690 | 1220 | 7640 |

TABLE 29B-continued

Cmax and AUC by Subject for Various Compositions in Part 2

| Subject | Lot 5Z (20%) Cmax | Lot 5Z (20%) AUC | Lot 3Z (25%) Cmax | Lot 3Z (25%) AUC | Lot 6Z (40%) Cmax | Lot 6Z (40%) AUC | Lot 1Z (IR) Cmax | Lot 1Z (IR) AUC |
|---|---|---|---|---|---|---|---|---|
| 81 | 595 | 3450 | 603 | 4000 | 514 | 3110 | 1470 | 5800 |
| 83 | 194 | 2360 | 575 | 2520 | 367 | 2320 | 609 | 2770 |
| 84 | 512 | 2980 | 736 | 3370 | 513 | 3230 | 912 | 5470 |
| 85 | 202 | 2240 | 364 | 2830 | 268 | 2260 | 564 | 3780 |
| 91 | 618 | 3320 | 453 | 2320 | 454 | 2130 | 958 | 4610 |
| 93 | 353 | 1460 | 118 | 1140 | 98.2 | 1090 | 245 | 1990 |
| 97 | 425 | 4130 | 634 | 3600 | 244 | 2690 | 570 | 5510 |
| 99 | 740 | 5150 | 923 | 5720 | 281 | 3490 | 781 | 6150 |
| 102 | 137 | 2410 | 261 | 2240 | 84.1 | 1820 | 300 | 2840 |
| 107 | 347 | 2090 | 331 | 3420 | 611 | 5370 | 798 | 4610 |
| 111 | 249 | 1390 | NC | NC | NC | NC | NC | NC |
| 112 | 133 | 2250 | 303 | 2840 | 295 | 2380 | 294 | 2920 |
| 113 | 1040 | 4640 | NC | NC | 856 | 3540 | 807 | 4580 |
| 114 | 283 | 3220 | NC | NC | 196 | 2950 | NC | NC |
| 115 | 514 | 3570 | 244 | 2480 | 238 | 2420 | 494 | 3660 |

NC = not calculated

TABLE 30A

Tmax (hours) by Subject for Various Compositions in Part 1

| Subject | Lot 2Z (10%) Tmax (hours) | Lot 4Z (15%) Tmax (hours) | Lot 3Z (25%) Tmax (hours) | Lot 3Z (25%) Fed State Tmax (hours) | Lot 1Z IR Tmax (hours) |
|---|---|---|---|---|---|
| 1 | 3.33 | 4.67 | 3.33 | 6 | 2.67 |
| 2 | 3.67 | 5.00 | 4.33 | NC | 3.67 |
| 5 | 4.33 | 4.33 | 3.67 | NC | 4.33 |
| 6 | 3.33 | NC | 3.33 | NC | 3.33 |
| 7 | 3 | 3 | 2.67 | 5.5 | 2.33 |
| 8 | NC | NC | NC | NC | 5.00 |
| 13 | 2 | 3.67 | 4 | 5.5 | 2.33 |
| 16 | 4.33 | 3.67 | 4.67 | 4.33 | 4 |
| 17 | 4.67 | 6.5 | 4 | 5.5 | 5 |
| 18 | 4.67 | 3.67 | 5 | 5.5 | 3.67 |
| 20 | 5 | 5 | 2.33 | 3.67 | 2.33 |
| 21 | NC | NC | 5.0 | NC | 4.40 |
| 22 | 4.33 | 4.67 | 4.67 | 7 | 4.67 |
| 23 | 4.33 | 4.33 | 4.33 | 5.5 | 4.33 |
| 25 | 5.5 | 5.5 | 5.5 | 5 | 6 |
| 26 | 2.33 | 3 | 4.33 | 6.5 | 1.67 |

NC = not calculated

TABLE 30B

Tmax (hours) by Subject for Various Compositions in Part 2

| Subject | Lot 5Z (20%) Tmax (hours) | Lot 3Z (25%) Tmax (hours) | Lot 6Z (40%) Tmax (hours) | Lot 1Z (IR) Tmax (hours) |
|---|---|---|---|---|
| 78 | 3.33 | 3.33 | 2.33 | 3.67 |
| 79 | 5.50 | 4.00 | 5.00 | 4.33 |
| 80 | 5.50 | 4.33 | 4.00 | 4.00 |
| 81 | 4.33 | 5.00 | 3.00 | 3.00 |
| 83 | 2.33 | 4.00 | 3.33 | 2.67 |
| 84 | 4.67 | 5.00 | 5.50 | 5.50 |
| 85 | 5.00 | 4.67 | 4.67 | 4.67 |
| 91 | 4.33 | 4.00 | 4.67 | 2.33 |
| 93 | 4.67 | 4.00 | 5.00 | 5.00 |
| 97 | 5.00 | 5.50 | 5.50 | 4.67 |
| 99 | 5.50 | 5.50 | 6.00 | 4.00 |
| 102 | 6.00 | 5.50 | 6.00 | 4.33 |
| 107 | 5.00 | 5.50 | 4.00 | 3.67 |
| 111 | 4.67 | NC | NC | NC |
| 112 | 7.00 | 5.00 | 4.67 | 4.00 |
| 113 | 4.67 | NC | 5.00 | 4.33 |

TABLE 30B-continued

Tmax (hours) by Subject for Various Compositions in Part 2

| Subject | Lot 5Z (20%) Tmax (hours) | Lot 3Z (25%) Tmax (hours) | Lot 6Z (40%) Tmax (hours) | Lot 1Z (IR) Tmax (hours) |
|---|---|---|---|---|
| 114 | 4.00 | NC | 4.33 | NC |
| 115 | 6.00 | 13.67 | 4.67 | 3.33 |

NC = not calculated

TABLE 31A $(AUC_{0-Tmax})/(AUC_{0-INF})$, for Various Compositions in Part 1

| Subject | Lot 1Z (IR) $AUC_{0-Tmax}/AUC_{0-INF}$ | Lot 2Z (10%) $AUC_{0-Tmax}/AUC_{0-INF}$ | Lot 4Z (15%) $AUC_{0-Tmax}/AUC_{0-INF}$ | Lot 3Z (25%) $AUC_{0-Tmax}/AUC_{0-INF}$ | Lot 3Z (25%) Fed State $AUC_{0-Tmax}/AUC_{0-INF}$ |
|---|---|---|---|---|---|
| 1 | 0.137 | 0.135 | 0.245 | 0.131 | 0.331 |
| 7 | 0.141 | 0.132 | 0.123 | 0.063 | 0.163 |
| 12 | 0.324 | 0.279 | 0.181 | 0.133 | 0.176 |
| 13 | 0.136 | 0.064 | 0.185 | 0.152 | 0.187 |
| 16 | 0.185 | 0.128 | 0.141 | 0.117 | 0.151 |
| 17 | 0.179 | 0.154 | 0.178 | 0.074 | 0.154 |
| 18 | 0.227 | 0.276 | 0.151 | 0.162 | 0.214 |
| 20 | 0.121 | 0.145 | 0.122 | 0.055 | 0.220 |
| 22 | 0.161 | 0.151 | 0.145 | 0.108 | 0.210 |
| 23 | 0.318 | 0.189 | 0.179 | 0.142 | 0.313 |
| 25 | 0.240 | 0.181 | 0.125 | 0.123 | 0.159 |
| 26 | 0.082 | 0.103 | 0.136 | 0.175 | 0.282 |
| Average | 0.19 ± 0.04 | 0.16 ± 0.04 | 0.16 ± 0.02 | 0.12 ± 0.02 | 0.21 ± 0.04 |

TABLE 31B $(AUC_{0-Tmax})/(AUC_{0-48})$, for Various Compositions in Part 1

| Subject | Lot 1Z (IR) $AUC_{0-Tmax}/AUC_{0-48}$ | Lot 2Z (10%) $AUC_{0-Tmax}/AUC_{0-48}$ | Lot 4Z (15%) $AUC_{0-Tmax}/AUC_{0-48}$ | Lot 3Z (25%) $AUC_{0-Tmax}/AUC_{0-48}$ | Lot 3Z (25%) Fed State $AUC_{0-Tmax}/AUC_{0-48}$ |
|---|---|---|---|---|---|
| 1 | 0.138 | 0.141 | 0.265 | 0.132 | 0.337 |
| 2 | 0.254 | 0.213 | 0.224 | 0.186 | NC |
| 5 | 0.243 | 0.315 | 0.216 | 0.154 | NC |
| 6 | 0.164 | 0.157 | NC | 0.168 | NC |
| 7 | 0.144 | 0.136 | 0.128 | 0.066 | 0.173 |
| 8 | 0.191 | NC | NC | NC | NC |
| 12 | 0.339 | 0.292 | 0.189 | 0.151 | 0.190 |
| 13 | 0.142 | 0.073 | 0.195 | 0.160 | 0.203 |
| 16 | 0.191 | 0.140 | 0.148 | 0.135 | 0.170 |
| 17 | 0.217 | 0.174 | 0.230 | 0.102 | 0.196 |
| 18 | 0.232 | 0.287 | 0.157 | 0.167 | 0.219 |
| 20 | 0.128 | 0.151 | 0.138 | 0.067 | 0.239 |
| 21 | 0.202 | NC | NC | 0.214 | NC |
| 22 | 0.176 | 0.167 | 0.177 | 0.138 | 0.292 |
| 23 | 0.323 | 0.193 | 0.184 | 0.152 | 0.323 |
| 25 | 0.248 | 0.202 | 0.133 | 0.135 | 0.174 |
| 26 | 0.085 | 0.107 | 0.146 | 0.188 | 0.317 |
| Average | 0.20 ± 0.3 | 0.18 ± 0.04 | 0.18 ± 0.02 | 0.15 ± 0.02 | 0.24 ± 0.04 |

NC = not calculated

TABLE 31C $(AUC_{0-Tmax})/(AUC_{0-48})$, for Various Compositions in Part 2

| Subject | Lot 1Z (IR) $AUC_{0-Tmax}/AUC_{0-48}$ | Lot 5Z (20%) $AUC_{0-Tmax}/AUC_{0-48}$ | Lot 3Z (25%) $AUC_{0-Tmax}/AUC_{0-48}$ | Lot 6Z (40%) $AUC_{0-Tmax}/AUC_{0-48}$ |
|---|---|---|---|---|
| 78 | 0.210 | 0.187 | 0.144 | 0.098 |
| 79 | 0.262 | 0.253 | 0.125 | 0.229 |
| 80 | 0.191 | 0.194 | 0.156 | 0.145 |

TABLE 31C-continued $(AUC_{0-Tmax})/(AUC_{0-48})$, for Various Compositions in Part 2

| Subject | Lot 1Z (IR) $AUC_{0-Tmax}$ $AUC_{0-48}$ | Lot 5Z (20%) $AUC_{0-Tmax}$ $AUC_{0-48}$ | Lot 3Z (25%) $AUC_{0-Tmax}$ $AUC_{0-48}$ | Lot 6Z (40%) $AUC_{0-Tmax}$ $AUC_{0-48}$ |
|---|---|---|---|---|
| 81 | 0.202 | 0.153 | 0.097 | 0.064 |
| 83 | 0.180 | 0.049 | 0.225 | 0.149 |
| 84 | 0.363 | 0.138 | 0.136 | 0.144 |
| 85 | 0.242 | 0.204 | 0.131 | 0.078 |
| 91 | 0.141 | 0.194 | 0.129 | 0.195 |
| 93 | 0.279 | 0.181 | 0.200 | 0.186 |
| 97 | 0.285 | 0.248 | 0.267 | 0.155 |
| 99 | 0.206 | 0.202 | 0.225 | 0.192 |
| 102 | 0.182 | 0.163 | 0.152 | 0.127 |
| 107 | 0.215 | 0.298 | 0.180 | 0.131 |
| 111 | NC | 0.218 | NC | NC |
| 112 | 0.208 | 0.224 | 0.199 | 0.161 |
| 113 | 0.235 | 0.170 | NC | 0.208 |
| 114 | NC | 0.152 | NC | 0.126 |
| 115 | 0.200 | 0.256 | 0.106 | 0.115 |
| Average | 0.23 ± 0.03 | 0.19 ± 0.03 | 0.17 ± 0.03 | 0.15 ± 0.02 |

NC = not calculated

The present inventors have discovered that the kinetics of amisulpride's gastrointestinal absorption is uneven and leads to transiently high drug concentrations at Tmax, and that the kinetics of amisulpride permeability across the blood-brain barrier appear to be unique among what is known about antipsychotics' brain occupancies. In addition, the present inventors have discovered that amisulpride isomers have durations of brain pharmacodynamics that extend well beyond the plasma pharmacokinetics. Thus in various embodiments, the inventors provide MR drug formulations with kinetics to reduce the Cmax of the therapeutic agents (85:15 R:S amisulpride) while still achieving the brain occupancies that provide therapeutic effects.

In addition, measurements of QT interval prolongation were also conducted in this study. The subjects were administered a single solid oral dose of a fixed ratio composition of (R)-amisulpride to (S)-amisulpride of 85:15 by weight at total composition amounts of 200 mg (170 mg R-amisulpride:30 mg S-amisulpride) in various formulations. Specifically, QT interval measurements for the subjects in this study were conducted on an IR formulation (Lot 1Z), three modified formulations given in a fasted stated (i.e. the formulations of Lot 2Z, Lot 3Z and Lot 4Z), and one modified release formulation given in a fed state (i.e. formulation of Lot 3Z fed state)

QT interval measurements for the subjects in this study were made by continuous 12-lead ECGs recorded with Holter monitors for a minimum of 25 hours post-dose. The Holter monitor was attached to the subjects prior to initiating the continuous recording. The Holter monitor was started approximately 2 to 3 hours prior to dosing and continued post-dose. ECGs were extracted from the continuous recording by a central ECG laboratory from at least 3 pre-dose time-points (−45, −30 and −15 minutes) and at 13 post-dose time points, at the following times: 20, 45, 80, 120, 160, 200, 240, 280 minutes (±5 minutes) post dose and at 5.5, 6.5, 7.5, 9, 12 and 24 h (±10 minutes) post dose. At each time point, subjects were supine for at least 10 minutes prior to and 5 minutes after the extraction time point. The central ECG laboratory used an advanced computer-assisted and statistical process to extract ECGs from continuous recordings. During the specified ECG extraction windows, 10-second digital 12-lead ECG tracings were extracted from continuous recordings by identifying periods of recordings with the lowest available heart rate variability and noise. At each time point specified, up to 10 ECG replicates were extracted. All readable cardiac cycles from these ECG replicates were assessed for multiple quality metrics, including beat stability, heart rate changes, noise, and other parameters, and were categorized into high and low confidence ranks. All low confidence beats were fully reviewed and adjudicated manually by ECG technicians using pass-fail criteria. The beats found acceptable by manual review were included in the analysis.

Baseline data was obtained, respectively, for 14, 13, 16, and 13 subjects in treatment periods with Lot 2Z, Lot 4Z, Lot 3Z, and Lot 3Z given in a fed state, and from 17 subjects administered the IR formulation of Lot 1Z. Baseline HR and QTcF were within expectations for a healthy adult population with mean baseline HR across treatments between 60.2 and 61.8 bpm and mean baseline QTcF across treatments between 402.9 and 414.5 ms. The measured baseline values of heart rate (HR) and QTcF are given in Table 32, where n is the number of subjects, SD is standard deviation, SE is standard error, L 90% CI is the lower 90% confidence interval, and U 90% CI is the upper 90% confidence interval.

TABLE 32

Baseline Parameters

| Parameter | Statistics | LOT 2Z | LOT 4Z | LOT 3Z | LOT 3Z fed state | LOT 1Z |
|---|---|---|---|---|---|---|
| QTcF (ms) | n | 14 | 13 | 16 | 13 | 17 |
|  | Mean (SD) | 411.4 (19.83) | 407.5 (18.76) | 412.7 (19.97) | 402.9 (18.81) | 414.5 (20.26) |
|  | SE | 5.30 | 5.20 | 4.99 | 5.22 | 4.91 |
|  | L 90% CI | 402.03 | 398.25 | 403.98 | 393.57 | 405.97 |
|  | U 90% CI | 420.80 | 416.79 | 421.48 | 412.16 | 423.12 |
|  | Median | 409.5 | 403.5 | 411.0 | 398.1 | 408.6 |
| HR (bpm) | n | 14 | 13 | 16 | 13 | 17 |
|  | Mean (SD) | 61.8 (6.39) | 61.4 (6.79) | 60.8 (7.96) | 60.2 (6.57) | 60.9 (8.51) |
|  | SE | 1.71 | 1.88 | 1.99 | 1.82 | 2.06 |
|  | L 90% CI | 58.75 | 58.00 | 57.34 | 56.92 | 57.30 |
|  | U 90% CI | 64.80 | 64.71 | 64.32 | 63.41 | 64.51 |
|  | Median | 62.0 | 60.2 | 59.3 | 57.6 | 57.7 |

A summary of the observed values for HR and change from baseline, ΔHR, are presented in Table 33, and the observed values for QTcF and change from baseline, ΔQTcF, are presented in Table 34. In Tables 33 and 34, SE is standard error, L 90% CI is the lower 90% confidence interval, and U 90% CI is the upper 90% confidence interval, Min is the minimum observed value, Max the maximum observed value, and n the number of subjects.

Mean change-from-baseline HR (ΔHR) was similar across treatments, except for the Lot 3Z fed state treatment, in which mean ΔHR increased immediately after dosing, likely due to the effect of food digestion on HR. In the first 240 minutes after dosing, mean ΔHR on the other treatments ranged from −1.6 to 3.2 bpm, while mean ΔHR on the Lot 3Z fed state treatment reached 10.8 bpm at 20 minutes post-dose. From 280 minutes through 24 hours post-dose, mean ΔHR ranged from 1.9 to 10.9 bpm across all treatments, with very similar patterns across treatment periods.

Mean change-from-baseline QTcF (ΔQTcF) was largest at 280 minutes post-dose for all treatments, with mean ΔQTcF on Lot 1Z (IR formulation) and Lot 2Z reaching 14.4 and 14.1 ms, respectively.

TABLE 33

Summary of observed values and change-from-baseline values of HR

| Time Point | Parameter | Statistics | LOT 2Z (10%) | LOT 4Z (15%) | LOT 3Z (25%) | LOT 3Z fed state | LOT 1Z (IR) |
|---|---|---|---|---|---|---|---|
| Baseline | HR (bpm) | n | 14 | 13 | 16 | 13 | 17 |
| | | Mean (SD) | 61.8 (6.4) | 61.4 (6.8) | 60.8 (8.0) | 60.2 (6.6) | 60.9 (8.5) |
| | | SE | 1.71 | 1.88 | 1.99 | 1.82 | 2.06 |
| | | Median | 62 | 60.2 | 59.3 | 57.6 | 57.7 |
| | | L 90% CI | 58.75 | 58.00 | 57.34 | 56.92 | 57.30 |
| | | U 90% CI | 64.80 | 64.71 | 64.32 | 63.41 | 64.51 |
| | | Min, Max | 51, 76 | 54, 77 | 51, 76 | 53, 77 | 52, 87 |
| 20 min Post-dose | HR (bpm) | n | 14 | 13 | 16 | 13 | 17 |
| | | Mean (SD) | 61.4 (6.0) | 61.6 (6.5) | 60.3 (7.6) | 71.1 (8 5) | 59.4 (7.4) |
| | | SE | 1.60 | 1.81 | 1.90 | 2.36 | 1.80 |
| | | Median | 61.5 | 60.2 | 59.3 | 70 | 58.5 |
| | | L 90% CI | 58.60 | 58.35 | 56.93 | 66.91 | 56.23 |
| | | U 90% CI | 64.28 | 64.81 | 63.58 | 75.31 | 62.53 |
| | | Min, Max | 52, 74 | 54, 78 | 50, 76 | 59, 87 | 47, 78 |
| | ΔHR (bpm) | n | 14 | 13 | 16 | 13 | 17 |
| | | Mean (SD) | −0.3 (2.9) | 0.2 (2.3) | −0.6 (3.2) | 10.9 (4.4) | −1.5 (4.4) |
| | | SE | 0.79 | 0.63 | 0.81 | 1.23 | 1.07 |
| | | Median | −0.6 | 0 | −0.1 | 11.9 | −1.1 |
| | | L 90% CI | −1.72 | −0.90 | −1.98 | 8.75 | −3.39 |
| | | U 90% CI | 1.06 | 1.35 | 0.84 | 13.14 | 0.33 |
| | | Min, Max | −5, 3 | −5, 4 | −6, 7 | 2, 16 | −10, 6 |
| 45 min Post-dose | HR (bpm) | n | 14 | 13 | 16 | 13 | 17 |
| | | Mean (SD) | 61.3 (6.9) | 61.6 (7.1) | 60.0 (7.1) | 68.2 (6.9) | 60.6 (7.0) |
| | | SE | 1.84 | 1.98 | 1.77 | 1.91 | 1.70 |
| | | Median | 61 | 62.4 | 59.7 | 68.3 | 59.9 |
| | | L 90% CI | (8.05 | 58.03 | 56.89 | 64.84 | 57.67 |
| | | U 90% CI | 64.57 | 65.08 | 63.10 | 71.66 | 63.60 |
| | | Min, Max | 53, 78 | 53, 79 | 49, 77 | 60, 83 | 48, 77 |
| | ΔHR (bpm) | n | 14 | 13 | 16 | 13 | 17 |
| | | Mean (SD) | −0.5 (3.4) | 0.2 (4.5) | −0.8 (3.2) | 8.1 (3.9) | −0.3 (4.7) |
| | | SE | 0.90 | 1.26 | 0.80 | 1.07 | 1.14 |
| | | Median | −1.4 | 1.4 | −0.9 | 8.2 | 0.7 |
| | | L 90% CI | −2.05 | −2.04 | −2.24 | 6.18 | −2.27 |
| | | U 90% CI | 1.13 | 2.45 | 0.56 | 9.99 | 1.72 |
| | | Min, Max | −6, 5 | −13, 4 | −9, 4 | 2, 14 | −10, 8 |
| 80 min Post-dose | HR (bpm) | n | 14 | 13 | 16 | 13 | 17 |
| | | Mean (SD) | 60.5 (7.1) | 59.8 (6.0) | 59.6 (8.7) | 66.7 (6.9) | 59.7 (7.6) |
| | | SE | 1.90 | 1.67 | 2.17 | 1.91 | 1.83 |
| | | Median | 59.4 | 59.8 | 59 | 66.3 | 55.9 |
| | | L 90% CI | 57.10 | 56.84 | 55.80 | 63.31 | 56.47 |
| | | U 90% CI | 63.85 | 62.80 | 63.40 | 70.11 | 62.86 |
| | | Min, Max | 49, 75 | 52, 74 | 45, 77 | 59, 84 | 50, 77 |
| | ΔHR (bpm) | n | 14 | 13 | 16 | 13 | 17 |
| | | Mean (SD) | −1.3 (2.9) | −1.5 (4.2) | −1.2 (3.9) | 6.5 (3.9) | −1.2 (4.9) |
| | | SE | 0.77 | 1.15 | 0.97 | 1.07 | 1.19 |
| | | Median | −2.2 | −0.4 | −1.6 | 6.8 | −0.1 |
| | | L 90% CI | −2.65 | −3.59 | −2.93 | 4.64 | −3.33 |
| | | U 90% CI | 0.06 | 0.52 | 0.47 | 8.45 | 0.85 |
| | | Min, Max | −6, 4 | −12, 3 | −6, 6 | −1, 15 | −14, 7 |
| 120 min Post-dose | HR (bpm) | n | 13 | 13 | 16 | 13 | 17 |
| | | Mean (SD) | 62.3 (8.4) | 62.7 (7.0) | 59.6 (8.2) | 65.4 (6.4) | 60.9 (8.4) |
| | | SE | 2.34 | 1.93 | 2.06 | 1.77 | 2.03 |
| | | Median | 62 | 61.9 | 58.4 | 64 | 58.8 |
| | | L 90% CI | 58.10 | 59.29 | 55.94 | 62.23 | 57.38 |
| | | U 90% CI | 66.45 | 66.18 | 63.16 | 68.53 | 64.47 |
| | | Min, Max | 51, 79 | 54, 79 | 46, 77 | 58, 81 | 46, 78 |
| | ΔHR (bpm) | n | 13 | 13 | 16 | 13 | 17 |
| | | Mean (SD) | 0.6 (4.2) | 1.4 (4.7) | −1.3 (5.3) | 5.2 (4.5) | 0.0 (4.8) |
| | | SE | 1.16 | 1.29 | 1.32 | 1.25 | 1.16 |
| | | Median | 2.2 | 2.7 | −0.5 | 6.2 | 0.6 |
| | | L 90% CI | −1.48 | −0.92 | −3.60 | 2.98 | −2.00 |
| | | U 90% CI | 2.64 | 3.69 | 1.04 | 7.45 | 2.04 |
| | | Min, Max | −8, 6 | −13, 5 | −11, 7 | −3, 13 | −9, 8 |

TABLE 33-continued

Summary of observed values and change-from-baseline values of HR

| Time Point | Parameter | Statistics | LOT 2Z (10%) | LOT 4Z (15%) | LOT 3Z (25%) | LOT 3Z fed state | LOT 1Z (IR) |
|---|---|---|---|---|---|---|---|
| 160 min Post-dose | HR (bpm) | n | 14 | 13 | 16 | 13 | 17 |
| | | Mean (SD) | 63.3 (7.6) | 62.5 (8.0) | 61.2 (8.4) | 64.9 (6.6) | 59.9 (7.2) |
| | | SE | 2.03 | 2.21 | 2.09 | 1.82 | 1.75 |
| | | Median | 63.4 | 62.1 | 59.2 | 65 | 58.8 |
| | | L 90% CI | 59.69 | 58.56 | 57.53 | 61.63 | 56.85 |
| | | U 90% CI | 66.88 | 66.43 | 64.86 | 68.12 | 62.96 |
| | | Min, Max | 52, 78 | 53, 82 | 52, 77 | 55, 81 | 49, 78 |
| | ΔHR (bpm) | n | 14 | 13 | 16 | 13 | 17 |
| | | Mean (SD) | 1.5 (2.9) | 1.1 (3.3) | 0.4 (4.0) | 4.7 (4.8) | −1.0 (5.5) |
| | | SE | 0.79 | 0.93 | 1.01 | 1.33 | 1.34 |
| | | Median | 2 | 0.4 | 1.1 | 5.8 | −0.1 |
| | | L 90% CI | 0.12 | −0.51 | −1.40 | 2.33 | −3.35 |
| | | U 90% CI | 2.91 | 2.80 | 2.13 | 7.09 | 1.35 |
| | | Min, Max | −3, 9 | −5, 7 | −8, 8 | −4, 12 | −12, 9 |
| 200 min Post-dose | HR (bpm) | n | 14 | 13 | 16 | 13 | 17 |
| | | Mean (SD) | 63.9 (6.4) | 62.6 (7.0) | 60.7 (7.3) | 64.8 (7.2) | 61.9 (8.3) |
| | | SE | 1.70 | 1.95 | 1.83 | 2.00 | 2.00 |
| | | Median | 64.3 | 62.8 | 59.5 | 64 | 61.8 |
| | | L 90% CI | 60.88 | 59.15 | 57.50 | 61.27 | 58.43 |
| | | U 90% CI | 66.89 | 66.11 | 63.93 | 68.39 | 65.41 |
| | | Min, Max | 53, 74 | 54, 79 | 52, 74 | 56, 82 | 46, 80 |
| | ΔHR (bpm) | n | 14 | 13 | 16 | 13 | 17 |
| | | Mean (SD) | 2.1 (2.8) | 1.3 (1.8) | −0.1 (4.2) | 4.7 (4.8) | 1.0 (5.5) |
| | | SE | 0.76 | 0.50 | 1.05 | 1.32 | 1.34 |
| | | Median | 2.3 | 1.4 | 1.1 | 5.1 | 2.5 |
| | | L 90% CI | 0.77 | 0.38 | −1.95 | 2.32 | −1.33 |
| | | U 90% CI | 3.45 | 2.17 | 1.72 | 7.02 | 3.36 |
| | | Min, Max | −3, 8 | −1, 4 | −7, 9 | −1, 16 | −10, 10 |
| 240 min Post-dose | HR (bpm) | n | 14 | 13 | 16 | 13 | 17 |
| | | Mean (SD) | 64.5 (8.1) | 64.5 (7.6) | 61.0 (8.2) | 64.3 (7.4) | 62.2 (9.4) |
| | | SE | 2.17 | 2.10 | 2.06 | 2.04 | 2.28 |
| | | Median | 62.3 | 63.9 | 59.4 | 63.5 | 60 |
| | | L 90% CI | 60.66 | 60.77 | 57.39 | 60.65 | 58.21 |
| | | U 90% CI | 68.34 | 68.27 | 64.61 | 67.93 | 66.16 |
| | | Min, Max | 53, 83 | 55, 84 | 47, 77 | 55, 83 | 46, 82 |
| | ΔHR (bpm) | n | 14 | 13 | 16 | 13 | 17 |
| | | Mean (SD) | 2.7 (4.4) | 3.2 (3.7) | 0.2 (4.3) | 4.1 (3.7) | 1.3 (5.8) |
| | | SE | 1.18 | 1.04 | 1.09 | 1.03 | 1.41 |
| | | Median | 2.4 | 3.3 | 1.3 | 4 | 1.6 |
| | | L 90% CI | 0.64 | 1.31 | −1.74 | 2.29 | −1.18 |
| | | U 90% CI | 4.82 | 5.01 | 2.07 | 5.96 | 3.74 |
| | | Min, Max | −5, 12 | −5, 8 | −7, 7 | −1, 12 | −8, 14 |
| 280 min Post-dose | HR (bpm) | n | 14 | 13 | 15 | 13 | 17 |
| | | Mean (SD) | 71.1 (9.3) | 71.2 (8.1) | 70.6 (9.7) | 66.4 (7.0) | 69.4 (9.9) |
| | | SE | 2.50 | 2.25 | 2.50 | 1.95 | 2.41 |
| | | Median | 69.8 | 70.4 | 68.3 | 68.5 | 70.3 |
| | | L 90% CI | 66.70 | 67.15 | 66.19 | 62.91 | 65.17 |
| | | U 90% CI | 75.54 | 75.16 | 74.99 | 69.85 | 73.59 |
| | | Min, Max | 53, 88 | 56, 84 | 58, 91 | 55, 79 | 50, 86 |
| | ΔHR (bpm) | n | 14 | 13 | 15 | 13 | 17 |
| | | Mean (SD) | 9.3 (5.9) | 9.8 (4.9) | 9.2 (7.4) | 6.2 (5.6) | 8.5 (7.4) |
| | | SE | 1.57 | 1.35 | 1.92 | 1.56 | 1.80 |
| | | Median | 9.9 | 10.2 | 9.5 | 5.2 | 9.5 |
| | | L 90% CI | 6.57 | 7.39 | 5.80 | 3.44 | 5.32 |
| | | U 90% CI | 12.13 | 12.22 | 12.56 | 8.99 | 11.62 |
| | | Min, Max | −3, 18 | 2, 18 | −2, 21 | −2, 16 | −4, 19 |
| 5.5 h Post-dose | HR (bpm) | n | 13 | 13 | 16 | 13 | 17 |
| | | Mean (SD) | 71.1 (6.9) | 72.1 (8.0) | 68.7 (9.8) | 69.5 (7.4) | 69.5 (8.3) |
| | | SE | 1.91 | 2.22 | 2.44 | 2.05 | 2.02 |
| | | Median | 68.4 | 71.2 | 68.8 | 68.7 | 70.8 |
| | | L 90% CI | 67.73 | 68.20 | 64.44 | 65.81 | 65.94 |
| | | U 90% CI | 74.53 | 76.10 | 72.99 | 73.11 | 73.01 |
| | | Min, Max | 63, 84 | 56, 84 | 53, 84 | 60, 85 | 55, 85 |
| | | n | 13 | 13 | 16 | 13 | 17 |
| | ΔHR (bpm) | Mean (SD) | 9.2 (4.8) | 10.8 (6.0) | 7.9 (6.7) | 9.3 (6.1) | 8.6 (7.2) |
| | | SE | 1.34 | 1.67 | 1.68 | 1.69 | 1.75 |
| | | Median | 8.9 | 11 | 6.5 | 5.9 | 8.5 |
| | | L 90% CI | 6.84 | 7.82 | 4.94 | 6.28 | 5.51 |
| | | U 90% CI | 11.61 | 13.77 | 10.82 | 12.31 | 11.62 |
| | | Min, Max | 4, 21 | −0, 24 | −1, 23 | 2, 21 | −10, 21 |
| | | n | 14 | 13 | 15 | 13 | 17 |
| 6.5 h Post-dose | HR (bpm) | Mean (SD) | 72.0 (8.4) | 72.1 (10.1) | 70.9 (9.2) | 70.6 (8.1) | 70.6 (8.7) |
| | | SE | 2.25 | 2.80 | 2.36 | 2.24 | 2.12 |
| | | Median | 72.4 | 68.9 | 70 | 71.4 | 71.2 |
| | | L 90% CI | 68.03 | 67.15 | 66.72 | 66.58 | 66.87 |

TABLE 33-continued

Summary of observed values and change-from-baseline values of HR

| Time Point | Parameter | Statistics | LOT 2Z (10%) | LOT 4Z (15%) | LOT 3Z (25%) | LOT 3Z fed state | LOT 1Z (IR) |
|---|---|---|---|---|---|---|---|
| | | U 90% CI | 76.00 | 77.11 | 75.04 | 74.56 | 74.26 |
| | | Min, Max | 59, 89 | 59, 89 | 53, 85 | 59, 90 | 54, 88 |
| | | n | 14 | 13 | 15 | 13 | 17 |
| | ΔHR (bpm) | Mean (SD) | 10.2 (3.8) | 10.8 (6.6) | 9.5 (6.1) | 10.4 (5.9) | 9.7 (7.1) |
| | | SE | 1.03 | 1.82 | 1.57 | 1.63 | 1.72 |
| | | Median | 9.6 | 8.3 | 9.3 | 9.3 | 11.6 |
| | | L 90% CI | 8.43 | 7.52 | 6.72 | 7.50 | 6.65 |
| | | U 90% CI | 12.06 | 14.03 | 12.23 | 13.32 | 12.66 |
| | | Min, Max | 6, 19 | 4, 26 | 2, 23 | 2, 20 | −6, 20 |
| | | n | 14 | 13 | 16 | 13 | 17 |
| 7.5 h Post-dose | HR (bpm) | Mean (SD) | 70.0 (10.1) | 70.9 (10.7) | 66.9 (9.6) | 66.3 (8.8) | 68.2 (9.9) |
| | | SE | 2.69 | 2.96 | 2.40 | 2.44 | 2.41 |
| | | Median | 67.8 | 70.5 | 64.7 | 66 | 67.8 |
| | | L 90% CI | 65.22 | 65.67 | 62.67 | 61.94 | 63.98 |
| | | U 90% CI | 74.73 | 76.23 | 71.09 | 70.63 | 72.41 |
| | | Min, Max | 55, 92 | 57, 87 | 53, 86 | 57, 87 | 50, 89 |
| | | n | 14 | 13 | 16 | 13 | 17 |
| | ΔHR (bpm) | Mean (SD) | 8.2 (6.1) | 9.6 (6.0) | 6.1 (6.7) | 6.1 (6.5) | 7.3 (6.5) |
| | | SE | 1.62 | 1.66 | 1.67 | 1.81 | 1.57 |
| | | Median | 7.6 | 8.8 | 3.7 | 4.3 | 8.4 |
| | | L 90% CI | 5.33 | 6.64 | 3.12 | 2.90 | 4.55 |
| | | U 90% CI | 11.07 | 12.55 | 8.98 | 9.34 | 10.02 |
| | | Min, Max | −1, 19 | 3, 23 | −4, 21 | −4, 16 | −7, 17 |
| | | n | 14 | 13 | 16 | 13 | 17 |
| 9 h Post-dose | HR (bpm) | Mean (SD) | 66.9 (8.4) | 66.6 (8.7) | 63.2 (10.2) | 62.2 (7.5) | 65.0 (10.1) |
| | | SE | 2.25 | 2.40 | 2.54 | 2.07 | 2.45 |
| | | Median | 66.1 | 64.3 | 60.4 | 61.8 | 63.5 |
| | | L 90% CI | 62.93 | 62.34 | 58.77 | 58.49 | 60.71 |
| | | U 90% CI | 70.88 | 70.90 | 67.68 | 65.88 | 69.26 |
| | | Min, Max | 55, 84 | 58, 85 | 51, 86 | 52, 81 | 48, 88 |
| | | n | 14 | 13 | 16 | 13 | 17 |
| | ΔHR (bpm) | Mean (SD) | 5.1 (4.4) | 5.3 (4.4) | 2.4 (7.1) | 2.0 (4.0) | 4.1 (6.2) |
| | | SE | 1.16 | 1.23 | 1.78 | 1.11 | 1.50 |
| | | Median | 4.4 | 3.6 | 1.4 | 3.1 | 3.4 |
| | | L 90% CI | 3.07 | 3.07 | −0.73 | 0.04 | 1.46 |
| | | U 90% CI | 7.19 | 7.46 | 5.52 | 4.00 | 6.70 |
| | | Min, Max | −1, 13 | −1, 16 | −10, 15 | −3, 10 | −7, 13 |
| | | n | 14 | 13 | 15 | 13 | 17 |
| 12 h Post-dose | HR (bpm) | Mean (SD) | 69.3 (8.0) | 69.7 (9.5) | 66.9 (8.2) | 68.1 (7.0) | 67.0 (9.7) |
| | | SE | 2.13 | 2.65 | 2.12 | 1.95 | 2.36 |
| | | Median | 67.9 | 69 | 66.7 | 67.4 | 68.2 |
| | | L 90% CI | 65.56 | 65.01 | 63.21 | 64.67 | 62.92 |
| | | U 90% CI | 73.13 | 74.45 | 70.69 | 71.62 | 71.14 |
| | | Min, Max | 58, 85 | 55, 84 | 55, 80 | 59, 80 | 51, 92 |
| | | n | 14 | 13 | 15 | 13 | 17 |
| | ΔHR (bpm) | Mean (SD) | 7.6 (3.7) | 8.4 (5.4) | 6.5 (4.9) | 8.0 (4.0) | 6.1 (5.0) |
| | | SE | 1.00 | 1.51 | 1.27 | 1.10 | 1.22 |
| | | Median | 7.7 | 8.4 | 6.7 | 8.5 | 5.5 |
| | | L 90% CI | 5.81 | 5.68 | 4.24 | 6.02 | (3.99 |
| | | U 90% CI | 9.34 | 11.07 | 8.72 | 9.94 | 8.26 |
| | | Min, Max | 1, 14 | 1, 18 | −3, 18 | 2, 15 | −3, 15 |
| | | n | 11 | 13 | 16 | 13 | 17 |
| 24 h Post-dose | HR (bpm) | Mean (SD) | 67.0 (8.6) | 68.5 (9.0) | 65.2 (6.8) | 67.3 (7.2) | 66.9 (10.6) |
| | | SE | 2.60 | 2.50 | 1.70 | 2.00 | 2.56 |
| | | Median | 65.7 | 69.1 | 63.8 | 66.1 | 65.1 |
| | | L 90% CI | 62.26 | 64.03 | 62.26 | 63.75 | 62.38 |
| | | U 90% CI | 71.68 | 72.96 | 68.21 | 70.89 | 71.33 |
| | | Min, Max | 59, 83 | 52, 91 | 54, 80 | 58, 85 | 49, 91 |
| | | n | 11 | 13 | 16 | 13 | 17 |
| | ΔHR (bpm) | Mean (SD) | 4.4 (5.6) | 7.1 (5.8) | 4.4 (6.0) | 7.2 (5.4) | 6.0 (7.9) |
| | | SE | 1.67 | 1.60 | 1.50 | 1.49 | 1.92 |
| | | Median | 4.6 | 5.1 | 4.1 | 7.4 | 6.5 |
| | | L 90% CI | 1.36 | 4.2 | 1.78 | 4.49 | 2.60 |
| | | U 90% CI | 7.43 | 10.00 | 7.03 | 9.82 | 9.30 |
| | | Min, Max | −4, 14 | −1, 17 | −6, 14 | −4, 17 | −12, 18 |

TABLE 34

Summary of observed values and change-from-baseline values of QTcF

| Time Point | Parameter | Statistics | LOT 2Z (10%) | LOT 4Z (15%) | LOT 3Z (25%) | LOT 3Z fed state | LOT 1Z (IR) |
|---|---|---|---|---|---|---|---|
| Baseline | QTcF (ms) | n | 14 | 13 | 16 | 13 | 17 |
| | | Mean (SD) | 411.4 (19.8) | 407.5 (18.8) | 412.7 (20.0) | 402.9 (18.8) | 414.5 (20.3) |
| | | SE | 5.30 | 5.20 | 4.99 | 5.22 | 4.91 |
| | | Median | 409.5 | 403.5 | 411 | 398.1 | 408.6 |
| | | L 90% CI | 402.03 | 398.25 | 403.98 | 393.57 | 405.97 |
| | | U 90% CI | 420.80 | 416.79 | 421.48 | 412.16 | 423.12 |
| | | Min, Max | 380, 447 | 381, 445 | 375, 444 | 381, 443 | 381, 448 |
| 20 min Post-dose | QTcF (ms) | n | 14 | 13 | 16 | 13 | 17 |
| | | Mean (SD) | 413.1 (20.4) | 406.3 (19.9) | 411.3 (22.2) | 401.9 (18.2) | 414.0 (21.7) |
| | | SE | 5.44 | 5.52 | 5.55 | 5.04 | 5.25 |
| | | Median | 410.6 | 402.1 | 409.8 | 397.7 | 405.7 |
| | | L 90% CI | 403.44 | 396.47 | 401.56 | 392.94 | 404.78 |
| | | U 90% CI | 422.70 | 416.13 | 421.03 | 410.92 | 423.12 |
| | | Min, Max | 381, 452 | 377, 447 | 378, 453 | 382, 446 | 382, 450 |
| | ΔQTcF ms | n | 14 | 13 | 16 | 13 | 17 |
| | | Mean (SD) | 1.7 (5.0) | −1.2 (2.9) | −1.4 (5.8) | −0.9 (4.3) | −0.6 (3.7) |
| | | SE | 1.33 | 0.79 | 1.44 | 1.20 | 0.90 |
| | | Median | 1 | −1.3 | −0.1 | −0.4 | −0.9 |
| | | L 90% CI | −0.71 | −2.63 | −3.97 | −3.08 | −2.16 |
| | | U 90% CI | 4.02 | 0.19 | 1.09 | 1.21 | 0.98 |
| | | Min, Max | −5, 11 | −6, 3 | −13, 12 | −10, 6 | −7, 8 |
| 45 min Post-dose | QTcF (ms) | n | 14 | 13 | 16 | 13 | 17 |
| | | Mean (SD) | 412.7 (18.9) | 407.0 (19.9) | 412.7 (21.2) | 399.7 (19.2) | 416.0 (19.1) |
| | | SE | 5.06 | 5.51 | 5.31 | 5.32 | 4.63 |
| | | Median | 412.9 | 400.5 | 409.8 | 395.2 | 414.2 |
| | | L 90% CI | 403.73 | 397.16 | 403.36 | 390.21 | 407.95 |
| | | U 90% CI | 421.66 | 416.80 | 421.98 | 409.18 | 424.11 |
| | | Min, Max | 384, 445 | 375, 451 | 381, 449 | 374, 443 | 378, 454 |
| | ΔQTcF (ms) | n | 14 | 13 | 16 | 13 | 17 |
| | | Mean (SD) | 1.3 (4.1) | −0.5 (3.4) | −0.1 (3.9) | −3.2 (3.6) | 1.5 (4.7) |
| | | SE | 1.10 | 0.95 | 0.98 | 0.99 | 1.14 |
| | | Median | 0.2 | −1.3 | −1.5 | −2.9 | 2.9 |
| | | L 90% CI | −0.67 | −2.23 | −1.79 | −4.93 | −0.49 |
| | | U 90% CI | 3.24 | 1.16 | 1.67 | −1.41 | 3.47 |
| | | Min, Max | −5, 9 | −6, 5 | −5, 8 | −10, 4 | −9, 8 |
| 80 min Post-dose | QTcF (ms) | n | 14 | 13 | 16 | 13 | 17 |
| | | Mean (SD) | 415.5 (20.1) | 409.4 (20.0) | 414.9 (21.6) | 396.9 (19.2) | 420.1 (21.4) |
| | | SE | 5.38 | 5.55 | 5.41 | 5.32 | 5.20 |
| | | Median | 414.1 | 404.6 | 413.6 | 395.9 | 417.9 |
| | | L 90% CI | 405.95 | 399.48 | 405.45 | 387.38 | 410.98 |
| | | U 90% CI | 425.01 | 419.25 | 424.43 | 406.34 | 429.13 |
| | | Min, Max | 385, 447 | 380, 454 | 384, 453 | 372, 443 | 381, 456 |
| | ΔQTcF (ms) | n | 14 | 13 | 16 | 13 | 17 |
| | | Mean (SD) | 4.1 (4.1) | 1.8 (3.0) | 2.2 (4.6) | −6.0 (5.6) | 5.5 (4.1) |
| | | SE | 1.10 | 0.84 | 1.16 | 1.55 | 1.00 |
| | | Median | 4.8 | 1.1 | 1.7 | −5.6 | 5.4 |
| | | L 90% CI | 2.11 | 0.35 | 0.18 | −8.76 | 3.76 |
| | | U 90% CI | 6.02 | 3.34 | 4.24 | −3.24 | 7.26 |
| | | Min, Max | −2, 13 | −2, 9 | −5, 12 | −17, 0 | −1, 13 |
| 120 min Post-dose | QTcF (ms) | n | 13 | 13 | 16 | 13 | 17 |
| | | Mean (SD) | 416.0 (22.9) | 408.9 (19.1) | 414.2 (21.7) | 397.2 (19.1) | 421.7 (21.4) |
| | | SE | 6.36 | 5.30 | 5.42 | 5.28 | 5.18 |
| | | Median | 416.1 | 402.9 | 412.6 | 389.7 | 431 |
| | | L 90% CI | 404.68 | 399.48 | 404.64 | 387.78 | 412.62 |
| | | U 90% CI | 427.34 | 418.38 | 423.66 | 406.61 | 430.72 |
| | | Min, Max | 385, 454 | 379, 450 | 382, 450 | 375, 444 | 380, 457 |
| | ΔQTcF (ms) | n | 13 | 13 | 16 | 13 | 17 |
| | | Mean (SD) | 5.9 (6.6) | 1.4 (4.1) | 1.4 (4.1) | −5.7 (5.2) | 7.1 (8.1) |
| | | SE | 1.84 | 1.14 | 1.02 | 1.44 | 1.96 |
| | | Median | 3.3 | 0 | 1.2 | −4.6 | 6.3 |
| | | L 90% CI | 2.66 | −0.62 | −0.37 | −8.24 | 3.71 |
| | | U 90% CI | 9.23 | 3.43 | 3.21 | −3.11 | 10.54 |
| | | Min, Max | −1, 21 | −6, 7 | −5, 11 | −16, 4 | −4, 33 |
| 160 min Post-dose | QTcF (ms) | n | 14 | 13 | 16 | 13 | 17 |
| | | Mean (SD) | 420.3 (23.4) | 408.3 (17.8) | 417.9 (24.0) | 396.7 (18.5) | 425.2 (21.8) |
| | | SE | 6.24 | 4.95 | 6.00 | 5.13 | 5.28 |
| | | Median | 416.3 | 404.1 | 418.9 | 389.8 | 427.6 |
| | | L 90% CI | 409.20 | 399.48 | 407.40 | 387.55 | 416.03 |
| | | U 90% CI | 431.30 | 417.12 | 428.45 | 405.85 | 434.45 |
| | | Min, Max | 386, 458 | 378, 441 | 382, 456 | 376, 439 | 383, 464 |
| | ΔQTcF(ms) | n | 14 | 13 | 16 | 13 | 17 |
| | | Mean (SD) | 8.8 (8.6) | 0.8 (4.6) | 5.2 (5.9) | −6.2 (4.8) | 10.7 (12.3) |
| | | SE | 2.29 | 1.27 | 1.48 | 1.34 | 2.97 |
| | | Median | 6.3 | 0.6 | 4.8 | −5.7 | 7.6 |
| | | L 90% CI | 4.78 | −1.49 | 2.61 | −8.55 | 5.51 |

TABLE 34-continued

Summary of observed values and change-from-baseline values of QTcF

| Time Point | Parameter | Statistics | LOT 2Z (10%) | LOT 4Z (15%) | LOT 3Z (25%) | LOT 3Z fed state | LOT 1Z (IR) |
|---|---|---|---|---|---|---|---|
| | | U 90% CI | 12.90 | 3.04 | 7.78 | −3.78 | 15.89 |
| | | Min, Max | −2, 27 | −8, 8 | −6, 18 | −17, 2 | −6, 38 |
| 200 min Post-dose | QTcF (ms) | n | 14 | 13 | 16 | 13 | 17 |
| | | Mean (SD) | 423.9 (24.1) | 411.8 (21.8) | 421.3 (25.1) | 398.5 (18.4) | 425.4 (22.1) |
| | | SE | 6.44 | 6.05 | 6.27 | 5.10 | 5.35 |
| | | Median | 423 | 409.9 | 421.4 | 389.9 | 421.8 |
| | | L 90% CI | 412.48 | 401.02 | 410.35 | 389.39 | 416.04 |
| | | U 90% CI | 435.28 | 422.60 | 432.33 | 407.56 | 434.72 |
| | | Min, Max | 386, 476 | 378, 458 | 387, 474 | 379, 441 | 384, 469 |
| | ΔQTcF (ms) | n | 14 | 13 | 16 | 13 | 17 |
| | | Mean (SD) | 12.5 (11.3) | 4.3 (7.2) | 8.6 (8.8) | −4.4 (5.9) | 10.8 (9.2) |
| | | SE | 3.02 | 1.99 | 2.19 | 1.63 | 2.24 |
| | | Median | 7.6 | 3.1 | 7.8 | −2.9 | 9.1 |
| | | L 90% CI | 7.12 | 0.74 | 4.77 | −7.30 | 6.93 |
| | | U 90% CI | 17.82 | 7.84 | 12.45 | −1.48 | 14.74 |
| | | Min, Max | −2, 34 | −4, 22 | −5, 36 | −18, 4 | −3, 37 |
| 240 min Post-dose | QTcF (ms) | n | 14 | 13 | 16 | 13 | 17 |
| | | Mean (SD) | 421.5 (23.3) | 413.2 (24.1) | 418.6 (22.5) | 399.6 (19.6) | 423.3 (20.1) |
| | | SE | 6.21 | 6.68 | 5.63 | 5.44 | 4.86 |
| | | Median | 418 | 407.1 | 418.1 | 396.9 | 424.6 |
| | | L 90% CI | 410.45 | 401.25 | 408.75 | 389.89 | 414.79 |
| | | U 90% CI | 432.46 | 425.06 | 428.48 | 409.27 | 431.77 |
| | | Min, Max | 390, 475 | 377, 462 | 389, 462 | 375, 444 | 384, 456 |
| | ΔQTcF (ms) | n | 14 | 13 | 16 | 13 | 17 |
| | | Mean (SD) | 10.0 (7.4) | 5.6 (11.1) | 5.9 (6.2) | −3.3 (5.5) | 8.7 (7.9) |
| | | SE | 1.97 | 3.08 | 1.54 | 1.54 | 1.92 |
| | | Median | 7.9 | 5.5 | 4.5 | −1.7 | 8.5 |
| | | L 90% CI | 6.57 | (0.14 | 3.19 | −6.02 | 5.38 |
| | | U 90% CI | 13.53 | 11.13 | 8.58 | −0.54 | 12.09 |
| | | Min, Max | 0, 28 | −6, 35 | −0, 25 | −15, 4 | −5, 25 |
| 280 min Post-dose | QTcF (ms) | n | 14 | 13 | 15 | 13 | 17 |
| | | Mean (SD) | 425.4 (23.5) | 415.1 (21.5) | 423.2 (26.6) | 404.2 (20.7) | 429.0 (23.9) |
| | | SE | 6.28 | 5.96 | 6.87 | 5.75 | 5.80 |
| | | Median | 424.2 | 406.1 | 419.7 | 398.6 | 428 |
| | | L 90% CI | 414.27 | 404.49 | 411.10 | 393.94 | 418.88 |
| | | U 90% CI | 436.50 | 425.74 | 435.29 | 414.45 | 439.13 |
| | | Min, Max | 390, 479 | 383, 453 | 389, 481 | 378, 454 | 387, 470 |
| | ΔQTcF (ms) | n | 14 | 13 | 15 | 13 | 17 |
| | | Mean (SD) | 14.0 (10.6) | 7.6 (11.9) | 10.9 (11.2) | 1.3 (8.8) | 14.5 (10.4) |
| | | SE | 2.85 | 3.31 | 2.89 | 2.44 | 2.53 |
| | | Median | 13 | 4.4 | 11.2 | 2.7 | 15.1 |
| | | L 90% CI | 8.93 | 1.70 | 5.78 | −3.01 | 10.05 |
| | | U 90% CI | 19.01 | 13.49 | 15.97 | 5.67 | 18.87 |
| | | Min, Max | −6, 32 | −12, 30 | −7, 43 | −15, 15 | −7, 35 |
| 5.5 h Post-dose | QTcF (ms) | n | 13 | 13 | 16 | 13 | 17 |
| | | Mean (SD) | 420.4 (22.1) | 408.3 (18.2) | 416.1 (28.2) | 403.7 (17.8) | 420.8 (25.2) |
| | | SE | 6.12 | 5.06 | 7.04 | 4.94 | 6.11 |
| | | Median | 417.1 | 405.8 | 409.1 | 396.1 | 419 |
| | | L 90% CI | 409.53 | 399.30 | 403.77 | 394.88 | 410.10 |
| | | U 90% CI | 431.34 | 417.34 | 428.45 | 412.49 | 431.43 |
| | | Min, Max | 385, 475 | 377, 439 | 377, 478 | 385, 444 | 380, 467 |
| | ΔQTcF (ms) | n | 13 | 13 | 16 | 13 | 17 |
| | | Mean (SD) | 6.6 (10.2) | 0.8 (11.1) | 3.4 (13.0) | 0.8 (7.5) | 6.2 (10.2) |
| | | SE | 2.83 | 3.07 | 3.24 | 2.09 | 2.46 |
| | | Median | 8.2 | 4.2 | 1.6 | 3.3 | 4.3 |
| | | L 90% CI | 1.58 | −4.67 | −2.30 | −2.90 | 1.92 |
| | | U 90% CI | 11.66 | 6.26 | 9.07 | 4.54 | 10.52 |
| | | Min, Max | −9, 27 | −26, 13 | −18, 40 | −12, 10 | −15, 24 |
| 6.5 h Post-dose | QTcF (ms) | n | 14 | 13 | 15 | 13 | 17 |
| | | Mean (SD) | 414.1 (24.2) | 405.2 (16.8) | 414.9 (25.3) | 403.2 (19.4) | 415.0 (21.7) |
| | | SE | 6.46 | 4.66 | 6.52 | 5.38 | 5.27 |
| | | Median | 411.1 | 403.3 | 407.6 | 398.5 | 413.8 |
| | | L 90% CI | 402.65 | 396.93 | 403.37 | 393.65 | 405.79 |
| | | U 90% CI | 425.53 | 413.53 | 426.36 | 412.82 | 424.18 |
| | | Min, Max | 379, 469 | 379, 428 | 383, 473 | 384, 454 | 380, 452 |
| | ΔQTcF (ms) | n | 14 | 13 | 15 | 13 | 17 |
| | | Mean (SD) | 2.7 (8.5) | −2.3 (7.1) | 2.5 (10.3) | 0.4 (6.9) | 0.4 (6.5) |
| | | SE | 2.27 | 1.97 | 2.66 | 1.90 | 1.57 |
| | | Median | 0.5 | −2.3 | −1 | −2 | −1.1 |
| | | L 90% CI | −1.35 | −5.79 | −2.15 | −3.03 | −2.30 |
| | | U 90% CI | 6.70 | 1.21 | 7.24 | 3.76 | 3.18 |
| | | Min, Max | −8, 22 | −17, 6 | −8, 36 | −9, 12 | −11, 12 |
| 7.5 h Post-dose | QTcF (ms) | n | 14 | 13 | 16 | 13 | 17 |
| | | Mean (SD) | 410.1 (21.7) | 403.3 (15.9) | 410.0 (21.7) | 399.3 (18.5) | 412.9 (20.5) |
| | | SE | 5.80 | 4.42 | 5.42 | 5.13 | 4.98 |

TABLE 34-continued

Summary of observed values and change-from-baseline values of QTcF

| Time Point | Parameter | Statistics | LOT 2Z (10%) | LOT 4Z (15%) | LOT 3Z (25%) | LOT 3Z fed state | LOT 1Z (IR) |
|---|---|---|---|---|---|---|---|
| | | Median | 408.5 | 402.5 | 405.8 | 396 | 409.1 |
| | | L 90% CI | 399.79 | 395.43 | 400.49 | 390.14 | 404.22 |
| | | U 90% CI | 420.32 | 411.18 | 419.49 | 408.44 | 421.61 |
| | | Min, Max | 372, 448 | 376, 425 | 376, 449 | 379, 442 | 380, 455 |
| | ΔQTcF (ms) | n | 14 | 13 | 16 | 13 | 17 |
| | | Mean (SD) | −1.4 (8.4) | −4.2 (9.1) | −2.7 (6.8) | −3.6 (6.6) | −1.6 (8.4) |
| | | SE | 2.26 | 2.51 | 1.69 | 1.83 | 2.04 |
| | | Median | −1.5 | −4.2 | −3.1 | −3.5 | −1.5 |
| | | L 90% CI | −5.36 | −8.70 | −5.70 | −6.85 | −5.19 |
| | | U 90% CI | 2.64 | 0.26 | 0.23 | −0.31 | 1.93 |
| | | Min, Max | −15, 14 | −20, 10 | −14, 11 | −17, 10 | −18, 11 |
| 9 h Post-dose | QTcF (ms) | n | 14 | 13 | 16 | 13 | 17 |
| | | Mean (SD) | 412.0 (23.5) | 406.6 (17.5) | 410.9 (21.3) | 400.8 (18.2) | 413.8 (20.4) |
| | | SE | 6.28 | 4.86 | 5.32 | 5.04 | 4.95 |
| | | Median | 406 | 405.1 | 410.3 | 392.8 | 418.7 |
| | | L 90% CI | 400.83 | 397.98 | 401.56 | 391.85 | 405.11 |
| | | U 90% CI | 423.08 | 415.30 | 420.22 | 409.80 | 422.41 |
| | | Min, Max | 380, 469 | 378, 437 | 379, 449 | 381, 437 | 380, 455 |
| | ΔQTcF (ms) | n | 14 | 13 | 16 | 13 | 17 |
| | | Mean (SD) | 0.5 (10.2) | −0.9 (8.5) | −1.8 (5.8) | −2.0 (5.7) | −0.8 (5.6) |
| | | SE | 2.72 | 2.36 | 1.45 | 1.59 | 1.36 |
| | | Median | −0.3 | 0.7 | −1.5 | −2.8 | −1 |
| | | L 90% CI | −4.27 | −5.09 | −4.38 | −4.87 | −3.15 |
| | | U 90% CI | 5.36 | 3.34 | 0.69 | 0.80 | 1.59 |
| | | Min, Max | −14, 28 | −18, 14 | −14, 9 | −11, 6 | −11, 11 |
| 12 h Post-dose | QTcF (ms) | n | 14 | 13 | 15 | 13 | 17 |
| | | Mean (SD) | 411.6 (22.0) | 410.9 (22.3) | 411.1 (20.3) | 400.7 (18.7) | 412.5 (19.5) |
| | | SE | 5.87 | 6.19 | 5.25 | 5.19 | 4.73 |
| | | Median | 410.9 | 407.1 | 413.5 | 401.9 | 414.3 |
| | | L 90% CI | 401.20 | 399.89 | 401.89 | 391.44 | (404.19 |
| | | U 90% CI | 421.99 | 421.97 | 420.38 | 409.93 | 420.71 |
| | | Min, Max | 376, 459 | 379, 460 | 380, 448 | 376, 443 | 375, 445 |
| | ΔQTcF (ms) | n | 14 | 13 | 15 | 13 | 17 |
| | | Mean (SD) | 0.2 (8.8) | 3.4 (8.3) | −2.5 (6.3) | −2.2 (8.1) | −2.1 (7.2) |
| | | SE | 2.34 | 2.30 | 1.64 | 2.25 | 1.75 |
| | | Median | −2.1 | 1.4 | −3 | −2.3 | −2.2 |
| | | L 90% CI | −3.96 | −0.68 | −5.34 | −6.18 | −5.15 |
| | | U 90% CI | 4.33 | 7.50 | 0.43 | 1.83 | 0.97 |
| | | Min, Max | −10, 18 | −12, 21 | −12, 8 | −16, 16 | −14, 10 |
| 24 h Post-dose | QTcF (ms) | n | 11 | 13 | 16 | 13 | 17 |
| | | Mean (SD) | 406.1 (21.5) | 403.9 (18.3) | 408.1 (22.5) | 398.0 (17.0) | 407.8 (20.6) |
| | | SE | 6.49 | 5.08 | 5.62 | 4.72 | 5.00 |
| | | Median | 406.8 | 403 | 403.5 | 392.2 | 399.4 |
| | | L 90% CI | 394.31 | 394.86 | 398.29 | 389.55 | 399.10 |
| | | U 90% CI | 417.82 | 412.96 | 417.98 | 406.40 | 416.57 |
| | | Min, Max | 377, 442 | 378, 436 | 378, 455 | 376, 434 | 378, 447 |
| | ΔQTcF (ms) | n | 11 | 13 | 16 | 13 | 17 |
| | | Mean (SD) | −3.3 (7.8) | −3.6 (3.3) | −4.6 (10.1) | −4.9 (5.5) | −6.7 (7.8) |
| | | SE | 2.35 | 0.91 | 2.52 | 1.52 | 1.89 |
| | | Median | −5.7 | −2.9 | −5.2 | −6.5 | −6.9 |
| | | L 90% CI | −7.59 | −5.23 | −9.01 | −7.60 | −10.01 |
| | | U 90% CI | 0.94 | −1.99 | −0.17 | −2.17 | −3.41 |
| | | Min, Max | −12, 17 | −9, 2 | −30, 13 | −13, 6 | −25, 6 |

The effect of amisulpride (enantiomers and total) on change-from-baseline QTcF and heart rate (ΔQTcF and ΔHR) was evaluated based on a linear mixed-effects model at each nominal post-dosing time point ("by-time point analysis") using the intersection union test. In the concentration-QTc analysis (primary analysis), the full model included ΔQTcF as the dependent variable, time-matched plasma concentrations of R- and S- and total amisulpride enantiomers as the explanatory variates, centered baseline QTcF (i.e., baseline QTcF for individual subject subtracting the population mean baseline QTcF for all subjects) as an additional covariate, a fixed intercept, and random effect for both intercept and slopes per subject, when applicable. A pre-specified model selection procedure was then performed to choose a primary model from among the full model and reduced models from possible first order combinations (without quadratic and interaction terms) among these 3 analytes of concentrations of R- and S-enantiomers and total amisulpride (including models with only 1 analyte and with any 2 analytes). In the concentration-QTc analysis, all models from the possible first order combinations among the 3 analytes (S-amisulpride, R-amisulpride, and total of amisulpride enantiomers) were considered. The total of amisulpride enantiomers (total amisulpride) was used as the primary model since the concentration value of total amisulpride enantiomers is the sum of S-amisulpride and R-amisulpride, and the 2 concentrations of S- and R- were observed to be highly correlated.

This analysis of the observations yielded an estimated population slope of the concentration-QTc relationship of 0.031 ms per ng/mL (90% CI: 0.0257 to 0.0369) for total amisulpride with an intercept of −2.3 ms (90% CI: −4.88 to 0.27). The slope for the relationship was found to be statistically significant at the 0.1 level, while the intercept was not. Table 35 presents the results of this analysis, where SE is standard error, df degrees of freedom, and CI confidence interval.

TABLE 35

Linear mixed-effects total amisulpride concentration-QTc relationship model parameters determined form experimental data

| Parameter | Value | SE | df | t-Value | P Value | 90% CI |
|---|---|---|---|---|---|---|
| Intercept (ms) | −2.31 | 1.4151 | 9.6 | −1.63 | 0.1355 | −4.881, 0.269 |
| Total Amisulpride Slope (ms per ng/mL) | 0.031 | 0.0032 | 17.0 | 9.71 | <0.0001 | 0.0257, 0.0369 |
| Centered Baseline Effect (ms) | −0.23 | 0.0394 | 100.1 | −5.79 | <0.0001 | −0.293, −0.162 |

The observations and a linear mixed-effects model parameters derived therefrom was used to estimate the ΔQTcF at the observed Cmax of the formulation Lots studied. This data is presented in Table 36 and shows the significant reduction in ΔQTcF for various modified release formulations of amisulpride provided herein compared to a comparable immediate release formulation. For example, the formulation of 4Z showed a reduction in ΔQTcF relative to Lot 1Z (IR) of about 45% at Cmax relative to the IR formulation. The formulation of Lot 3Z, administered in the fed state, showed a reduction in in ΔQTcF relative to Lot 1Z (IR) of about 55% at Cmax relative to the IR formulation; and Lot 3Z, administered in the fasted state, showed a reduction in in ΔQTcF relative to Lot 1Z (IR) of about 60% at Cmax relative to the IR formulation. As important as the relative reduction, Lots 3Z and 4Z showed a ΔQTcF prolongation (relative to baseline) of less than 8 ms, and for Lot 3Z less than 6 ms.

TABLE 36

Estimated ΔQTcF at observed geometric mean Cmax

| Treatment | Geometric Mean $C_{max}$ (ng/mL) (90% CI) of total amisulpride | ΔQTcF (ms) (90% CI) |
|---|---|---|
| LOT 2Z (10%) | 454.8 (347.64; 595.10) | 11.94 (9.10, 14.78) |
| LOT 4Z (15%) | 301.9 (224.05; 406.81) | 7.15 (4.65, 9.65) |
| LOT 3Z (25%) | 236.0 (184.86; 301.33) | 5.09 (2.66, 7.52) |
| LOT 3Z (25%) fed state | 260.3 (217.85; 311.01) | 5.85 (3.40, 8.30) |
| LOT 1Z (IR) | 493.3 (400.32; 607.87) | 13.15 (10.19, 16.11) |

TABLE 37

Figure 23:
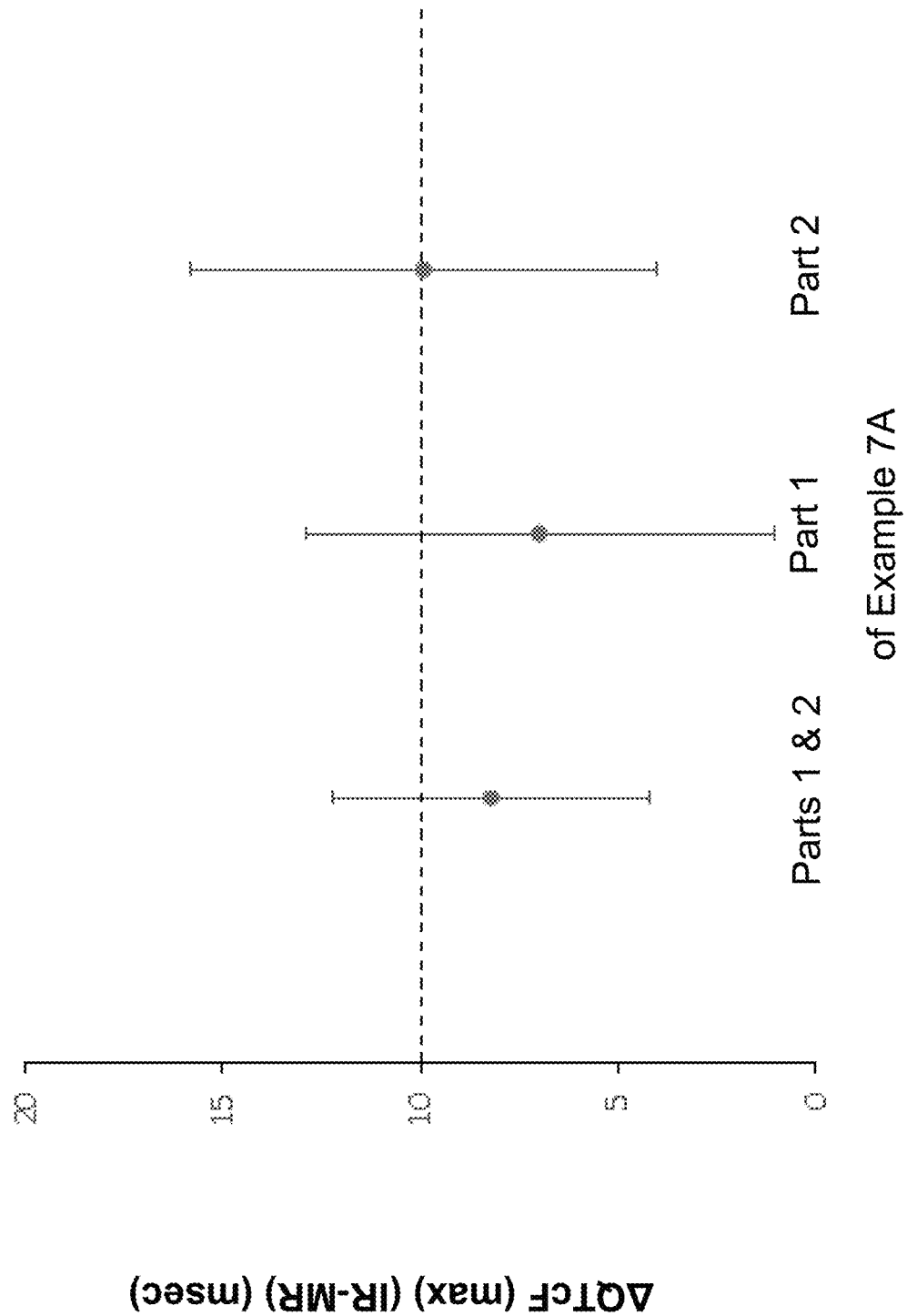
FIG. 23 compares the difference (IR-MR) between AQTcF max for IR and modified release (MR) formulations for the subjects of Example 7A Parts 1 and 2, the error bars represent the ±90% confidence intervals.

ΔQTcF (max) (IR-MR) (msec) and ±90% Confidence Interval (CI) of data plotted in FIG. 23

| Subjects | Average ΔQTcF (max) (IR-MR) (msec) | 90% CI Lower | 90% CI Upper |
|---|---|---|---|
| Parts 1 & 2 | 8.21 | 4.21 | 12.2 |
| Part 1 | 6.99 | 1.06 | 12.9 |
| Part 2 | 9.93 | 4.05 | 15.8 |

Example 7B: Human Clinical Studies (MAD/PET Imaging)

The therapeutic effects of amisulpride enantiomers occur by direct interactions with dopamine D2 and serotonin 5-HT7 receptors in the brain. However, measuring directly drug concentration in the brain is not feasible. Dopamine D2 receptor occupancy by Positron Emission Tomography (PET) in human subjects was used in this study as a surrogate to measure the magnitude of effect of amisulpride in the brain, as binding to a pharmacological target, relative to the plasma pharmacokinetics measured directly by collecting plasma samples over time post administration.

In these human clinical studies, single solid oral doses of a fixed ratio composition of (R)-amisulpride to (S)-amisulpride of 85:15 by weight were administered to healthy volunteers at total composition amounts of 200 mg (170 mg R-amisulpride:30 mg S-amisulpride) and 400 mg (340 mg R-amisulpride:60 mg S-amisulpride). Two formulations and two dosing regimens were studied, an IR formulation comprising 200 mg of API (substantially in accord with Lot 1Z of Table 25), and a 25% extended release agent formulation comprising 200 mg of API (substantially in accord with Lot 3Z of TABLE 24A), studied in two dosage regimens, a 1 tablet/day regimen and a 2 tablets/day regimen (i.e. for a total of 400 mg of API per day).

Subjects in this study were divided into five cohorts and received 7 doses of a given formulation in a once per day dosage regimen. Specifically, subjects received either a 200 mg or 400 mg total daily dose of API once per day formulated as either an immediate release (IR) or modified release formulation, over a period of 7 days with each dose approximately 24 hours apart.

Day 1 of the study was defined as the day upon which a subject received the first dose of any formulation used in the study. The first cohort comprised 19 subjects randomly assigned to receive the IR formulation once daily for a total daily dose of either 200 mg API (n=9) or 400 mg API (n=10). Cohorts 2-5 comprised 18 subjects total, and each subject received a modified release formulation comprising 200 mg of API (substantially in accord with Lot 3Z of Table 24A), in one of two dosage regimens, in a total once daily dose of either 200 mg (n=8) API or 400 mg (n=10) API.

A summary of the parameters and protocols used in the PET study of this example are provided in Table 38 and are further described in the accompanying text below. Prior to dosing, all subjects received a structural brain T1-weighted high resolution magnetic resonance imaging (MRI) scan and a baseline PET scan. The MRI scan of a subject was used for anatomical co-registration with their respective PET scan images for the image analysis. The PET scans of this study utilized [$^{11}$C]-propyl-hexahydro-naphtho-oxazin (11C—PHNO) as the imaging ligand and up to 0.3 μg/kg of the imaging ligand was administered intravenously as a single bolus injection before the start of a PET scan.

TABLE 38

Summary of PET Imaging Study Parameters and Protocols

| | |
|---|---|
| Imaging Ligand: | [$^{11}$C]-propyl-hexahydro-naphtho-oxazin (11C—PHNO) |
| Administration: | up to 0.3 µg/kg of the imaging ligand, single bolus intravenous injection before the start of a PET scan. Specific activities ranged from 17-35 Gbq/µmol (mean = 24.6 Gbq/µmol, SD = 5.9 Gbq/µmol) |
| Timing of Scan: | 27.5 h ± 1 h after a given dose |
| Instrumentation: | Siemens PET/CT Hi-Rez Biograph 6 scanner, or Siemens PET/CT Biograph 6 TruePoint with TrueV scanner |
| Data Acquisition Sampling Type: | dynamic emission |
| Acquisition Duration: | 90 minute duration and frame durations of 8 × 15 s, 3 × 60 s, 5 × 120 s, 5 × 300 s, 5 × 600 s |
| Image Processing/ Reconstruction: | Fourier rebinning and 2D filtered discrete inverse Fourier transform algorithm with 5 mm isotropic Gaussian filter on a 128 × 128 matrix with 2.6 zoom giving 2 mm isotropic voxels |
| Corrections (applied for): | attenuation, randoms, scatter |
| D2 Occupancy Determination: | Regional estimate of the binding potential relative to the non-displaceable component ($BP_{ND}$): $$\Delta BP_{ND} = 100 \times \left(1 - \frac{BP_{ND}^{post-dose}}{BP_{ND}^{baseline}}\right)..$$ |
| Quantitative Analysis: | MIAKAT software package (version 4.2.6.1), simplified reference tissue model (SRTM) |
| Reference Region: | Cerebellum |
| Primary Brain Regions for D2 Occupancy: | dorsal caudate, dorsal putamen |
| Primary Brain Region for D3 Occupancy: | substantia nigra |
| Brain Regions for mixed D2/D3 Occupancy: | ventral striatum, globus pallidus, thalamus |

In this study, subjects received two to four PET scans: thirty three subjects received 4 PET scans, 2 subjects received three PET scans and 2 subjects received 2 PET scans. Of the 33 subjects receiving four PET scans, 28 subjects received scans according to the planned schedule: (1) an initial baseline PET scan, (2) a PET scan conducted 27.5 h±1 h following the first dose (i.e. on Day 2), (3) a PET scan conducted 27.5 h±1 h following the seventh, and last, dose (i.e. on Day 8), and (4) PET scan conducted approximately 5-7 days after the last dose. The PET scans of Day 2 of the study were conducted before administration of the second dose, and the second dose was administered within 2 hours after completion of the PET scan. Some subjects did not complete the full set of planned scans or did not have them at the planned timepoints due to radiochemistry issues.

Prior to administration of 11C—PHNO and initiation of the post dose PET scans, venous blood samples were taken from each subject to determine blood plasma concentrations of amisulpride (R-, S- and total amisulpride).

During the dosing portion of the study subjects resided in the clinical unit and were admitted the day before the receiving the first dose and discharged on Day 9, i.e. 48 hours post final dose. On the night before Day 1 and Day 7, subjects were provided meals but were required to refrain from all food and drink (except water) for ≥8 hours prior to dosing. A light snack was provided upon waking, no later than 2 hours prior to dosing, on Day 1 and Day 7. Lunch was provided at approximately 4 hours post-dose, and an evening meal at approximately 10 hours post-dose and an evening snack at approximately 14 hours post-dose. Subjects were discharged from the clinical unit on Day 9, and returned on Day 11 or 12 for the final PET scan.

PET experiments were conducted using 11C—PHNO. [$^{11}$C]—PHNO is formed in situ by the reaction of [$^{11}$C]-propionyl chloride with the PET precursor despropyl-PHNO. GMP grade precursor was supplied by ABX with specification set to >95% for purity (as measured by HPLC). [$^{11}$C]—PHNO was purified by solid phase extraction and reformulated in a solution of 10% ethanol in normal saline. Specific activities delivered ranged from 7.5-48.5 GBq/µmol (mean: 25.2 GBq/µmol, SD: 8.0 GBq/µmol). Radiochemical purity was calculated as 100% for all scans.

All dynamic [$^{11}$C]—PHNO PET scans were acquired on Siemens PET/CT scanners (two similar scanners were used: Hi-Rez Biograph 6 and Biograph 6 TruePoint with TrueV, Siemens Healthcare, Erlangen, Germany). A low-dose CT scan was performed immediately before each PET study in order to estimate attenuation. Following intravenous bolus injection of the radiotracer ([$^{11}$C]—PHNO), dynamic emission data were acquired for 90 minutes (frame durations: 8×15 s, 3×60 s, 5×120 s, 5×300 s, 5×600 s). The dynamic images were reconstructed using Fourier rebinning and a 2D filtered discrete inverse Fourier transform algorithm with 5 mm isotropic Gaussian filter on a 128×128 matrix with 2.6 zoom giving 2 mm isotropic voxels. Corrections were applied for attenuation, randoms and scatter.

Dopamine D2 receptor occupancy was calculated for each PET scan via regional estimate of the binding potential relative to the non-displaceable component (BPND). Quantitative analysis of PET images was performed using the simplified reference tissue model (SRTM) with the cerebellum serving as the reference region. Primary brain regions considered for D2 receptor occupancy were the dorsal caudate and dorsalputamen. D3 receptor occupancy was assessed using substantia nigra. Ventral striatum, globus pallidus, and thalamus were also selected to include regions of mixed D2/D3 receptor expression.

Following repeated dosing, the immediate release (IR) and modified release D2 receptor occupancies were very similar to each other, and to the single dose IR values. At the final (washout) scans in this study, the D2 signal had returned to baseline values. The $D_3$ data were markedly more variable, and showed a decrease in BPND that persisted to the washout scan.

The following formula was used to determine the dopamine D2 receptor occupancy based upon D2 receptor occupancy in the dorsal caudate and dorsal putamen $$\Delta BP_{ND} = 100 \times \left(1 - \frac{BP_{ND}^{post-dose}}{BP_{ND}^{baeeline}}\right)$$

D3 and mixed D2/D3 receptor occupancy was not used to determine D2 receptor occupancy.

TABLE 39A

Various PK Parameters by Subject for Subjects who were Administered a Modified Release Tablet Formulation Substantially Similar to Lot 3Z in Example 7B

| Total Daily Dose (mg) | Day | Subject | Tmax (hr) | Cmax (ng/mL) | $AUC_{0-24}$ (hr*ng/mL) |
|---|---|---|---|---|---|
| 200 | 1 | 320 | 3.67 | 492 | 2110 |
| 200 | 1 | 321 | 4 | 226 | 1530 |
| 200 | 1 | 326 | 4 | 371 | 1550 |
| 200 | 1 | 327 | 4 | 135 | 838 |
| 200 | 1 | 328 | 6.5 | 118 | 986 |
| 200 | 1 | 329 | 5.5 | 86.8 | 1070 |
| 200 | 1 | 332 | 3.67 | 179 | 1080 |
| 200 | 1 | 333 | 5.5 | 64.1 | 745 |
| 200 | 1 | 336 | 4 | 279 | 1860 |
| 200 | 1 | 337 | 5.5 | 183 | 1320 |
| 200 | 3 | 320 | 5 | 295 | NC |
| 200 | 3 | 321 | 5 | 395 | NC |
| 200 | 3 | 326 | 4 | 683 | NC |
| 200 | 3 | 327 | 6 | 197 | NC |
| 200 | 3 | 328 | 6 | 139 | NC |
| 200 | 3 | 329 | 2.67 | 123 | NC |
| 200 | 3 | 332 | 8 | 93.9 | NC |
| 200 | 3 | 333 | 2 | 164 | NC |
| 200 | 3 | 336 | 4 | 279 | NC |
| 200 | 3 | 337 | 6 | 264 | NC |
| 200 | 7 | 320 | 5 | 177 | 1530 |
| 200 | 7 | 321 | 3 | 187 | 2300 |
| 200 | 7 | 328 | 4.33 | 411 | 2500 |
| 200 | 7 | 326 | 4.33 | 510 | 2580 |
| 200 | 7 | 327 | 4.33 | 205 | 2340 |
| 200 | 7 | 329 | 4 | 208 | 2060 |
| 200 | 7 | 332 | 4.67 | 318 | 3490 |
| 200 | 7 | 333 | 4 | 222 | 1640 |
| 200 | 7 | 336 | 4 | 235 | 2320 |
| 200 | 7 | 337 | 5.5 | 619 | 3400 |
| 400 | 1 | 322 | 4.33 | 101 | 1700 |
| 400 | 1 | 323 | 5.5 | 717 | 4230 |
| 400 | 1 | 324 | 5 | 164 | 1220 |
| 400 | 1 | 325 | 5.5 | 757 | 3910 |
| 400 | 1 | 330 | 5.5 | 1080 | 3440 |
| 400 | 1 | 331 | 3 | 535 | 5020 |
| 400 | 1 | 334 | 5 | 293 | 2780 |
| 400 | 1 | 335 | 4 | 247 | 1540 |
| 400 | 3 | 322 | 5 | 731 | NC |
| 400 | 3 | 323 | 2 | 312 | NC |
| 400 | 3 | 324 | 6 | 438 | NC |
| 400 | 3 | 325 | 6 | 785 | NC |
| 400 | 3 | 330 | 5 | 251 | NC |
| 400 | 3 | 331 | 5 | 527 | NC |
| 400 | 3 | 334 | 4 | 566 | NC |
| 400 | 3 | 335 | 2.67 | 559 | NC |
| 400 | 7 | 322 | 4 | 1040 | 6130 |
| 400 | 7 | 323 | 3.67 | 601 | 5460 |
| 400 | 7 | 324 | 4.33 | 166 | 2560 |
| 400 | 7 | 325 | 6 | 1040 | 7950 |
| 400 | 7 | 330 | 5.5 | 505 | 3120 |
| 400 | 7 | 331 | 4.33 | 1040 | 7800 |
| 400 | 7 | 334 | 2.67 | 955 | 10800 |
| 400 | 7 | 335 | 4 | 411 | 3450 |

NC = not calculated

TABLE 39B

Various PK Parameters by Subject for Subject who were Administered an Immediate Release Tablet Formulation Substantially Similar to Lot 1Z in Example 7B

| Total Daily Dose (mg) | Day | Subject | Tmax (hr) | Cmax (ng/mL) | $AUC_{0-24}$ (hr*ng/mL) |
|---|---|---|---|---|---|
| 200 | 1 | 301 | 4 | 190 | 1520 |
| 200 | 1 | 304 | 2.33 | 1100 | 5640 |
| 200 | 1 | 305 | 5.5 | 381 | 2750 |
| 200 | 1 | 308 | 1.67 | 236 | 2420 |
| 200 | 1 | 310 | 5.5 | 263 | 2210 |

TABLE 39B-continued

Various PK Parameters by Subject for Subject who were Administered an Immediate Release Tablet Formulation Substantially Similar to Lot 1Z in Example 7B

| Total Daily Dose (mg) | Day | Subject | Tmax (hr) | Cmax (ng/mL) | $AUC_{0-24}$ (hr*ng/mL) |
|---|---|---|---|---|---|
| 200 | 1 | 312 | 4.67 | 615 | 3250 |
| 200 | 1 | 314 | 5 | 153 | 961 |
| 200 | 1 | 316 | 2.33 | 595 | 3550 |
| 200 | 1 | 318 | 5 | 407 | 1820 |
| 200 | 3 | 301 | 6 | 360 | NC |
| 200 | 3 | 304 | 4 | 517 | NC |
| 200 | 3 | 305 | 1 | 350 | NC |
| 200 | 3 | 308 | 2.33 | 422 | NC |
| 200 | 3 | 310 | 5 | 303 | NC |
| 200 | 3 | 312 | 5 | 353 | NC |
| 200 | 3 | 314 | 5 | 243 | NC |
| 200 | 3 | 316 | 4 | 952 | NC |
| 200 | 3 | 318 | 5 | 658 | NC |
| 200 | 7 | 301 | 3.67 | 256 | 2050 |
| 200 | 7 | 304 | 1.67 | 1040 | 4420 |
| 200 | 7 | 305 | 2 | 298 | 2810 |
| 200 | 7 | 308 | 4.67 | 399 | 4880 |
| 200 | 7 | 310 | 6 | 294 | 3250 |
| 200 | 7 | 312 | 5 | 616 | 3580 |
| 200 | 7 | 314 | 2 | 170 | 2050 |
| 200 | 7 | 316 | 2.67 | 578 | 4250 |
| 200 | 7 | 318 | 4.33 | 579 | 2930 |
| 400 | 1 | 302 | 3 | 1230 | 7380 |
| 400 | 1 | 303 | 5 | 466 | 3460 |
| 400 | 1 | 306 | 2.33 | 835 | 5810 |
| 400 | 1 | 307 | 5 | 874 | 6500 |
| 400 | 1 | 309 | 5.5 | 1050 | 4450 |
| 400 | 1 | 311 | 4.33 | 1420 | 6250 |
| 400 | 1 | 313 | 3.33 | 1140 | 4810 |
| 400 | 1 | 315 | 5 | 1280 | 4660 |
| 400 | 1 | 317 | 5 | 1280 | 7610 |
| 400 | 1 | 319 | 3.67 | 1040 | 6380 |
| 400 | 3 | 302 | 2 | 1510 | NC |
| 400 | 3 | 303 | 1.67 | 667 | NC |
| 400 | 3 | 306 | 4 | 1700 | NC |
| 400 | 3 | 307 | 5 | 854 | NC |
| 400 | 3 | 309 | 3 | 1000 | NC |
| 400 | 3 | 311 | 4 | 1660 | NC |
| 400 | 3 | 313 | 5 | 579 | NC |
| 400 | 3 | 315 | 3 | 1410 | NC |
| 400 | 3 | 317 | 3 | 985 | NC |
| 400 | 3 | 319 | 2.33 | 1370 | NC |
| 400 | 7 | 302 | 0.5 | 454 | 5310 |
| 400 | 7 | 303 | 3.33 | 781 | 5830 |
| 400 | 7 | 306 | NC | NC | NC |
| 400 | 7 | 307 | 4.67 | 657 | 9350 |
| 400 | 7 | 309 | 5.5 | 509 | 4210 |
| 400 | 7 | 311 | 4.33 | 916 | 6980 |
| 400 | 7 | 313 | 4.67 | 447 | 5360 |
| 400 | 7 | 315 | 3.33 | 1800 | 7430 |
| 400 | 7 | 317 | 3 | 1660 | 9780 |
| 400 | 7 | 319 | 4.33 | 1340 | 8880 |

NC = not calculated

TABLE 40A

D2 Receptor Occupancy (RO) % by Subject in Example 7B

| | 200 mg Total Daily Dose | | | | 400 mg Total Daily Dose | | | |
|---|---|---|---|---|---|---|---|---|
| | MR (Lot 3Z) | | IR (Lot 1Z) | | MR (Lot 3Z) | | IR (Lot 1Z) | |
| Day Measured* | Subject | D2 RO (%) | Subject | D2 RO (%) | Subject | D2 RO (%) | Subject | D2 RO (%) |
| 2 | 320 | 28 | 301 | 26 | 322 | 30 | 302 | NC |
| 2 | 321 | 25 | 304 | 35 | 323 | 23 | 303 | 33 |
| 2 | 328 | 16 | 305 | 30 | 324 | 17 | 306 | 40 |
| 2 | 329 | 22 | 308 | 29 | 325 | 33 | 307 | 51 |

TABLE 40A-continued

D2 Receptor Occupancy (RO) % by Subject in Example 7B

| | 200 mg Total Daily Dose | | | | 400 mg Total Daily Dose | | | |
|---|---|---|---|---|---|---|---|---|
| Day Measured* | Subject | MR (Lot 3Z) D2 RO (%) | Subject | IR (Lot 1Z) D2 RO (%) | Subject | MR (Lot 3Z) D2 RO (%) | Subject | IR (Lot 1Z) D2 RO (%) |
| 2 | 332 | 20 | 310 | 22 | 330 | 29 | 309 | 39 |
| 2 | 333 | 21 | 312 | 27 | 331 | 42 | 311 | 43 |
| 2 | 336 | 13 | 314 | 29 | 334 | 25 | 313 | 30 |
| 2 | 337 | 20 | 316 | 27 | 335 | 23 | 315 | 36 |
| 2 | | | 318 | 16 | | | 317 | 33 |
| 2 | | | | | | | 319 | 34 |
| | Average | 21 ± 4 | | 27 ± 5 | | 28 ± 7 | | 38 ± 6 |
| 8 | 320 | 32 | 301 | 27 | 322 | 30 | 302 | 34 |
| 8 | 321 | 39 | 304 | NC | 323 | 32 | 303 | NC |
| 8 | 328 | 33 | 305 | 28 | 324 | 35 | 307 | 49 |
| 8 | 329 | 21 | 308 | 37 | 325 | 44 | 309 | 32 |
| 8 | 332 | 38 | 310 | 34 | 330 | 26 | 311 | 32 |
| 8 | 333 | 24 | 312 | 31 | 331 | 36 | 313 | 40 |
| 8 | 336 | 20 | 314 | 35 | 334 | 50 | 315 | 36 |
| 8 | 337 | 32 | 316 | 34 | 335 | 37 | 317 | 24 |
| 8 | | | 318 | 19 | | | 319 | 38 |
| | Average | 30 ± 7 | | 31 ± 5 | | 36 ± 7 | | 36 ± 7 |

NC = not calculated
*Measurements on Day 2 were conducted within 27 ± 1 hours of administration of the first dose, and measurements on Day 8 were conducted within 27 ± 1 hours of administration of the seventh dose.

TABLE 40B

Figure 25:
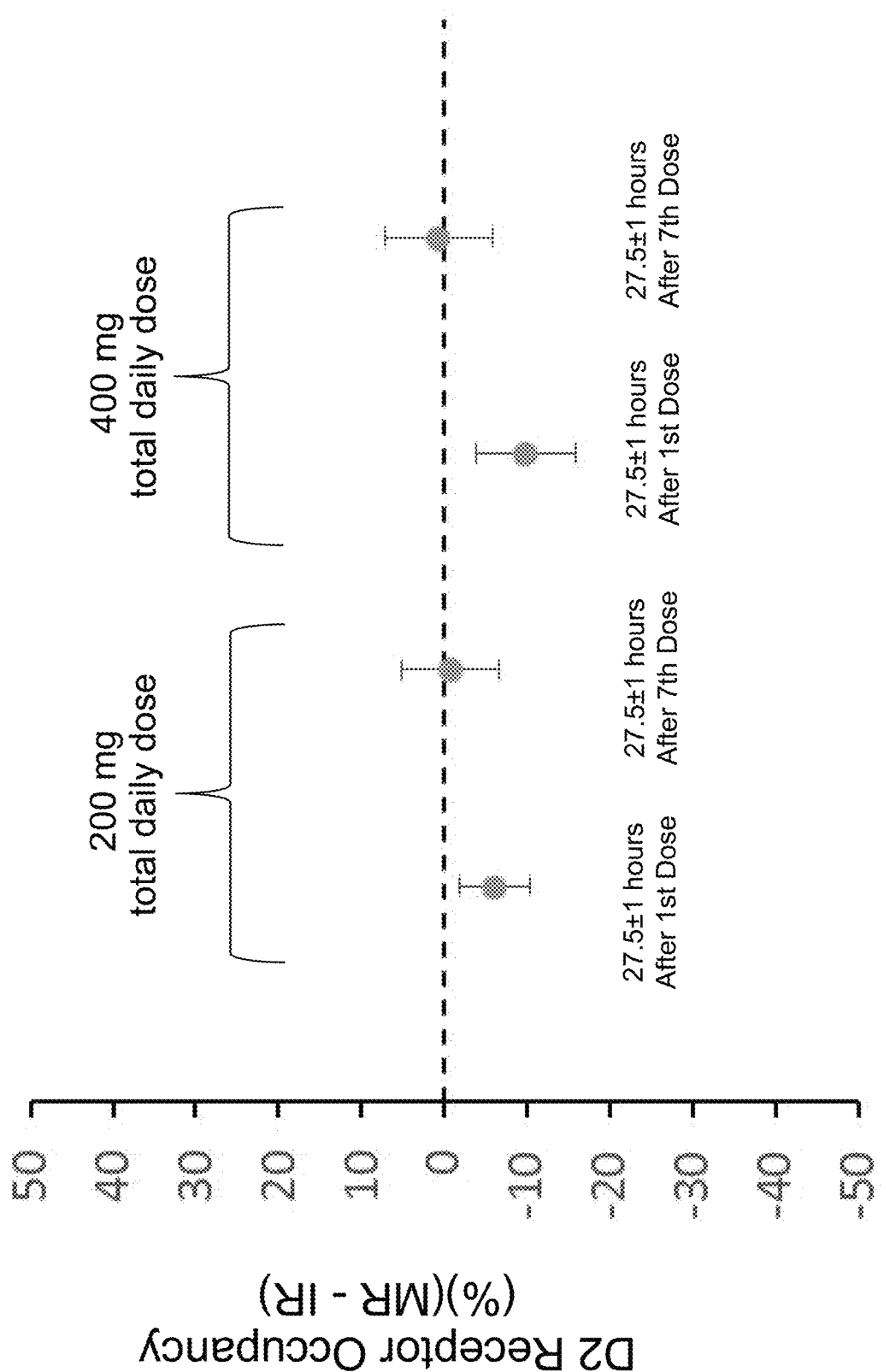
FIG. 25 compares the difference (MR-IR) between D2 receptor occupancy measured for IR and modified release (MR) formulations for the subjects of Example 7B, the error bars represent the ±90% confidence intervals.

Example 7B D2 RO % (MR-IR) and ±90% Confidence Interval (CI) of data plotted in FIG. 25

| Total Daily Dose (mg) | Day | % RO % (MR AR) | 90% CI Lower | 90% CI Upper |
|---|---|---|---|---|
| 200 | 1 | −6.15 | −10.5 | −1.85 |
| 200 | 7 | −0.75 | −6.60 | 5.10 |
| 400 | 1 | −9.92 | −15.9 | −3.94 |
| 400 | 7 | 0.63 | −5.95 | 7.20 |

TABLE 40C

Figure 28B:
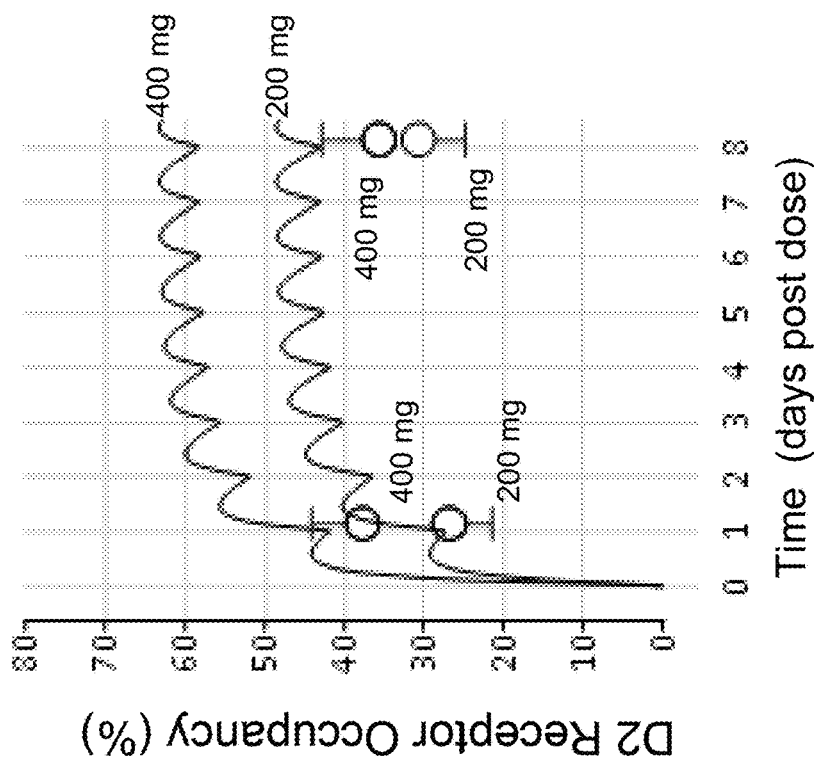
FIG. 28B compares observed D2 receptor occupancy as measured in Example 7B (white circles where total daily does is indicated) to predicted accumulation (solid lines, dosage for prediction is indicated).
Figure 28A:
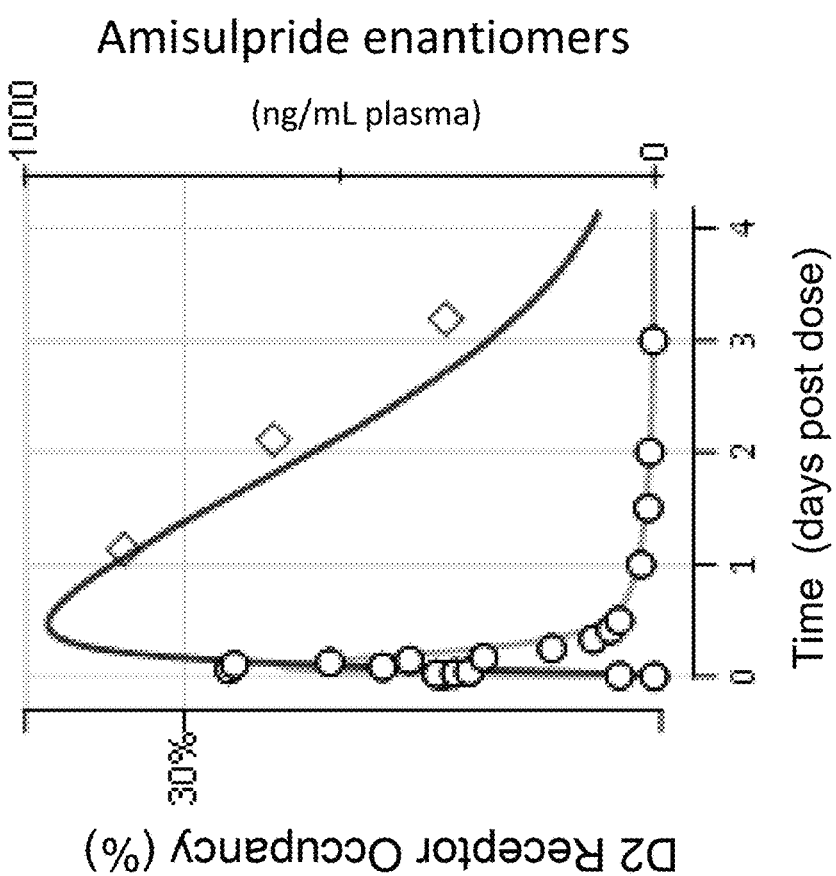
FIG. 28A presents data for a single subject comparing the amisulpride blood plasma concentration as a function of time (white circles) to D2 receptor occupancy (white diamonds) as a function of time following a single day dosing.

Data Plotted in FIG. 28A

| White Diamonds | | White Circles Plasma |  |
|---|---|---|---|
| Time (hr) | D2 RO (%) | Time (hr) | Concentration (ng/mL) |
| 27.27 | 33.5 | 0.167 | 55.4 |
| 50.7 | 24.4 | 0.333 | 334 |
| 76.65 | 13.9 | 0.5 | 346 |
| | | 0.667 | 316 |
| | | 1 | 294 |
| | | 1.5 | 677 |
| | | 2 | 432 |
| | | 2.5 | 668 |
| | | 3 | 516 |
| | | 3.5 | 389 |
| | | 4 | 272 |
| | | 6 | 163 |
| | | 8 | 96.8 |
| | | 10 | 69.9 |
| | | 12 | 55.6 |
| | | 24 | 21.2 |
| | | 36 | 9.84 |
| | | 48 | 7.02 |
| | | 72 | 1.48 |

It was surprisingly discovered, that embodiments of the modified release pharmaceutical formulations of the present inventions can provide substantially the same efficacy as comparable immediate release formulations at both lower blood plasma maximum concentrations (Cmax) and total blood plasma concentration (AUC), and with reduced adverse events and/or side effects.

Referring to FIGS. 22C, 22H, 22J, 26A, 26B, 27A and 27B it can be seen that the modified release formulations used in this study provide both a lower Cmax a AUC relative to the comparator immediate release formulation. While FIGS. 24A-D show that the modified release formulation provided substantially similar D2 receptor occupancy of that of a comparable immediate release formulation. It was discovered in this study that brain D2 receptor occupancy (RO) correlated more with an exposure sustained above a threshold (e.g., 100 ng/mL) than with Cmax or AUC itself. The comparison of pharmacokinetic (PK) parameters between immediate release (IR) and modified release (MR) formulations indicated that Cmax and total AUC were insufficient to explain the observed D2 receptor occupancy.

In addition, the modified release formulations of the present inventions show reduced side effects (e.g. QT prolongation) compared to comparable immediate release formulations. The modified release formulations resulted in substantially lower QTc prolongation than the same dose of the IR formulation. FIG. 23 illustrates the improved safety (reduced QT prolongation) provided by the modified release formulation in this study.

Mean estimates of the QTc prolongation for the 200 mg IR formulations tested in these studies were consistently above 10 ms threshold (13 and 14 ms at geometric mean Cmax values of 490 and 580 ng/mL in subjects in Examples 7A Parts 1 and 2, respectively) and were successfully reduced to 5 and 8 ms (at geometric means of 240 and 370 ng/mL, respectively) for the 200 mg modified release formulations.

These studies demonstrated that embodiments of the modified release formulations of the present inventions similar to Lot 3Z, provided as 200 mg or 400 mg daily doses of the API, provided markedly lower Cmax (for a 200 mg total daily dose the modified release formulation (MR) population geometric mean Cmax was 314 ng/mL and for a 400 mg daily dose of MR population geometric mean Cmax was 484 ng/mL vs. a population geometric mean Cmax of 599 ng/mL for a 200 mg total daily dose of the IR formulation), and achieved clinically meaningful reduction in QT prolongation relative to a comparable IR form, while maintaining substantially similar brain occupancy (D2 recpetors) at steady state as compared to the same dose given in comparable IR form. The modified release formulations thus provided an improved therapeutic index for brain occupancy versus QTc prolongation relative to comparable immediate release formulations.

Figures 24A, 24B:
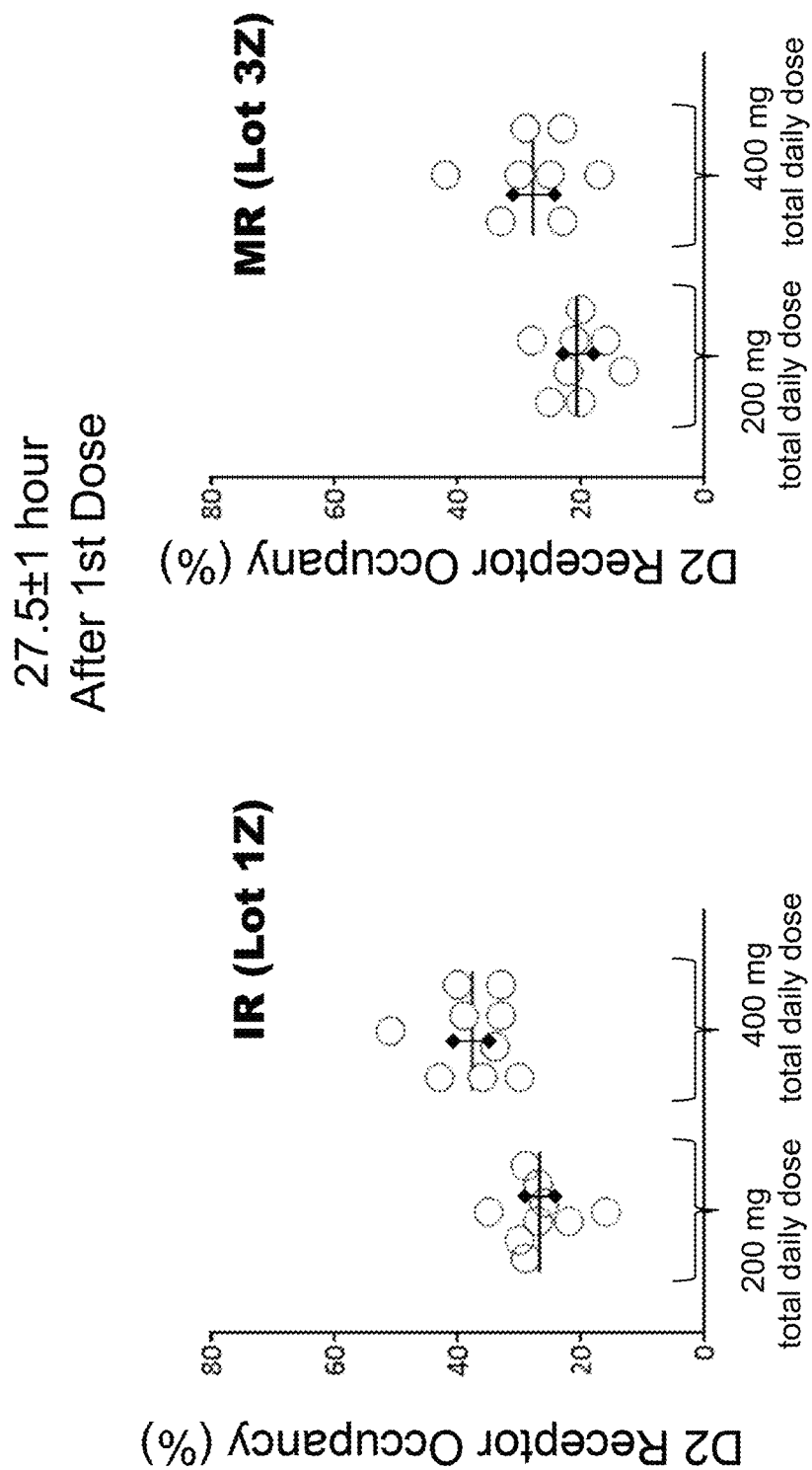
FIGS. 24A-24D present data on D2 receptor occupancy for the subjects of Example 7B.

Referring more specifically to the figures, FIGS. 24A and 24B compare brain D2 receptor occupancies percentages for subjects 27±1 hour after receiving a first ($1^{st}$) total daily dose of either 200 mg or 400 mg of API as: an immediate release (IR) formulation (as tablets with a formulation substantially similar to Lot 1Z), in FIG. 24A; and a modified release (MR) formulation (as tablets with a formulation substantially similar to Lot 3Z) in FIG. 24B.

Figures 24C, 24D:
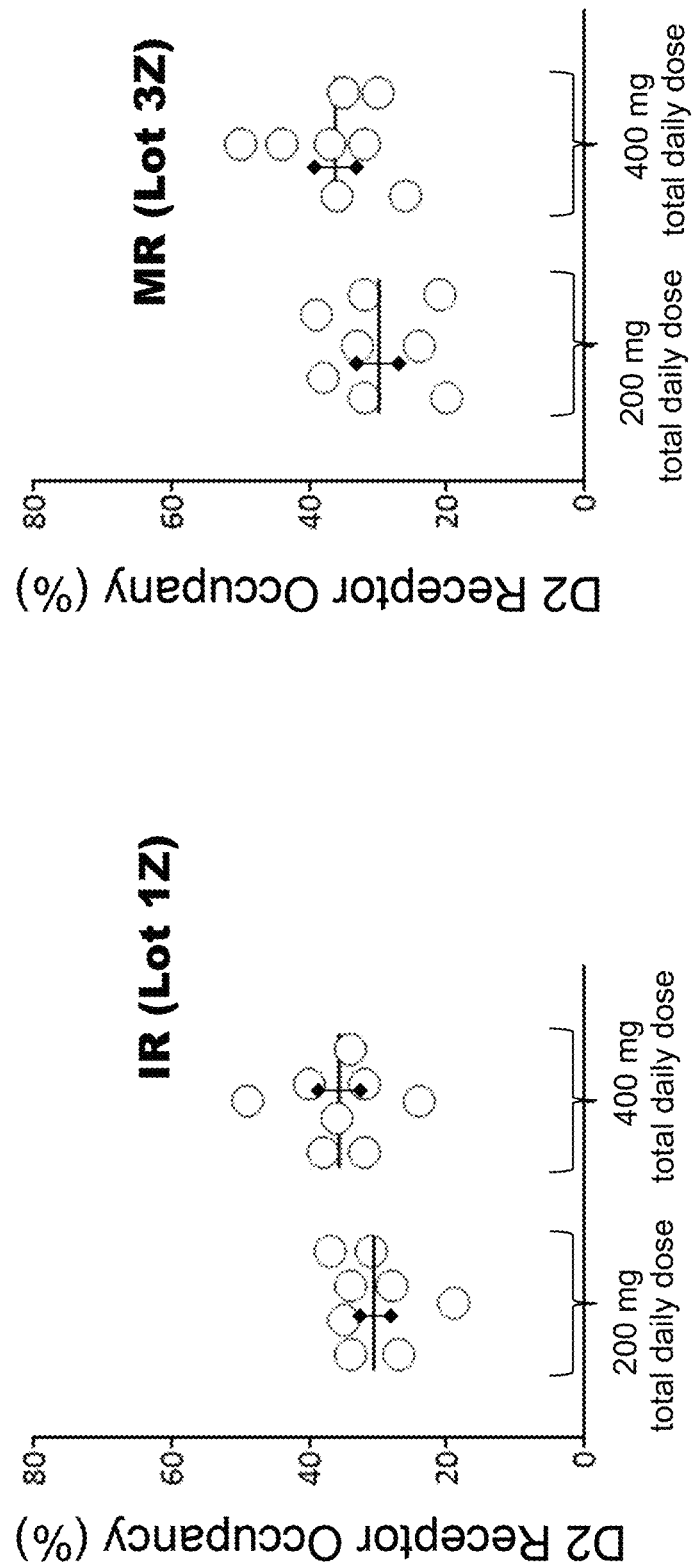

FIGS. 24C and 24D compare brain D2 receptor occupancies percentages for subjects 27±1 hour after receiving a seventh ($7^{th}$) total daily dose of either 200 mg or 400 mg of API as: an immediate release (IR) formulation (as tablets with a formulation substantially similar to Lot 1Z), in FIG. 24C; and a modified release (MR) formulation (as tablets with a formulation substantially similar to Lot 3Z) in FIG. 24D.

The data plotted in FIGS. 24A, 24B, 24C and 24 D is presented in Table 40A. The circles in FIGS. 24A, 24B, 24C and 24 D represent data for individual subjects which have been displaced for clarity, the horizontal bars represent the average for the respective group of data points, and vertical error bars are the ±1 standard deviations for the associated average, also presented in Table 40A.

Figure 26A:
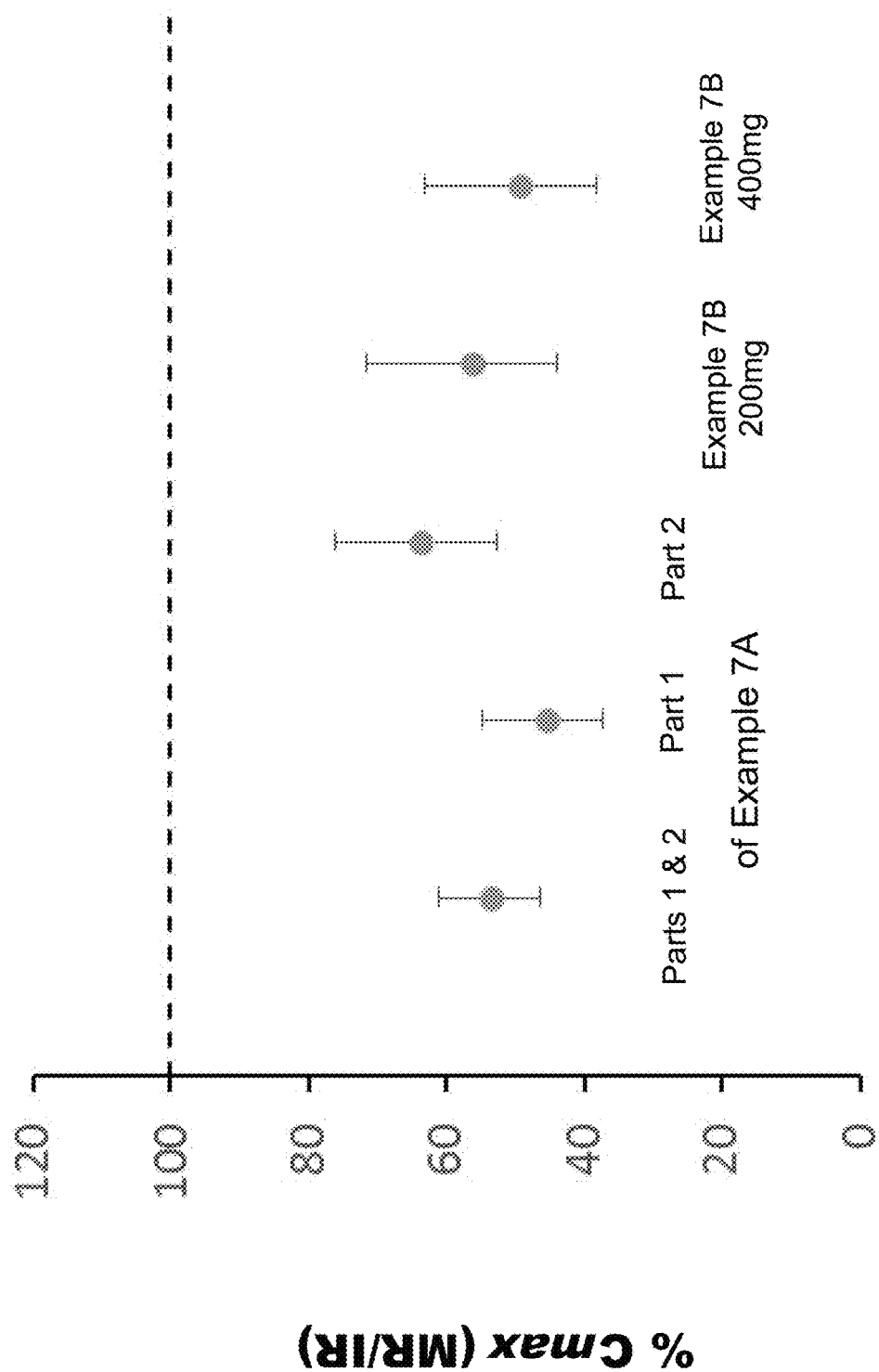
FIG. 26A presents normalized Cmax data from Example 7A (Part 1, Part 2, and Parts 1 & 2 combined) and Example 7B. The Cmax for subjects of Example 7A has been normalized for each subject to the Cmax value of that subject when administered the IR tablet (i.e. a tablet having a composition substantially similar to that of Lot 1Z). The normalized Cmax data for Example 7B is the geometric mean Cmax of subjects administered a modified release (MR) composition substantially similar to that of Lot 3Z normalized by the geometric mean Cmax of the subjects administered the IR tablet having a composition substantially similar to that of Lot 1Z. The error bars represent the ±90% confidence intervals.
Figure 26B:
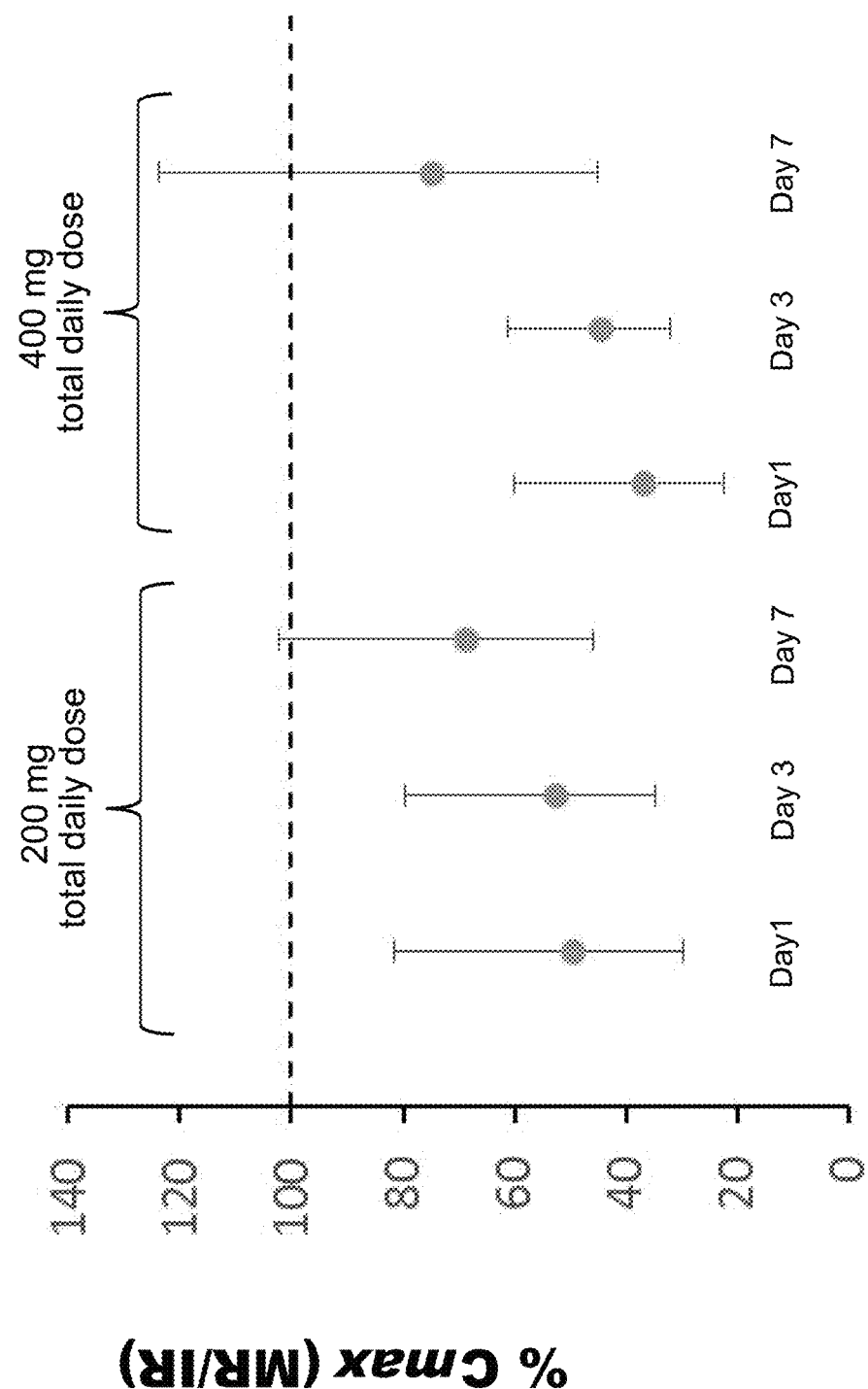
FIG. 26B presents normalized Cmax data for Example 7B as measured on Day 1, Day 3 and Day 7, where the geometric mean Cmax of subjects administered a modified release (MR) composition substantially similar to that of Lot 3Z is normalized by the geometric mean Cmax of the subjects administered the IR tablet having a composition substantially similar to that of Lot 1Z. The error bars represent the ±90% confidence intervals.

It was discovered in this study that brain D2 receptor occupancy is substantially similar between the immediate release (IR) and modified release (MR) formulations despite the difference in maximum blood plasma concentrations (Cmax) and total blood plasma concentration over time (represented by AUC) between these formulations. This can be more readily seen through a comparison of FIG. 25, FIG. 26A, FIG. 26B, FIG. 27A and FIG. 27B. FIG. 25 plots the difference between the average observed D2 RO for subjects administered the MR formulation and that observed for subjects administered the IR formulation in this study, measured 27±1 hour after receiving the first daily dose and the seventh daily does (where blood plasma concentration has reached a steady state). FIG. 25 illustrates that the D2 RO percentage is substantially similar between the immediate release and modified release formulations of this study. FIGS. 26A and 26B present modified release formulation Cmax normalized by the Cmax for an immediate release formulation administered at the same total daily dose as the MR formulation, and presented as a percentage where a value of 100 indicates Cmax IR equals Cmax MR.

Figure 27A:
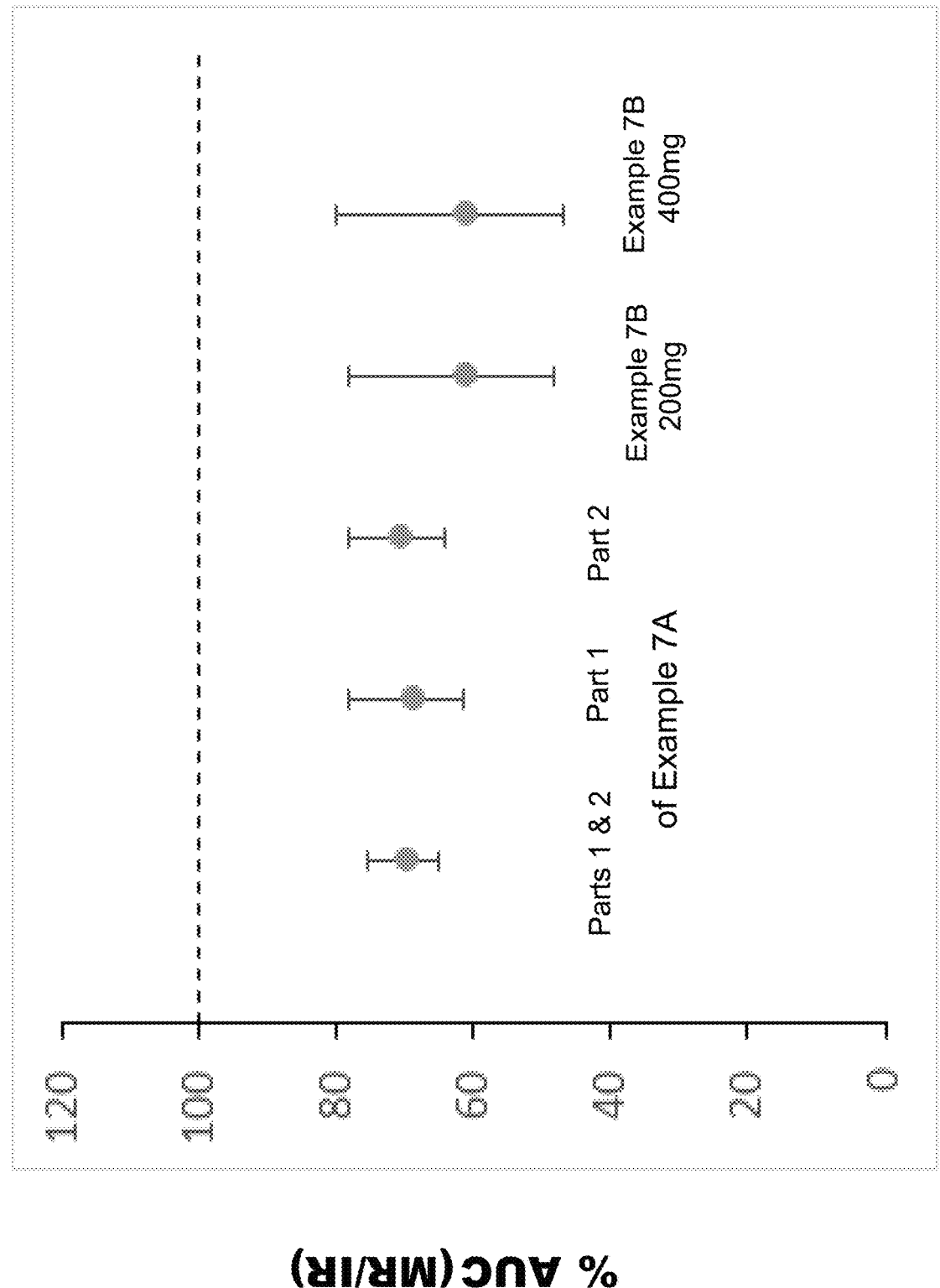
FIG. 27A presents normalized AUC data from Example 7A (Part 1, Part 2, and Parts 1 & 2 combined) and Example 7B (Days 1 & 7 combined). $AUC_{0-INF}$ values are used for the subjects of Example 7A and $AUC_{0-24}$ are used for the subjects of Example 7B. The AUC for subjects of Example 7A has been normalized for each subject to the AUC value of that subject when administered the IR tablet (i.e. a tablet having a composition substantially similar to that of Lot 1Z). The normalized AUC data for Example 7B is the geometric mean AUC of subjects administered a modified release (MR) composition substantially similar to that of Lot 3Z normalized by the geometric mean AUC of the subjects in Example 7B administered the IR tablet having a composition substantially similar to that of Lot 1Z. The error bars represent the ±90% confidence intervals.

FIG. 26A includes date presented in Examples 7A Parts 1 and 2, as well as Example 7B, while FIG. 26B presents data for Example 7B at several time points during the course of the study (i.e. Day 1, Day 3, and Day 7). FIG. 27A includes date presented in Examples 7A Parts 1 and 2, as well as Example 7B, while FIG. 27B presents data for Example 7B at several time points during the course of the study (i.e. Day 1 and Day 7).

Figure 27B:
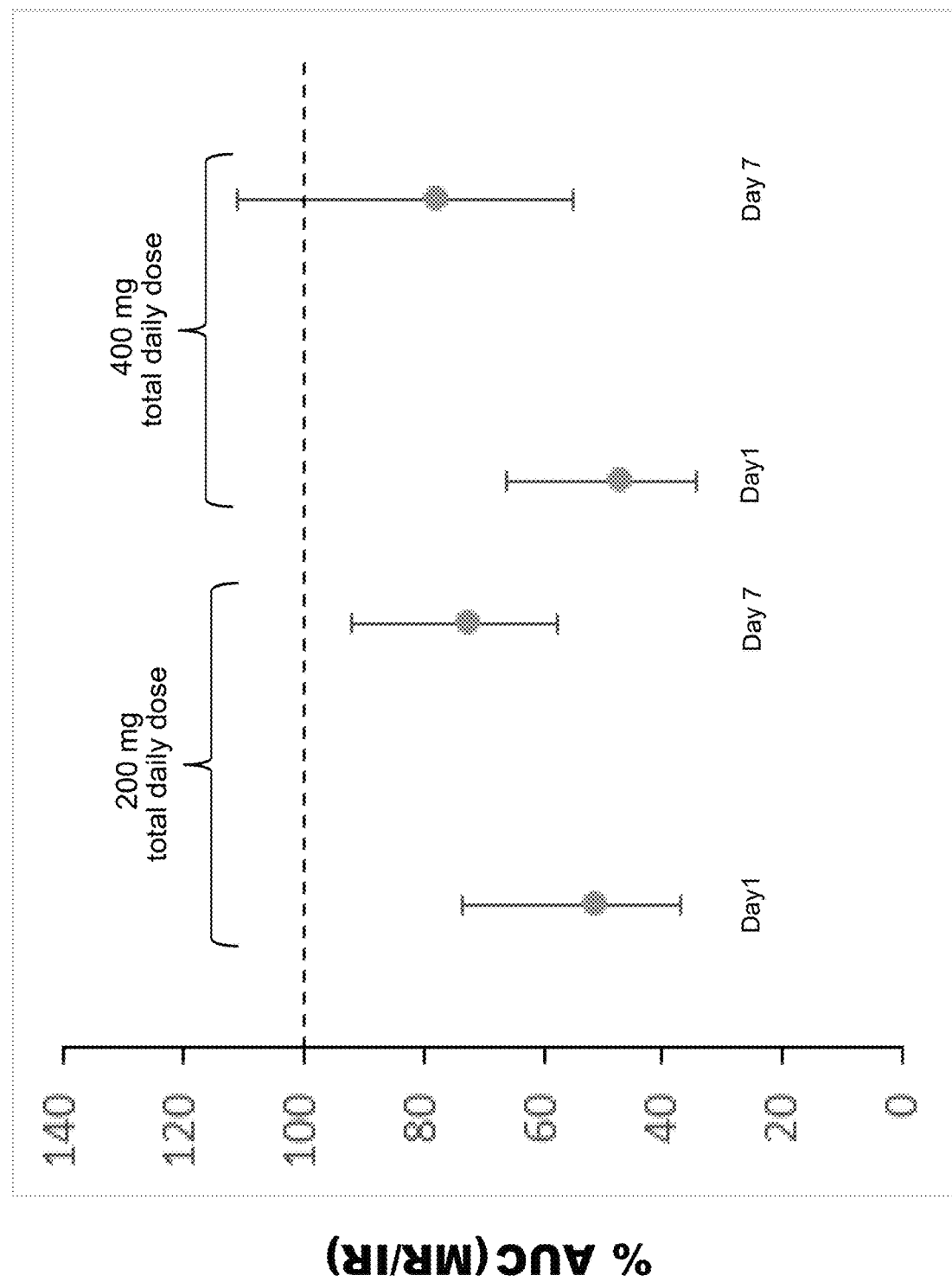
FIG. 27B presents normalized $AUC_{0-24}$ data for Example 7B as measured on Day 1 and Day 7, where the geometric mean $AUC_{0-24}$ of subjects administered a modified release (MR) composition substantially similar to that of Lot 3Z is normalized by the geometric mean $AUC_{0-24}$ of the subjects administered the IR tablet having a composition substantially similar to that of Lot 1Z. The error bars represent the ±90% confidence intervals.

FIGS. 26A and 26B show that the Cmax of the MR formulations is consistently less than that of the IR formulations and FIGS. 27A and 27B show that the AUC of the MR formulations is consistently less than that of the IR formulations, while FIG. 25 shows that the D2 RO % is substantially the same between the IR and MR formulations of this study. Thus, the present MR formulations present an increased therapeutic index relative to the IR formulations, and the data of these studies indicate that the MR formulations of this study (for example a formulation comprising about 25% of an extended release agent) can provide substantially similar therapeutic effect at reduced blood plasma concentrations (and thus with potentially less undesirable side effects) than a comparable IR formulation.

In addition, it was discovered that embodiments of the modified release formulations of the present inventions show a marked pharmacokinetic (PK) and pharmacodynamics (PD) disconnect in amisulpride brain occupancy relative to amisulpride blood plasma concentration, that cannot be accounted for or predicted with traditional models. It was discovered in these studies (Examples 7A Parts 1 & 2 and Example 7B) that amisulpride exhibits: (1) time-hysteresis: the clearance from plasma is rapid compared to the washout of brain occupancy, (2) dose-response: occupancy increases with dose and receptor binding is not saturated, and (3) lack-of-accumulation: brain occupancy does not accumulate substantially to steady state.

The comparison of PK parameters between IR and MR (modified release) formulations indicated that Cmax and total AUC were insufficient to explain the observed brain occupancies under traditional models. For example, conventional linear direct effect (fails to account for observed hysteresis), Emax direct effect (fails to account for observed hysteresis and dose response), receptor binding with effect-compartment (fails to account for observed lack of accumulation), concentration-difference (fails to account for observed hysteresis), and ratio (fails to account for observed lack of accumulation) models.

The observed time-hysteresis (the clearance from plasma is rapid compared to the washout of brain occupancy) can be discerned, for example, in the data of FIGS. 22C, 22H, 22J and Tables 26A-C (showing amisulpride blood plasma concentration over time) to the observed D2 receptor occupancy (see, for example FIGS. 24A-B and FIG. 28A) it was surprisingly discovered that single oral doses resulted in brain occupancies that far outlasted (approximately a 5-day washout for D2 receptor occupancy) the plasma PK (approximately 24-hour washout observed for blood plasma concertation). Referring to FIG. 28A, this observed behavior is illustrated for a single subject in these studies, where the amisulpride blood plasma concertation as a function of time (white circles) is compared to D2 receptor occupancy (white diamonds) as a function of time. Hysteresis was observed in all subjects where D2 receptor occupancy was measured, and this long duration of brain occupancy was unexpected.

The observed D2 receptor occupancy and pharmacokinetics for the modified release formulation support the conclusion that lasting effects due to these distribution kinetics would also be present at serotonin 5-HT7 receptors for the modified release formulations of the present inventions, and thus supports the conclusion that the therapeutic effect associated with 5-HT7 receptor occupancy will be substantially similar between the modified release formulations of the present invention and comparable IR formulations.

The observed dose-response (occupancy increases with dose and receptor binding is not saturated), can be discerned, for example, in the data of FIGS. 24A-D and 25.

The observed lack-of-accumulation (brain occupancy does not accumulate substantially to steady state) can be discerned, for example, in comparing FIGS. 24A and 24B to FIGS. 24C and 24D, and is further illustrated in FIG. 28B. FIG. 28B compares observed D2 receptor occupancy as measured in Example 7B (white circles where total daily dose is indicated) to predicted accumulation (solid lines, dosage for prediction is indicated); where the prediction was made using a traditional receptor-binding model using single dose data from the studies of Example 7A. In marked contrast to the predictions by the traditional receptor-binding model, brain occupancy did not accumulate over 7 daily doses.

Without being held to theory, the inventors have developed a novel distribution model having an additional transit step in the effect (brain) compartment, that accurately matches the measured data and recapitulated the three key observations above: time-hysteresis, dose-response, and lack-of-accumulation. Both simulations and analytical solutions employing the novel distribution model describe how the reduced blood plasma exposures with modified release (MR) formulations can still attain brain D2 receptor occupancies equivalent to those observed for the immediate release (IR) formulations. In this novel model, transient increases in plasma concentration do not appreciably change brain occupancy when they occur over shorter time durations, consistent with the experimental observations in these studies.

TABLE 41A

Cmax and ±90% Confidence Interval (CI) of data plotted in FIG. 26A

| Subjects | Total Daily Dose (mg) | % Cmax (MR/IR) | 90% CI Lower | 90% CI Upper |
| --- | --- | --- | --- | --- |
| Parts 1 & 2 Example 7A | 200 | 53.2 | 46.4 | 61.0 |
| Parts 1 Example 7A | 200 | 45.1 | 37.2 | 54.7 |
| Parts 2 Example 7A | 200 | 63.4 | 52.8 | 76.1 |
| Example 7B | 200 | 56.1 | 43.9 | 71.7 |
| Example 7B | 400 | 49.2 | 38.3 | 63.1 |

TABLE 41B

Example 7B Cmax and ±90% Confidence Interval (CI) of data plotted in FIG. 26B

| Total Daily Dose (mg) | Day | % Cmax (MR/IR) | 90% CI Lower | 90% CI Upper |
| --- | --- | --- | --- | --- |
| 200 | 1 | 49.1 | 29.6 | 81.6 |
| 200 | 3 | 52.5 | 34.7 | 79.5 |
| 200 | 7 | 68.5 | 45.9 | 102 |
| 400 | 1 | 36.6 | 22.3 | 60.1 |
| 400 | 3 | 44.3 | 32.2 | 61.1 |
| 400 | 7 | 74.5 | 44.9 | 124 |

TABLE 41C

Normalized AUC and ±90% Confidence Interval (CI) of data plotted in FIG. 27A

| Subjects | Total Daily Dose (mg) | % AUC (MR/IR) | 90% CI Lower | 90% CI Upper |
| --- | --- | --- | --- | --- |
| Parts 1 & 2 Example 7A | 200 | 70.0 | 64.9 | 75.5 |
| Parts 1 Example 7A | 200 | 69.3 | 61.3 | 78.3 |
| Parts 2 Example 7A | 200 | 70.8 | 64.2 | 78.1 |
| Example 7B | 200 | 61.5 | 48.3 | 78.3 |
| Example 7B | 400 | 61.5 | 47.1 | 80.2 |

TABLE 41D

Normalized AUC and ±90% Confidence Interval (CI) of data plotted in FIG. 27B

| Total Daily Dose (mg) | Day | % AUC (MR/IR) | 90% CI Lower | 90% CI Upper |
| --- | --- | --- | --- | --- |
| 200 | 1 | 52.0 | 36.8 | 73.4 |
| 200 | 7 | 72.8 | 57.7 | 92 |
| 400 | 1 | 47.8 | 34.4 | 66.3 |
| 400 | 7 | 78.3 | 55.2 | 111 |

Crystal Forms of Enantiomeric Amisulpride

In various embodiments, are provided a distinct polymorph of (R)-(+)-amisulpride, (S)-(−)-amisulpride, or both, is used in various embodiments of the compositions, formulations, methods and medicaments.

Polymorphism is the ability of an element or compound to crystallize into distinct crystalline phases. Although the term polymorph implies more than one morphology, the term is still used in the art, and herein, to refer to a crystalline structure of a compound as a polymorph even when only one crystalline phase is currently known. Thus, polymorphs are distinct solids sharing the same molecular formula as other polymorphs and the amorphous (non-crystalline) phase, however since the properties of any solid depends on its structure, polymorphs often exhibit physical properties distinct from each other and the amorphous phase, such as different solubility profiles, different melting points, different dissolution profiles, different thermal stability, different photostability, different hygroscopic properties, different shelf life, different suspension properties and different physiological absorption rates. Inclusion of a solvent in the crystalline solid leads to solvates, and in the case of water as a solvent, hydrates, often leads to a distinct crystalline form with one or more physical properties that are distinctly different from the non-solvated and non-hydrated (e.g., free base) crystalline form. In various embodiments, Form A and A' are anhydrous, e.g., substantially free of water and solvent.

As used herein, the term "polymorph" refers to different crystal structures achieved by a particular chemical entity. As used herein, the term "solvate" refers to a crystal form where a stoichiometric or non-stoichiometric amount of solvent, or mixture of solvents, is incorporated into the crystal structure. Similarly, the term "hydrate" refers to a crystal form where a stoichiometric or non-stoichiometric amount of water is incorporated into the crystal structure.

In various embodiments, (R)-amisulpride and (S)-amisulpride are independently provided in a free base crystal form, and thus without any water or solvent incorporated into the crystal structure. It has been found that (R)-amisulpride and (S)-amisulpride can exist in at least one such free base crystal form, or polymorph, which is referred to herein as Form A for crystalline (R)-amisulpride, and Form A' for crystalline (S)-amisulpride.

Form A and Form A' are also described U.S. patent application Ser. No. 16/209,263 filed on Dec. 4, 2018, and is hereby incorporated herein by reference in its entirety.

Crystal forms of amisulpride, enantiomeric amisulpride, and crystalline forms of their salts, hydrates and solvates may be characterized and differentiated using a number of conventional analytical techniques, including but not limited to X-ray powder diffraction (XRPD) patterns, nuclear magnetic resonance (NMR) spectra, Raman spectra, Infrared (IR) absorption spectra, dynamic vapor sorption (DVS), Differential Scanning calorimetry (DSC), and melting point.

Chemical purity may be characterized using a number of conventional analytical techniques, including but not limited to high performance liquid chromatography (HPLC) and gas chromatography (GC). For example, one skilled in the art could use a reverse phase gradient HPLC method or a reverse phase isocratic HPLC method to determine organic impurities, a headspace GC method to determine residual solvents, coulometric titration (Karl Fischer) to determine water content, and a reverse phase isocratic HPLC method or a polar organic phase isocratic HPLC method to determine the amount of drug product in a sample. Chiral purity (also known as enantiomeric purity) may be characterized using a number of conventional analytical techniques, including but not limited to chiral high performance liquid chromatography (HPLC).

In various embodiments, the crystal forms of racemic amisulpride, enantiomeric amisulpride, and enantiomeric amisulpride solvates are characterized by X-ray powder diffraction (XRPD). XRPD is a technique of characterizing a powdered sample of a material by measuring the diffraction of X-rays by the material. The result of an XRPD experiment is a diffraction pattern. Each crystalline solid produces a distinctive diffraction pattern containing sharp peaks as a function of the scattering angle 2θ (2-theta). Both the positions (corresponding to lattice spacing) and the relative intensity of the peaks in a diffraction pattern are indicative of a particular phase and material. This provides a "fingerprint" for comparison to other materials. In contrast to a crystalline pattern comprising a series of sharp peaks, amorphous materials (liquids, glasses etc.) produce a broad background signal in a diffraction pattern.

It is to be understood that the apparatus employed, humidity, temperature, orientation of the powder crystals, and other parameters involved in obtaining an XRPD pattern may cause some variability in the appearance, intensities, and positions of the lines in the diffraction pattern. An XRPD pattern that is "substantially in accord with" that of a Figure (FIG.) provided herein (e.g., FIG. 11B) is an XRPD pattern that would be considered by one skilled in the art to represent a compound possessing the same crystal form as the compound that provided the XRPD pattern of that Figure. That is, the XRPD pattern may be identical to that of the Figure, or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns.

Figure 11A:
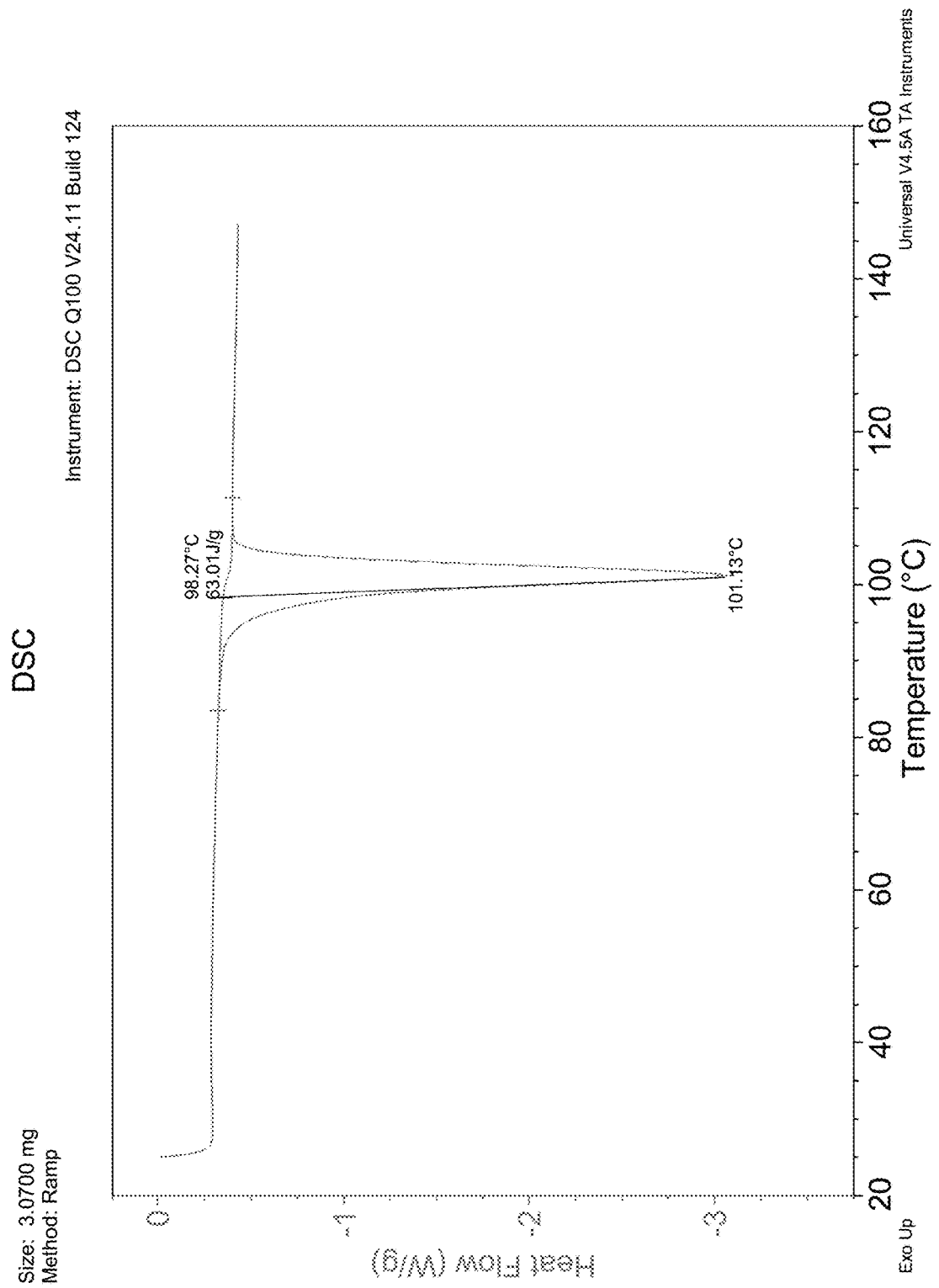
FIGS. 11A-11C present various analytical data and images for Form A crystals of (R)-amisulpride, where
Figure 11B:
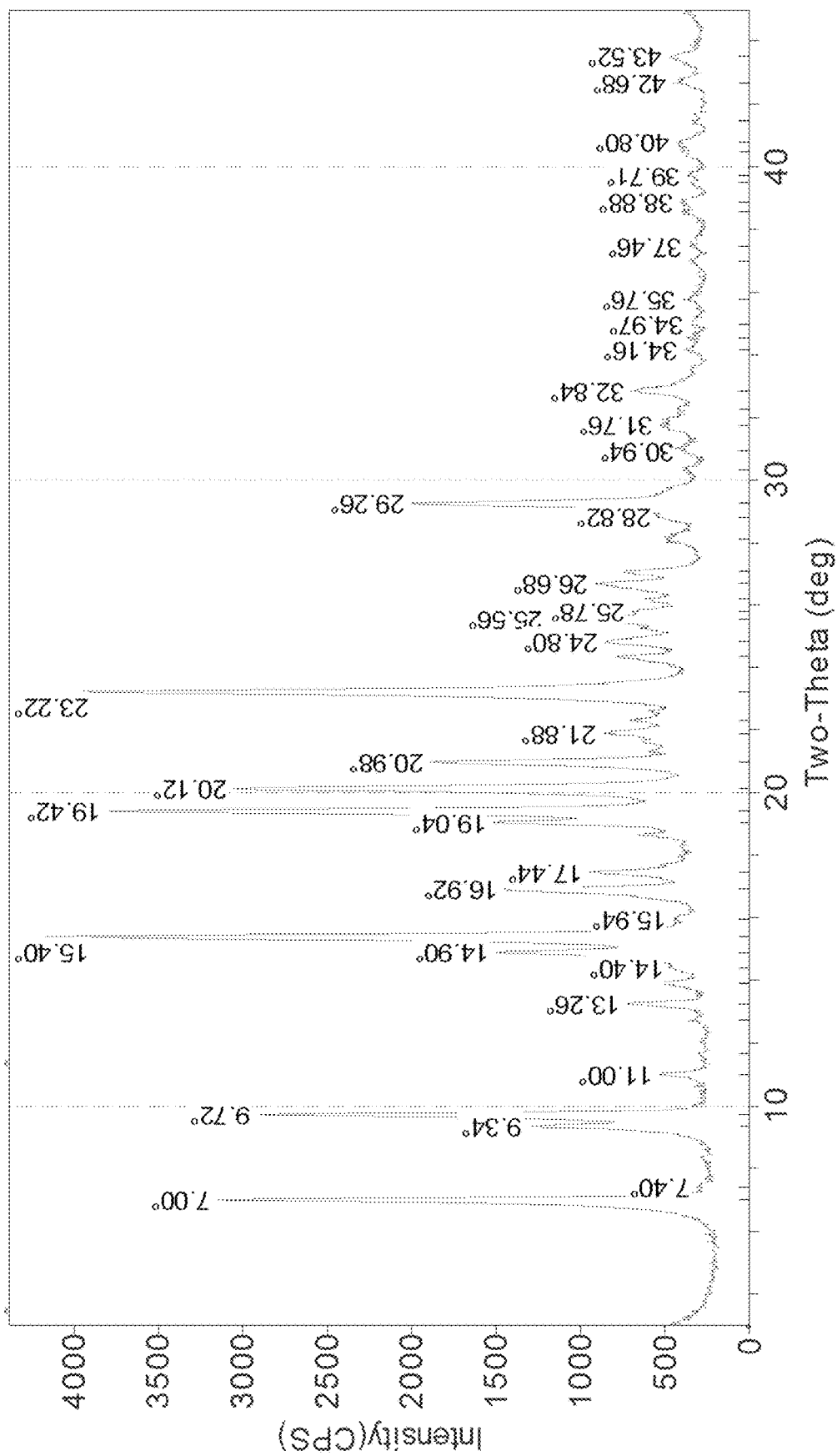
Figure 12A:
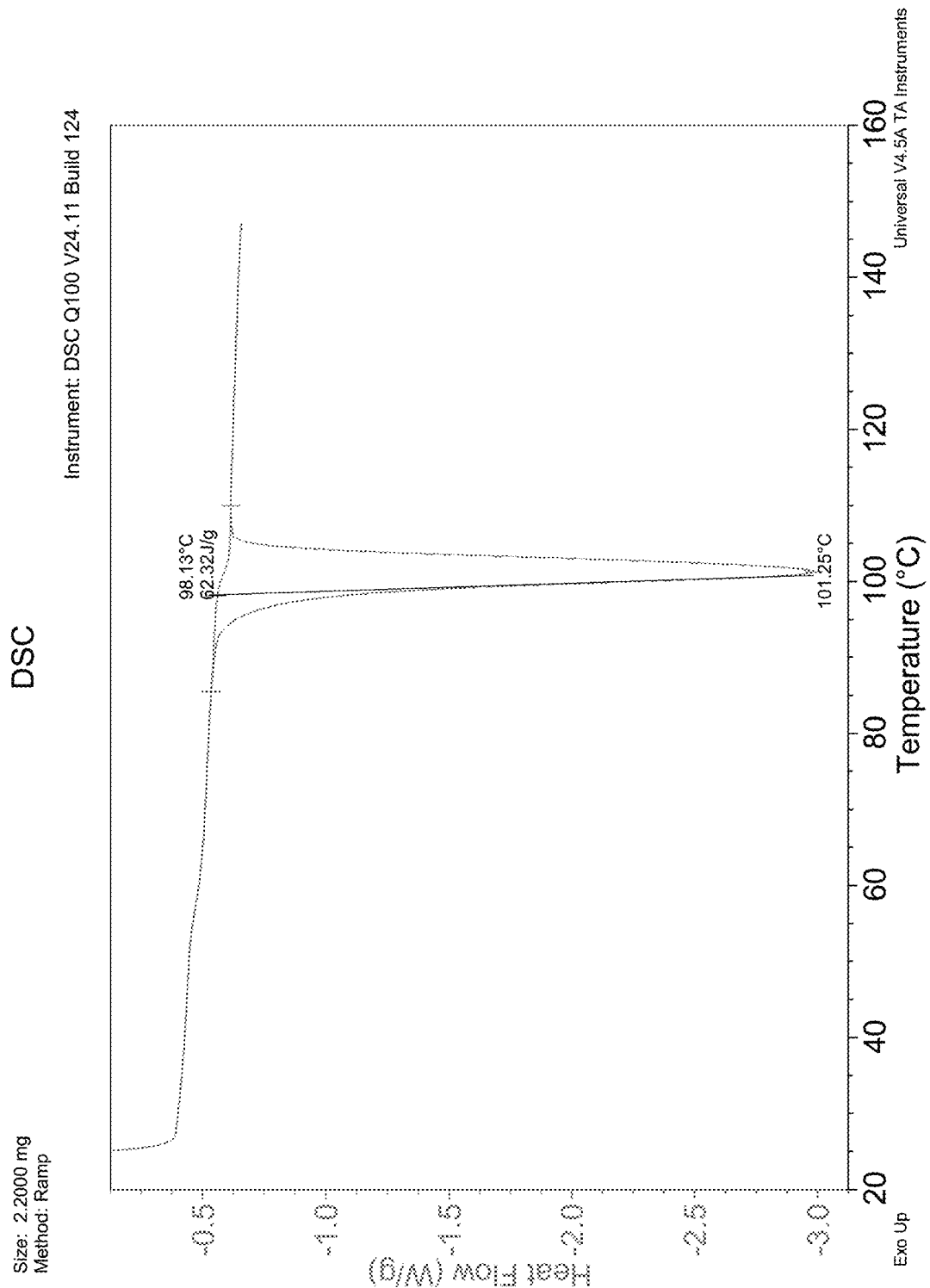
FIGS. 12A-12D present various analytical data and images for Form A' crystals of (S)-amisulpride, where
Figure 12B:
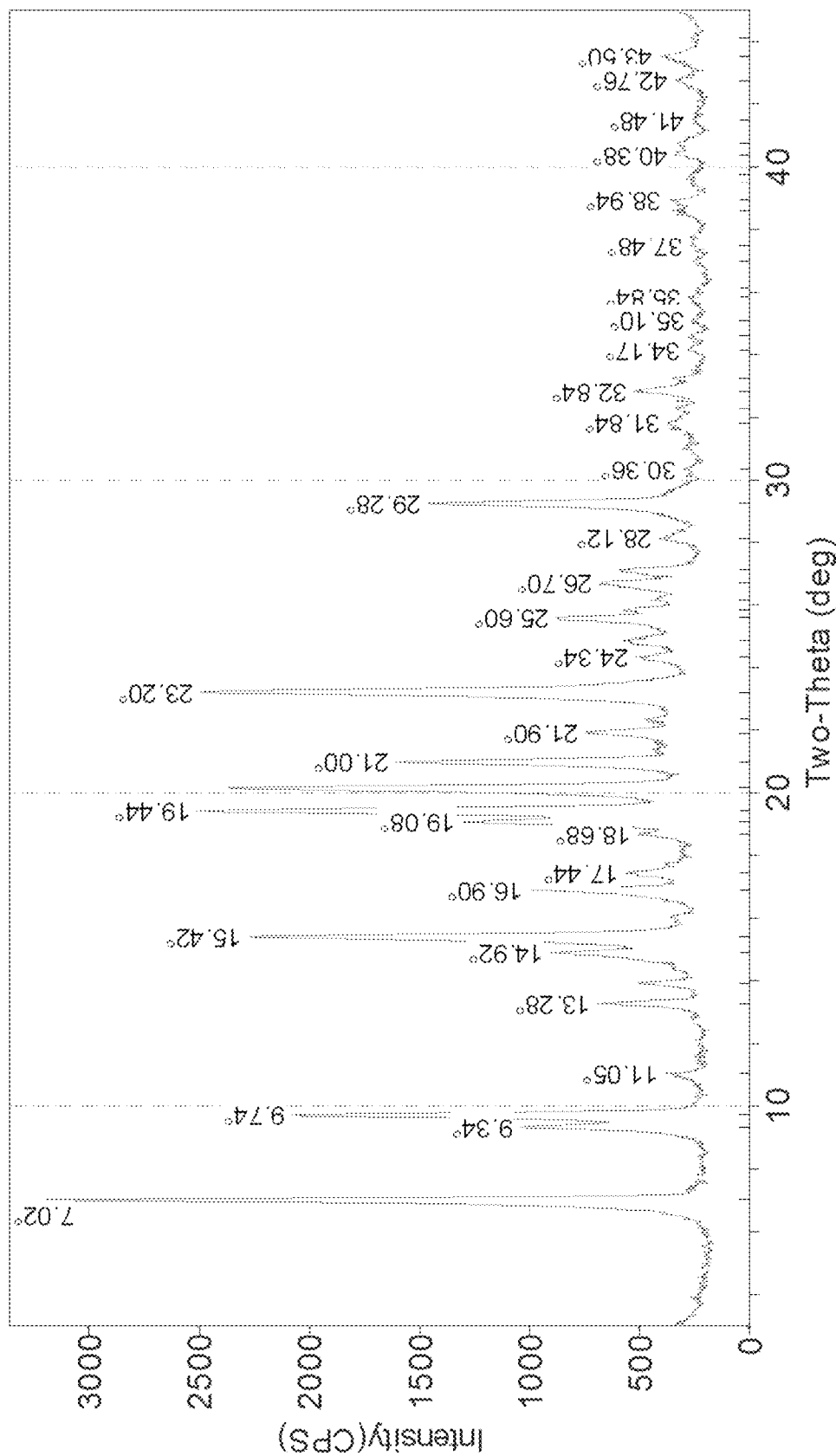

For example, one skilled in the art could use a chiral HPLC method (e.g. polar organic mode isocratic HPLC) to determine the enantiomeric identity of an amisulpride sample and if, for example, the sample is identified as (R)-amisulpride, one skilled in the art can overlay an XRPD pattern of the amisulpride sample with FIG. 11B and/or FIG. 12B, and using expertise and knowledge in the art, readily determine whether the XRPD pattern of the sample is substantially in accordance with the XRPD pattern of crystalline (R)-amisulpride of Form A presented in FIG. 11B. If, for example, HPLC identifies the sample as being (R)-amisulpride and the sample XRPD pattern is substantially in accord with FIG. 11B, the sample can be readily and accurately identified as (R)-amisulpride of Form A.

In various embodiments, the crystal forms of racemic amisulpride, enantiomeric amisulpride, and enantiomeric amisulpride solvates are characterized by melting point. Melting points were determined by conventional methods such as capillary tube and may exhibit a range over which complete melting occurs, or in the case of a single number, a melt point of that temperature ±1° C.

In various embodiments, the crystal forms of racemic amisulpride, enantiomeric amisulpride, and enantiomeric amisulpride solvates are characterized by differential scanning calorimetry (DSC). DSC is a thermoanalytical technique in which the difference in the amount of heat required to increase the temperature of a sample and a reference is measured as a function of temperature. Both the sample and reference are maintained at substantially the same temperature throughout the experiment. The result of a DSC experiment is a curve of heat flow versus temperature, called a DSC thermogram.

In various embodiments, the hygroscopicity of crystal forms of racemic amisulpride, enantiomeric amisulpride, and enantiomeric amisulpride solvates are characterized by dynamic vapor sorption (DVS). DVS is a gravimetric technique that measures how much of a solvent is absorbed by a sample by varying the vapor concentration surrounding the sample (e.g., relative humidity) and measuring the change in mass. In the present application, DVS is used to generate water sorption isotherms, which represent the equilibrium amount of vapor sorbed as a function of steady state relative vapor pressure at a constant temperature.

As used herein, the term "substantially non-hygroscopic" refers to a compound exhibiting less than a 1% maximum mass change in water sorption isotherms, at 25° C. scanned over 0 to 95% relative humidity, as measured by dynamic vapor sorption (DVS).

In various embodiments, the compositions use new crystalline forms of enantiomeric amisulpride, Form A and Form A'. Forms A and A' have been found to be a distinct polymorph, different from the crystalline form of a racemic amisulpride, having a distinctly different structure and XRPD pattern, as well as physical properties. Table 42 compares various properties and data on Form A crystals of (R)-amisulpride and Form A' crystals of (S)-amisulpride where the Figure (FIG.) references are to figures in the present application. The Specific Rotation data was obtained by polarimetry, the compound was dissolved in methanol at nominal concentration of c=1 using the 589 nm (Sodium Line). It is to be understood that upon dissolution of the compound it is no longer of a crystalline form, thus one of ordinary skill in the art will understand that the specific rotation in Table 42 refers to that of the non-crystalline compound.

TABLE 42

Physical Properties of Forms A and A'

Figure 11C:
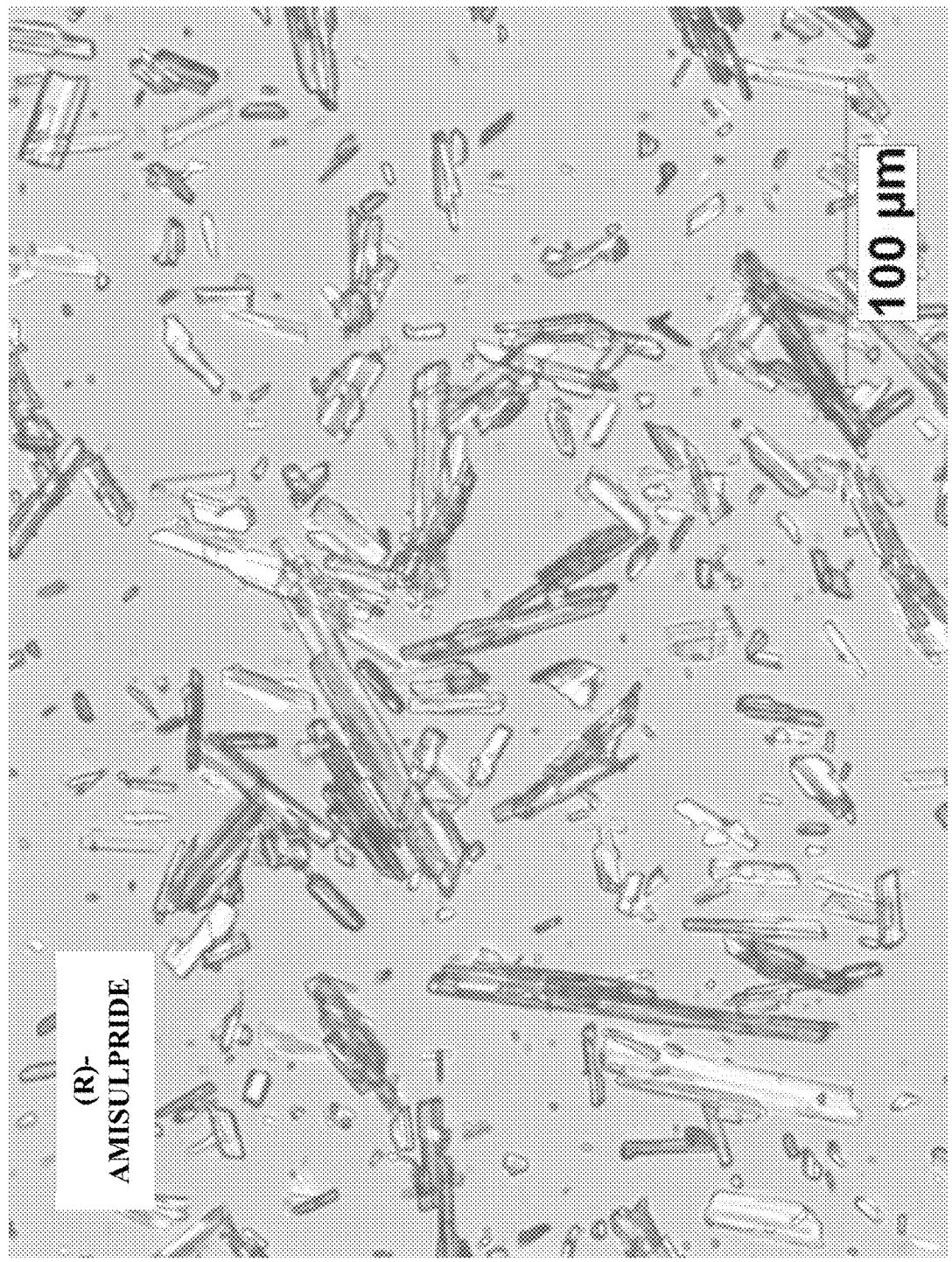
Figure 12C:
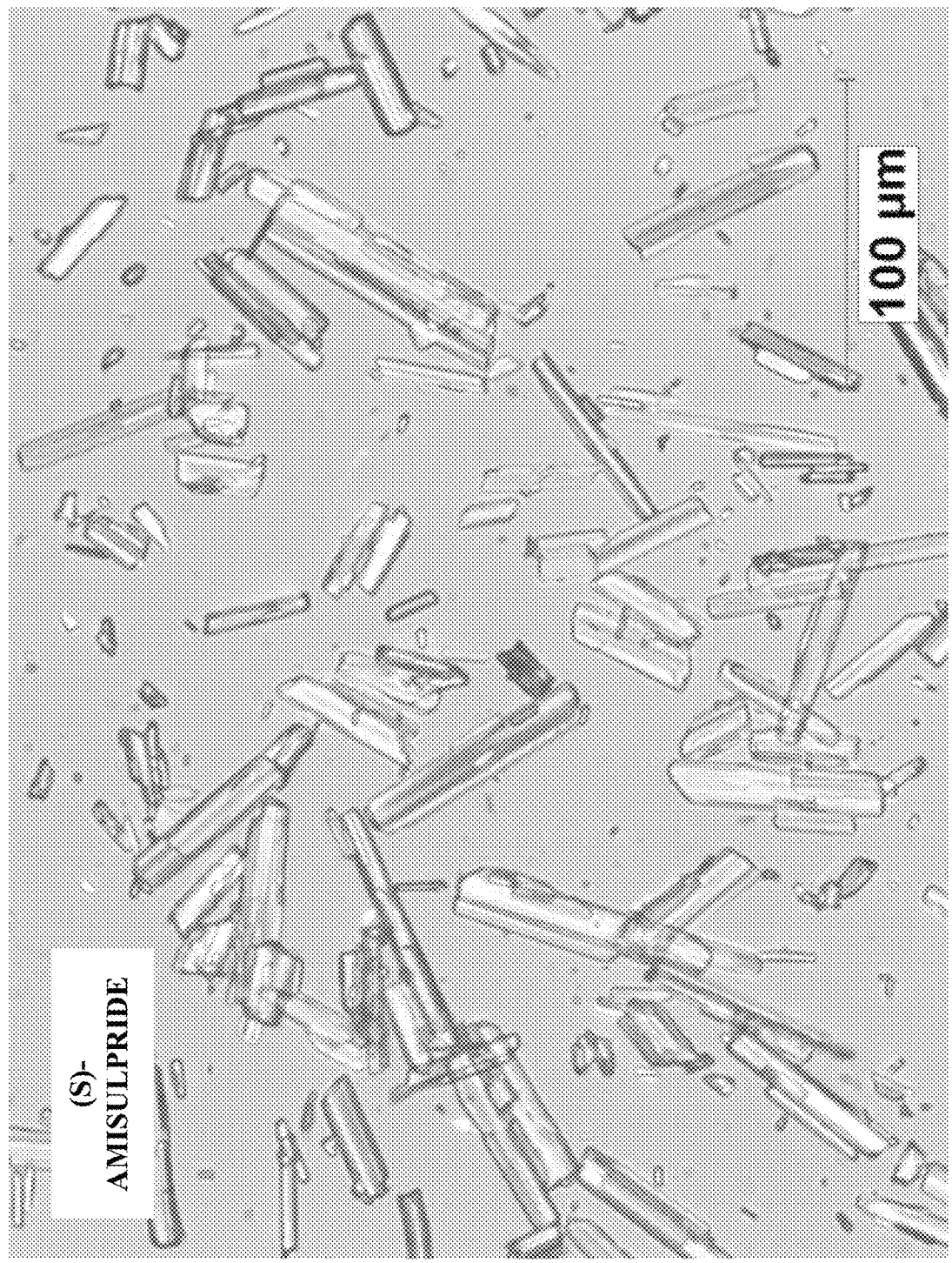

|  | (R)-amisulpride Form A | (S)-amisulpride Form A' |
|---|---|---|
| # of Solid Phases | 1 | 1 |
| Melting Point, °C | 102 | 102 |
| DSC Thermograph | FIG. 11A | FIG. 12A |
| XRPD Pattern | FIG. 11B | FIG. 12B |
| Micrograph Image | FIG. 11C | FIG. 12C |
| Specific Rotation | $[\alpha]^{20}_D = -5.0 \cdot 10^1$ (MeOH, c = 1) | $[\alpha]^{20}_D = -5.0 \cdot 10^1$ (MeOH, c = 1) |
| Solubility (mg/mL): |  |  |
| Water (solution pH) | 2 (10.2) | 2 (10.3) |

TABLE 42-continued

Physical Properties of Forms A and A'

|  | (R)-amisulpride Form A | (S)-amisulpride Form A' |
|---|---|---|
| 0.05M Acetate Buffer (solution pH) | >100 (4.5) | >100 (4.5) |
| Ethyl Acetate | 3.9 | 3.9 |
| Acetone/MtBE 1:4 | 8 | 8 |
| Acetone/MtBE 1:9 | 2 | 2 |
| Simulated Gastric Fluid (no enzyme) | >100 (pH adjusted to 1.1) | >100 (pH adjusted to 1.2) |
| Simulated Intestinal Fluid (no enzyme) | >100 (pH adjusted to 6.7) | >100 (pH adjusted to 6.9) |

In various embodiments, Form A is a crystalline form of (R)-amisulpride characterized by an XRPD pattern comprising peaks, in terms of 2-theta, at 7.0±0.2°, 9.7±0.2°, and 19.4±0.2°. In various embodiments, the crystalline form of (R)-amisulpride is characterized by three or more peaks in its XRPD pattern selected from those at 7.0±0.2°, 9.7±0.2°, 15.4±0.2°, 19.4±0.2°, 20.1±0.2°, 21.0±0.2°, 23.2±0.2°, and 29.3±0.2°, in terms of 2-theta. In various embodiments, Form A of (R)-amisulpride is characterized by an XRPD pattern substantially in accord with FIG. 11B.

In various embodiments, the crystalline Form A of (R)-amisulpride is characterized by the following properties, an XRPD pattern comprising peaks, in terms of 2-theta, at 7.0±0.2°, 9.7±0.2°, and 15.4±0.2°, a melting point of 102±3° C., a chiral purity of greater than about 99%, a chemical purity greater than about 99%, a residual solvent content of less than about 1000 ppm, and is substantially non-hygroscopic.

In various embodiments, the crystalline Form A of (R)-amisulpride is characterized by the following properties, an XRPD pattern comprising peaks, in terms of 2-theta, at 7.0±0.2°, 9.7±0.2°, and 15.4±0.2° and one or more of the following:
(a) the powder x-ray diffraction pattern further comprising peaks, in terms of 2-theta, at 19.4±0.2° and 29.3±0.2°;
(b) the powder x-ray diffraction pattern further comprising peaks, in terms of 2-theta, at 20.1±0.2°, 21.0±0.2°, and 23.2±0.2°;
(c) a melting point of 102±3° C.;
(d) a differential scanning calorimetry thermogram comprising a peak at 101±3° C.;
(e) a differential scanning calorimetry thermogram substantially in accord with FIG. 11A;
(f) a chiral purity of greater than about: (i) 90%, (ii) 95%, (iii) 97%, (iv) 99%, (v) 99.5%, (vi) 99.7%, or (vii) 99.9%;
(g) a chemical purity of greater than about: (i) 80%, (ii) 90%, (iii) 95%, (iv) 97%, (v) 99%, (vi) 99.5%, (vii) 99.7%, or (viii) 99.9%;
(h) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm; and
(i) as measured by dynamic vapor sorption (DVS), at 25° C. scanned over 0 to 95% relative humidity, a maximum mass change in water sorption isotherms of less than about (i) 2%, (ii) 1%, (iii) 0.5%, or (iv) 0.4%.

In various embodiments, the crystalline Form A' of (S)-amisulpride is characterized by an XRPD pattern comprising peaks, in terms of 2-theta, at 7.0±0.2°, 9.7±0.2°, and 19.4±0.2°. In various embodiments, the crystalline form of (S)-amisulpride is Form A' characterized by three or more peaks in its XRPD pattern selected from those at 7.0±0.2°, 9.7±0.2°, 15.4±0.2°, 19.4±0.2°, 20.1±0.2°, 21.0±0.2°, 23.2±0.2°, and 29.3±0.2°, in terms of 2-theta. In various embodiments, Form A' of (S)-amisulpride is characterized by an XRPD pattern substantially in accord with FIG. 12B.

In various embodiments, the crystalline Form A' of (S)-amisulpride is characterized by the following properties, an XRPD pattern comprising peaks, in terms of 2-theta, at 7.0±0.2°, 9.7±0.2°, and 15.4±0.2°, a melting point of 102±3° C., a chiral purity of greater than about 99%, a chemical purity greater than about 99%, a residual solvent content of less than about 1000 ppm, and is substantially non-hygroscopic.

In various embodiments, the crystalline Form A' of (S)-amisulpride is characterized by the following properties, an XRPD pattern comprising peaks, in terms of 2-theta, at 7.0±0.2°, 9.7±0.2°, and 15.4±0.2° and two or more of the following:
(a) the powder x-ray diffraction pattern further comprising peaks, in terms of 2-theta, at 19.4±0.2° and 29.3±0.2°;
(b) the powder x-ray diffraction pattern further comprising peaks, in terms of 2-theta, at 20.1±0.2°, 21.0±0.2°, and 23.2±0.2°;
(c) a melting point of 102±3° C.;
(d) a differential scanning calorimetry thermogram comprising a peak at 101±3° C.;
(e) a differential scanning calorimetry thermogram substantially in accord with FIG. 12A;
(f) a chiral purity of greater than about: (i) 90%, (ii) 95%, (iii) 97%, (iv) 99%, (v) 99.5%, (vi) 99.7%, or (vii) 99.9%;
(g) a chemical purity of greater than about: (i) 80%, (ii) 90%, (iii) 95%, (iv) 97%, (v) 99%, (vi) 99.5%, (vii) 99.7%, or (viii) 99.9%;
(h) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm; and
(i) as measured by dynamic vapor sorption (DVS), at 25° C. scanned over 0 to 95% relative humidity, a maximum mass change in water sorption isotherms of less than about (i) 2%, (ii) 1%, (iii) 0.5%, or (iv) 0.4%.

In various embodiments, crystalline enantiomeric amisulpride of Form A is characterized at least in part by having an XRPD pattern comprising peaks, in terms of 2-theta, at 7.0±0.2°, 9.7±0.2°, and 19.4±0.2° and not having a peak, in terms of 2-theta, at 6.6±0.3° that has a height greater than about 5% of the highest of the peaks at 7.0±0.2°, 9.7±0.2°, and 19.4±0.2°.

In various embodiments, crystalline enantiomeric amisulpride of Form A' is characterized at least in part by having an XRPD pattern comprising peaks, in terms of 2-theta, at 7.0±0.2°, 9.7±0.2°, and 19.4±0.2° and not having a peak, in terms of 2-theta, at 6.6±0.3° that has a height greater than about 5% of the highest of the peaks at 7.0±0.2°, 9.7±0.2°, and 19.4±0.2°.

In various embodiments, XRPD information and patterns are used to characterize Forms A and A'. FIGS. 11B and 12B XRPD patterns for, respectively, (R)-amisulpride Form A and (S)-amisulpride Form A'. Tables 43-46 present further information and details on XRPD patterns obtained for Forms A and A'.

The XRPD patterns of both (R)-amisulpride Form A (FIG. 11B) and (S)-amisulpride Form A' (FIG. 12B) show prominent peaks, in terms of 2-theta, at 7.0±0.2°, 9.7±0.2°, 15.4±0.2°, 19.4±0.2°, 20.1±0.2°, 21.0±0.2°, 23.2±0.2°, and 29.3±0.2°.

In various embodiments, Form A of (R)-(+)-amisulpride characterized by a powder x-ray diffraction pattern comprising peaks, in terms of 2-theta, at 7.0±0.2°, 9.7±0.2°, and 15.4±0.2°. In some embodiment, Form A of (R)-(+)-amisulpride is further characterized by the powder x-ray diffraction pattern further comprising peaks, in terms of 2-theta, at 9.3±0.2°, and 19.4±0.2°. In some embodiment, Form A of (R)-(+)-amisulpride is further characterized by the powder x-ray diffraction pattern further comprising peaks, in terms of 2-theta, at 14.9±0.2°, 16.9±0.2°, and 20.1±0.2°. In some embodiment, Form A of (R)-(+)-amisulpride is further characterized by the powder x-ray diffraction pattern further comprising peaks, in terms of 2-theta, at 19.0±0.2°, 21.0±0.2°, and 23.2±0.2°.

In various embodiments, Form A' of (S)-(−)-amisulpride characterized by a powder x-ray diffraction pattern comprising peaks, in terms of 2-theta, at 7.0±0.2°, 9.7±0.2°, and 15.4±0.2°. In some embodiments, Form A' of (S)-(−)-amisulpride is further characterized by the powder x-ray diffraction pattern further comprising peaks, in terms of 2-theta, at 9.3±0.2°, and 19.4±0.2°. In some embodiments, Form A' of (S)-(−)-amisulpride is further characterized by the powder x-ray diffraction pattern further comprising peaks, in terms of 2-theta, at 14.9±0.2°, 16.9±0.2°, and 20.2±0.2°. In some embodiments, Form A' of (S)-(−)-amisulpride is further characterized by the powder x-ray diffraction pattern further comprising peaks, in terms of 2-theta, at 19.1±0.2°, 21.0±0.2°, and 23.2±0.2°.

The DSC thermograms of FIGS. 11A and 12A were obtained using TA Instruments Q100 differential scanning calorimeter. Each sample was heated in a sealed pan under a 50 mL/min nitrogen purge at a heating rate of 10° C./min, from a starting temperature of 25° C. up to a final temperature of 150° C. or 200° C.

The micrograph images of FIGS. 11C and 12C were obtained using the Nikon Microphot polarizing light microscope. Samples were prepared in Isopar G/3% Lecithin, and imaged using cross-polarized light with a quarter wave plate.

The XRPD patterns of FIGS. 11B and 12B were performed using a Rigaku MiniFlex II Desktop X-Ray diffractometer using Cu radiation. The tube voltage and amperage were set to 30 kV and 15 mA, respectively. The scattering slit was fixed at 1.25° and the receiving slit was fixed at 0.3 mm. Diffracted radiation was detected by a NaI scintillation detector. A θ-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder. In FIGS. 11B and 12B, 2-Theta angles in degrees (x-axis) are plotted against peak intensity in terms of the count rate per second (y-axis).

Crystals of (R)-Amisulpride Form A

For single crystal structure determination, a colorless needle having approximate dimensions of 0.25×0.04×0.02 mm$^3$, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 16528 reflections in the range 3.5080°<θ<77.2950°. The data was collected to a maximum diffraction angle (2θ) of 155.296°, at a temperature of 100 K. A total of 35826 reflections were collected, of which 12849 were unique. Lorentz and polarization corrections were applied to the data. The linear absorption coefficient is 1.728 mm$^{-1}$ for Cu Kα radiation. An empirical absorption correction using CRYSALISPRO was applied (CrysAlisPro 1.171.38.41r (Rigaku Oxford Diffraction, 2015). Transmission coefficients ranged from 0.659 to 1.000. Intensities of equivalent reflections were averaged. The agreement factor for the averaging was 5.72% based on intensity.

Figure 29:
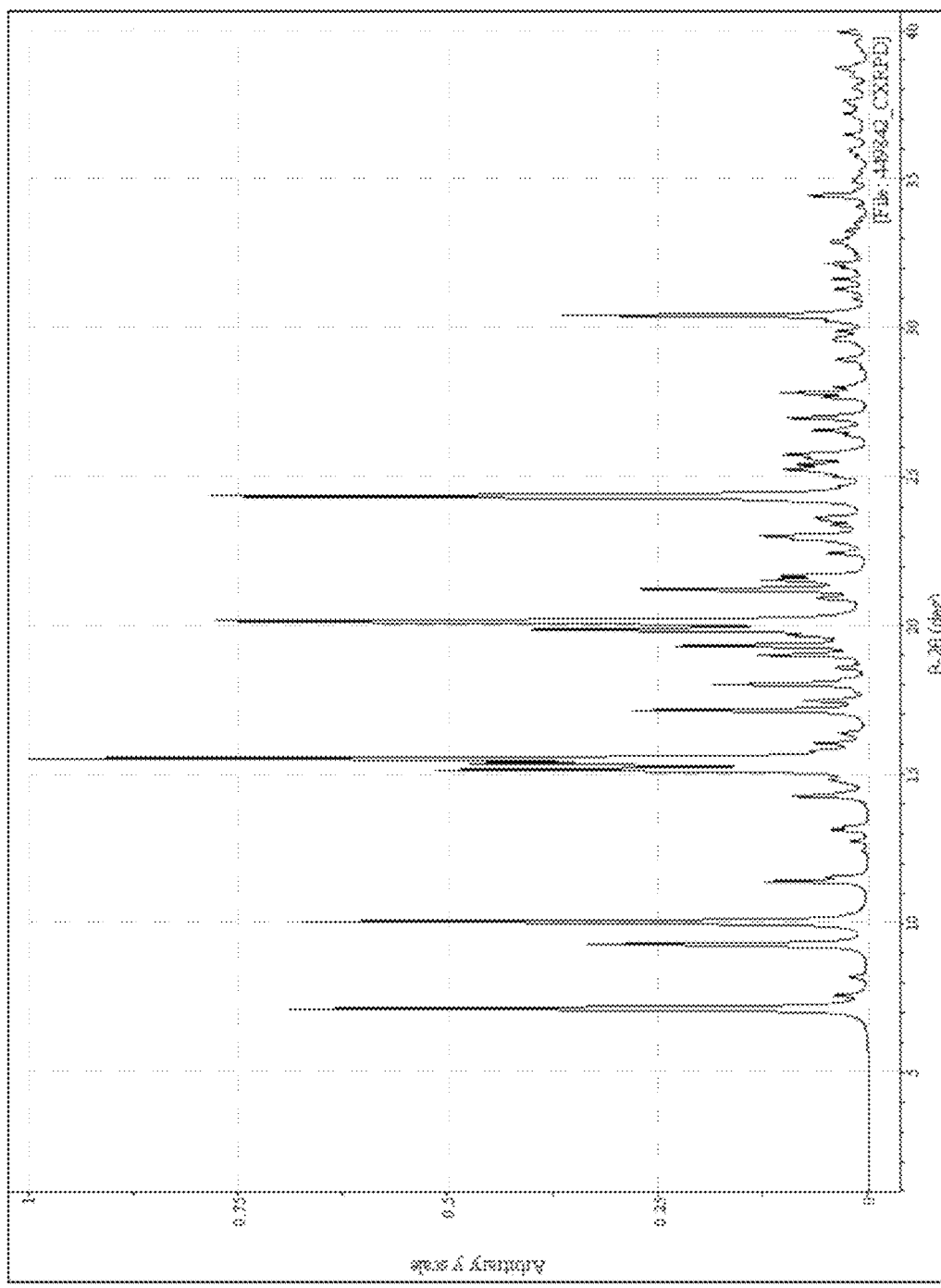
FIG. 29 presents a calculated XRPD based on single crystal structure determination for (R)-amisulpride Form A.

A calculated XRPD pattern was generated for Cu radiation using MERCURY and the atomic coordinates, space group, and unit cell parameters from the single crystal structure (Macrae, C. F. et al., J. *J. Appl. Cryst.*, 2006, 39, 453-457). It is to be understood that because the single crystal data are collected at low temperatures (100 K), peak shifts may be evident between the pattern calculated from low temperature data and room temperature experimental powder diffraction patterns, particularly at high diffraction angles. FIG. 29 shows the calculated XRPD pattern of Form A.

In various embodiments, the crystal system of (R)-amisulpride Form A crystals is triclinic and the space group is P1. Referring to FIG. 11C, by microscopy the solids consisted of birefringent spherulites of long needles. Further details of the crystal data and crystallographic data collection parameters are summarized in Table 43 and a listing of the peaks of the experimental XRPD of FIG. 11B are listed in Table 44. The calculated XRPD pattern of Form A is shown in FIG. 29.

In some embodiment, the crystalline form of (R)-(+)-amisulpride is characterized by single crystal x-ray diffraction having a P1 space group and cell formula units (Z) of 4. In some embodiments, crystalline form of (R)-(+)-amisulpride has unit cell parameters: a is about 12.3 Å, b is about 12.8 Å, c is about 14.1 Å, α is about 64.0°, β is about 73.4°, and γ is about 75.9°.

TABLE 43

(R)-amisulpride Form A Single Crystal Data and Data Collection Parameters

| | |
|---|---|
| Empirical formula | $C_{17}H_{27}N_3O_4S$ |
| Molecular weight (g mol$^{-1}$) | 369.47 |
| Temperature (K) | 100 |
| Wavelength (Å) | 1.54184 |
| Crystal system | triclinic |
| Space group | P1 |
| Unit cell parameters | |
| a = 12.3348(4) Å | α = 64.033(4)° |
| b = 12.8343(6) Å | β = 73.431(3)° |
| c = 14.1403(6) Å | γ = 75.881(3)° |
| Unit cell volume (Å$^3$) | 1910.47(15) |
| Cell formula units, Z | 4 |
| Calculated density (g cm$^{-3}$) | 1.285 |
| Absorption coefficient (mm$^{-1}$) | 1.728 |
| F(000) | 792 |
| Crystal size (mm$^3$) | 0.25 × 0.04 × 0.02 |
| Reflections used for cell measurement | 16528 |
| θ range for cell measurement | 3.5080° -77.2950° |
| Total reflections collected | 35826 |
| Index ranges | −15 ≤ h ≤ 15; −16 ≤ k ≤ 16; −17 ≤ l ≤ 17 |
| θ range for data collection | $θ_{min}$ = 3.552°, $θ_{max}$ = 77.648° |
| Completeness to $θ_{max}$ | 97.6% |
| Completeness to $θ_{full}$ = 67.684° | 99.8% |
| Absorption correction | multi-scan |
| Transmission coefficient range | 0.659-1.000 |
| Refinement method | full matrix least-squares on F$^2$ |
| Independent reflections | 12849 [$R_{int}$ = 0.0572, $R_σ$ = 0.0533] |
| Reflections [I>2σ(I)] | 11460 |
| Reflections/restraints/parameters | 12849/3/954 |
| Goodness-of-fit on F$^2$ | S = 1.02 |
| Final residuals [I > 2σ(I)] | R = 0.0607, $R_w$ = 0.1675 |
| Final residuals [all reflections] | R = 0.0658, $R_w$ = 0.1739 |
| Largest diff. peak and hole (e Å$^{-3}$) | 0.640, −0.670 |
| Max/mean shift/standard uncertainty | 0.000/0.000 |

TABLE 43-continued (R)-amisulpride Form A Single Crystal Data and Data Collection Parameters

| | |
|---|---|
| Empirical formula | $C_{17}H_{27}N_3O_4S$ |
| Absolute structure determination | Flack parameter: 0.009(18) |
| | Hooft parameter: 0.007(12) |
| | Friedel coverage: 60.2% |

TABLE 44

(R)-amisulpride Form A XRPD (FIG. 11B) Peak List

| 2-Theta | Relative Height |
|---|---|
| 7.00 | 75 |
| 7.42 | 1.6 |
| 9.34 | 26.9 |
| 9.72 | 68.3 |
| 9.95 | 1.5 |
| 11.00 | 6.7 |
| 11.66 | 1.2 |
| 12.72 | 2.3 |
| 13.26 | 11.3 |
| 13.90 | 5.2 |
| 14.41 | 4.8 |
| 14.72 | 13.5 |
| 14.90 | 31 |
| 15.40 | 100 |
| 15.94 | 4 |
| 16.64 | 7.9 |
| 16.92 | 28 |
| 17.44 | 14.8 |
| 17.70 | 4 |
| 18.66 | 7.5 |
| 19.04 | 29.3 |
| 19.42 | 87 |
| 20.12 | 63.7 |
| 20.98 | 34.8 |
| 21.62 | 3.5 |
| 21.88 | 7.8 |
| 22.32 | 3.8 |
| 22.61 | 2.5 |
| 23.22 | 89.3 |
| 24.34 | 8.1 |
| 24.80 | 8.7 |
| 25.26 | 3 |
| 25.56 | 17 |
| 25.78 | 4.3 |
| 26.20 | 3.2 |
| 26.68 | 15.8 |
| 27.10 | 11.3 |
| 28.12 | 3.5 |
| 28.28 | 2.6 |
| 28.82 | 5.2 |
| 29.26 | 42.2 |
| 29.56 | 5.9 |
| 29.76 | 3.7 |
| 30.32 | 1.9 |
| 30.92 | 1.7 |
| 31.02 | 2.6 |
| 31.70 | 4.3 |
| 31.94 | 3.8 |
| 32.26 | 2.2 |
| 32.84 | 8.9 |
| 33.22 | 2.7 |
| 34.16 | 2.7 |
| 34.55 | 2.2 |
| 34.97 | 1.7 |
| 35.24 | 1.1 |
| 35.48 | 0.9 |
| 35.76 | 2.9 |
| 37.00 | 1.9 |
| 37.44 | 1.3 |
| 38.58 | 3.2 |
| 38.88 | 3.4 |
| 39.50 | 1.6 |
| 39.76 | 2.1 |
| 40.38 | 2.5 |
| 40.80 | 3.7 |
| 41.39 | 1.4 |
| 41.68 | 1.5 |
| 42.68 | 3.7 |
| 43.28 | 2.8 |
| 43.52 | 4.7 |

Crystals of (S)-Amisulpride Form A'

For single crystal structure determination, a colorless needle having approximate dimensions of 0.20×0.04×0.02 mm³, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 14943 reflections in the range 3.5170°<θ<77.9740°. The data was collected to a maximum diffraction angle (2θ) of 156.71°, at a temperature of 100 K. A total of 36278 reflections were collected, of which 12840 were unique. Lorentz and polarization corrections were applied to the data. The linear absorption coefficient is 1.728 mm-1 for Cu Kα radiation. An empirical absorption correction using CRYSALISPRO was applied (CrysAlisPro 1.171.38.41r (Rigaku Oxford Diffraction, 2015). Transmission coefficients ranged from 0.791 to 1.000. Intensities of equivalent reflections were averaged. The agreement factor for the averaging was 5.83% based on intensity.

Figure 30:
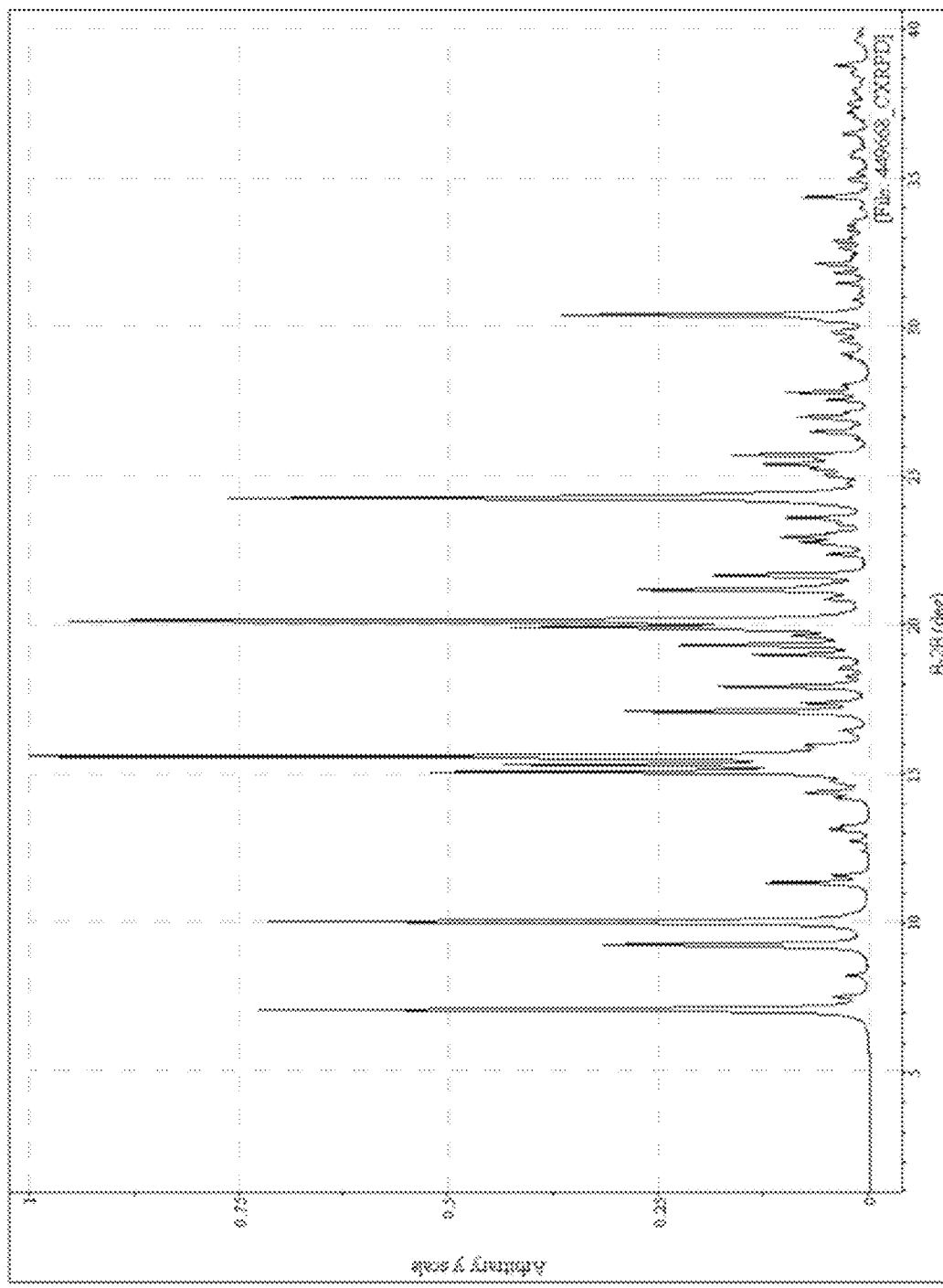
FIG. 30 presents a calculated XRPD based on single crystal structure determination for (S)-amisulpride Form A'.

A calculated XRPD pattern was generated for Cu radiation using MERCURY and the atomic coordinates, space group, and unit cell parameters from the single crystal structure (Macrae, C. F. et al., J. J. Appl. Cryst., 2006, 39, 453-457). It is to be understood that because the single crystal data are collected at low temperatures (100 K), peak shifts may be evident between the pattern calculated from low temperature data and room temperature experimental powder diffraction patterns, particularly at high diffraction angles. FIG. 30 shows the calculated XRPD pattern of Form A'.

In various embodiments, the crystal system of (S)-amisulpride Form A' crystals is triclinic and the space group is P1. Referring to FIG. 12C, by microscopy the solids consisted of birefringent spherulites of long needles. Further details of the crystal data and crystallographic data collection parameters are summarized in Table 45 and a listing of the peaks of the experimental XRPD of FIG. 12B are listed in Table 46. The calculated XRPD pattern of Form A' is shown in FIG. 30.

In some embodiments, the crystalline form of (S)-(−)-amisulpride is characterized by single crystal x-ray diffraction having a P1 space group and cell formula units (Z) of 4. In some embodiments, the crystalline form of (S)-(−)-amisulpride has unit cell parameters: α is about 12.4 Å, b is about 12.8 Å, c is about 14.1 Å, α is about 64.2°, β is about 73.6°, and γ is about 75.8°.

TABLE 45

(S)-amisulpride Form A' Single Crystal Data and Data Collection Parameters

| | |
|---|---|
| Empirical formula | $C_{17}H_{27}N_3O_4S$ |
| Formula weight (g mol$^{-1}$) | 369.47 |
| Temperature (K) | 100 |
| Wavelength (Å) | 1.54184 |
| Crystal system | triclinic |
| Space group | P1 |
| Unit cell parameters | |
| a = 12.3795(4) Å | α = 64.246(3)° |
| b = 12.7526(4) Å | β = 73.598(3)° |
| c = 14.1438(4) Å | γ = 75.797(3)° |
| Unit cell volume (Å$^3$) | 1909.71(11) |
| Cell formula units, Z | 4 |
| Calculated density (g cm$^{-3}$) | 1.285 |
| Absorption coefficient (mm$^{-1}$) | 1.728 |
| F(000) | 792 |
| Crystal size (mm$^3$) | 0.2 × 0.04 × 0.02 |
| Reflections used for cell measurement | 14943 |
| ϑ range for cell measurement | 3.5170°–77.9740° |
| Total reflections collected | 36278 |
| Index ranges | −15 ≤ h ≤ 14; −16 ≤ k ≤ 16; −17 ≤ l ≤ 17 |
| ϑ range for data collection | $ϑ_{min}$ = 3.542°, $ϑ_{max}$ = 78.355° |
| Completeness to $θ_{max}$ | 97.6% |
| Completeness to $θ_{full}$ = 67.684° | 99.9% |
| Absorption correction | multi-scan |
| Transmission coefficient range | 0.791-1.000 |
| Refinement method | full matrix least-squares on $F^2$ |
| Independent reflections | 12840 [$R_{int}$ = 0.0583, $R_σ$ = 0.0539] |
| Reflections [I>2σ(I)] | 11066 |
| Reflections/restraints/parameters | 12840/3/956 |
| Goodness-of-fit on $F^2$ | S = 1.08 |
| Final residuals [I>2σ(I)] | R = 0.0613, $R_w$ = 0.1732 |
| Final residuals [all reflections] | R = 0.0694, $R_w$ = 0.1817 |
| Largest diff. peak and hole (e Å$^{-3}$) | 0.470, −0.468 |
| Max/mean shift/standard uncertainty | 0.000/0.000 |
| Absolute structure determination | Flack parameter: 0.008(18) |
| | Hooft parameter: 0.019(12) |
| | Friedel coverage: 58.8% |

TABLE 46

(S)-amisulpride Form A' XRPD (FIG. 12B) Peak List

| 2-Theta | Relative Height |
|---|---|
| 7.02 | 100 |
| 9.34 | 28 |
| 9.74 | 62 |
| 11.05 | 5.6 |
| 13.28 | 15.2 |
| 13.94 | 7.8 |
| 14.92 | 20 |
| 15.42 | 66.2 |
| 16.90 | 23.9 |
| 17.44 | 8.9 |
| 18.68 | 7.4 |
| 19.08 | 34.2 |
| 19.44 | 74.4 |
| 20.16 | 70 |
| 21.00 | 41.2 |
| 21.9 | 12 |
| 22.36 | 3.1 |
| 23.20 | 72.1 |
| 24.34 | 5.7 |
| 24.87 | 7 |
| 25.60 | 16.9 |
| 25.84 | 6.2 |
| 26.17 | 2.3 |
| 26.70 | 14.8 |
| 27.12 | 12.1 |
| 28.12 | 5.2 |
| 29.28 | 40.4 |
| 30.36 | 2.2 |
| 31.84 | 3.8 |
| 32.30 | 2.4 |
| 32.84 | 9 |
| 33.26 | 3.7 |
| 34.17 | 2.5 |
| 34.64 | 2 |
| 35.10 | 1.8 |
| 35.84 | 2.8 |
| 36.14 | 1.6 |
| 37.00 | 1.6 |
| 37.48 | 2.1 |
| 38.60 | 4.8 |
| 38.94 | 5.2 |
| 39.52 | 1.6 |
| 39.75 | 2.1 |
| 40.38 | 4.1 |
| 40.76 | 4.2 |
| 41.48 | 1.8 |
| 42.76 | 3.6 |
| 43.50 | 5.7 |
| 44.12 | 1.1 |

In various embodiments, the crystalline Form A of (R)-amisulpride is characterized by an XRPD pattern comprising peaks, in terms of 2-theta, at two or more of 7.0±0.2°, 9.7±0.2°, and 19.4±0.2°, and a DSC thermogram having a peak at 101±3° C. In various preferred embodiments, the DSC thermogram has a single peak at 101±3° C.

In various embodiments, the a crystalline Form A of (R)-amisulpride is characterized by an XRPD pattern comprising peaks, in terms of 2-theta, at two or more of 7.0±0.2°, 9.7±0.2°, and 19.4±0.2°, and a differential scanning calorimetry thermogram substantially in accord with FIG. 11A.

In various embodiments, the crystalline Form A' of (S)-amisulpride is characterized by an XRPD pattern comprising peaks, in terms of 2-theta, at two or more of 7.0±0.2°, 9.7±0.2°, and 19.4±0.2°, and a DSC thermogram having a peak at 101±3° C. In various preferred embodiments, the DSC thermogram has a single peak at 101±3° C.

In various embodiments, the crystalline Form A' of (S)-amisulpride is characterized by an XRPD pattern comprising peaks, in terms of 2-theta, at two or more of 7.0±0.2°, 9.7±0.2°, and 19.4±0.2°, and a differential scanning calorimetry thermogram substantially in accord with FIG. 12A.

In various embodiments, the crystalline Forms A and A' of enantiomeric amisulpride is substantially non-hygroscopic. In various embodiments, crystalline (R)-amisulpride of Form A has a maximum mass change of less than about 2%, less than about 1%, or less than about 0.5%, in water sorption isotherms as measured by dynamic vapor sorption (DVS), at 25° C. scanned over 0 to 95% relative humidity. In various embodiments, crystalline (S)-amisulpride of Form A' has a maximum mass change of less than about 2%, less than about 1%, or less than about 0.5%, in water sorption isotherms as measured by dynamic vapor sorption (DVS), at 25° C. scanned over 0 to 95% relative humidity.

Figure 12D:
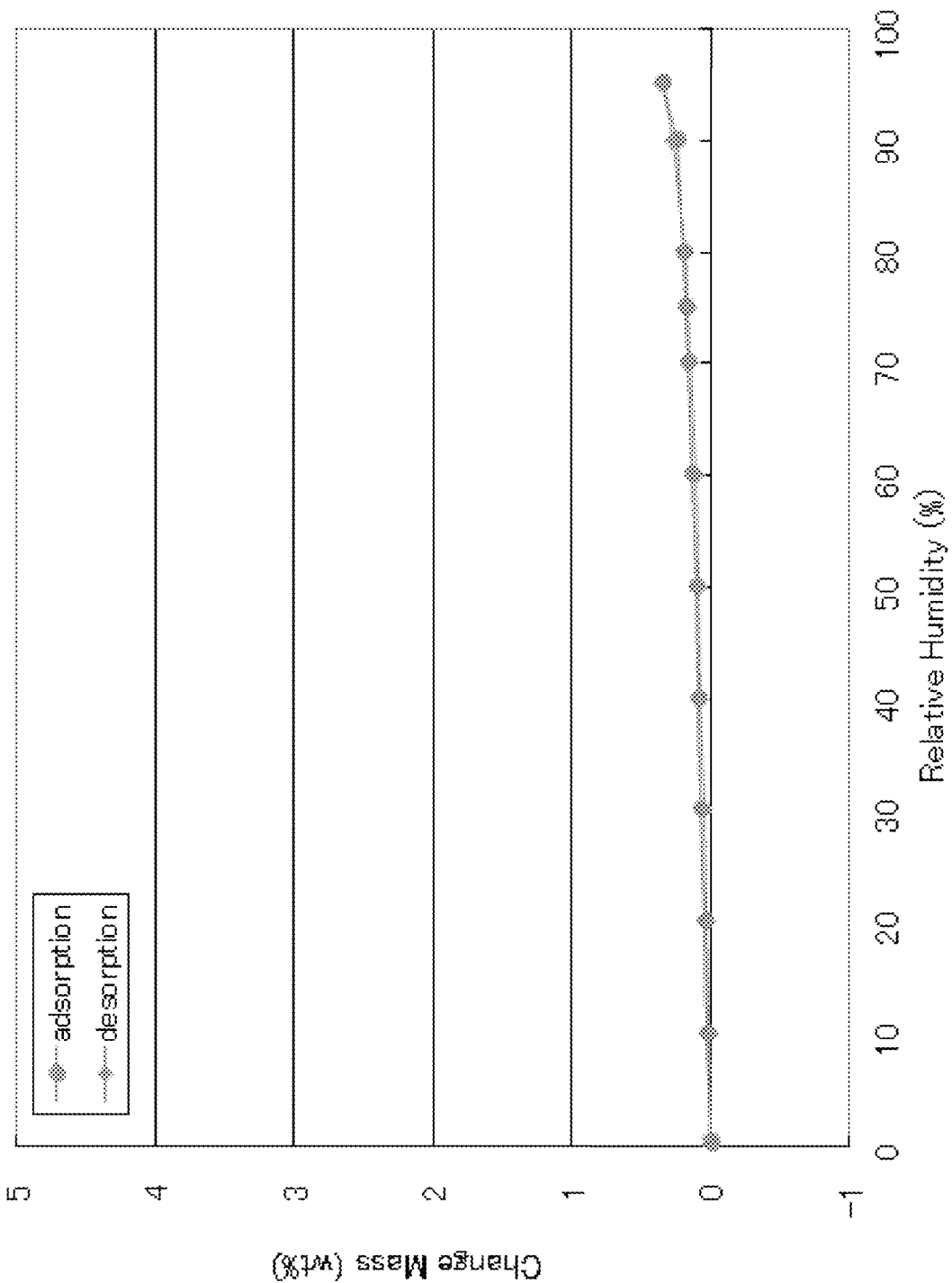

FIG. 12D shows a DVS water sorption isotherm for 19.077 mg of (S)-amisulpride crystal Form A' and Table 47 lists the data plotted in FIG. 12D. As can be seen, crystalline (S)-amisulpride Form A' is substantially non-hygroscopic, exhibiting a maximum mass change of only 0.35%.

TABLE 47

(S)-amisulpride Form A' DVS Water Sorption Isotherm of FIG. 12D

| Relative Humidity % | Change Mass (wt %) | Time/step (min) |
|---|---|---|
| 0 | 0.00 | 60.72 |
| 10 | 0.03 | 33.25 |
| 20 | 0.05 | 31.89 |
| 30 | 0.07 | 32.20 |
| 40 | 0.09 | 31.53 |
| 50 | 0.11 | 31.95 |
| 60 | 0.13 | 31.87 |
| 70 | 0.16 | 31.10 |
| 75 | 0.18 | 31.28 |
| 80 | 0.19 | 31.43 |
| 90 | 0.25 | 31.97 |
| 95 | 0.34 | 32.77 |
| 95 | 0.35 | 36.47 |
| 90 | 0.28 | 31.35 |
| 80 | 0.17 | 32.11 |
| 75 | 0.16 | 31.01 |
| 70 | 0.14 | 31.50 |
| 60 | 0.11 | 32.10 |
| 50 | 0.08 | 32.12 |
| 40 | 0.07 | 31.41 |
| 30 | 0.05 | 62.67 |
| 20 | 0.03 | 32.05 |
| 10 | 0.01 | 31.00 |
| 1 | −0.01 | 32.02 |

In various aspects, provided are methods of making enantiomeric amisulpride crystalline polymorphs of Form A and Form A'. Various embodiments of the methods described below produce novel crystal forms and various embodiments of these methods are in themselves novel.

As used in the context of the methods of the present inventions, the term "Form A" or "Form A'" refers to a method that produces a crystalline form of enantiomeric amisulpride having a powder x-ray crystal pattern comprising peaks, in terms of 2-theta, at least at 7.0±0.2°, 9.7±0.2°, and one or more peaks at 15.4±0.2° and/or 19.4±0.2°; and preferably with additional peaks, in terms of 2-theta, at two or more of: 15.4±0.2°, 19.4±0.2°, 20.1±0.2°, 21.0±0.2°, 23.2±0.2°, and 29.3±0.2°; and in various preferred embodiments an powder x-ray crystal pattern substantially in accord with FIG. 11B, in the case of (R)-amisulpride, and FIG. 12B in the case of (S)-amisulpride.

Producing high yields of a specific crystalline form, and thus high purity of that crystalline form, is often limited by the formation of amorphous products and other crystalline forms that may, for example, be kinetically favored. It has been discovered through experimentation that making crystalline enantiomeric amisulpride is complicated by the fact that traditional methods result in non-crystalline (amorphous) enantiomeric amisulpride, including methods that produce crystalline racemic amisulpride.

It has been discovered that formation of certain enantiomeric amisulpride solvates as intermediates followed by conversion to the free base allows for isolation of a crystalline form of enantiomeric amisulpride (having a powder x-ray crystal pattern comprising peaks, in terms of 2-theta, at least at 7.0±0.2°, 9.7±0.2°, and one or more peaks at 15.4±0.2° and/or 19.4±0.2°) that is greater than 90% by weight, greater than 95% by weight, greater than 97% by weight, greater than 99% by weight; or greater than 99.5% by weight of the enantiomeric amisulpride starting material.

In various embodiments, methods of making crystalline enantiomeric amisulpride, characterized by an XRPD pattern comprising peaks, in terms of 2-theta, at least at 7.0±0.2°, 9.7±0.2°, and one or more peaks at 15.4±0.2° and/or 19.4±0.2°, comprise: (a) providing either (R)-amisulpride or (S)-amisulpride as a starting material, where (R)-amisulpride is provided as the starting material when crystalline (R)-amisulpride is the desired product and (S)-amisulpride is provided as the starting material when crystalline (S)-amisulpride is the desired product; (b) solvating the starting material with a first solvent where the first solvent is a carbonyl containing compound having 5 carbons or less; (c) freeing the solvated starting material from the first solvent by adding a second solvent other than water to form a mixture with a starting material solubility of less than about 20 wt/wt %; and then (d) isolating the crystalline form of the starting material having a powder x-ray crystal pattern comprising peaks, in terms of 2-theta, at least at 7.0±0.2°, 9.7±0.2°, and 19.4±0.2°.

In various embodiments, the methods start with the provision of either (R)-amisulpride or (S)-amisulpride to make, respectively, crystalline (R)-amisulpride or crystalline (S)-amisulpride. It is to be understood that there are many acceptable ways to separate the enantiomers of amisulpride to provide an enantiomeric starting material for the methods of the present inventions. Examples 8 and 10 provide an in situ method for making enantiomerically enriched amisulpride starting material.

It is to be understood that the enantiomeric amisulpride starting materials are not necessarily crystalline, and often are amorphous or a mixture of amorphous and crystalline form. In addition to separation of enantiomers from a racemic starting material, suitable enantiomeric starting materials for the methods of the present inventions can also be directly synthesized.

It is to be understood that the ultimate chiral purity of the crystalline form of the starting material is limited by the chiral purity of the starting material. However, in various embodiments, it has been found that the methods produce the crystalline form of the starting material that has a chiral purity that is no less than the chiral purity of the starting material. Thus, in various embodiments, the present methods of making crystalline enantiomeric amisulpride (characterized by an XRPD pattern comprising peaks, in terms of 2-theta, at least at 7.0±0.2°, 9.7±0.2°, and one or more peaks at 15.4±0.2° and/or 19.4±0.2°) provide said crystalline enantiomeric amisulpride having one or more of: a greater than about 90% chiral purity where the starting material has a greater than about 90% chiral purity; a greater than about 95% chiral purity where the starting material has a greater than about 95% chiral purity; a greater than about 97% chiral purity where the starting material has a greater than about 97% chiral purity; a greater than about 99% chiral purity where the starting material has a greater than about 99% chiral purity.

It has been unexpectedly found that by proper selection of the first solvent, an intermediate solvate can be formed that upon subsequent conversion to the free base can provide an amisulpride product where greater than 90% by weight, greater than 95% by weight, greater than 97% by weight, greater than 99% by weight; or greater than 99.5% by weight of amisulpride product is in the form of crystalline enantiomeric amisulpride of starting material, characterized by an XRPD pattern comprising peaks, in terms of 2-theta, at least at 7.0±0.2°, 9.7±0.2°, and one or more peaks at 15.4±0.2° and/or 19.4±0.2°.

The first solvent is a carbonyl containing compound having 5 carbons or less. Preferably, the first solvent has a water content of less than 3% by weight, more preferably less than 1% by weight, and more preferably less than 0.5% by weight. It has been found that excess water in the first solvent interferes with, and can even prohibit, proper crystallization. Examples of such larger carbonyl containing solvent include cyclohexanone. In various embodiments, the first solvent is an aldehyde, ketone or ester. In various embodiments, the first solvent is ethyl acetate, propyl acetate, or methyl ethyl ketone; and in various preferred embodiments the first solvent is ethyl acetate.

In various embodiments, the step of solvating includes basifying; for example, by addition of a basic aqueous solution. In various embodiments, a basic solution sufficient to raise the pH to greater than 9.5, preferably to about 10, and in various embodiments between about 9.5 and about 11, is added. In various embodiments, aqueous solutions of potassium carbonate are employed. It is to be understood that a variety of basic solutions can be used to basify including, but not limited to, potassium carbonate, sodium carbonate, sodium hydroxide, and the like.

In various embodiments, the solvating step comprises multiple separations between any aqueous phase and organic phase of the solvent system of the solvating step, as may result, for example, from basifying; the desired products being preferentially partitioned into the organic phase. In various embodiments, the aqueous/organic solvent system is heated to 30-40° C. to facilitate separation.

In various embodiments, subsequent to basifying, the organic phase is concentrated and a stoichiometric excess of the first solvent is added one or more times to facilitate complete conversion to the solvate. In addition, in various embodiments, repeated concentration and addition of the first solvent facilitates producing a concentrated solvate solution having less than about 1 wt % water, less than about 0.7 wt % water, or less than about 0.4 wt % water, as determined by Karl Fischer titration.

In various embodiments, the reaction mixture is seeded with the desired crystalline form, (for example, seeding with crystalline (S)-amisulpride of Form A' where the desired product is crystalline (S)-amisulpride of Form A') prior to addition of the second solvent. In various embodiments, the step of solvating includes formation of a slurry by, for example, seeding the reaction mixture the desired crystalline form and cooling the reaction mixture below about 40° C., in various embodiments below about 30° C., and preferably below about 20° C.

Following formation of the enantiomeric starting material solvate, (i.e., (R)-amisulpride solvate with the first solvent or a (S)-amisulpride solvate with the first solvent) the solvate is freed from the enantiomeric starting material to form the free base of the enantiomeric starting material under conditions that allow for the isolation of crystalline enantiomeric amisulpride characterized by an XRPD pattern comprising peaks, in terms of 2-theta, at least at 7.0±0.2°, 9.7±0.2°, and one or more peaks at 15.4±0.2° and/or 19.4±0.2°. In various embodiments, the reaction mixture is seeded with the desired crystalline form, (for example, seeding with crystalline (S)-amisulpride of Form A' where the desired product is crystalline (S)-amisulpride of Form A') prior to addition of the second solvent. In various embodiments, the step of freeing comprises cooling the reaction mixture to below about 40° C.

As used herein, the term "solvating" refers to the combination of (R)-amisulpride or (S)-amisulpride with a solvent.

As used herein, the terms "isolating" and "freeing" refer to separating the desired product from the environment in which it was formed or detected. For example, separation can include compositions containing at least about 50%, at least about 60%, at least about 70%, at least about 80%, at least about 90%, at least about 95%, at least about 97%, or at least about 99% by weight of the desired product.

In various embodiments, a second solvent (other than water) is added to form a mixture with a starting material solubility of less than about 20 wt/wt %; less than about 10 wt/wt %; or less than about 5 wt/wt %. One of skill in the art will understand that in various embodiments the second solvent can be considered an anti-solvent as it lowers the solubility of the mixture with respect to the desired product. It is to be understood that a variety of compounds can be used as a second solvent including, but not limited to, methyl t-butyl ether, toluene, heptane, isopropanol, and the like. In various embodiments the second solvent is methyl t-butyl ether (MtBE).

A variety of procedures can be used to isolate the desired enantiomeric crystalline form of the starting material. In various embodiments, the step of isolating comprises one or more of: (a) adding an anti-solvent; (b) cooling the mixture to below about 30° C., and in various embodiments between about 10° C. and about 20° C.; and (c) adding seed crystal of the R-enantiomer or S-enantiomer. In various embodiments, the step of isolating comprises adding an anti-solvent and/or cooling the reaction mixture. In various embodiments use is made of seed crystals of the crystalline formed desired, and seed crystals can be obtained by one of skill in the art using the teachings provided herein.

For example, Example 12 teaches methods of producing crystalline (R)-amisulpride ethyl acetate solvate. The product of these examples upon drying above about 30° C., desolvates and converts to crystals of crystalline (R)-amisulpride free base of Form A and amorphous. Similarly, for example, Example 14 teaches a method producing crystalline (S)-amisulpride ethyl acetate solvate. The product of these examples upon drying above about 30° C., desolvates and converts to crystals of crystalline (S)-amisulpride free base of Form A' and amorphous. Although the fraction of the solvate that converts to Form A or Form A' in the above examples is low, it is sufficient for obtaining seed crystals.

In various embodiments, the step of isolating the crystalline form comprises seeding the reaction mixture with the desired crystalline form, (for example, seeding with crystalline (S)-amisulpride of Form A' where the desired product is crystalline (S)-amisulpride of Form A') prior to addition of the second solvent, and, in various embodiments, a slurry is then formed by cooling the reaction mixture below about 40° C., in various embodiments below about 30° C., and preferably below about 20° C.

In various embodiments, the step of isolating comprises filtering a slurry comprising the desired crystalline form of the enantiomeric amisulpride free base, washing the solid residue with a solvent system comprising the second solvent and the first solvent, and drying the residue. In various embodiments, the wt/wt ratio of the second solvent to first solvent (second solvent:first solvent) is greater than about 1:9, and in various embodiments between about 1:9 to about 4:1. In various embodiments where the second solvent is MtBE and the first solvent ethyl acetate, the MtBe:ethyl acetate ratio is preferably about 3:1.

In various embodiments, the methods of the present inventions for making crystalline enantiomeric amisulpride, characterized by an XRPD pattern comprising peaks, in terms of 2-theta, at least at 7.0±0.2°, 9.7±0.2°, and one or more peaks at 15.4±0.2° and/or 19.4±0.2°, comprise recrystallization. In the Examples, example methods that do not show a recrystallization step are noted as forming a "crude freebase," however it is to be understood that this nomenclature is used only for distinguishing the examples.

Recrystallization can be performed by a variety of techniques. In various embodiments, a step of recrystallization comprises (a) dissolving the crystalline enantiomeric amisulpride material in a solvent/anti-solvent solution; (b) cooling the solution comprising the starting material and the solvent/anti-solvent solution; and (c) adding a seed crystal of the R or S enantiomeric amisulpride material. In various embodiments the step of dissolving includes heating of the solution, to a temperature greater than 40° C. and below about 70° C., and preferably between about 50° C. and about 65° C., and preferably about 60° C.

A variety of solvent/anti-solvent systems can be used. For example, in various embodiments the solvent is acetone and the anti-solvent is methyl t-butyl ether. In various embodiments, the solvent is isopropanol (IPA) and the anti-solvent is heptane. As understood by those of skill in the art, care must be taken in selection of the solvent/anti-solvent system. For example, the inventors have found that in the IPA/heptane system a second liquid phase can form before seeding if the heptane to IPA ratio is greater than 1:1, that if a large excess of IPA is added the seeds will dissolve then crystallize upon addition of heptane antisolvent and cooling, and that a preferred IPA:heptane:product ratio is 36:32:32.

Non-limiting examples of various embodiments of making crystalline enantiomeric amisulpride of Forms A and A', or characterized by an XRPD pattern comprising peaks, in terms of 2-theta, at least at 7.0±0.2°, 9.7±0.2°, and one or more peaks at 15.4±0.2° and/or 19.4±0.2°, are further illustrated and described in Examples 8, 9, 10 and 11.

Aspects, embodiments, and features of the preparation and characterization of crystal forms of enantiomeric amisulpride may be further understood from the following examples, which should not be construed as limiting the scope of the present inventions.

Crystal Forms of Enantiomeric Amisulpride Examples

It is to be understood that the enantiomeric amisulpride starting materials are not necessarily crystalline, and often are amorphous or a mixture of amorphous and crystalline form. In addition to separation of enantiomers from a racemic starting material, suitable enantiomeric starting materials can also be directly synthesized.

Example 8: Synthesis of R-4-Amino-N-[(1-ethyl-2-pyrrolidinyl)methyl]-5-(ethylsulfonyl)-2-methoxybenzamide (Crude Freebase)

150 g of 4-amino-5-(ethylsulfonyl)-2-methoxybenzoic acid and 2000 g of acetone were placed in a flask. The solution was cooled to −9° C., and 74.3 mL of ethyl chloroformate was added to the flask. Then 88.9 mL of 4-methyl morpholine was added over 1 hour. 81.4 g of (R)-(1-ethylpyrrolidin-2-yl)methanamine was added and the mixture stirred for 16 h. The reaction was then concentrated and 800 g of water and 300 g of ethyl acetate were added. The mixture was agitated and the organic layer removed, which contained the R-4-Amino-N-[(1-ethyl-2-pyrrolidinyl)methyl]-5-(ethylsulfonyl)-2-methoxybenzamide starting material. The solution containing the starting material was basified by the addition of aqueous 20 wt % potassium carbonate and 2.5 L of ethyl acetate was added. The aqueous layer was removed. The organic layer was washed twice with water and concentrated to dryness. Then 800 g of ethyl acetate was added and the mixture was concentrated. This was repeated once. The resulting oil was dissolved into 800 g of ethyl acetate and concentrated to 600 mL. The solution was stirred at 30° C. and a slurry formed. The resulting slurry was cooled to 20° C. and agitated. 600 g of methyl t-butyl ether was added and the mixture stirred. The slurry was then filtered, washed with 3:1 wt/wt methyl t-butyl ether:ethyl acetate and dried. 165 g of R-4-Amino-N-[(1-ethyl-2-pyrrolidinyl)methyl]-5-(ethylsulfonyl)-2-methoxybenzamide was obtained as a crystalline solid.

Example 9: Recrystallization of R-4-Amino-N-[(1-ethyl-2-pyrrolidinyl)methyl]-5-(ethylsulfonyl)-2-methoxybenzamide (Freebase Crystal Form A)

603.05 g of R-4-Amino-N-[(1-ethyl-2-pyrrolidinyl)methyl]-5-(ethylsulfonyl)-2-methoxybenzamide (prepared substantially according to Example 8) and 500.3 g of isopropanol were added to a flask with a stir bar and stopper. The flask was heated to 40° C. to form a solution. The solution was then polish filtered and transferred to a reactor at 40° C. with agitator, nitrogen line, thermocouple and cooling water, using 122.81 g of isopropanol to rinse the flask and polish filter. 603.2 g of heptane was added and the solution was agitated. The reactor was cooled to a jacket temperature of 35° C. and 6.91 g of isopropanol was added to the reactor drop wise to create a clear solution. The solution was agitated and then seeded with 972 mg of R-4-Amino-N-[(1-ethyl-2-pyrrolidinyl)methyl]-5-(ethylsulfonyl)-2-methoxybenzamide (Form A) and then agitated. The reactor was then cooled to 20° C. and then agitated. 1889.24 g of heptane was added using an external pump. Following agitation, the slurry was filtered, washed with 15:85 wt/wt isopropanol:heptane and dried. 531.7 g of R-4-Amino-N-[(1-ethyl-2-pyrrolidinyl)methyl]-5-(ethylsulfonyl)-2-methoxybenzamide of crystal Form A, having greater than 97% chiral purity, and greater than 99% chemical purity, was obtained, representing a yield of about 88%.

Figure 13:
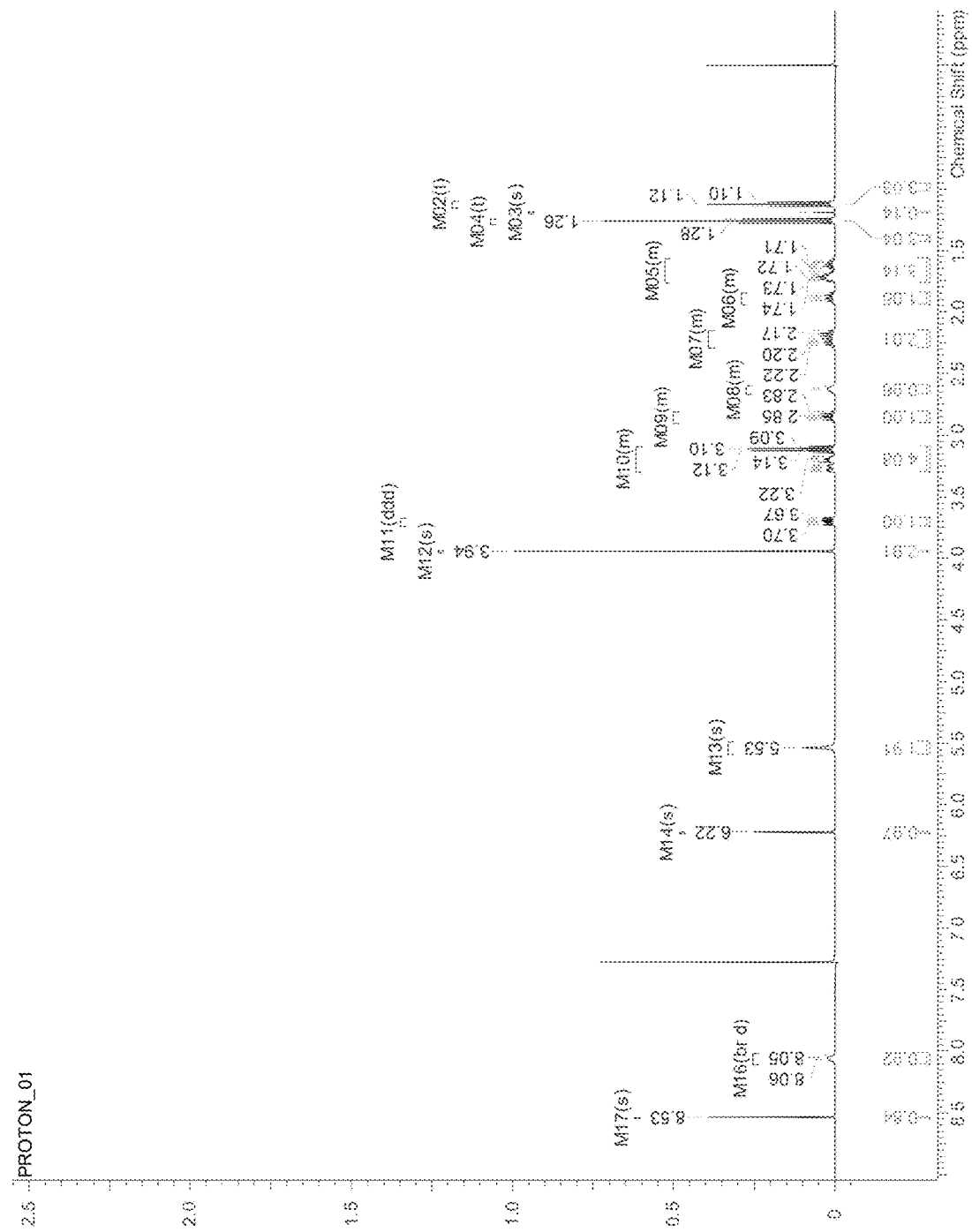
FIG. 13 is an NMR spectrum of an R-4-Amino-N-[(1-ethyl-2-pyrrolidinyl)methyl]-5-(ethylsulfonyl)-2-methoxybenzamide freebase of crystal Form A'.

An NMR spectrum of the R-4-Amino-N-[(1-ethyl-2-pyrrolidinyl)methyl]-5-(ethylsulfonyl)-2-methoxybenzamide obtained in Example 9 is illustrated in FIG. 13, having the following characteristics: $^1$H NMR (400 MHz, CHLOROFORM-d) δ ppm 1.12 (t, J=7.24 Hz, 3H) 1.26 (t, J=7.43 Hz, 3H) 1.56-1.76 (m, 3H) 1.84-1.94 (m, 1H) 2.15-2.29 (m, 2H) 2.59-2.66 (m, 1H) 2.81-2.90 (m, 1H) 3.08-3.29 (m, 4H) 3.70 (ddd, J=13.69, 7.24, 2.93 Hz, 1H) 3.94 (s, 3H) 5.53 (s, 2H) 6.22 (s, 1H) 8.06 (br d, J=4.70 Hz, 1H) 8.53 (s, 1H).

Referring to FIGS. 11A-11C, FIGS. 11A-11C present data on the R-4-Amino-N-[(1-ethyl-2-pyrrolidinyl)methyl]-5-(ethylsulfonyl)-2-methoxybenzamide, (R)-amisulpride, of crystal Form A obtained in Example 9. FIG. 11A is a DSC thermogram for crystal Form A of (R)-amisulpride obtained in Example 9; FIG. 11B a XRPD pattern for crystal Form A of (R)-amisulpride obtained in Example 9; and FIG. 11C a micrograph image crystals of crystal Form A of the (R)-amisulpride obtained in Example 8.

Example 10: Synthesis of S-4-Amino-N-[(1-ethyl-2-pyrrolidinyl)methyl]-5-(ethylsulfonyl)-2-methoxybenzamide (Crude Freebase)

153 g of 4-amino-5-(ethylsulfonyl)-2-methoxybenzoic acid and 789 g of acetone were placed in a flask fitted with a stir bar, a thermocouple and a nitrogen line. The solution was cooled to −8° C., and then 70.4 g of ethyl chloroformate was added to the flask. An addition funnel was fitted to the flask and 79.3 g of 4-methyl morpholine was added drop wise, maintaining the temperature below 0° C. The mixture was agitated at −8° C. and then 55 g of (S)-(1-ethylpyrrolidin-2-yl)methanamine was added drop wise. The mixture was agitated at 0° C. for 1 hour, warmed to ambient temperature and then further agitated at ambient temperature to provide S-4-Amino-N-[(1-ethyl-2-pyrrolidinyl)methyl]-5-(ethylsulfonyl)-2-methoxybenzamide starting material. The reaction was then concentrated to minimum volume and 822 g of water, followed by 311 g of ethyl acetate, was added. The mixture was agitated and the organic layer removed. The solution was heated to 35° ° C. and 755 g of ethyl acetate and 326 g of 40 wt % potassium carbonate (aq) were added. The mixture was agitated, the phases allowed to separate, and the aqueous layer removed. Then 296 g of water of water was added, the mixture agitated, the phases allowed to separate and the aqueous layer removed. 302 g of water was added, the mixture agitated, the phases allowed to separate and the aqueous layer removed. The organic layer was transferred to a flask with a mechanical stirrer, a thermocouple and a nitrogen line. The organic layer was concentrated to dryness and 531 g of ethyl acetate was added. After agitation, the solution was concentrated to 400 mL. Then 305 g of ethyl acetate was added and the solution was concentrated to 400 mL and was 0.35 wt % water by Karl Fischer titration. The solution was then cooled to 30° C. and seeded with 300 mg of S-4-Amino-N-[(1-ethyl-2-pyrrolidinyl)methyl]-5-(ethylsulfonyl)-2-methoxybenzamide and a slurry formed. The solution was then cooled to 20° C. and agitated, and 495 g of methyl t-butyl ether was added. The slurry was then filtered, washed with 3:1 wt/wt methyl t-butyl ether:ethyl acetate and dried. 160.7 g of S-4-Amino-N-[(1-ethyl-2-pyrrolidinyl)methyl]-5-(ethylsulfonyl)-2-methoxybenzamide was obtained as a crystalline solid, representing a yield of about 74%.

Example 11: Recrystallization of: S-4-Amino-N-[(1-ethyl-2-pyrrolidinyl)methyl]-5-(ethylsulfonyl)-2-methoxybenzamide (Freebase Crystal Form A')

300.19 g of S-4-Amino-N-[(1-ethyl-2-pyrrolidinyl)methyl]-5-(ethylsulfonyl)-2-methoxybenzamide (prepared substantially according to Example 10) and 240.2 g of isopropanol were added to a flask with a stir bar and stopper. The flask was heated to 40° C. to form a solution. The solution was then polish filtered and transferred to a reactor at 40° C. with agitator, nitrogen line, thermocouple and cooling water, using 59.8 g of isopropanol to rinse the flask and polish filter. 300.4 g of heptane was added and the solution agitated. The reactor was cooled to a jacket temperature of 35° C. and 6.91 g of isopropanol was added to the reactor drop wise to create a clear solution. The solution was agitated and then seeded with 602 mg of S-4-Amino-N-[(1-ethyl-2-pyrrolidinyl)methyl]-5-(ethylsulfonyl)-2-methoxybenzamide (Form A') and then agitated. The reactor was then cooled to 20° C. and agitated. 1399.86 g of heptane was added using an external pump. Following agitation, the slurry was filtered, washed with 15:85 isopropanol:heptane and dried. 281.03 g of S-4-Amino-N-[(1-ethyl-2-pyrrolidinyl)methyl]-5-(ethylsulfonyl)-2-methoxybenzamide of crystal Form A' having greater than 97% chiral purity, and greater than 98% chemical purity, was obtained, representing a yield of about 91%.

Figure 14:
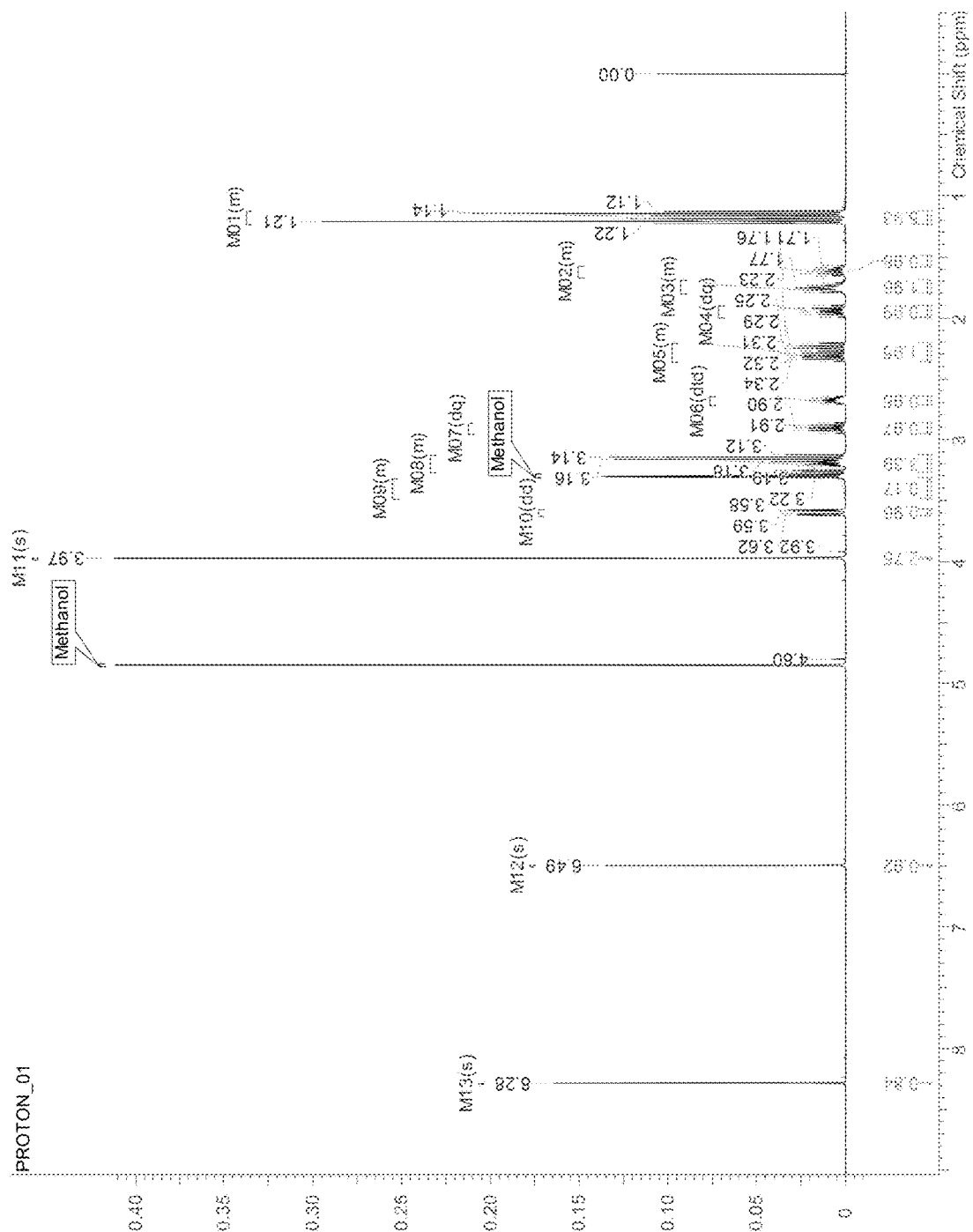
FIG. 14 is an NMR spectrum of an S-4-Amino-N-[(1-ethyl-2-pyrrolidinyl)methyl]-5-(ethylsulfonyl)-2-methoxybenzamide freebase of crystal Form A'.

An NMR spectrum of the S-4-Amino-N-[(1-ethyl-2-pyrrolidinyl)methyl]-5-(ethylsulfonyl)-2-methoxybenzamide obtained in Example 11 is illustrated in FIG. 14, having the following characteristics: $^1$H NMR (400 MHz, METHANOL-$d_4$) δ ppm 1.12-1.23 (m, 6H) 1.57-1.66 (m, 1H) 1.68-1.80 (m, 2H) 1.95 (dq, J=12.18, 8.33 Hz, 1H) 2.20-2.36 (m, 2H) 2.68 (dtd, J=8.61, 6.26, 6.26, 3.91 Hz, 1H) 2.91 (dq, J=12.08, 7.32 Hz, 1H) 3.12-3.27 (m, 3H) 3.32-3.48 (m, 1H) 3.60 (dd, J=13.30, 3.91 Hz, 1H) 3.97 (s, 3H) 6.49 (s, 1H) 8.28 (s, 1H).

Referring to FIGS. 12A-12C, FIGS. 12A-12C present data on the S-4-Amino-N-[(1-ethyl-2-pyrrolidinyl)methyl]-5-(ethylsulfonyl)-2-methoxybenzamide, (S)-amisulpride, of crystal Form A' obtained in Example 11. FIG. 12A is a DSC thermogram for crystal Form A' of (S)-amisulpride obtained in Example 11; FIG. 12B a XRPD pattern for crystal Form A' of (S)-amisulpride obtained in Example 11; and FIG. 12C a micrograph image showing crystals of crystal Form A' of the (S)-amisulpride obtained in Example 11.

Example 12: General Overview of Preparation of R-4-Amino-N-[(1-ethyl-2-pyrrolidinyl)methyl]-5-(ethylsulfonyl)-2-methoxybenzamide In overview, R-4-Amino-N-[(1-ethyl-2-pyrrolidinyl)methyl]-5-(ethylsulfonyl)-2-methoxybenzamide of Form A can be prepared in two steps: Step 1 Preparation of Crude (R)-amisulpride; and Step 2 Recrystallization of the Crude (R)-amisulpride to crystalline (R)-amisulpride of Form A.

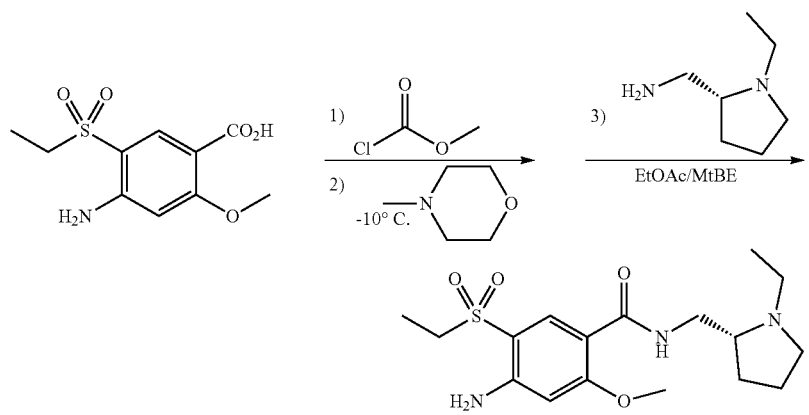

Step 1, Examples 12 and 13

Step 1 in general comprises mixing 4-Amino-5-(ethylsulfonyl)-2-methoxybenzoic acid with ethyl chloroformate and then reacting with (R)-(1-ethyl pyrrolidin-2-yl)methanamine to form R-4-Amino-N-[(1-ethyl-2-pyrrolidinyl)methyl]-5-(ethylsulfonyl)-2-methoxybenzamide hydrochloride. Other coupling reagents such as methyl, isopropyl and isobutyl chloroformates and dimethoxytriazinechloride are also suitable for carrying out the coupling reaction. The resulting product is extracted into water and washed with ethyl acetate. The R-4-Amino-N-[(1-ethyl-2-pyrrolidinyl)methyl]-5-(ethylsulfonyl)-2-methoxybenzamide hydrochloride is converted to freebase, dissolved into ethyl acetate and washed with base and water. The ethyl acetate solution is then dried and concentrated. The ethyl acetate solvate of R-4-Amino-N-[(1-ethyl-2-pyrrolidinyl)methyl]-5-(ethylsulfonyl)-2-methoxybenzamide crystallizes and is converted to R-4-Amino-N-[(1-ethyl-2-pyrrolidinyl)methyl]-5-(ethylsulfonyl)-2-methoxybenzamide (crude freebase) by the addition of methyl-tert butyl ether. The R-4-Amino-N-[(1-ethyl-2-pyrrolidinyl)methyl]-5-(ethylsulfonyl)-2-methoxybenzamide (crude freebase) is then isolated by filtration.

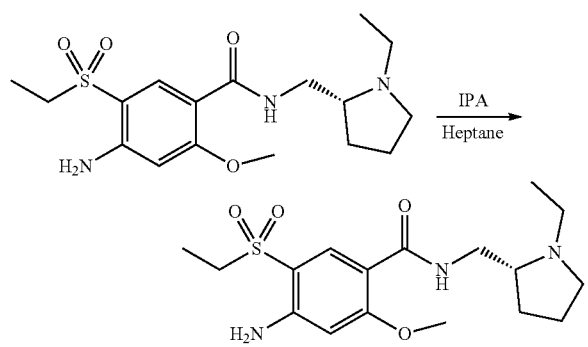

Step 2, Examples 12 and 13

Step 2 in general comprises dissolving the R-4-Amino-N-[(1-ethyl-2-pyrrolidinyl)methyl]-5-(ethylsulfonyl)-2-methoxybenzamide (crude freebase) of Step 1 into isopropanol and polish filtering. The isopropanol solution is concentrated, diluted with n-heptane and seeded with Form A to yield R-4-Amino-N-[(1-ethyl-2-pyrrolidinyl)methyl]-5-(ethylsulfonyl)-2-methoxybenzamide freebase crystals. The mixture is then cooled and filtered to yield crystalline R-4-Amino-N-[(1-ethyl-2-pyrrolidinyl)methyl]-5-(ethylsulfonyl)-2-methoxybenzamide substantially of Form A.

It is to be understood that during the crystallization of R-4-Amino-N-[(1-ethyl-2-pyrrolidinyl)methyl]-5-(ethylsulfonyl)-2-methoxybenzamide (crude freebase) the amount of water in the ethyl acetate solvent affects the crystallization and is preferably less than 0.5%. Accordingly the water content is preferably monitored during the distillation of the ethyl acetate solution, such as for example by coulometric titration (Karl Fischer). For example, in various embodiments coulometric titration (Karl Fischer) was performed by non-aqueous, perchloric acid titration where approximately 300 mg of sample, accurately weighed, was dissolved in about 50 mL of glacial acetic acid and titrated with 0.1 N perchloric acid and the end-point determined potentiometrically. The weight of sample was corrected for water content and residual solvent content prior to assay calculation. The drying of the isolated solid is also preferably monitored. In various embodiments, the reaction of Step 1 is considered complete when the amount of 4-amino-5-(ethylsulfonyl)-2-methoxybenzoic acid in the reaction mixture is less than or equal to 10 A % (where A % refers to Area % by HPLC) and/or when the amount of 4-amino-5-(ethylsulfonyl)-2-methoxybenzoic acid in the reaction mixture is less than or equal to 10 mol %.

Example 13: Detailed Overview of Preparation of R-4-Amino-N-[(1-ethyl-2-pyrrolidinyl)methyl]-5-(ethylsulfonyl)-2-methoxybenzamide of Form A Step 1: To a mixture of 4-amino-5-(ethylsulfonyl)-2-methoxybenzoic acid in acetone at −10° C. and ethyl chloroformate, 4-methylmorpholine is added at a rate (exothermic) so as to maintain the internal temperature below −5° C. The reaction is stirred for 1 hour at −10° C. and then (R)-(1-ethyl pyrrolidin-2-yl)methanamine is added. After stirring for 2 hours the reaction mixture is concentrated and diluted with water and ethyl acetate. The ethyl acetate layer is removed and the aqueous layer is basified with potassium carbonate. Ethyl acetate is added and the aqueous layer removed. The organic layer is washed with water twice and concentrated. The mixture is diluted with ethyl acetate and concentrated until water content of the ethyl acetate solution is below 0.5%. The solution is seeded at 31° C. with 1 wt % Form A and stirred at the nucleation temperature for 2 h. The mixture is cooled to 20° C. and stirred for 1 h. The slurry is diluted with methyl tert butylether (MtBE) and stirred for 2 h at 20 C. The suspension is filtered and the product cake is washed with MtBE/ethyl acetate. The wet-cake is dried under vacuum at 40° C. 5° C. to constant weight to yield R-4-Amino-N-[(1-ethyl-2-pyrrolidinyl)methyl]-5-(ethylsulfonyl)-2-methoxybenzamide (crude).

Step 2: Isopropanol and R-4-Amino-N-[(1-ethyl-2-pyrrolidinyl)methyl]-5-(ethylsulfonyl)-2-methoxybenzamide (crude) are mixed together. The mixture is heated to 50° C. to achieve dissolution and then passed through a filter. The filtrate is concentrated and cooled to 40° C. n-Heptane is added and the resulting solution is cooled to 28° C. and seeded with Form A. The resulting slurry is cooled to 23° C. and stirred for 1.5 h at this temperature. More n-heptane is added and the slurry is stirred at 22° C. for 13 h. The suspension is filtered and the product cake is washed with isopropanol/N-heptane. The wet-cake is dried under vacuum at 40° C. 5° C. to constant weight to yield R-4-Amino-N-[(1-ethyl-2-pyrrolidinyl)methyl]-5-(ethylsulfonyl)-2-methoxybenzamide of Form A.

Figure 15A:
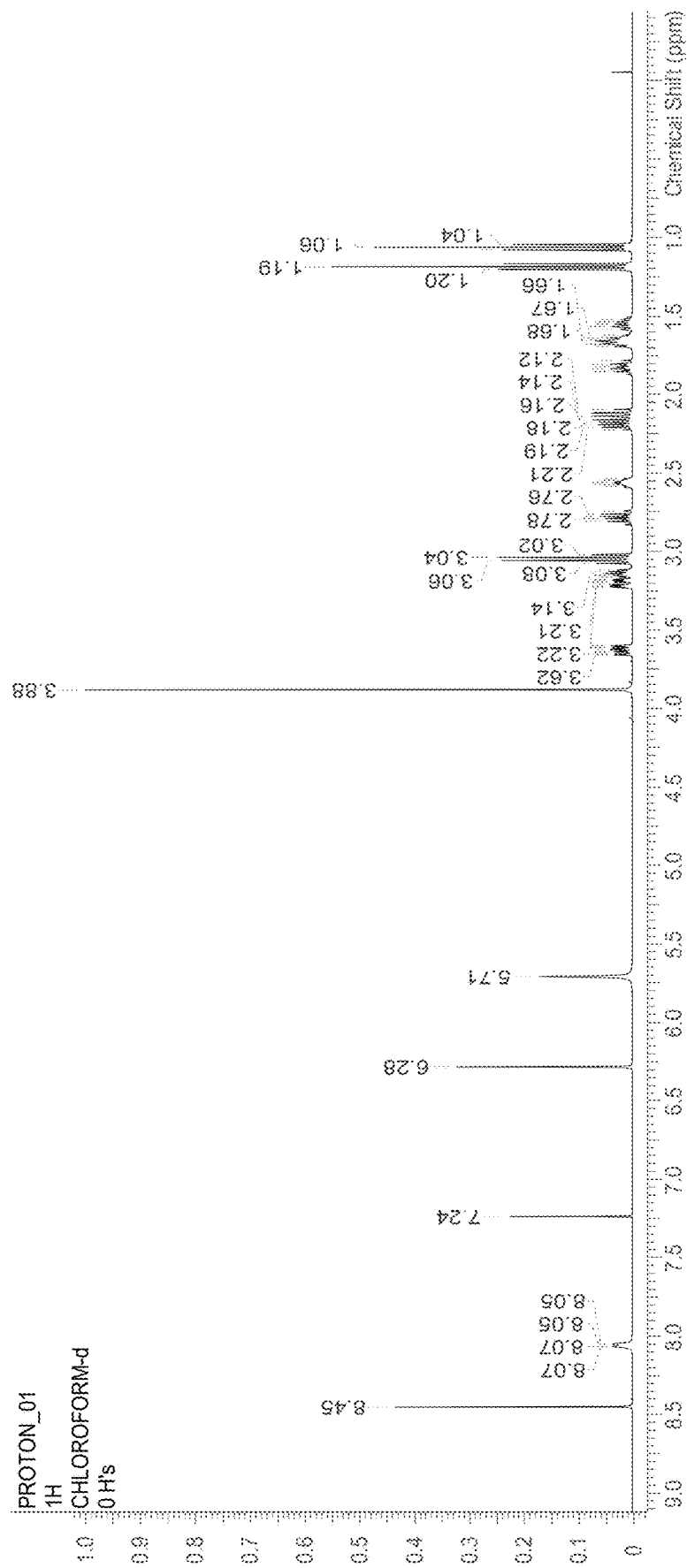
FIG. 15A is an NMR spectrum of an R-4-Amino-N-[(1-ethyl-2-pyrrolidinyl)methyl]-5-(ethylsulfonyl)-2-methoxybenzamide freebase of crystal Form A.
Figure 15B:
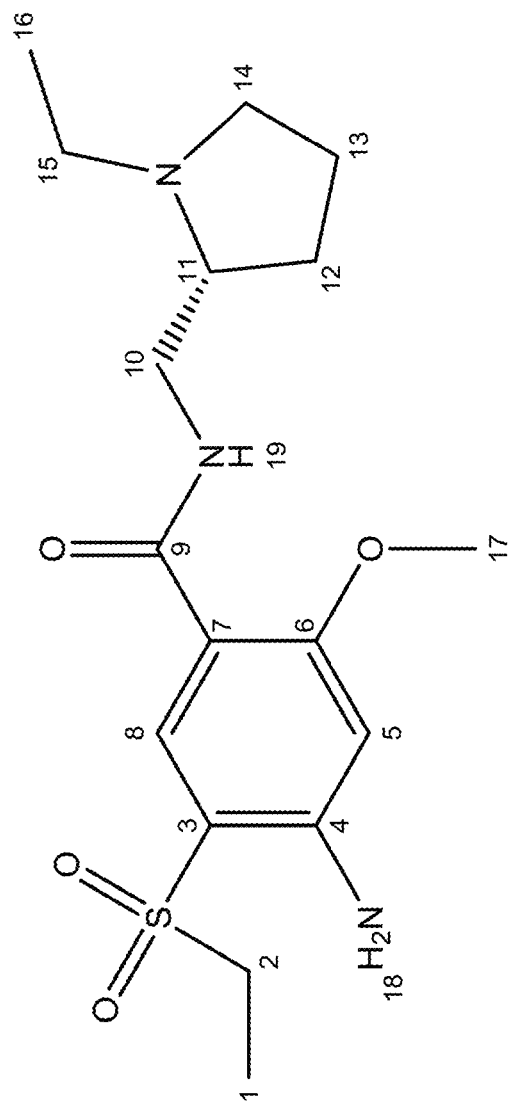
FIG. 15B illustrates the number sequence used for the assignment of peaks in FIG. 15A.

An NMR spectrum of the R-4-Amino-N-[(1-ethyl-2-pyrrolidinyl)methyl]-5-(ethylsulfonyl)-2-methoxybenzamide of Form A obtained by the methods of Examples 12 and 13 is illustrated in FIG. 15A, and FIG. 15B provides the number scheme used for the assignments of Table 48 based on the NMR spectrum of FIG. 15A, where the following notation is used in Table 48: s: singlet, d: doublet, br s: broad singlet, br d broad doublet, ddd: doublet of doublets of doublets, t: triplet, q: quadruplet; m: multiplet, tt: triplet of triplets; dq: doublet of quadruplets.

TABLE 48

Assignment of $^1$H NMR Spectrum of FIG. 15A

| Carbon (see FIG. 15B) | Chemical Shift | Details |
|---|---|---|
| 1 | 1.19-1.20 | t, J = 7.24 Hz, 3 H |
| 2 | 3.02-3.08 | q, J = 7.43 Hz, 2 H |
| 5 | 6.28 | s, 1 H |
| 8 | 8.45 | s, 1 H |
| 10a, b | 3.18-3.23 | ddd, J = 13.50, 4.89, 2.74 Hz, 1 H |
|  | 3.60-3.66 | ddd, J = 13.69, 7.04, 2.74 Hz, 1 H |
| 11 | 2.53-2.64 | m, 1 H |
| 12a, b | 1.52-1.59 | m, 1 H |
|  | 1.79-1.85 | m, 1 H |
| 13 | 1.64-1.69 | m, 2 H |
| 14a, b | 2.09-2.15 | m, 1 H |
|  | 3.12-3.17 | m, 1 H |
| 15a, b | 2.18-2.21 | m, 1 H |
|  | 2.74-2.81 | dq, J = 11.93, 7.37 Hz, 1 H |
| 16 | 1.04-1.06 | t, J = 7.04 Hz, 3 H |
| 17 | 3.88 | s, 3 H |
| 18 | 5.71 | s, 2 H |
| 19 | 8.05-8.07 | br dd, J = 7.04, 2.35 Hz, 1 H |

Figure 16A:
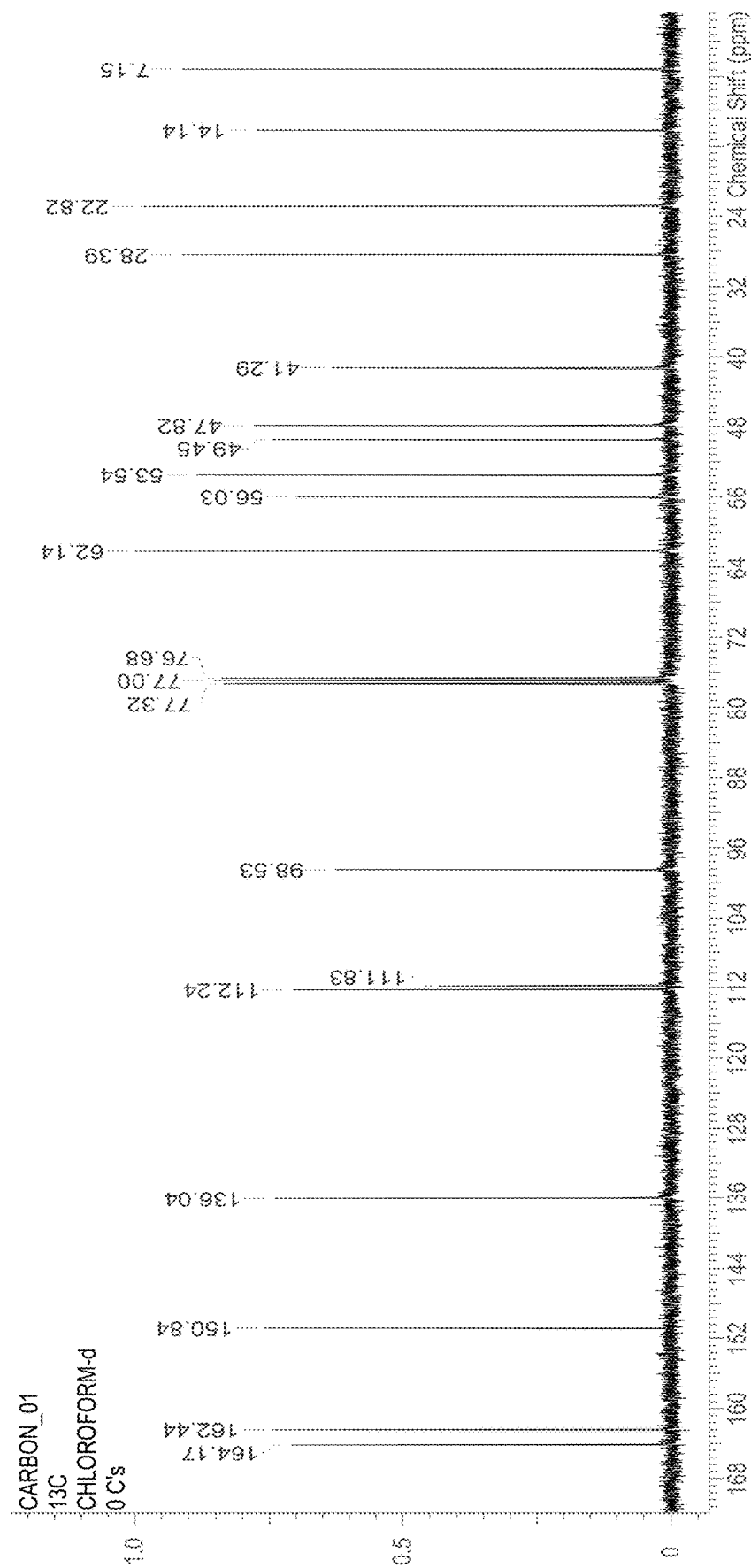
FIG. 16A is an $^{13}$C NMR spectrum of an R-4-Amino-N-[(1-ethyl-2-pyrrolidinyl)methyl]-5-(ethylsulfonyl)-2-methoxybenzamide freebase of crystal Form A.
Figure 16B:
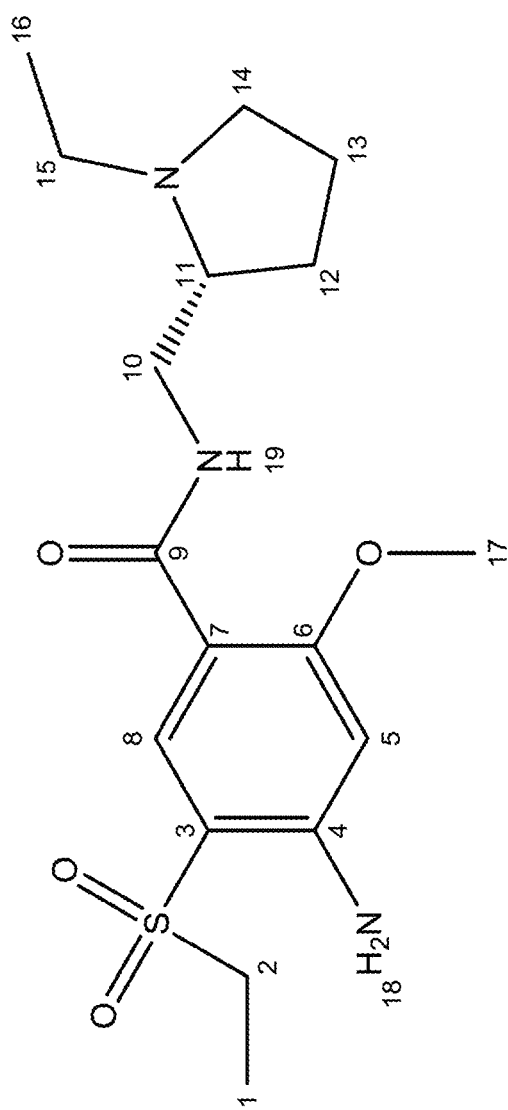
FIG. 16B illustrates the number scheme used for the assignment of peaks in FIG. 16A.

A $^{13}$C NMR spectrum of the R-4-Amino-N-[(1-ethyl-2-pyrrolidinyl)methyl]-5-(ethylsulfonyl)-2-methoxybenzamide of Form A obtained by the methods of Examples 12 and 13 is illustrated in FIG. 16A, and FIG. 16B provides the number scheme used for the assignments of Table 49 based on the $^{13}$C NMR spectrum of FIG. 16A.

TABLE 49

Assignment of $^{13}$C NMR Spectrum of FIG. 16A

| Chemical Shift (ppm) | Assignment (see FIG. 16B) |
|---|---|
| 7.15 | 1 |
| 49.45 | 2 |
| 112.24 | 3 |
| 111.83 | 4 |
| 98.53 | 5 |
| 162.44 | 6 |
| 150.84 | 7 |
| 136.04 | 8 |
| 164.17 | 9 |
| 41.29 | 10 |
| 62.14 | 11 |
| 28.39 | 12 |
| 22.82 | 13 |
| 53.54 | 14 |
| 47.82 | 15 |
| 14.14 | 16 |
| 56.03 | 17 |

Example 14: General Overview of Preparation of S-4-Amino-N-[(1-ethyl-2-pyrrolidinyl)methyl]-5-(ethylsulfonyl)-2-methoxybenzamide In overview, S-4-Amino-N-[(1-ethyl-2-pyrrolidinyl) methyl]-5-(ethylsulfonyl)-2-methoxybenzamide of Form A' can be prepared in two steps: Step 1 Preparation of Crude (S)-amisulpride; and Step 2 Recrystallization of the Crude (S)-amisulpride to crystalline (S)-amisulpride of Form A'.

concentrated. The ethyl acetate solvate of S-4-Amino-N-[(1-ethyl-2-pyrrolidinyl)methyl]-5-(ethylsulfonyl)-2-methoxybenzamide crystallizes and is desolvated by the addition of methyl-tert butyl ether. The S-4-Amino-N-[(1-ethyl-2-pyrrolidinyl)methyl]-5-(ethylsulfonyl)-2-methoxybenzamide (crude freebase) is isolated by filtration.

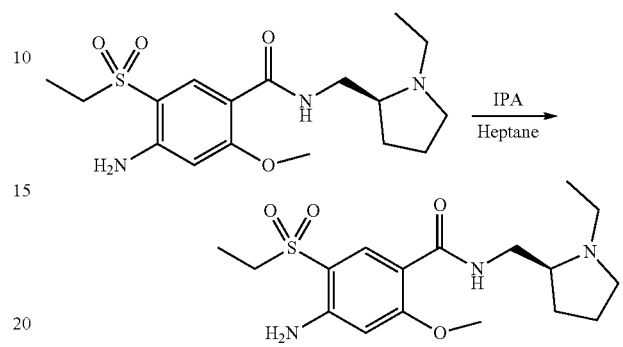

Step 2, Examples 14 and 15

Step 2 in general comprises dissolving the S-4-Amino-N-[(1-ethyl-2-pyrrolidinyl)methyl]-5-(ethylsulfonyl)-2-methoxybenzamide (crude freebase) of into isopropanol and polish filtering. The isopropanol solution is concentrated, diluted with n-heptane and seeded with Form A' to yield a slurry of S-4-Amino-N-[(1-ethyl-2-pyrrolidinyl)methyl]-5-(ethylsulfonyl)-2-methoxybenzamide. The mixture is cooled and filtered to yield crystalline S-4-Amino-N-[(1-ethyl-2-pyrrolidinyl)methyl]-5-(ethylsulfonyl)-2-methoxybenzamide substantially of Form A'.

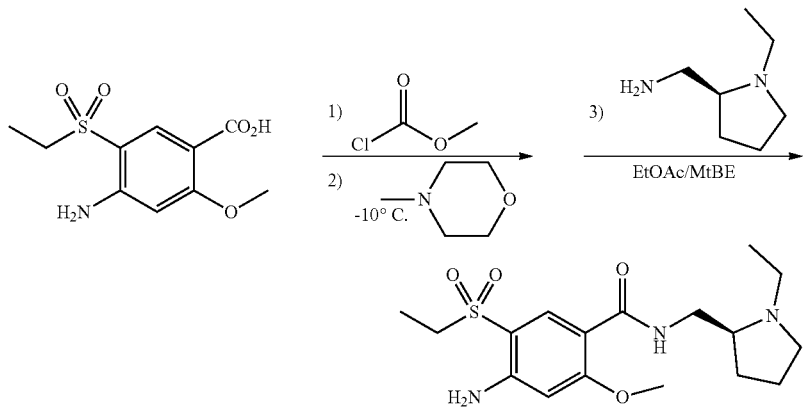

Step 1, Examples 14 and 15

Step 1 in general comprises reacting 4-Amino-5-(ethylsulfonyl)-2-methoxybenzoic acid with ethyl chloroformate and then adding (S)-(1-ethyl pyrrolidin-2-yl)methanamine to form S-4-Amino-N-[(1-ethyl-2-pyrrolidinyl)methyl]-5-(ethylsulfonyl)-2-methoxybenzamide hydrochloride. The resulting product is extracted into water and washed with ethyl acetate. S-4-Amino-N-[(1-ethyl-2-pyrrolidinyl) methyl]-5-(ethylsulfonyl)-2-methoxybenzamide hydrochloride is converted to freebase by the addition of aqueous potassium carbonate, dissolved into ethyl acetate and washed with water. The ethyl acetate solution is dried and It is to be understood that during the crystallization of S-4-Amino-N-[(1-ethyl-2-pyrrolidinyl)methyl]-5-(ethylsulfonyl)-2-methoxybenzamide (crude freebase) the amount of water in the ethyl acetate solvent affects the crystallization and is preferably less than 0.5%. Accordingly the water content is preferably monitored during the distillation of the ethyl acetate solution, such as for example by coulometric titration (Karl Fischer). For example, in various embodiments coulometric titration (Karl Fischer) was performed by non-aqueous, perchloric acid titration where approximately 300 mg of sample, accurately weighed, was dissolved in about 50 mL of glacial acetic acid and titrated with 0.1 N perchloric acid and the end-point determined potentiometrically. The weight of sample was corrected for water content and residual solvent content prior to assay calculation. The drying of the isolated solid is also preferably monitored. In various embodiments, the reaction of Step 1 is considered complete when the amount of 4-amino-5-(ethylsulfonyl)-2-methoxybenzoic acid in the reaction mixture is less than or equal to 10 A % (where A % refers to Area % by HPLC) and/or when the amount of 4-amino-5-(ethylsulfonyl)-2-methoxybenzoic acid in the reaction mixture is less than or equal to 10 mol %.

Example 15: Detailed Overview of Preparation of S-4-Amino-N-[(1-ethyl-2-pyrrolidinyl)methyl]-5-(ethylsulfonyl)-2-methoxybenzamide of Form A'

Step 1: To a solution of 4-amino-5-(ethylsulfonyl)-2-methoxybenzoic acid in acetone at −10° C. is added ethyl chloroformate. 4-Methylmorpholine is added at a rate (exothermic) so as to maintain the internal temperature below −5° C. The reaction is stirred for 1 hour at −10° C. and then (S)-(1-ethyl pyrrolidin-2-yl)methanamine is added. After stirring for 2 hours the reaction mixture is concentrated and diluted with water and ethyl acetate. The ethyl acetate layer is removed and the aqueous layer is basified with potassium carbonate. Ethyl acetate is then added and the aqueous layer removed. The organic layer is washed with water twice and concentrated. The mixture is diluted with ethyl acetate and concentrated until the water content of the ethyl acetate solution is below 0.5%. The solution is seeded at 31° C. with 1 wt % S-4-Amino-N-[(1-ethyl-2-pyrrolidinyl)methyl]-5-(ethylsulfonyl)-2-methoxybenzamide of Form A' and stirred at the nucleation temperature for 2 h. The mixture is cooled to 20° C. and stirred for 1 h. The slurry is then diluted with methyl tert butylether (MtBE) and stirred for 2 h at 20° C. The suspension is then filtered and the product cake is washed with MtBE/ethyl acetate. The wet-cake is dried under vacuum at 40° C. 5° C. to constant weight to yield S-4-Amino-N-[(1-ethyl-2-pyrrolidinyl)methyl]-5-(ethylsulfonyl)-2-methoxybenzamide (crude).

Step 2: Isopropanol is added to S-4-Amino-N-[(1-ethyl-2-pyrrolidinyl)methyl]-5-(ethylsulfonyl)-2-methoxybenzamide (crude) and the mixture is heated to 50° C. to achieve dissolution. The resulting solution is then passed through a filter. The filtrate is concentrated and cooled to 40° C. n-Heptane is then added and the resulting solution is cooled to 28° C. and seeded. The resulting slurry is cooled to 23° C. and stirred for 1.5 h at this temperature. More n-heptane is added and the slurry is stirred at 22° C. for 13 h. The suspension is then filtered and the product cake is washed with isopropanol/n-heptane. The wet-cake is dried under vacuum at 40° C. 5° C. to constant weight to yield S-4-Amino-N-[(1-ethyl-2-pyrrolidinyl)methyl]-5-(ethylsulfonyl)-2-methoxybenzamide substantially of Form A'.

Figure 17A:
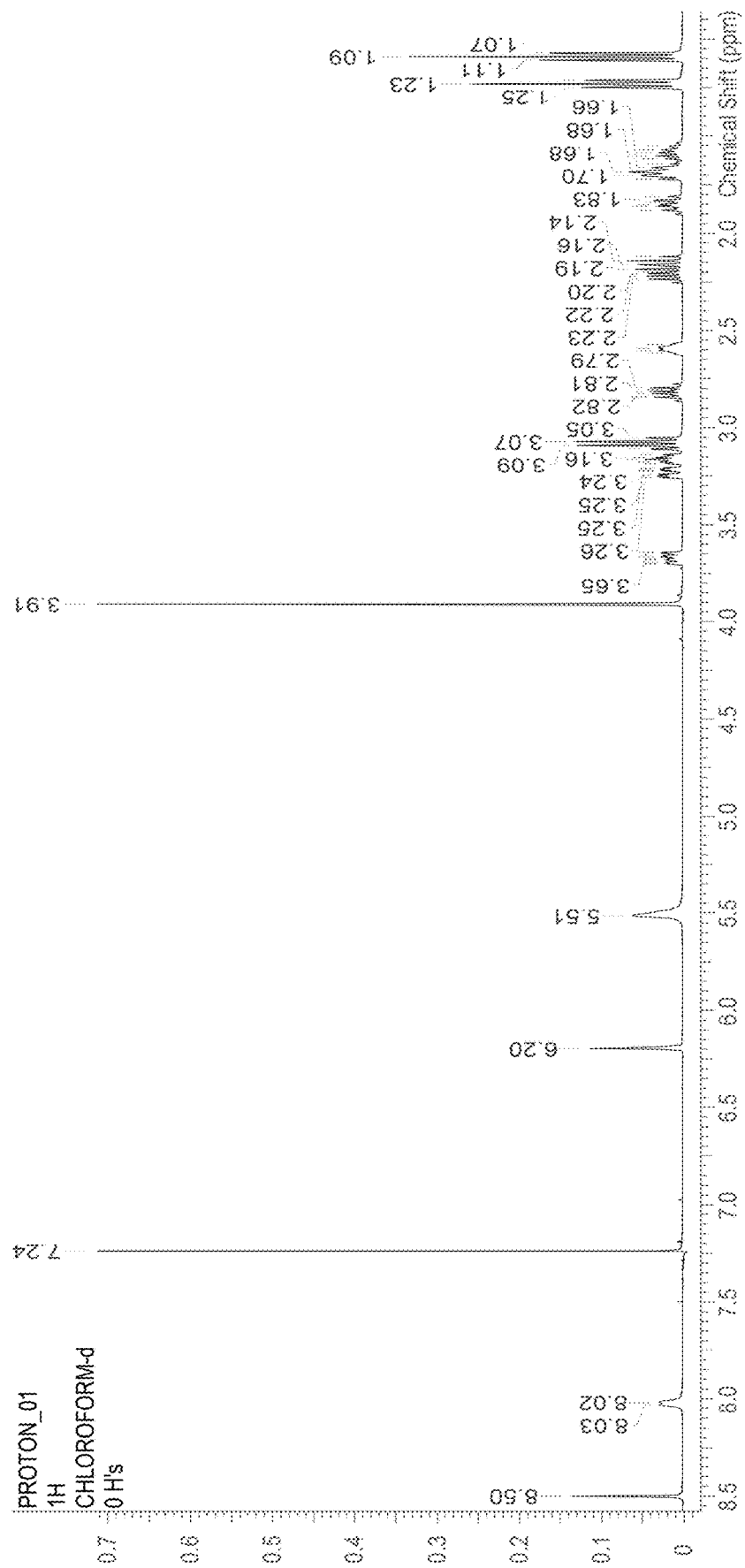
FIG. 17A is an NMR spectrum of an S-4-Amino-N-[(1-ethyl-2-pyrrolidinyl)methyl]-5-(ethylsulfonyl)-2-methoxybenzamide freebase of crystal Form A'.
Figure 17B:
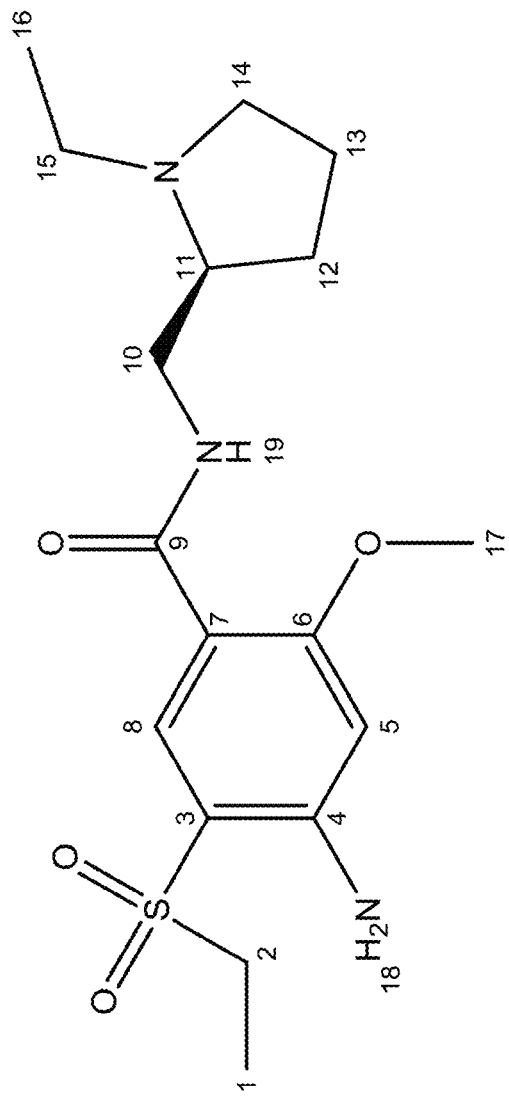
FIG. 17B illustrates the number sequence used for the assignment of peaks in FIG. 17A.

An NMR spectrum of the S-4-Amino-N-[(1-ethyl-2-pyrrolidinyl)methyl]-5-(ethylsulfonyl)-2-methoxybenzamide of Form A' obtained by the methods of Examples 14 and 15 is illustrated in FIG. 17A, and FIG. 17B provides the number scheme used for the assignments of Table 50 based on the NMR spectrum of FIG. 17A, where the following notation is used in Table 50: s: singlet, d: doublet, br s: broad singlet, br broad doublet, ddd: doublet of doublets of doublets, t: triplet, q: quadruplet; m: multiplet, tt: triplet of triplets; dq: doublet of quadruplets.

TABLE 50

Assignment of 1-E1 NMR Spectrum of FIG. 17A

| Carbon (see FIG. 17B) | Chemical Shift | Details |
|---|---|---|
| 1 | 1.21-1.25 | t, J = 7.43 Hz, 3 H |
| 2 | 3.05-3.11 | q, J= 7.30 Hz, 2 H |
| 5 | 6.20 | s, 1 H |
| 8 | 8.50 | s, 1 H |
| 10a, b | 3.22-3.26 | ddd, J = 13.69, 4.89, 2.93 Hz, 1 H |
|  | 3.64-3.70 | ddd, J = 13.69, 7.04, 2.74 Hz, 1 H |
| 11 | 2.57-2.61 | m, 1 H |
| 12a, b | 1.57-1.64 | m, 1 H |
|  | 1.83-1.88 | m, 1 H |
| 13 | 1.66-1.72 | m, 2 H |
| 14a, b | 2.12-2.16 | m, 1 H |
|  | 3.13-3.18 | m, 1 H |
| 15a, b | 2.19-2.23 | m, 1 H |
|  | 2.79-2.84 | dq, J = 12.13, 7.43 Hz, 1 H |
| 16 | 1.07-1.11 | t, J = 7.24 Hz, 3 H |
| 17 | 3.91 | s, 3 H |
| 18 | 5.51 | br s, 2 H |
| 19 | 8.02-8.03 | br d, J = 5.1 Hz, 1 H |

Figure 18A:
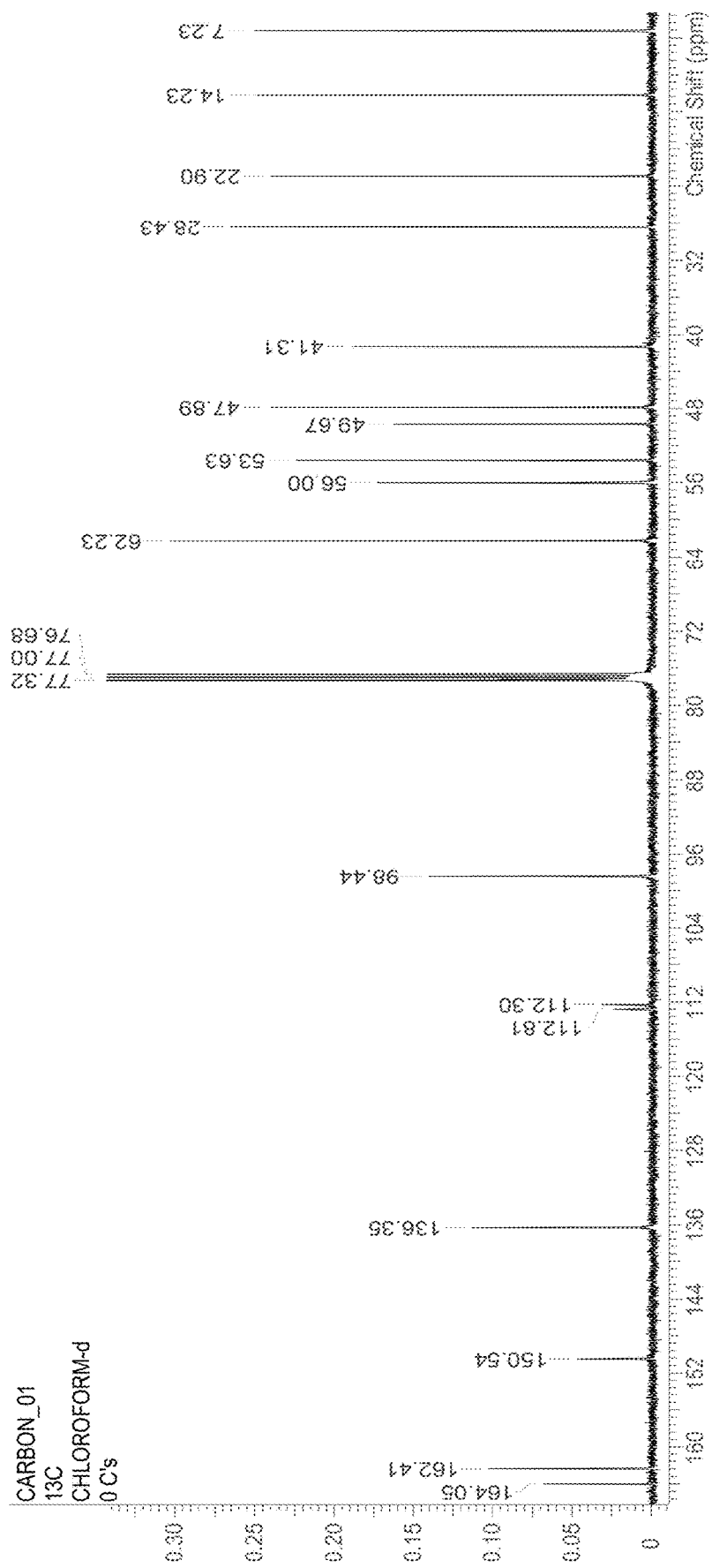
FIG. 18A is an $^{13}$C NMR spectrum of an S-4-Amino-N-[(1-ethyl-2-pyrrolidinyl)methyl]-5-(ethylsulfonyl)-2-methoxybenzamide freebase of crystal Form A'.
Figure 18B:
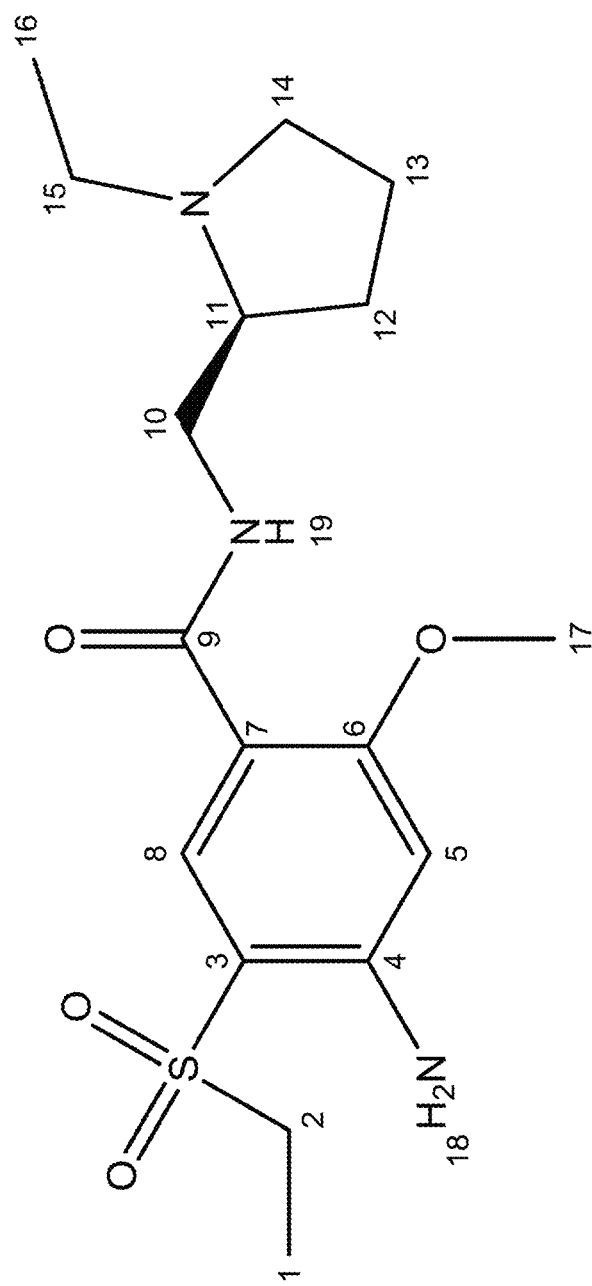
FIG. 18B illustrates the number scheme used for the assignment of peaks in FIG. 18A.

A $^{13}$C NMR spectrum of the S-4-Amino-N-[(1-ethyl-2-pyrrolidinyl)methyl]-5-(ethyl sulfonyl)-2-metoxybenzamide of Form A' obtained by the methods of Examples 14 and 15 is illustrated in FIG. 18A, and FIG. 18B provides the number scheme used for the assignments of Table 51 based on the $^{13}$C NMR spectrum of FIG. 18A.

TABLE 51

Assignment of $^{13}$C NMR Spectrum of FIG. 18A

| Chemical Shift (ppm) | Assignment (see FIG. 18 B) |
|---|---|
| 7.23 | 1 |
| 49.67 | 2 |
| 112.81 | 3 |
| 112.30 | 4 |
| 98.44 | 5 |
| 162.41 | 6 |
| 150.54 | 7 |
| 136.35 | 8 |
| 164.05 | 9 |
| 41.31 | 10 |
| 62.23 | 11 |
| 28.43 | 12 |
| 22.90 | 13 |
| 53.63 | 14 |
| 47.89 | 15 |
| 14.23 | 16 |
| 56.00 | 17 |

The present inventions also include the following aspects and embodiments.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when administered to a subject population, the pharmaceutical composition results in a maximum QT interval prolongation relative to baseline over the time period of 12 hours after administration that, compared to an immediate release composition having the same total daily amount of amisulpride as the pharmaceutical composition, is (a) at least about 75% less than that of said immediate release composition; (b) at least about 65% less than that of said immediate release composition; (c) at least about 60% less than that of said immediate release composition; (d) at least about 55% less than that of said immediate release composition; or (e) at least about 50% less than that of said immediate release composition. In various embodiments, the maximum QT interval prolongation relative to baseline is the population average maximum QTcF interval prolongation relative to baseline.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said pharmaceutical composition is administered to a subject population it is effective to provide in the subject after administration an occupancy of dopamine D2 receptors that, compared to an immediate release composition having the same total daily amount of amisulpride as the pharmaceutical composition, is (a) at least 85% of the dopamine D2 receptors occupancy of said immediate release composition; (b) at least 90% of the dopamine D2 receptors occupancy of said immediate release composition; or (c) at least 95% of the dopamine D2 receptors occupancy of said immediate release composition.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said pharmaceutical composition is administered to a subject population effective to provide in the subject after administration: (1) an occupancy of dopamine D2 receptors between (a) about 20% and about 60% at about 27 hours after administration; or (b) about 20% and about 60% at about 27 hours after administration; and (2) an occupancy of dopamine D2 receptors that is substantially similar to that achieved by an immediate release composition having the same total daily amount of amisulpride as the pharmaceutical composition.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said pharmaceutical composition is administered to a subject population it provides, compared to an immediate release composition having the same total daily amount of amisulpride as the pharmaceutical composition, a blood plasma Cmax of amisulpride that is (a) less than about 75% of the Cmax of said immediate release composition; (b) less than about 65% of the Cmax of said immediate release composition; (c) is less than about 60% of the Cmax of said immediate release composition; (d) less than about 55% of the Cmax of said immediate release composition; or (e) less than about 50% of the Cmax of said immediate release composition.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein said pharmaceutical composition when administered to a subject population is effective in minimizing the difference between Cmin and Cmax of amisulpride compared to an immediate release composition having the same total daily amount of amisulpride as the pharmaceutical composition, wherein the value of Cmin is that at about 9 hours after administration.

It is to be understood that in each of the aspects above, provided are embodiments wherein the immediate release composition having the same total daily amount of amisulpride as the pharmaceutical composition is the immediate release composition described in Table 25 and having the same total daily amount of amisulpride as the pharmaceutical composition.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when administered to a subject population, said pharmaceutical composition results in a maximum QT interval prolongation, over the time period of 12 hours after administration, of (a) less than about 0.45 milliseconds (ms) per 10 mg of amisulpride; (b) less than about 0.40 milliseconds (ms) per 10 mg of amisulpride; (c) less than about 0.35 milliseconds (ms) per 10 mg of amisulpride; (d) less than about 0.30 milliseconds (ms) per 10 mg of amisulpride; (e) less than about 0.25 milliseconds (ms) per 10 mg of amisulpride; (f) less than about 0.20 milliseconds (ms) per 10 mg of amisulpride; (g) less than about 0.15 milliseconds (ms) per 10 mg of amisulpride; (h) less than about 0.10 milliseconds (ms) per 10 mg of amisulpride; (i) less than about 0.05 milliseconds (ms) per 10 mg of amisulpride; or (j) less than about 0.02 milliseconds (ms) per 10 mg of amisulpride. In various embodiments, the maximum QT interval prolongation relative to baseline is the population average maximum QTcF interval prolongation relative to baseline.

In various aspects, provided are pharmaceutical compositions in a solid oral dosage form, the solid oral dosage form comprising, about 200 mg of amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when administered to a subject population, said pharmaceutical composition results in a population maximum QTcF interval prolongation relative to baseline of (a) less than about 10 milliseconds (ms) over the time period of 12 hours after administration; (b) less than about 9 milliseconds (ms) over the time period of 12 hours after administration; (c) less than about 8 milliseconds (ms) over the time period of 12 hours after administration; (d) less than about 7 milliseconds (ms) over the time period of 12 hours after administration; (e) less than about 6 milliseconds (ms) over the time period of 12 hours after administration; or (f) less than about 5 milliseconds (ms) over the time period of 12 hours after administration. In various embodiments, the maximum QTcF interval prolongation relative to baseline is the population average maximum QTcF interval prolongation relative to baseline.

In various aspects, provided are pharmaceutical compositions in a solid oral dosage form, the solid oral dosage form comprising, about 200 mg of amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when administered to a subject population, said pharmaceutical composition is effective to provide at geometric mean Cmax a QTcF interval prolongation relative to baseline that is (a) less than about 10 milliseconds (ms); (b) less than about 9 milliseconds (ms); (c) less than about 8 milliseconds (ms); (d) less than about 7 milliseconds (ms); (e) is less than about 6 milliseconds (ms); or (f) less than about 5 milliseconds (ms). In various embodiments, the maximum QTcF interval prolongation relative to baseline is the population average maximum QTcF interval prolongation relative to baseline.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said composition is administered to a subject population it provides a Cmax/Cmin ratio of amisulpride, wherein the value of Cmin is determined within about 9 hours after administration, that is (a) less than about 2; (b) less than about 1.9; or (c) less than about 1.8. In various embodiments, (a) the values of Cmax and Cmin are determined within about 9 hours after administration; and/or (b) the value of Cmin is that at about 9 hours after administration.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said pharmaceutical composition is administered to a subject population (i) the area under the curve (AUC) of blood plasma concentration versus time of amisulpride from administration to Tmax ($AUC_{0-Tmax}$) is less than about 19% of the area under the curve from administration to about 48 hours ($AUC_{0-48}$); and (ii) Tmax of amisulpride is between about 4 hours and about 6 hours after administration.

In various aspects, provided are pharmaceutical compositions in a solid oral dosage form, the solid oral dosage form comprising amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when a solid oral dosage form is administered to a subject population the the population mean time to Cmax (Tmax) of amisulpride is between about 4 hours and about 6 hours after administration and the area under the curve (AUC) of blood plasma concentration versus time of amisulpride from administration to Tmax ($AUC_{0-Tmax}$) is (a) less than about 18% of the area under the curve from administration to 48 hours ($AUC_{0-48}$); (b) less than about 17% of $AUC_{0-48}$; (c) less than about 15% of $AUC_{0-48}$; or (d) less than about 13% of $AUC_{0-48}$.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein the solid oral dosage form when dissolution tested using a two-stage in vitro gastrointestinal simulation dissolution test (a) releases less than about 30% of the amisulpride after 1 hour, releases more than about 20% and less than about 60% of the amisulpride after 3 hours, and releases more than about 30% and less than about 100% of the amisulpride after 6 hours; (b) releases less than about 30% of the amisulpride after 1 hour, releases more than 20% and less than about 60% of the amisulpride after 3 hours, and releases more than about 30% and less than 75% of the amisulpride after 6 hours; (c) releases less than about 20% of the amisulpride after 1 hour, releases more than about 20% and less than about 50% of the amisulpride after 3 hours, and releases more than about 30% and less than about 75% of the amisulpride after 6 hours; (d) releases more than about 30% and less than about 50% of the amisulpride after 6 hours; (e) releases no more than about 30% of the amisulpride after 1 hour, releases between about 30% and about 75% of the amisulpride after about 3 hours, and releases more than about 75% of the amisulpride after about 12 hours; and/or (f) releases more than about 75% of the amisulpride after about 6 hours.

It is to be understood that in each of the aspects above, provided are embodiments wherein (a) the two-stage gastrointestinal simulation dissolution test comprises in the first stage 500 ml of an aqueous media having a pH of about 2 and adding after 1 hour 400 ml of an aqueous buffer media such that the second stage pH is 6.8; where the temperature in both stages of the two-stage in vitro gastrointestinal simulation dissolution test is about 37° C.; and/or (b) wherein the two-stage gastrointestinal simulation dissolution test is conducted in a paddle apparatus substantially in accord with that described in one of more of: (a) United States Pharmacopeia Convention (USP) Apparatus 2 of Chapter 711 Dissolution; USP41-NF36 General Chapter <711> Dissolution, and (b) Japanese Pharmacopeia (P) General test <6.10>.

In various aspects, provided are pharmaceutical compositions in a solid oral dosage form for reducing QT interval prolongation, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, wherein said solid oral dosage form is formulated for extended release. In various embodiments, the solid oral dosage form when dissolution tested using the two-stage in vitro dissolution test described in Table 5 in the paddle apparatus described in United States Pharmacopeia Convention (USP) Apparatus 2 of Chapter 711 Dissolution; USP41-NF36 General Chapter <711> Dissolution has a dissolution profile substantially the same as (a) the profile of Lot 3C in FIG. 1C; or (b) the profile of Lot 2C in FIG. 1C.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein the solid oral dosage form when dissolution tested using the two-stage in vitro dissolution test described in Table 5 in the paddle apparatus described in United States Pharmacopeia Convention (USP) Apparatus 2 of Chapter 711 Dissolution; USP41-NF36 General Chapter <711> Dissolution has a dissolution profile substantially the same as (a) the profile of Lot 3C in FIG. 1C; (b) the profile of Lot 2C in FIG. 1C; (c) the profile of Lot 3Z used in the study of Example 7A, Part 1 or Part 2 in FIG. 1D; (d) the profile of Lot 3Z used in fed state study of Example 7A, Part 1 in FIG. 1D; (e) the profile of Lot 3Z used in MAD/PET study of Example 7B in FIG. 1D; (f) the profile of Lot 4Z in FIG. 1D; (g) the profile of Lot 5Z in FIG. 1D; (h) the profile of Lot 6Z in FIG. 1D; (i) the profile of Lot 7C in FIG. 1E over the time period from 0 to 6 hours; (j) the profile of Lot 8C in FIG. 1E over the time period from 0 to 6 hours; (k) the profile of Lot 7C in FIG. 1E over the time period from 0 to 6 hours; (l) the profile of Lot 8C in FIG. 1E over the time period from 0 to 6 hours.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and an extended release agent, wherein the solid oral dosage form when dissolution tested using the two-stage in vitro dissolution test described in Table 5 in the paddle apparatus described in United States Pharmacopeia Convention (USP) Apparatus 2 of Chapter 711 Dissolution; USP41-NF36 General Chapter <711> Dissolution has a dissolution profile substantially the same as the profile of Lot 3Z used in the study of one or more of (a) Example 7B; (b) Example 7A Part 1; or (c) Example 7A Part 2 in FIG. 1D.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said pharmaceutical composition is administered to a subject population it provides a plasma concentration profile substantially the same as (a) the profile of Lot 4Z in FIG. 22B; or (b) the profile of Lot 4Z in FIG. 22F In various aspects and embodiments, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said pharmaceutical composition is administered to a subject population it provides a plasma concentration profile substantially the same as (a) the profile of Lot 3Z in FIG. 22C; (b) the profile of Lot 3Z Fed State in FIG. 22D; (c) the profile of Lot 3Z in FIG. 22H; (d) the profile of Lot 3Z Fed State in FIG. 22I; or (e) the profile of Lot 3Z in FIG. 22J.

In various aspects and embodiments, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said pharmaceutical composition is administered to a subject population it provides a plasma concentration profile substantially the same as (a) the profile of Lot 5Z in FIG. 22G; or (b) the profile of Lot 6Z in FIG. 22K.

It is to be understood that in each of the aspects above, provided are embodiments wherein the enantiomeric ratio of (R)-(+)-amisulpride to (S)-(−)-amisulpride is (a) from about 65:35 to about 88:12 by weight of free base; (b) from about 75:25 to about 88:12 by weight of free base; (c) from about 80:20 to about 88:12 by weight of free base; (d) from about 85:15 to about 90:10 by weight of free base; or (e) is about 85:15 by weight of free base.

It is to be understood that in each of the aspects above, provided are embodiments wherein the amisulpride is in (a) an amount from about 85 mg to about 600 mg of (R)-(+)-amisulpride, or a pharmaceutically acceptable salt thereof, by weight of free base; and an amount from about 15 mg to about 100 mg of (S)-(−)-amisulpride, or a pharmaceutically acceptable salt thereof, by weight of free base; (b) an amount from about 170 mg to about 340 mg of (R)-(+)-amisulpride, or a pharmaceutically acceptable salt thereof, by weight of free base; and an amount from about 30 mg to about 60 mg of (S)-(−)-amisulpride, or a pharmaceutically acceptable salt thereof, by weight of free base; (c) about 85 mg of (R)-(+)-amisulpride, or a pharmaceutically acceptable salt thereof, by weight of free base; and about 15 mg of (S)-(−)-amisulpride, or a pharmaceutically acceptable salt thereof, by weight of free base; (d) about 170 mg of (R)-(+)-amisulpride, or a pharmaceutically acceptable salt thereof, by weight of free base; and about 30 mg of (S)-(−)-amisulpride, or a pharmaceutically acceptable salt thereof, by weight of free base; or (e) about 340 mg of (R)-(+)-amisulpride, or a pharmaceutically acceptable salt thereof, by weight of free base; and about 60 mg of (S)-(−)-amisulpride, or a pharmaceutically acceptable salt thereof, by weight of free base.

It is to be understood that in each of the aspects above, provided are embodiments wherein, the combined amount of (R)-(+)-amisulpride and (S)-(−)-amisulpride, or pharmaceutically acceptable salts thereof, is (a) about 100 mg, about 200 mg, about 300 mg, about 400 mg, about 500 mg, about 600 mg or about 700 mg by weight of free base; (b) from about 50 mg to about 1000 mg by weight of free base; (c) about 200 mg to about 600 mg by weight of free base; (d) from about 100 mg to about 500 mg by weight of free base; (e) from about 200 mg to about 400 mg by weight of free base; (f) about 200 mg to about 700 mg by weight of free base; (g) about 100 mg by weight of free base; (h) about 160 mg by weight of free base; (i) about 200 mg by weight of free base (j) about 300 mg by weight of free base; (k) about 400 mg by weight of free base; (l) about 500 mg by weight of free base; (m) about 600 mg by weight of free base; or (n) about 700 mg by weight of free base.

It is to be understood that in each of the aspects above, provided are embodiments wherein the solid oral dosage form comprises: a granular component admixed with an extra-granular component, the granular component comprising amisulpride and a binder; and the extra-granular component comprising, an extended release agent. In various embodiments, (a) the extragranular component further comprises a filler; (b) the extended release agent comprises a biopolymer; and/or (c) the biopolymer comprises hypromellose. In various embodiments, (a) the extended release agent in an amount between about 10% and about 50% by total dosage form weight; (b) the extended release agent comprises hypromellose in an amount between about 10% and about 50% by total dosage form weight; (c) the amisulpride is in an amount between about 30% and about 50% by total dosage form weight. In various embodiments, the granules comprise (a) between about 60% to about 80% by weight of amisulpride, between about 10% to about 30% by weight of filler, and between about 1% to about 5% by weight of binder; (b) between about 70% to about 80% by weight of amisulpride, between about 20% to about 25% by weight of filler, and between about 1% to about 5% by weight of binder. In various embodiments, the granular component comprises: between about 73% to about 78% by weight of amisulpride, between about 10% to about 12% by weight of a D-mannitol, between about 10% to about 12% by weight of a pregelatinized starch, and between about 1% to about 3% by weight of polyvinyl alcohol, based on the weight of the granular component.

It is to be understood that in each of the embodiments and aspects above, provided are embodiments wherein the solid oral dosage form is a tablet. In various embodiments, the tablet (granules plus extragranular component) comprises (a) between about 20% to about 70% by total tablet weight of granules of extended release agent; (b) between about 10% to about 50% by total tablet weight of extended release agent; (c) a combined amount of filler in both granular and extragranular between about 6% to about 60% by total tablet weight; (d) a combined amount of filler in both granular and extragranular between about 10% to about 50% by total tablet weight. In various embodiments, the tablet (granules plus extragranular component) comprises between about 1% to about 2% by total tablet weight of a lubricant, and in various embodiments the lubricant is magnesium stearate. In various embodiments, the tablet (granules plus extragranular component) comprises (a) comprises between about 34% to about 39% by total tablet weight of a D-mannitol, and about 15% by total tablet weight of hypromellose; (b) between about 24% to about 29% by total tablet weight of a D-mannitol, and about 25% by total tablet weight of hypromellose; and/or (c) between about 4% to about 9% by total tablet weight of a D-mannitol, and about 45% by total tablet weight of hypromellose.

It is to be understood that in each of the embodiments and aspects above, provided are embodiments wherein the pharmaceutical composition is effective to provide after administration a maximum QT interval prolongation, over the time period of 12 hours after administration, of (a) less than about 0.45 milliseconds (ms) per 10 mg of amisulpride; (b) less than about 0.30 milliseconds (ms) per 10 mg of amisulpride; (c) less than about 0.20 milliseconds (ms) per 10 mg of amisulpride; (d) less than about 0.15 milliseconds (ms) per 10 mg of amisulpride; (e) less than about 0.10 milliseconds (ms) per 10 mg of amisulpride; (f) less than about 0.05 milliseconds (ms) per 10 mg of amisulpride; or (g) less than about 0.02 milliseconds (ms) per 10 mg of amisulpride.

It is to be understood that in each of the embodiments and aspects above, provided are embodiments wherein the pharmaceutical composition is effective to provide a population maximum QTcF interval prolongation relative to baseline of (a) less than about 10 milliseconds (ms) over the time period of 12 hours after administration; (b) less than about 9 milliseconds (ms) over the time period of 12 hours after administration; (c) less than about 8 milliseconds (ms) over the time period of 12 hours after administration; (d) less than about 7 milliseconds (ms) over the time period of 12 hours after administration; (e) less than about 6 milliseconds (ms) over the time period of 12 hours after administration; or (f) less than about 5 milliseconds (ms) over the time period of 12 hours after administration. In various embodiments, the maximum QTcF interval prolongation relative to baseline is the population average maximum QTcF interval prolongation relative to baseline.

It is to be understood that in each of the embodiments and aspects above, provided are embodiments wherein the pharmaceutical composition is effective to provide at geometric mean Cmax a QTcF interval prolongation relative to baseline that is (a) less than about 10 milliseconds (ms); (b) less than about 9 milliseconds (ms); (c) less than about 8 milliseconds (ms); (d) less than about 7 milliseconds (ms); (e) is less than about 6 milliseconds (ms); or (f) less than about 5 milliseconds (ms).

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, the one or more excipients comprising an extended release agent, wherein when said composition is administered to a subject population it provides a Cmax/Cmin ratio of amisulpride, wherein the value of Cmin is determined within about 9 hours after administration, that is (a) less than about 2; (b) less than about 1.9; or (c) less than about 1.8. In various embodiments, (a) the values of Cmax and Cmin are determined within about 9 hours after administration; and/or (b) the value of Cmin is that at about 9 hours after administration.

It is to be understood that in each of the embodiments and aspects above, provided are embodiments wherein the pharmaceutical composition is effective to provide after administration an occupancy of dopamine D2 receptors of (a) about 20% to about 60%; or (b) about 30% to about 50%.

It is to be understood that in each of the embodiments and aspects above, provided are embodiments wherein the pharmaceutical composition when administered to a subject population provides a Tmax between about 4 hours and about 6 hours after administration.

It is to be understood that in each of the embodiments and aspects above, provided are embodiments wherein the modified release composition when administered to a subject population provides a magnitude of QT prolongation that is less than that of a comparable immediate release composition.

It is to be understood that in each of the embodiments and aspects above, provided are embodiments wherein the modified release composition when administered to a subject population provides a reduced incidence of QT prolongation that is less than that of a comparable immediate release composition.

It is to be understood that in each of the aspects above, provided are embodiments wherein when a solid oral dosage form is administered to a subject population the area under the curve (AUC) of blood plasma concentration versus time of amisulpride from administration to Tmax ($AUC_{0-Tmax}$) is (a) less than about 18% of the area under the curve from administration to 48 hours ($AUC_{0-48}$); (b) less than about 17% $AUC_{0-48}$; (c) less than about 15% $AUC_{0-48}$; or (d) less than about 13% of $AUC_{0-48}$.

In various aspects, provided are pharmaceutical compositions in a solid oral dosage form, the solid oral dosage form comprising, about 170 mg of (R)-(+)-amisulpride, or a pharmaceutically acceptable salt thereof, by weight of free base; and about 30 mg of (S)-(−)-amisulpride, or a pharmaceutically acceptable salt thereof, by weight of free base; and an extended release agent, wherein when said pharmaceutical composition is administered to a subject population it is effective to provide after administration: (a) maximum QTcF interval prolongation relative to baseline is less than about 8 milliseconds (ms) over the time period of 12 hours after administration; (b) an occupancy of dopamine D2 receptors between about 20% and about 60% about 27 hours after administration; and (c) an occupancy of dopamine D2 receptors about 27 hours after administration that is at least 85% of the dopamine D2 receptors occupancy achieved by an immediate release composition having the same total daily amount of amisulpride as the pharmaceutical composition.

In various aspects, provided are pharmaceutical compositions in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, and the amount of (S)-(−)-amisulpride is less than about 100 mg; and an extended release agent, wherein when said solid oral dosage form is administered to a subject population it is effective to provide in the subject about 27 hours after administration: (1) an occupancy of dopamine D2 receptors between about 20% and about 60%; and; (2) an occupancy of dopamine D2 receptors that is at least 85% of the dopamine D2 receptors occupancy achieved by an immediate release composition having the same total daily amount of amisulpride as the pharmaceutical composition.

It is to be understood that in each of the embodiments and aspects above, provided are embodiments where applicable Cmax is (a) mean Cmax; (b) geometric mean Cmax; or (c) average Cmax. It is to be understood that in each of the embodiments and aspects above, provided are embodiments where applicable Cmin is (a) mean Cmin; (b) geometric mean Cmin; or (c) average Cmin. It is to be understood that in each of the embodiments and aspects above, provided are embodiments where applicable Tmax is (a) mean Tmax; (b) geometricamean Tmax; or (c) average Tmax. It is to be understood that in each of the embodiments and aspects above, provided are embodiments where applicable maximum QT interval prolongation is (a) mean maximum QT interval prolongation; (b) geometric mean maximum QT interval prolongation; or (c) average maximum QT interval prolongation. It is to be understood that in each of the aspects above, provided are embodiments wherein when applicable the D2 receptor occupancy is the average D2 receptor occupancy.

It is to be understood that in each of the aspects above, provided are embodiments wherein when applicable the occupancy of D2 receptors is measured using Positron Emission Tomography (PET) as described in Table 38 and accompanying text.

It is to be understood that in each of the aspects above, provided are embodiments wherein the (R)-(+)-amisulpride is crystalline (R)-(+)-amisulpride of crystal Form A; and the (S)-(−)-amisulpride is crystalline (S)-(−)-amisulpride of crystal Form A'; wherein Form A is characterized by a powder x-ray diffraction pattern comprising peaks, in terms of 2-theta, at 7.0±0.2°, 9.7±0.2°, and 15.4±0.2°; and Form A' is characterized by a powder x-ray diffraction pattern comprising peaks, in terms of 2-theta, at 7.0±0.2°, 9.7±0.2°, and 15.4±0.2°.

In various aspects and embodiments, provided are methods of treating a psychiatric disorder in a subject comprising administering to the subject a solid oral dosage form according to any of the aspects and embodiments of pharmaceutical compositions above and/or providing to a subject for the treatment of a psychiatric disorder a medicament comprising a pharmaceutical composition above. In various embodiments, the psychiatric disorder treated is (a) a depressive disorder; (b) bipolar disorder; (c) bipolar depression; (d) major depressive disorder (MDD); (e) major depressive disorder with mixed features (MDD-MF); (f) treatment resistant depression (TRD); (g) schizophrenia; (h) one or more of schizophrenia and negative symptoms of schizophrenia; or (i) two or more of schizophrenia, negative symptoms of schizophrenia, treatment resistant depression, bipolar disorder and depression.

In various aspects and embodiments, provided are methods of treating a psychiatric disorder in a subject comprising administering to the subject a solid oral dosage form according to any of the aspects and embodiments of pharmaceutical compositions above and/or providing to a subject for the treatment of a psychiatric disorder a medicament comprising a pharmaceutical composition above wherein the psychiatric disorder is selected from schizophrenia, negative symptoms of schizophrenia, treatment resistant depression, bipolar disorder and depression.

In various aspects and embodiments, provided are methods of treating bipolar disorder comprising administering to a subject in need thereof an effective amount of a solid oral dosage form according to any of the aspects and embodiments of pharmaceutical compositions above and/or providing to a subject for the treatment of a psychiatric disorder a medicament comprising a pharmaceutical composition above. In various embodiments, the bipolar disorder is bipolar depression.

It is to be understood that in each of the embodiments and aspects above, provided are embodiments of the methods above wherein the solid oral dosage form is effective to provide in the subject after administration (a) a suppression of the time in rapid eye movement (REM) sleep as characterized by a decrease in REM sleep by an amount greater than 10 minutes; (b) a suppression of the time in rapid eye movement (REM) sleep as characterized by a decrease in REM sleep by an amount about 15 minutes to about 45 minutes; or (c) a suppression of the time in rapid eye movement (REM) sleep as characterized by a decrease in REM sleep by an amount about 15 minutes to about 30 minutes.

It is to be understood that in each of the embodiments and aspects above, provided are embodiments of the methods above wherein the solid oral dosage form is effective to provide in the subject after administration (a) a suppression of the time in rapid eye movement (REM) sleep as characterized by a latency to REM sleep by an amount greater than 20 minutes; or (b) a suppression of the time in rapid eye movement (REM) sleep as characterized by a latency to REM sleep by an amount greater than 30 minutes;

It is to be understood that in each of the embodiments and aspects above, provided are embodiments of the methods above wherein the solid oral dosage form is effective to provide in the subject after administration (a) a suppression of the time in rapid eye movement (REM) sleep as characterized by a decrease in total REM sleep time relative to total sleep time by an amount greater than 5%; or (b) a suppression of the time in rapid eye movement (REM) sleep as characterized by a decrease in total REM sleep time relative to total sleep time by an amount greater than 6.5%.

It is to be understood that in each of the embodiments and aspects above, provided are embodiments wherein the pharmaceutical composition is administered once daily. In various embodiments administration comprises administering once daily to a subject in need thereof an effective amount of a pharmaceutical composition according to any one of the aspects and embodiments above.

It is to be understood that in each of the embodiments and aspects above, provided are embodiments wherein when said pharmaceutical composition is first administered to a subject population it provides: (1) a blood plasma Cmax of amisulpride, compared to an immediate release composition having the same total daily amount of amisulpride as the pharmaceutical composition, that is less than about 80% of the Cmax of said immediate release composition; (2) a AUC from 0 to 24 hours after administration ($AUC_{0-24}$) of amisulpride, compared to an immediate release composition having the same total daily amount of amisulpride as the pharmaceutical composition, that is (a) less than about 70% of the $AUC_{0-24}$ of said immediate release composition.

It is to be understood that in each of the embodiments and aspects above, provided are embodiments wherein when said pharmaceutical composition is first administered to a subject population it provides: (1) a steady state blood plasma Cmax of amisulpride, compared to an immediate release composition having the same total daily amount of amisulpride as the pharmaceutical composition, that is less than about 80% of the Cmax of said immediate release composition; and (2) a steady state AUC from 0 to 24 hours after administration ($AUC_{0-24}$) of amisulpride, compared to an immediate release composition having the same total daily amount of amisulpride as the pharmaceutical composition, that is less than about 80% of the $AUC_{0-24}$ of said immediate release composition. In various embodiments, the steady state blood plasma Cmax and steady state AUC are achieved after single daily dosage administration of the pharmaceutical composition over one week.

It is to be understood that in each of the aspects above, provided are embodiments wherein the solid oral dosage form provides a therapeutically effective plasma concentration over a period of 24 hours to treat a psychiatric disorder when administered to a subject.

The present inventions also include the following aspects and embodiments. The following aspects and embodiments are listed with numerical references for convenience in exposition and reference, such numerical listing and reference is not meant to be construed in a limiting sense.

Embodiment 1, a method of treating bipolar depression comprising: administering between about 200 mg to about 400 mg per day of amisulpride by weight of free base as a solid oral dosage form to a subject, the solid oral dosage form comprising amisulpride in the form of an unequal mixture of (R)-(+)-amisulpride and (S)-(−)-amisulpride, or pharmaceutically acceptable salts thereof, wherein the enantiomeric ratio of (R)-(+)-amisulpride to (S)-(−)-amisulpride is about 85:15 by weight of free base, and an extended release agent in an amount between about 10% to about 50% by total solid oral dosage form weight; wherein said administration provides a subject population average maximum QT interval prolongation relative to baseline that is less than 12 milliseconds (ms).

Embodiment 2, the method of embodiment 1, wherein said administration is once per day.

Embodiment 3, the method of embodiment 1, wherein said solid oral dosage form is a tablet.

Embodiment 4, the method of embodiment 1, wherein the population average maximum QT interval prolongation relative to baseline is the population average maximum QTcF interval prolongation relative to baseline over the time period of 12 hours after said administration.

Embodiment 5, the method of embodiment 1, wherein the population average maximum QT interval prolongation relative to baseline is less than 11 milliseconds (ms).

Embodiment 6, the method of embodiment 1, wherein the population average maximum QT interval prolongation relative to baseline is less than 10 milliseconds (ms).

Embodiment 7, the method of embodiment 1, wherein said administration is about 200 mg per day of amisulpride by weight of free base.

Embodiment 8, the method of embodiment 7, wherein the population average maximum QT interval prolongation relative to baseline is less than 9 milliseconds (ms).

Embodiment 9, the method of embodiment 1, wherein the extended release agent comprises a matrix forming agent.

Embodiment 10, the method of embodiment 9, wherein the matrix forming agent comprises one or more cellulosic ethers.

Embodiment 11, the method of embodiment 1, wherein the extended release agent is in an amount between about 20% to about 40% by total solid oral dosage form weight.

Embodiment 12, the method of embodiment 1, wherein the extended release agent comprises hydroxypropyl methylcellulose in an amount between about 20% to about 30% by total solid oral dosage form weight.

Embodiment 13, the method of embodiment 1, wherein said administration provides about 27 hours after said administration a subject population average occupancy of dopamine D2 receptors between about 20% and about 60%, when the occupancy of D2 receptors is measured using Positron Emission Tomography (PET) substantially as described in Table 38 and accompanying text.

Embodiment 14, the method of embodiment 1, wherein said administration provides: (a) a blood plasma population geometric mean Cmax of amisulpride that is less than about 80% of the population geometric mean Cmax achieved by an immediate release composition having the same total daily amount of amisulpride as the solid oral dosage form, and (b) a population geometric mean AUC from 0 to 24 hours after administration ($AUC_{0-24}$) of amisulpride that is less than about 80% of the population geometric mean $AUC_{0-24}$ achieved by an immediate release composition having the same total daily amount of amisulpride as the solid oral dosage form.

Embodiment 15, the method of embodiment 14, wherein said immediate release composition is the immediate release composition substantially as described in Table 25 and having the same total daily amount of amisulpride as the pharmaceutical composition.

Embodiment 16, a method of treating bipolar depression comprising: administering between about 200 mg to about 400 mg per day of amisulpride by weight of free base as a tablet to a subject, the tablet comprising amisulpride in the form of an unequal mixture of (R)-(+)-amisulpride and (S)-(−)-amisulpride, or pharmaceutically acceptable salts thereof, wherein the enantiomeric ratio of (R)-(+)-amisulpride to (S)-(−)-amisulpride is 85:15 by weight of free base, and an extended release agent in an amount between about 10% to about 50% by total tablet weight; wherein said administration provides a subject population average maximum QT interval prolongation relative to baseline that is less than about 0.4 milliseconds (ms) per 10 mg of amisulpride.

Embodiment 17, the method of embodiment 16, wherein said administration is once per day.

Embodiment 18, the method of embodiment 16, wherein the population average maximum QT interval prolongation relative to baseline is the population average maximum QTcF interval prolongation relative to baseline over the time period of 12 hours after said administration.

Embodiment 19, the method of embodiment 16, wherein the population average maximum QT interval prolongation relative to baseline is less than about 0.35 milliseconds (ms) per 10 mg of amisulpride.

Embodiment 20, the method of embodiment 16, wherein the population average maximum QT interval prolongation relative to baseline is less than about 0.3 milliseconds (ms) per 10 mg of amisulpride.

Embodiment 21, the method of embodiment 16, wherein the extended release agent comprises a matrix forming agent.

Embodiment 22, the method of embodiment 21, wherein the matrix forming agent comprises one or more cellulosic ethers.

Embodiment 23, the method of embodiment 22, wherein the extended release agent comprises hydroxypropyl methylcellulose in an amount between about 20% to about 40% by total tablet weight.

Embodiment 24, the method of embodiment 16, wherein said administration provides about 27 hours after said administration a subject population average occupancy of dopamine D2 receptors between about 20% and about 60%, when the occupancy of D2 receptors is measured using Positron Emission Tomography (PET) substantially as described in Table 38 and accompanying text.

Embodiment 25, the method of embodiment 16, wherein said administration provides a population Cmax/Cmin ratio of amisulpride that is less than about 2, wherein the values of Cmax and Cmin are determined within 9 hours after administration.

Embodiment 26, the method of embodiment 16, wherein said administration provides: a. a blood plasma population geometric mean Cmax of amisulpride that is less than about 80% of the population geometric mean Cmax achieved by an immediate release composition having the same total daily amount of amisulpride as the pharmaceutical composition, and b. a population geometric mean AUC from 0 to 24 hours after administration ($AUC_{0-24}$) of amisulpride that is less than about 80% of the population geometric mean $AUC_{0-24}$ achieved by an immediate release composition having the same total daily amount of amisulpride as the pharmaceutical composition.

Embodiment 27, the method of embodiment 26, wherein said immediate release composition is the immediate release composition substantially as described in Table 25 and having the same total daily amount of amisulpride as the pharmaceutical composition Embodiment 28, a method of treating bipolar depression comprising:
administering between about 200 mg to about 400 mg per day of amisulpride by weight of free base as a solid oral dosage form to a subject, the solid oral dosage form comprising amisulpride in the form of an unequal mixture of (R)-(+)-amisulpride and (S)-(−)-amisulpride, or pharmaceutically acceptable salts thereof, wherein the enantiomeric ratio of (R)-(+)-amisulpride to (S)-(−)-amisulpride is 85:15 by weight of free base, and an extended release agent in an amount between about 10% to about 50% by total solid oral dosage form weight; wherein said administration provides: a subject population average maximum QTcF interval prolongation relative to baseline that is less than 12 milliseconds (ms) over the time period of 12 hours after said administration, and about 27 hours after said administration a subject population average occupancy of dopamine D2 receptors between about 20% and about 60%.

Embodiment 29, the method of embodiment 28, wherein said administration is once per day.

Embodiment 30, the method of embodiment 28, wherein said solid oral dosage form is a tablet.

Embodiment 31, the method of embodiment 28, wherein the occupancy of D2 receptors is measured using Positron Emission Tomography (PET) substantially as described in Table 38 and accompanying text.

Embodiment 32, the method of embodiment 28, wherein the extended release agent comprises a matrix forming agent.

Embodiment 33, the method of embodiment 32, wherein the matrix forming agent comprises one or more cellulosic ethers.

Embodiment 34, the method of embodiment 28, wherein the extended release agent comprises hydroxypropyl methylcellulose in an amount between about 20% to about 40%/by total solid oral dosage form weight.

Embodiment 35, the method of embodiment 28, wherein said administration provides a population Cmax/Cmin ratio of amisulpride that is less than about 2, wherein the values of Cmax and Cmin are determined within 9 hours after administration.

Embodiment 36, the method of embodiment 28, wherein said administration provides: a. a blood plasma population geometric mean Cmax of amisulpride that is less than about 80% of the population geometric mean Cmax achieved by an immediate release composition having the same total daily amount of amisulpride as the pharmaceutical composition, and b. a population geometric mean AUC from 0 to 24 hours after administration ($AUC_{0-24}$) of amisulpride that is less than about 80% of the population geometric mean $AUC_{0-24}$ achieved by an immediate release composition having the same total daily amount of amisulpride as the pharmaceutical composition.

Embodiment 37, the method of embodiment 36, wherein said immediate release composition is the immediate release composition substantially as described in Table 25 and having the same total daily amount of amisulpride as the pharmaceutical composition Embodiment 38, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+) amisulpride is greater than the amount of (S)-(−)-amisulpride; and one or more pharmaceutically acceptable excipients, wherein when administered to a subject population, said pharmaceutical composition provides a population average maximum QT interval prolongation relative to baseline over the time period of 12 hours after administration of: (a) less than about 0.45 milliseconds (ms) per 10 mg of amisulpride; or (b) less than about 0.40 milliseconds (ms) per 10 mg of amisulpride; or (c) less than about 0.35 milliseconds (ms) per 10 mg of amisulpride; or (d) less than about 0.30 milliseconds (ms) per 10 mg of amisulpride; or (e) less than about 0.25 milliseconds (ms) per 10 mg of amisulpride; or (f) less than about 0.20 milliseconds (ms) per 10 mg of amisulpride; or (g) less than about 0.15 milliseconds (ms) per 10 mg of amisulpride; or (h) less than about 0.10 milliseconds (ms) per 10 mg of amisulpride; or (i) less than about 0.05 milliseconds (ms) per 10 mg of amisulpride or (j) less than about 0.02 milliseconds (ms) per 10 mg of amisulpride.

Embodiment 39, the pharmaceutical composition of embodiment 38, wherein the population average maximum QT interval prolongation relative to baseline is the population average maximum QTcF interval prolongation relative to baseline.

Embodiment 40, the pharmaceutical composition of embodiment 38, wherein the combined amount of (R)-(+)-amisulpride and (S)-(−)-amisulpride, or pharmaceutically acceptable salts thereof, is: (a) about 100 mg; or (b) about 160 mg; or (c) about 200 mg; or (d) about 300 mg; or (e) about 400 mg; or (f) about 500 mg; or (g) or about 600 mg by weight of free base.

Embodiment 41, a pharmaceutical composition in a solid oral dosage form, the solid oral dosage form comprising, 200 mg of amisulpride in the form of an unequal mixture of (R)-(+) amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, wherein when administered to a subject population provides a population average maximum QTcF interval prolongation relative to baseline over the time period of 12 hours after administration of: (a) less than about 10 milliseconds (ms); or (b) less than about 9 milliseconds (ms); or (c) less than about 8 milliseconds (ms); or (d) less than about 7 milliseconds (ms); or (e) less than about 6 milliseconds (ms); or (f) less than about 5 milliseconds (ms).

Embodiment 42, the pharmaceutical composition of embodiment 41, wherein the population average maximum QTcF interval prolongation relative to baseline is the population average maximum QTcF interval prolongation relative to baseline at geometric mean Cmax.

Embodiment 43, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+) amisulpride is greater than the amount of (S)-(−)-amisulpride; and one or more pharmaceutically acceptable excipients, wherein when administered to a subject population, the pharmaceutical composition provides a population average maximum QT interval prolongation relative to baseline over the time period of 12 hours after administration, compared to an immediate release composition having the same total daily amount of amisulpride as the pharmaceutical composition, that is: (a) at least about 75% less than that of said immediate release composition; or (b) at least about 65% less than that of said immediate release composition; or (c) at least about 60% less than that of said immediate release composition; or (d) at least about 55% less than that of said immediate release composition; or (e) at least about 50% less than that of said immediate release composition.

Embodiment 44, the pharmaceutical composition of embodiment 43, wherein the population average maximum QT interval prolongation relative to baseline is the population average maximum QTcF interval prolongation relative to baseline.

Embodiment 45, the pharmaceutical composition of embodiment 43, wherein said immediate release composition is the immediate release composition substantially as described in Table 25 and having the same total daily amount of amisulpride as the pharmaceutical composition.

Embodiment 46, the pharmaceutical composition of embodiment 43, wherein the combined amount of (R)-(+)-amisulpride and (S)-(−)-amisulpride, or pharmaceutically acceptable salts thereof, is: (a) about 100 mg; or (b) about 160 mg; or (c) about 200 mg; or (d) about 300 mg; or (e) about 400 mg; or (f) about 500 mg; or (g) or about 600 mg by weight of free base.

Embodiment 47, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and one or more pharmaceutically acceptable excipients, wherein when said pharmaceutical composition is administered to a subject population provides at about 27 hours after administration a population average occupancy of dopamine D2 receptors that is: (a) at least 85% of the dopamine D2 receptors occupancy achieved by an immediate release composition having the same total daily amount of amisulpride as the pharmaceutical composition; or (b) at least 90% of the dopamine D2 receptors occupancy achieved by an immediate release composition having the same total daily amount of amisulpride as the pharmaceutical composition; or (c) at least 95% of the dopamine D2 receptors occupancy achieved by an immediate release composition having the same total daily amount of amisulpride as the pharmaceutical composition.

Embodiment 48, the pharmaceutical composition of embodiment 47, wherein said immediate release composition is the immediate release composition substantially as described in Table 25 and having the same total daily amount of amisulpride as the pharmaceutical composition.

Embodiment 49, the pharmaceutical composition of embodiment 47, wherein the combined amount of (R)-(+)-amisulpride and (S)-(−)-amisulpride, or pharmaceutically acceptable salts thereof, is: (a) about 100 mg; or (b) about 160 mg; or (c) about 200 mg; or (d) about 300 mg; or (e) about 400 mg; or (f) about 500 mg; or (g) or about 600 mg by weight of free base.

Embodiment 50, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, and one or more pharmaceutically acceptable excipients, wherein said pharmaceutical composition when administered to a subject population is effective in minimizing the difference between Cmin and Cmax of amisulpride compared to an immediate release composition having the same total daily amount of amisulpride as the pharmaceutical composition, wherein the value of Cmin is determined within about 9 hours after administration.

Embodiment 51, the pharmaceutical composition of embodiment 50, wherein the combined amount of (R)-(+)-amisulpride and (S)-(−)-amisulpride, or pharmaceutically acceptable salts thereof, is: (a) about 100 mg; or (b) about 160 mg; or (c) about 200 mg; or (d) about 300 mg; or (e) about 400 mg; or (f) about 500 mg; or (g) or about 600 mg by weight of free base.

Embodiment 52, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, and one or more pharmaceutically acceptable excipients, wherein when said composition is administered to a subject population provides a Cmax/Cmin ratio of amisulpride, wherein the value of Cmin is determined within about 9 hours after administration, that is: (a) less than about 2; or (b) less than about 1.9; or (c) less than about 1.8.

Embodiment 53, the pharmaceutical composition of embodiment 52, wherein the values of Cmax and Cmin are the population geometric mean values and the values are determined within about 9 hours after administration.

Embodiment 54, the pharmaceutical composition of embodiment 52, wherein the solid oral dosage when administered in a total amount of amisulpride of 200 mg provides a blood plasma population geometric mean Cmax of (a) less than about 350 ng/mL; (b) less than about 300 ng/mL; or (c) less than about 250 ng/mL.

Embodiment 55, the pharmaceutical composition of embodiment 52, wherein the solid oral dosage when administered in a total amount of amisulpride of 400 mg provides a blood plasma population geometric mean Cmax of (a) less than about 500 ng/mL; (b) less than about 475 ng/mL; or (c) less than about 450 ng/mL Embodiment 56, the pharmaceutical composition of embodiment 52, wherein the combined amount of (R)-(+)-amisulpride and (S)-(−)-amisulpride, or pharmaceutically acceptable salts thereof, is: (a) about 100 mg; or (b) about 160 mg; or (c) about 200 mg; or (d) about 300 mg; or (e) about 400 mg; or (f) about 500 mg; or (g) or about 600 mg by weight of free base.

Embodiment 57, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+) amisulpride is greater than the amount of (S)-(−)-amisulpride; and an extended release agent, wherein the solid oral dosage form when dissolution tested using a two-stage in vitro gastrointestinal simulation dissolution test: (a) releases less than about 30% of the amisulpride after 1 hour, releases more than about 20% and less than about 60% of the amisulpride after 3 hours, and releases more than about 30% and less than about 100% of the amisulpride after 6 hours; or (b) releases less than about 30% of the amisulpride after 1 hour, releases more than 20% and less than about 60% of the amisulpride after 3 hours, and releases more than about 30% and less than 75% of the amisulpride after 6 hours; or (c) releases less than about 20% of the amisulpride after 1 hour, releases more than about 20% and less than about 50% of the amisulpride after 3 hours, and releases more than about 30% and less than about 75% of the amisulpride after 6 hours; or (d) releases less than about 20% of the amisulpride after 1 hour, releases more than about 20% and less than about 50% of the amisulpride after 3 hours, and releases more than about 30% and less than about 50% of the amisulpride after 6 hours; or (e) releases no more than about 30% of the amisulpride after 1 hour, releases between about 30% and about 75% of the amisulpride after about 3 hours, and releases more than about 75% of the amisulpride after about 12 hours; or (f) releases less than about 30% of the amisulpride after 1 hour, releases more than about 20% and less than about 60% of the amisulpride after 3 hours, releases more than about 30% and less than about 100% of the amisulpride after 6 hours, and releases more than about 75% of the amisulpride after about 10 hours; or (g) releases less than about 30% of the amisulpride after 1 hour, releases more than about 20% and less than about 60% of the amisulpride after 3 hours, releases more than about 30% and less than about 100% of the amisulpride after 6 hours, and releases more than about 75% of the amisulpride after about 8 hours; or (h) releases less than about 30% of the amisulpride after 1 hour, releases more than about 20% and less than about 60% of the amisulpride after 3 hours, releases more than about 30% and less than about 75% of the amisulpride after 6 hours, and releases more than about 75% of the amisulpride after about 10 hours; or (i) releases less than about 20% of the amisulpride after 1 hour, releases more than about 20% and less than about 60% of the amisulpride after 3 hours, releases more than about 30% and less than about 100% of the amisulpride after 6 hours, and releases more than about 75% of the amisulpride after about 10 hours; or (j) releases less than about 30% of the amisulpride after 1 hour, releases more than about 20% and less than about 60% of the amisulpride after 3 hours, releases more than about 30% and less than about 50% of the amisulpride after 6 hours, and releases more than about 75% of the amisulpride after about 10 hours.

Embodiment 58, the pharmaceutical composition of embodiment 57, wherein the two-stage gastrointestinal simulation dissolution test comprises in the first stage 500 ml of an aqueous media having a pH of about 2 and adding after 1 hour 400 ml of an aqueous buffer media such that the second stage pH is 6.8; where the temperature in both stages of the two-stage in vitro gastrointestinal simulation dissolution test is about 37° C.

Embodiment 59, the pharmaceutical composition of embodiment 57, wherein the two-stage gastrointestinal simulation dissolution test is conducted in a paddle apparatus substantially in accord with that described in one of more of: (a) United States Pharmacopeia Convention (USP) Apparatus 2 of Chapter 711 Dissolution; USP41-NF36 General Chapter <711> Dissolution, and (b) Japanese Pharmacopeia (JP) General test <6.10>.

Embodiment 60, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and an extended release agent, wherein the solid oral dosage form when dissolution tested using the two-stage in vitro dissolution test described in Table 5 in the paddle apparatus described in United States Pharmacopeia Convention (USP) Apparatus 2 of Chapter 711 Dissolution; USP41-NF36 General Chapter <711> Dissolution has a dissolution profile substantially the same as: (a) the profile of Lot 3C in FIG. 1C; or (b) the profile of Lot 2C in FIG. 1C; or (c) the profile of Lot 3Z used in the study of Example 7A, Part 1 or Part 2 in FIG. 1D; or (d) the profile of Lot 3Z used in fed state study of Example 7A, Part 1 in FIG. 1D; or (e) the profile of Lot 3Z used in MAD/PET study of Example 7B in FIG. 1D; or (f) the profile of Lot 4Z in FIG. 1D; or (g) the profile of Lot 5Z in FIG. 1D; or (h) the profile of Lot 6Z in FIG. 1D; or (i) the profile of Lot 7C in FIG. 1E over the time period from 0 to 6 hours; or (j) the profile of Lot 8C in FIG. 1E over the time period from 0 to 6 hours; or (k) the profile of Lot 3Z used in the study of Example 7B, Example 7A Part 1, or (l) the profile of Lot 3Z used in the study of Example 7A Part 2 in FIG. 1D.

Embodiment 61, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+) amisulpride is greater than the amount of (S)-(−)-amisulpride; and an extended release agent, wherein when said pharmaceutical composition is administered to a subject population provides a plasma concentration profile substantially the same as: (a) the profile of Lot 4Z in FIG. 22B; or (b) the profile of Lot 3Z in FIG. 22C; or (c) the profile of Lot 3Z Fed State in FIG. 22D; (d) the profile of Lot 4Z in FIG. 22F; or (e) the profile of Lot 3Z in FIG. 22H; or (f) the profile of Lot 3Z Fed State in FIG. 22I; or (g) the profile of Lot 3Z in FIG. 22J; or (h) the profile of Lot 5Z in FIG. 22G; or (i) the profile of Lot 6Z in FIG. 22K.

Embodiment 62, a pharmaceutical composition in a solid oral dosage form, the solid oral dosage form comprising, amisulpride in the form of an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride; and an extended release agent, wherein when said solid oral dosage form is administered to a subject population provides: (i) a population geometric mean Tmax of amisulpride is between about 4 hours and about 6 hours after administration; and (ii) a AUC to Tmax ($AUC_{0\text{-}Tmax}$) that is less than about: (a) 19% of the area under the curve from administration to about 48 hours ($AUC_{0\text{-}48}$); or (b) 18% of the population mean area under the curve from administration to about 48 hours ($AUC_{0\text{-}48}$); or (c) 17% of the area under the curve from administration to 48 hours ($AUC_{0\text{-}48}$); or (d) 16% of the area under the curve from administration to 48 hours ($AUC_{0\text{-}48}$); or (e) 15% of the area under the curve from administration to 48 hours ($AUC_{0\text{-}48}$); or (f) 14% of the area under the curve from administration to 48 hours ($AUC_{0\text{-}48}$); or (g) 13% of the area under the curve from administration to 48 hours ($AUC_{0\text{-}48}$); or (h) 12% of the area under the curve from administration to 48 hours ($AUC_{0\text{-}48}$).

Embodiment 63, the pharmaceutical composition of any one of embodiments 40, 41, 46, 47, 51, and 56 wherein the enantiomeric ratio of (R)-(+)-amisulpride to (S)-(−)-amisulpride, or pharmaceutically acceptable salts thereof, is about 85:15 by weight of free base.

Embodiment 64, the pharmaceutical composition of embodiment 63, wherein the one or more pharmaceutically acceptable excipients comprise an extended release agent.

Embodiment 65, the pharmaceutical composition of embodiment 64, wherein the extended release agent is in an amount: (a) between about 10% and about 50% by total solid oral dosage form weight; or (b) between about 30% and about 50% by total solid oral dosage form weight; or (c) between about 20% and about 40% by total solid oral dosage form weight; or (d) between about 20% and about 30% by total solid oral dosage form weight.

Embodiment 66, the pharmaceutical composition of embodiment 65, wherein the solid oral dosage form is a tablet.

Embodiment 67, the pharmaceutical composition of embodiment 66, wherein the extended release agent comprises a matrix forming agent.

Embodiment 68, the pharmaceutical composition of embodiment 67, wherein the matrix forming agent comprises one or more cellulosic ethers.

Embodiment 69, the pharmaceutical composition of embodiment 66, wherein the extended release agent comprises hydroxypropyl methylcellulose in an amount between about 20% to about 40% by total solid oral dosage form weight.

Embodiment 70, the pharmaceutical composition of embodiment 63, wherein the solid oral dosage form comprises by total solid oral dosage form weight: between about 35% to about 45% of said amisulpride, between about 20% to about 40% of a pharmaceutically acceptable filler, and between about 20% to about 35% of the extended release agent.

Embodiment 71, the pharmaceutical composition of embodiment 63, wherein when said pharmaceutical composition is administered to the subject population provides: (a) a blood plasma population geometric mean Cmax of amisulpride that is less than about 80% of the population geometric mean Cmax achieved by an immediate release composition having the same total daily amount of amisulpride as the pharmaceutical composition, and (b) a population geometric mean AUC from 0 to 24 hours after administration ($AUC_{0\text{-}24}$) of amisulpride that is less than about 80% of the population geometric mean $AUC_{0\text{-}24}$ achieved by an immediate release composition having the same total daily amount of amisulpride as the pharmaceutical composition.

Embodiment 72, the pharmaceutical composition of embodiment 71, wherein said immediate release composition is the immediate release composition substantially as described in Table 25 and having the same total daily amount of amisulpride as the pharmaceutical composition.

Embodiment 73, the pharmaceutical composition of embodiment 63, wherein when said pharmaceutical composition is administered to the subject population provides about 27 hours after said administration: (a) a population average occupancy of dopamine D2 receptors between about 20% and about 60%, or (b) a population average occupancy of dopamine D2 receptors between about 30% and about 50%; wherein the occupancy of D2 receptors is measured using Positron Emission Tomography (PET) substantially as described in Table 38 and accompanying text.

Embodiment 74, the pharmaceutical composition of embodiment 73, wherein the amount of (S)-(−)-amisulpride, or pharmaceutically acceptable salts thereof, is less than about 100 mg by weight of free base.

Embodiment 75, a method of treating a psychiatric disorder comprising administering a solid oral dosage form of embodiment 63.

Embodiment 76, the method of embodiment 75, wherein the solid oral dosage form is administered once per day in a total daily amount of between about 200 mg to about 400 mg per day of said amisulpride by weight of free base.

Embodiment 77, the method of embodiment 76, wherein the psychiatric disorder is: (a) a depressive disorder; or (b) bipolar disorder; or (c) bipolar depression; or (d) major depressive disorder (MDD); or (e) major depressive disorder with mixed features (MDD-MF); or (f) treatment resistant depression (TRD); or (g) schizophrenia; or (h) negative symptoms of schizophrenia.

Embodiment 78, the method of embodiment 76, wherein the psychiatric disorder is bipolar disorder; bipolar depression; or both.

Embodiment 79, a method of treating bipolar depression comprising administering a solid oral dosage form of embodiment 63 in once per day in a total daily amount of between about 200 mg to about 400 mg per day of said amisulpride by weight of free base.

Embodiment 80, a method of treating bipolar depression comprising administering a therapeutically effective amount of a pharmaceutical composition of embodiment 63.

Embodiment 81, the pharmaceutical composition of any one of embodiments 57, 60, 61, and 62, wherein the enantiomeric ratio of (R)-(+)-amisulpride to (S)-(−)-amisulpride, or pharmaceutically acceptable salts thereof, is about 85:15 by weight of free base.

Embodiment 82, the pharmaceutical composition of embodiment 81, wherein the extended release agent is in an amount: (a) between about 10% and about 50% by total solid oral dosage form weight; or (b) between about 30% and about 50% by total solid oral dosage form weight; or (c) between about 20% and about 40% by total solid oral dosage form weight; or (d) between about 20% and about 30% by total solid oral dosage form weight.

Embodiment 83, the pharmaceutical composition of embodiment 82, wherein the solid oral dosage form is a tablet.

Embodiment 84, the pharmaceutical composition of embodiment 83, wherein the extended release agent comprises a matrix forming agent.

Embodiment 85, the pharmaceutical composition of embodiment 83, wherein the matrix forming agent comprises one or more cellulosic ethers.

Embodiment 86, the pharmaceutical composition of embodiment 83, wherein the extended release agent comprises hydroxypropyl methylcellulose in an amount between about 20% to about 40% by total solid oral dosage form weight.

Embodiment 87, the pharmaceutical composition of embodiment 83, wherein the solid oral dosage form comprises one or more of (a) a filler; (b) a binder; and (c) a lubricant.

Embodiment 88, the pharmaceutical composition of embodiment 87, wherein the lubricant comprises magnesium stearate.

Embodiment 89, the pharmaceutical composition of embodiment 87, wherein the filler comprises D-mannitol and wherein the solid oral dosage form comprises between about 0.5% to about 2% by total tablet weight of a binder comprising polyvinyl alcohol.

Embodiment 90, the pharmaceutical composition of embodiment 81, wherein the solid oral dosage form comprises by total solid oral dosage form weight: between about 35% to about 45% of said amisulpride, between about 20% to about 40% of a pharmaceutically acceptable filler, and between about 20% to about 35% of the extended release.

Embodiment 91, the pharmaceutical composition of any one of embodiments 38, 41, 43, 47, 50, 52, 57, 60, 61, and 62, wherein the enantiomeric ratio of (R)-(+)-amisulpride to (S)-(−)-amisulpride is from about: (a) 65:35 to about 88:12 by weight of free base; or (b) 75:25 to about 88:12 by weight of free base; or (c) 80:20 to about 88:12 by weight of free base; or (d) 85:15 to about 90:10 by weight of free base.

Embodiment 92, the pharmaceutical composition of any one of embodiments 38, 43, 47, 50, 52, 57, 60, and 62, wherein the combined amount of (R)-(+)-amisulpride and (S)-(−)-amisulpride, or pharmaceutically acceptable salts thereof, is from: (a) about 50 mg to about 600 mg by weight of free base; or (b) about 200 mg to about 600 mg by weight of free base; or (c) about 100 mg to about 500 mg by weight of free base; or (d) about 100 mg to about 400 mg by weight of free base; or (e) about 200 mg to about 400 mg by weight of free base.

Embodiment 93, the pharmaceutical composition of embodiment 92, comprising: about 170 mg of (R)-(+)-amisulpride, or a pharmaceutically acceptable salt thereof, by weight of free base; and about 30 mg of (S)-(−)-amisulpride, or a pharmaceutically acceptable salt thereof, by weight of free base.

Embodiment 94, the pharmaceutical composition of embodiment 92, comprising: about 85 mg of (R)-(+)-amisulpride, or a pharmaceutically acceptable salt thereof, by weight of free base; and about 15 mg of (S)-(−)-amisulpride, or a pharmaceutically acceptable salt thereof, by weight of free base.

Embodiment 95, a pharmaceutical composition of any one of embodiments 47, 50, 52, 57, 60, 61, and 62, wherein when administered to a subject population provides a population average maximum QT interval prolongation relative to baseline over the time period of 12 hours after administration of: (a) less than about 0.45 milliseconds (ms) per 10 mg of amisulpride; or (b) less than about 0.40 milliseconds (ms) per 10 mg of amisulpride; or (c) less than about 0.35 milliseconds (ms) per 10 mg of amisulpride; or (d) less than about 0.30 milliseconds (ms) per 10 mg of amisulpride; or (e) less than about 0.25 milliseconds (ms) per 10 mg of amisulpride; or (f) less than about 0.20 milliseconds (ms) per 10 mg of amisulpride; or (g) less than about 0.15 milliseconds (ms) per 10 mg of amisulpride; or (h) less than about 0.10 milliseconds (ms) per 10 mg of amisulpride; or (i) less than about 0.05 milliseconds (ms) per 10 mg of amisulpride or (j) less than about 0.02 milliseconds (ms) per 10 mg of amisulpride.

Embodiment 96, a pharmaceutical composition of any one of embodiments 38, 41, 43, 47, 50, 52, 57, 60, and 61, wherein, when administered to a subject population provides, compared to an immediate release composition having the same total daily amount of amisulpride as the pharmaceutical composition, a blood plasma Cmax of amisulpride that is: (a) less than about 80% of the Cmax of said immediate release composition; (b) less than about 75% of the Cmax of said immediate release composition; or (c) less than about 65% of the Cmax of said immediate release composition; or (d) is less than about 60% of the Cmax of said immediate release composition; or (e) less than about 55% of the Cmax of said immediate release composition; or (f) less than about 50% of the Cmax of said immediate release composition.

Embodiment 97, a pharmaceutical composition of any one of embodiments 40, 41, 46, 47, 50, 56, 57, 60, 61, and 62, wherein, when administered to a subject population provides a suppression of the time in rapid eye movement (REM) sleep as characterized by: (a) a decrease in REM sleep by an amount greater than 10 minutes; or (b) a decrease in REM sleep by an amount about 15 minutes to about 45 minutes; or (c) a decrease in REM sleep by an amount about 15 minutes to about 30 minutes.

Embodiment 98, a pharmaceutical composition of any one of embodiments 40, 41, 46, 47, 50, 56, 57, 60, 61, and 62, wherein, when administered to a subject population provides a suppression of the time in rapid eye movement (REM) sleep as characterized by: (a) a latency to REM sleep by an amount greater than 20 minutes; or (b) a latency to REM sleep by an amount greater than 30 minutes.

Embodiment 99, a pharmaceutical composition of any one of embodiments 40, 41, 46, 47, 50, 56, 57, 60, 61, and 62, wherein, when administered to a subject population provides a suppression of the time in rapid eye movement (REM) sleep as characterized by: (a) a decrease in total REM sleep time relative to total sleep time by an amount greater than 5%; or (b) a decrease in total REM sleep time relative to total sleep time by an amount greater than 6.5%.

Embodiment 100, the pharmaceutical composition of any one of embodiments 40, 41, 46, 47, 50, 56, 57, 60, and 61, wherein the pharmaceutical composition when administered to a subject population provides a population geometric mean Tmax between about 4 hours and about 6 hours after administration.

Embodiment 101, a pharmaceutical composition in the form of a tablet, the tablet comprising, amisulpride in the form of an unequal mixture of (R)-(+)-amisulpride and (S)-(−)-amisulpride, or pharmaceutically acceptable salts thereof, wherein the enantiomeric ratio of (R)-(+)-amisulpride to (S)-(−)-amisulpride is from about 80:20 to about 88:12 by weight of free base, and the combined amount of (R)-(+)-amisulpride and (S)-(−)-amisulpride, or pharmaceutically acceptable salts thereof, is from about 100 mg to about 500 mg by weight of free base; and an extended release agent in an amount between about 10% and about 50% by total tablet weight.

Embodiment 102, the pharmaceutical composition of embodiment 101, wherein the combined amount of (R)-(+)-amisulpride and (S)-(−)-amisulpride, or pharmaceutically acceptable salts thereof, is about 200 mg by weight of free base and the enantiomeric ratio of (R)-(+)-amisulpride to (S)-(−)-amisulpride is 85:15 by weight of free base.

Embodiment 103, the pharmaceutical composition of embodiment 102, wherein the tablet comprises: between about 35% to about 45% by total tablet weight of amisulpride, between about 20% to about 40% by total tablet weight of a pharmaceutically acceptable filler, and between about 20% to about 30% by total tablet weight of the extended release agent.

Embodiment 104, the pharmaceutical composition of embodiment 103, wherein the extended release agent comprises hydroxypropyl methylcellulose.

Embodiment 105, the pharmaceutical composition of embodiment 104, wherein the hydroxypropyl methylcellulose has a median particle size that is 5-15 times larger than the median particle size of the amisulpride.

Embodiment 106, the pharmaceutical composition of embodiment 104, wherein the filler comprises D-mannitol and wherein the tablet comprises between about 0.5% to about 2% by total tablet weight of a binder comprising polyvinyl alcohol.

Embodiment 107, the pharmaceutical composition of embodiment 101, wherein the tablet comprises: a granular component admixed with an extra-granular component, the granular component comprising amisulpride and a binder; and the extra-granular component comprising, an extended release agent.

Embodiment 108, the pharmaceutical composition of embodiment 107, wherein the granular component comprises one or more of (a) a filler; and (b) a binder.

Embodiment 109, the pharmaceutical composition of embodiment 108, wherein the granules comprise: (a) between about 60% to about 80% by weight of amisulpride, between about 10% to about 30% by weight of filler, and between about 1% to about 5% by weight of binder; or (b) between about 70% to about 80% by weight of amisulpride, between about 20% to about 25% by weight of filler, and between about 1% to about 5% by weight of binder.

Embodiment 110, the pharmaceutical composition of embodiment 108, wherein the granular component comprises: between about 73% to about 78% by weight of amisulpride, between about 10% to about 12% by weight of a D-mannitol, between about 10% to about 12% by weight of a pregelatinized starch, and between about 1% to about 3% by weight of polyvinyl alcohol; based on the weight of the granular component.

Embodiment 111, the pharmaceutical composition of embodiment 107, wherein the extragranular component comprises one or more of (a) a filler; (b) a binder; and (c) a lubricant.

Embodiment 112, the pharmaceutical composition of embodiment 107, wherein the tablet (granules plus extragranular component) comprises: (a) between about 20% to about 70% by total tablet weight of granules of extended release agent; or (b) between about 10% to about 50% by total tablet weight of extended release agent.

Embodiment 113, the pharmaceutical composition of embodiment 107, wherein the tablet (granules plus extragranular component) comprises: (a) a combined amount of filler in both granular and extragranular between about 6% to about 60% by total tablet weight; or (b) a combined amount of filler in both granular and extragranular between about 10% to about 50% by total tablet weight.

Embodiment 114, the pharmaceutical composition of embodiment 107, wherein the tablet (granules plus extragranular component) comprises between about 1% to about 2% by total tablet weight of a lubricant.

Embodiment 115, the pharmaceutical composition of embodiment 115, wherein the lubricant is magnesium stearate.

Embodiment 116, the pharmaceutical composition of embodiment 107, wherein the tablet (granules plus extragranular component) comprises: (a) between about 34% to about 39% by total tablet weight of a D-mannitol, and about 15% by total tablet weight of hydroxypropyl methylcellulose; or (b) between about 24% to about 29% by total tablet weight of a D-mannitol, and about 25% by total tablet weight of hydroxypropyl methylcellulose; or (c) between about 4% to about 9% by total tablet weight of a D-mannitol, and about 45% by total tablet weight of hydroxypropyl methylcellulose.

Although the invention has been described with reference to a specific embodiment this description is not meant to be construed in a limiting sense. The invention being thus described, it is apparent that the same can be varied in many ways. Such variations are not to be regarded as a departure from the spirit and scope of the present invention, and all such modifications, alternatives, and equivalents as would be obvious to one skilled in the art are intended to be included within the scope of the following claims.

What is claimed is:

1. A method of alleviating and/or reducing bipolar depression comprising:

administering once per day between about 200 mg to about 400 mg per day of amisulpride by weight of free base as a solid oral dosage form to a subject, the solid oral dosage form comprising amisulpride in the form of an unequal mixture of (R)-(+)-amisulpride and (S)-(−)-amisulpride, or pharmaceutically acceptable salts thereof, wherein the enantiomeric ratio of (R)-(+)-amisulpride to (S)-(−)-amisulpride is 85:15 by weight of free base, and an extended release agent in an amount between about 10% to about 50% by total solid oral dosage form weight to provide a modified-release form;

wherein said administration provides:

a population geometric mean AUC from 0 to 24 hours after administration ($AUC_{0-24}$) of amisulpride that is less than about 80% of the population geometric mean $AUC_{0-24}$ achieved by an immediate release composition having the same enantiomeric ratio and same total daily amount of amisulpride as the solid oral dosage form, a subject population average maximum QTcF interval prolongation relative to baseline that is less than 12 milliseconds (ms) over the time period of 12 hours after said administration, and about 27 hours after said administration a subject population average occupancy of dopamine D2 receptors between about 20% and about 60%.

2. The method of claim 1, wherein said solid oral dosage form is a tablet.

3. The method of claim 1, wherein the occupancy of D2 receptors is measured using Positron Emission Tomography (PET).

4. The method of claim 1, wherein the extended release agent comprises a matrix forming agent.

5. The method of claim 4, wherein the matrix forming agent comprises one or more cellulosic ethers.

6. The method of claim 1, wherein the extended release agent comprises hydroxypropyl methylcellulose in an amount between about 20% to about 40% by total solid oral dosage form weight.

7. The method of claim 1, wherein said administration provides a population $C_{max}/C_{min}$ ratio of amisulpride that is less than about 2, wherein the values of $C_{max}$ and $C_{min}$ are determined within 9 hours after administration.

8. The method of claim 1, wherein said administration provides a $C_{max}$ that is less than 75% of the immediate release formulation.

9. The method of claim 1, wherein said administration provides a population geometric mean $T_{max}$ between about 4 hours and about 6 hours after administration.

10. The method of claim 1, wherein about 27 hours after said administration, the subject population average occupancy of dopamine D2 receptors is between about 30% and about 50%.

11. The method of claim 1, wherein the subject population average maximum QTcF interval prolongation relative to baseline that is less than 10 milliseconds (ms) over the time period of 12 hours after said administration.

12. The method of claim 1, wherein the subject population average maximum QTcF interval prolongation relative to baseline that is less than 9 milliseconds (ms) over the time period of 12 hours after said administration.

13. The method of claim 1, wherein the subject population average maximum QTcF interval prolongation relative to baseline that is less than 8 milliseconds (ms) over the time period of 12 hours after said administration.

14. The method of claim 1, wherein the subject population average maximum QTcF interval prolongation relative to baseline that is less than 7 milliseconds (ms) over the time period of 12 hours after said administration.

15. The method of claim 1, wherein the subject population average maximum QTcF interval prolongation relative to baseline that is less than 6 milliseconds (ms) over the time period of 12 hours after said administration.

16. The method of claim 1, wherein the subject population average maximum QTcF interval prolongation relative to baseline that is less than 5 milliseconds (ms) over the time period of 12 hours after said administration.

17. The method of claim 1, wherein about 200 mg per day of amisulpride by weight of free base as a solid oral dosage form is administered to the subject.

18. The method of claim 1, wherein about 300 mg per day of amisulpride by weight of free base as a solid oral dosage form is administered to the subject.

19. The method of claim 1, wherein about 400 mg per day of amisulpride by weight of free base as a solid oral dosage form is administered to the subject.

20. The method of claim 1, wherein the extended release agent is in an amount between about 20% to about 40% by total solid oral dosage form weight.

21. The method of claim 4, wherein the matrix forming agent comprises one or more cellulosic ethers, polymer coatings, polymer matrix systems, enzyme-activated systems, pH independent polymers, or pH dependent polymers.

22. The method of claim 1, wherein the extended release agent comprises one or more alginate material, carboxyvinyl polymer, sodium salts of carboxymethyl cellulose, propyl methyl cellulose, hydroxy propyl ethyl cellulose, hydroxy propyl cellulose, hydroxy ethyl cellulose, methyl cellulose, xanthan gum, polyethylene oxide, ammonio methacrylate copolymers type A and B as described in USP, polyacrylate dispersion 30% as described in Ph. Eur., or hydroxypropyl methylcellulose.

23. The method of claim 1, wherein the extended release agent comprises one or more hydroxypropylcellulose or hydroxypropyl methylcellulose.

24. The method of claim 1, wherein the extended release agent comprises hydroxypropyl methylcellulose in an amount between about 20% to about 30% by total solid oral dosage form weight.

25. The method of claim 1, wherein the extended release agent comprises hydroxypropyl methylcellulose in an amount of about 25% by total solid oral dosage form weight.

26. The method of claim 1, wherein about 200 mg per day of amisulpride by weight of free base as a solid oral dosage form is administered to the subject, and said administration provides a population geometric mean AUC from 0 to 24 hours after administration ($AUC_{0-24}$) of amisulpride that is less than about 1900 (ng*h/ml) after administration of a first dose of said solid oral dosage form.

27. The method of claim 26, wherein said administration provides a population geometric mean AUC from 0 to 24 hours after administration ($AUC_{0-24}$) of amisulpride that is less than about 2500 (ng*h/ml) after one week of administration of said solid oral dosage form in an amount of about 200 mg per day of amisulpride by weight of free base.

28. The method of claim 1, wherein about 400 mg per day of amisulpride by weight of free base as a solid oral dosage form is administered to the subject, and said administration provides a population geometric mean AUC from 0 to 24 hours after administration ($AUC_{0-24}$) of amisulpride that is less than about 4400 (ng*h/ml) after administration of a first dose of said solid oral dosage form.

29. The method of claim 28, wherein said administration provides a population geometric mean AUC from 0 to 24 hours after administration ($AUC_{0-24}$) of amisulpride that is less than about 5400 (ng*h/ml) after one week of administration of said solid oral dosage form in an amount of about 400 mg per day of amisulpride by weight of free base.

* * * * *